(12) United States Patent
Kato et al.

(10) Patent No.: US 10,944,057 B2
(45) Date of Patent: *Mar. 9, 2021

(54) COMPOUND, MATERIAL FOR ORGANIC ELECTROLUMINESCENCE DEVICES, ORGANIC ELECTROLUMINESCENCE DEVICE, AND ELECTRONIC EQUIPMENT

(71) Applicant: IDEMITSU KOSAN CO., LTD., Chiyoda-ku (JP)

(72) Inventors: Tomoki Kato, Ichihara (JP); Nobuhiro Yabunouchi, Sodegaura (JP); Masakazu Funahashi, Chiba (JP); Takahiro Fujiyama, Kisarazu (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 304 days.

This patent is subject to a terminal disclaimer.

(21) Appl. No.: 14/909,930

(22) PCT Filed: Jul. 13, 2015

(86) PCT No.: PCT/JP2015/070045
§ 371 (c)(1),
(2) Date: Feb. 3, 2016

(87) PCT Pub. No.: WO2016/006709
PCT Pub. Date: Jan. 14, 2016

(65) Prior Publication Data
US 2016/0176801 A1 Jun. 23, 2016

(30) Foreign Application Priority Data

Jul. 11, 2014 (JP) .............................. JP2014-143248
Jul. 11, 2014 (JP) .............................. JP2014-143249
(Continued)

(51) Int. Cl.
*H01L 51/00* (2006.01)
*C07D 333/76* (2006.01)
(Continued)

(52) U.S. Cl.
CPC .......... *H01L 51/006* (2013.01); *C07C 211/61* (2013.01); *C07D 209/82* (2013.01);
(Continued)

(58) Field of Classification Search
CPC ............... H01L 51/006; H01L 51/5012; H01L 51/0073; H01L 51/0074; H01L 51/0061;
(Continued)

(56) References Cited

U.S. PATENT DOCUMENTS

2003/1011886   6/2003   Oh et al.
2004/0157084 A1* 8/2004 Lee ...................... C07D 471/04
428/690

(Continued)

FOREIGN PATENT DOCUMENTS

CN      101341115 A   1/2009
CN      103755574 A   4/2014
(Continued)

OTHER PUBLICATIONS

International Search Report dated Oct. 6, 201 5 in PCT/JP2015/070045.
(Continued)

*Primary Examiner* — Michael Y Sun
(74) *Attorney, Agent, or Firm* — Oblon, McClelland, Maier & Neustadt, L.L.P.

(57) ABSTRACT

A compound represented by formula (A-0) or (B-0) is useful as a material for organic EL devices which realizes an organic EL device exhibiting high emission efficiency even when driving at a low voltage and has a long lifetime:
(Continued)

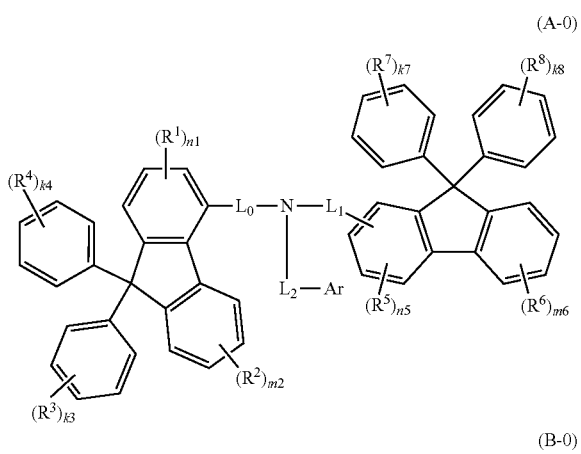

(A-0)

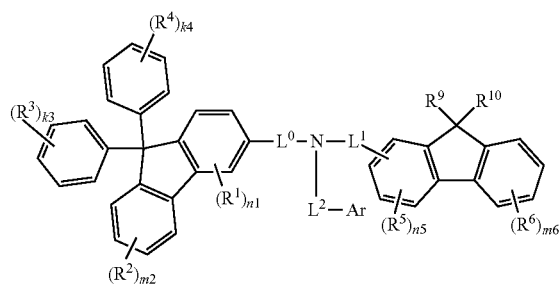

(B-0)

wherein $R^1$ to $R^{10}$, n1, m2, k3, k4, n5, m6, k7, k8, $L^0$ to $L^2$, and Ar are as defined in the description.

17 Claims, 1 Drawing Sheet

(30) Foreign Application Priority Data

Dec. 17, 2014 (JP) ............................. JP2014-255559
Dec. 17, 2014 (JP) ............................. JP2014-255562
Dec. 17, 2014 (JP) ............................. JP2014-255565

(51) Int. Cl.
  *C07D 307/91* (2006.01)
  *C09K 11/06* (2006.01)
  *H01L 51/50* (2006.01)
  *C07C 211/61* (2006.01)
  *C07D 209/82* (2006.01)
  *C07D 405/12* (2006.01)
  *C07D 209/86* (2006.01)

(52) U.S. Cl.
  CPC ......... *C07D 209/86* (2013.01); *C07D 307/91* (2013.01); *C07D 333/76* (2013.01); *C07D 405/12* (2013.01); *C09K 11/06* (2013.01); *H01L 51/0061* (2013.01); *H01L 51/0072* (2013.01); *H01L 51/0073* (2013.01); *H01L 51/0074* (2013.01); *H01L 51/50* (2013.01); *H01L 51/5012* (2013.01); *C07C 2603/18* (2017.05); *C07C 2603/42* (2017.05); *C09K 2211/1007* (2013.01); *C09K 2211/1011* (2013.01); *C09K 2211/1014* (2013.01); *C09K 2211/1018* (2013.01); *H01L 51/0052* (2013.01); *H01L 51/0054* (2013.01); *H01L 51/0058* (2013.01); *H01L 51/5016* (2013.01);

*H01L 51/5056* (2013.01); *H01L 51/5064* (2013.01); *H01L 51/5072* (2013.01); *H01L 51/5088* (2013.01); *H01L 51/5092* (2013.01)

(58) Field of Classification Search
  CPC . H01L 51/0072; H01L 51/50; H01L 51/5056; H01L 51/0052; H01L 51/6072; H01L 51/0054; H01L 51/0058; H01L 51/5016; H01L 51/5064; H01L 51/5072; H01L 51/5088; H01L 51/5092; C07D 209/82; C07D 405/12; C07D 307/91; C07D 333/76; C07D 209/86; C07C 211/61; C07C 2603/42; C07C 2603/18; C09K 11/06; C09K 2211/1007; C09K 2211/1011; C09K 2211/1014; C09K 2211/1018; C09K 2211/1092; C09K 2211/1088

See application file for complete search history.

(56) References Cited

U.S. PATENT DOCUMENTS

| | | |
|---|---|---|
| 2006/0232198 A1 | 10/2006 | Kawamura et al. |
| 2007/0278938 A1 | 12/2007 | Yabunouchi et al. |
| 2009/0115320 A1 | 5/2009 | Kawamura et al. |
| 2010/0033081 A1* | 2/2010 | Yamada ............... C07C 211/61 313/504 |
| 2012/0146014 A1 | 6/2012 | Kato |
| 2012/0181530 A1 | 7/2012 | Funyuu et al. |
| 2013/0105771 A1 | 5/2013 | Ryu et al. |
| 2014/0042411 A1 | 2/2014 | Fukuzaki |
| 2014/0291643 A1* | 10/2014 | Ogita ................. H01L 51/0061 257/40 |
| 2015/0065730 A1* | 3/2015 | Montenegro ......... C07C 211/54 548/440 |
| 2015/0179940 A1* | 6/2015 | Mujica-Fernaud ......................... H01L 51/0052 252/519.21 |
| 2015/0179953 A1 | 6/2015 | Mujica-Fernaud et al. |
| 2015/0243891 A1 | 8/2015 | Kato et al. |
| 2016/0301005 A1 | 10/2016 | Pfister et al. |
| 2017/0373254 A1 | 12/2017 | Lee et al. |

FOREIGN PATENT DOCUMENTS

| | | | |
|---|---|---|---|
| EP | 2 891 648 A1 | | 7/2015 |
| JP | 6-102683 A | | 4/1994 |
| JP | 10-95972 A | | 4/1998 |
| JP | 11-144875 A | | 5/1999 |
| JP | 11144875 A | * | 5/1999 |
| JP | 11-184119 A | | 7/1999 |
| JP | 2008-300503 A | | 12/2008 |
| JP | 2009-010364 A | | 1/2009 |
| JP | 2011-187959 A | | 9/2011 |
| KR | 10-2013-0096334 A | | 8/2013 |
| KR | 10-20113-0121597 A | | 11/2013 |
| KR | 10-2014-0024734 A | | 3/2014 |
| KR | 10-1389527 B1 | | 4/2014 |
| KR | 10-2014-0098502 A | | 8/2014 |
| KR | 10-2015-0007476 A | | 1/2015 |
| KR | 10-1530049 B1 | | 6/2015 |
| WO | WO 2011/021520 A1 | | 2/2011 |
| WO | 2012/011642 A1 | | 1/2012 |
| WO | WO 2013/087142 A1 | | 6/2013 |
| WO | WO 2013/182263 A1 | | 12/2013 |
| WO | WO 2014/015935 A2 | | 1/2014 |
| WO | WO 2014/015937 A1 | | 1/2014 |
| WO | WO 2014/034795 A1 | | 3/2014 |
| WO | WO 2014/088285 A1 | | 6/2014 |
| WO | WO 2014/112728 A1 | | 7/2014 |
| WO | WO 2015/041428 A1 | | 3/2015 |
| WO | 2015-082056 | | 6/2015 |

(56) References Cited

FOREIGN PATENT DOCUMENTS

WO    WO 2015/162912 A1    10/2015
WO    WO 2016/122150 A2    8/2016

OTHER PUBLICATIONS

Extended European Search Report dated Nov. 24, 2016 in Patent Application No. 15819013.2.
Office Action as received in the corresponding Chinese Patent Application No. 201580001554.6 dated May 21, 2016 w/English Translation.
Office Action dated Aug. 28, 2018 in the corresponding Japanese patent application with machine English translation (JP-OA 2016-504820).
Office Action dated Aug. 28, 2018 in the corresponding Japanese patent application with machine English translation (JP-OA 2015-560883.
Combined Office Action and Search Report dated Sep. 28, 2018 in Chinese Patent Application No. 201580001555.0 (with English translation of categories of cited documents).
Office Acton (Notification of Reasons for Refusal) dated Feb. 5, 2019 in Japanese Patent Application No. 2015-560883 with computer generated English translation.
Office Action (Notification of Reasons for Refusal) dated Feb. 5, 2019 in Japanese Patent Application No. 2016-504820 with computer generated English translation.
The Third Office Action dated Oct. 16, 2019 in Chinese Patent Application No. 201580001554.6 with computer-generated English translation, 12 pages.
The Second Office Action dated Feb. 22, 2019 in Chinese Patent Application No. 20158001549.5 with machine generated English translation.
Notification of Reasons for Refusal dated Mar. 5, 2019 in Japanese Patent Application No. 2016-504413 with machine generated English translation.
Office Action dated Nov. 8, 2018 in European Patent Application No. 15 818 448.1.
Office Action dated Nov. 16, 2018 in European Patent Application No. 15 818 619.7.
Office Action as received in the corresponding Chinese Patent Application No. 201580001549.5 dated Nov. 4, 2019 / English Translation not available, 10 pages.
Office Action dated Jun. 21, 2019 in European Patent Application No. 15 818 448.1.
The Second Office Action dated June 17, 2019 in Chinese Patent Appiication No. 201580001555.0 with machine generated English translation.
Chinese Office Action dated Apr. 28, 2020 in Patent Application No. 201580001554.6, 5 pages.
Chinese Office Action dated Apr. 3, 2020 in Chinese Patent Application No. 201580001555.0, 5 pages.
Office Action dated Dec. 13, 2018 in co-pending U.S. Appl. No. 15/308,461, 20 pages.
Office Action dated May 17, 2019 in co-pending U.S. Appl. No. 15/308,461, 16 pages.
Office Action dated Apr. 3, 2020 in co-pending U.S. Appl. No. 15/308,461, 21 pages.
Office Action dated Feb. 5, 2020 in European Patent Application No. 15 818 448.1 filed Jul. 13, 2015, 5 pages.
Office Action in Chinese Application No. 201580001549.5, dated Jul. 23, 2020.
Office Action in Chinese Application No. 201580001555.0: dated Jan. 13, 2021.

* cited by examiner

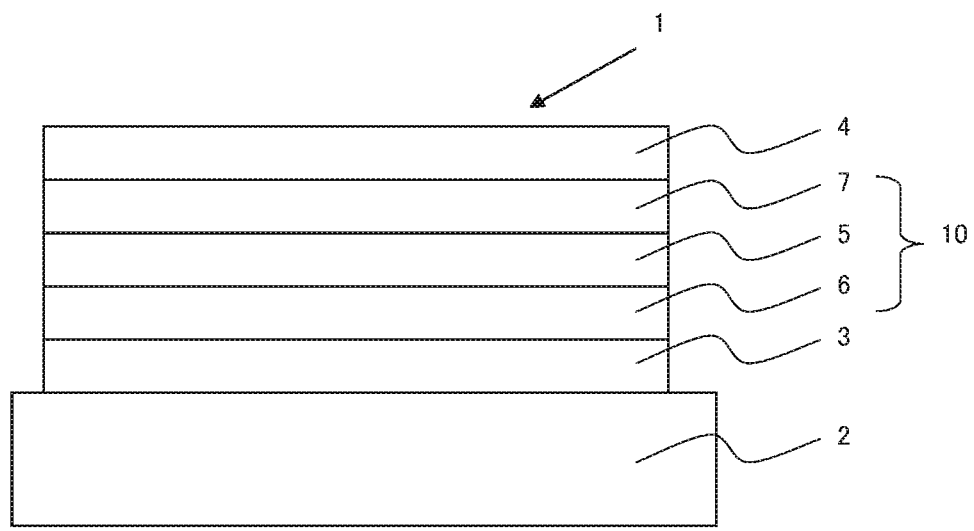

COMPOUND, MATERIAL FOR ORGANIC ELECTROLUMINESCENCE DEVICES, ORGANIC ELECTROLUMINESCENCE DEVICE, AND ELECTRONIC EQUIPMENT

TECHNICAL FIELD

The present invention relates to compounds, materials for organic electroluminescence devices comprising the compounds, organic electroluminescence devices comprising the compounds, and electronic equipment comprising the organic electroluminescence devices.

BACKGROUND ART

An organic electroluminescence device (also referred to as "organic EL device") is generally composed of an anode, a cathode, and one or more organic thin film layers which comprise a light emitting layer and are sandwiched between the anode and the cathode. When a voltage is applied between the electrodes, electrons are injected from the cathode and holes are injected from the anode into a light emitting region. The injected electrons recombine with the injected holes in the light emitting region to form excited states. When the excited states return to the ground state, the energy is released as light. Therefore, it is important for increasing the efficiency of an organic EL device to develop a compound which transports electrons or holes into a light emitting region efficiently and facilitates the recombination of electrons and holes.

The lower voltage drive of an organic EL device is effective for reducing the power consumption and also effective for improving the emission efficiency and the device lifetime. To reduce the driving voltage, a charge transporting material having a high electron mobility and/or a high hole mobility is required, and many proposals have been made on such a charge transporting material.

CITATION LIST

Patent Literature

Patent Literature 1: WO 2013/182263
Patent Literature 2: WO 2014/015935
Patent Literature 3: WO 2014/015937
Patent Literature 4: WO 2011/021520

SUMMARY OF INVENTION

Technical Problem

An object of the present invention is to provide an organic EL device which exhibits high emission efficiency even when driving at a lower voltage and has a long lifetime and also provide a material for organic EL devices which realizes such an organic EL device.

Solution to Problem

As a result of extensive research in view of achieving the above object, the inventors have found that a compound represented by formula (A-0) or (B-0) has a large energy gap and a high hole mobility, and further found that an organic EL device which is capable of driving at a lower voltage and has high emission efficiency and long lifetime is obtained by using the compound.

In an aspect of the invention, the following (1) to (4) are provided:
(1) a compound represented by formula (A-0) or (B-0):

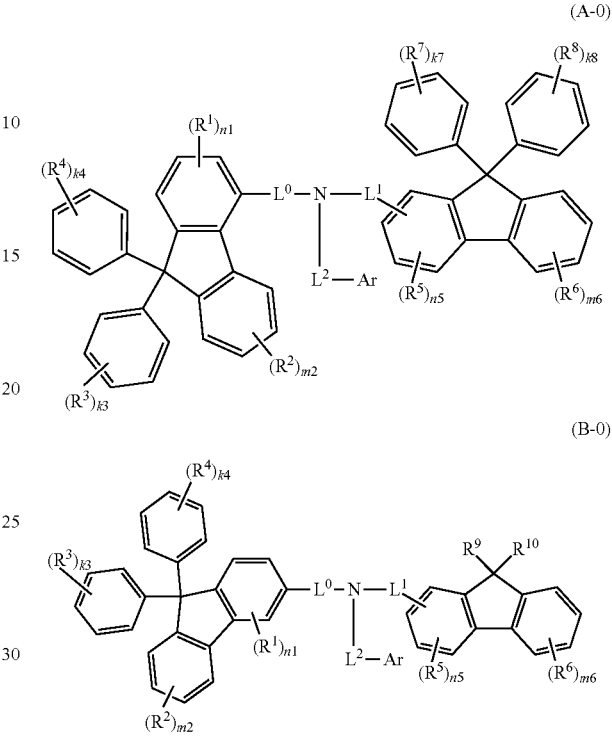

wherein $R^1$ to $R^8$ each independently represent a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group;
when $R^1$ to $R^8$ are each plurality in number, groups $R^1$ to groups $R^8$ may be the same or different, two selected from $R^5$ to $R^8$ in formula (A-0) may be bonded to each other to form a ring structure, and two selected from $R^5$ and $R^6$ in formula (B-0) may be bonded to each other to form a ring structure;
$R^9$ and $R^{10}$ each independently represent a substituted or unsubstituted phenyl group, and $R^9$ and $R^{10}$ may be bonded to each other to form a ring structure;
k3, k4, k7, and k8 each independently represent an integer of 0 to 5, m2 and m6 each independently represent an integer of 0 to 4, and n1 and n5 each independently represent an integer of 0 to 3;
$L^0$ to $L^2$ each independently represent a single bond, a substituted or unsubstituted arylene group having 6 to 50 ring carbon atoms, or a substituted or unsubstituted heteroarylene group having 5 to 50 ring atoms; and
Ar represents a substituted or unsubstituted aryl group having 6 to 50 ring carbon atoms or a substituted or unsubstituted heteroaryl group having 5 to 50 ring atoms;
(2) a material for organic electroluminescence devices comprising the compound according to (1);

(3) an organic electroluminescence device which comprises a cathode, an anode, and at least one organic thin film layer disposed between the cathode and the anode, wherein the at least one organic thin film layer comprises a light emitting layer and at least one layer of the at least one organic thin film layer comprises the compound according to (1); and
(4) an electronic equipment comprising the organic electroluminescence device according to (3).

Advantageous Effects of Invention

An organic EL device which exhibits high emission efficiency even when driving at a lower voltage and has a long lifetime is obtained by using the compound represented by formula (A-0) or (B-0) as the material for organic EL devices.

BRIEF DESCRIPTION OF DRAWINGS

FIG. 1 is a schematic illustration of the structure of an organic EL device in an aspect of the present invention.

DESCRIPTION OF EMBODIMENTS

The term of "XX to YY carbon atoms" referred to by "a substituted or unsubstituted group ZZ having XX to YY carbon atoms" used herein is the number of carbon atoms of the unsubstituted group ZZ and does not include any carbon atom in the substituent of the substituted group ZZ.

The term of "XX to YY atoms" referred to by "a substituted or unsubstituted group ZZ having XX to YY atoms" used herein is the number of atoms of the unsubstituted group ZZ and does not include any atom in the substituent of the substituted group ZZ.

The number of "ring carbon atoms" referred to herein means the number of the carbon atoms included in the atoms which are members forming the ring itself of a compound in which a series of atoms is bonded to form a ring (for example, a monocyclic compound, a fused ring compound, a cross-linked compound, a carbocyclic compound, and a heterocyclic compound). If the ring has a substituent, the carbon atom in the substituent is not included in the ring carbon atom. The same applies to the number of "ring carbon atom" described below, unless otherwise noted. For example, a benzene ring has 6 ring carbon atoms, a naphthalene ring has 10 ring carbon atoms, a pyridinyl group has 5 ring carbon atoms, and a furanyl group has 4 ring carbon atoms. If a benzene ring or a naphthalene ring has, for example, an alkyl substituent, the carbon atom in the alkyl substituent is not counted as the ring carbon atom of the benzene or naphthalene ring. In case of a fluorene ring to which a fluorene substituent is bonded (inclusive of a spirofluorene ring), the carbon atom in the fluorene substituent is not counted as the ring carbon atom of the fluorene ring.

The number of "ring atom" referred to herein means the number of the atoms which are members forming the ring itself (for example, a monocyclic ring, a fused ring, and a ring assembly) of a compound in which a series of atoms is bonded to form the ring (for example, a monocyclic compound, a fused ring compound, a cross-linked compound, a carbocyclic compound, and a heterocyclic compound). The atom not forming the ring (for example, hydrogen atom(s) for saturating the valence of the atom which forms the ring) and the atom in a substituent, if the ring is substituted, are not counted as the ring atom. The same applies to the number of "ring atoms" described below, unless otherwise noted. For example, a pyridine ring has 6 ring atoms, a quinazoline ring has 10 ring atoms, and a furan ring has 5 ring atoms. The hydrogen atom on the ring carbon atom of a pyridine ring or a quinazoline ring and the atom in a substituent are not counted as the ring atom. In case of a fluorene ring to which a fluorene substituent is bonded (inclusive of a spirofluorene ring), the atom in the fluorene substituent is not counted as the ring atom of the fluorene ring.

The definition of "hydrogen atom" used herein includes isotopes different in the neutron numbers, i.e., light hydrogen (protium), heavy hydrogen (deuterium), and tritium.

The terms of "heteroaryl group" and "heteroarylene group" used herein means a group having at least one hetero atom as a ring atom. The hetero atom is preferably at least one selected from a nitrogen atom, an oxygen atom, a sulfur atom, a silicon atom, and a selenium atom.

The optimal substituent referred to by "substituted or unsubstituted" used herein is preferably selected from the group consisting of an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; an aralkyl group having 7 to 51, preferably 7 to 30, more preferably 7 to 20 carbon atoms which includes an aryl group having 6 to 50, preferably 6 to 25, more preferably 6 to 18 ring carbon atoms; an amino group; an alkoxy group having an alkyl group having 1 to 50, preferably 1 to 18, more preferably 1 to 8 carbon atoms; an aryloxy group having an aryl group having 6 to 50, preferably 6 to 25, more preferably 6 to 18 ring carbon atoms; a mono-, di- or tri-substituted silyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a heteroaryl group having 5 to 50, preferably 5 to 24, more preferably 5 to 13 ring atoms; a haloalkyl group having 1 to 50, preferably 1 to 18, more preferably 1 to 8 carbon atoms; a halogen atom selected from a fluorine atom, a chlorine atom, a bromine atom and an iodine atom; a cyano group; a nitro group; a substituted sulfonyl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; a di-substituted phosphoryl group, wherein the substituent is selected from an alkyl group having 1 to 50, preferably 1 to 18, more preferably 1 to 8 carbon atoms and an aryl group having 6 to 50, preferably 6 to 25, more preferably 6 to 18 ring carbon atoms; an alkylsulfonyloxy group; an arylsulfonyloxy group; an alkylcarbonyloxy group; an arylcarbonyloxy group; a boron-containing group; a zinc-containing group; a tin-containing group; a silicon-containing group; a magnesium-containing group; a lithium-containing group; a hydroxyl group; an alkyl-substituted or aryl-substituted carbonyl group; a carboxyl group; a vinyl group; a (meth)acryloyl group; an epoxy group; and an oxetanyl group.

The optional substituent may further has the substituent mentioned above. The optional substituents may be bonded to each other to form a ring.

The term of "unsubstituted" referred to by "substituted or unsubstituted" used herein means that no hydrogen atom in a group is substituted by a substituent.

Of the above substituents, more preferred are an alkyl group having 1 to 50, preferably 1 to 18, more preferably 1 to 8 carbon atoms; a cycloalkyl group having 3 to 50, preferably 3 to 10, more preferably 3 to 8, still more preferably 5 or 6 ring carbon atoms; an aryl group having 6 to 50, preferably 6 to 25, more preferably 6 to 18 ring carbon atoms; a heteroaryl group having 5 to 50, preferably 5 to 24, more preferably 5 to 13 ring atoms; a halogen atom; and a cyano group.

In the present invention, those which are defined as being preferred can be selected arbitrarily and a combination thereof is a more preferred embodiment.

Compound

In an aspect of the invention, a compound represented by formula (A-0) (also referred to as "compound (A)") and a compound represented by formula (B-0) (also referred to as "compound (B)") are provided. The compound (A) and the compound (B) are useful as a material for organic electroluminescence devices.

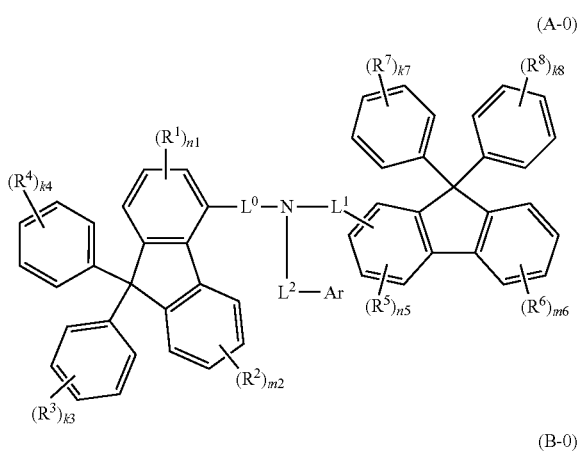

(A-0)

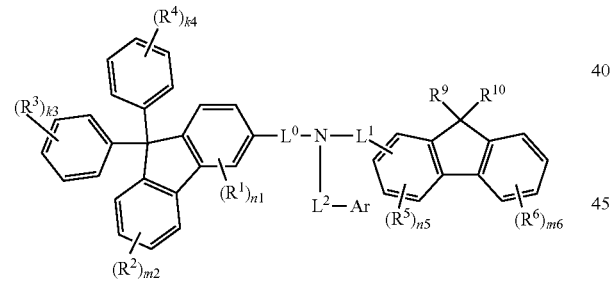

(B-0)

$R^1$ to $R^8$ in Formulae (A-0) and (B-0)

$R^1$ to $R^8$ in formula (A-0) and $R^1$ to $R^6$ in formula (B-0) (also collectively referred to as "$R^1$ to $R^8$") each represent a substituent which is bonded to a carbon atom of each benzene ring in each formula.

$R^1$ to $R^8$ each independently represent a substituted or unsubstituted alkyl group having 1 to 20, preferably 1 to 8, and more preferably 1 to 3 carbon atoms; a substituted or unsubstituted aryl group having 6 to 50, preferably 6 to 25, more preferably 6 to 18, and still more preferably 6 to 12 ring carbon atoms; a substituted or unsubstituted heteroaryl group having 5 to 50, preferably 5 to 10, more preferably 5 to 8, and still more preferably 5 or 6 ring atoms; a halogen atom; a substituted or unsubstituted fluoroalkyl group having 1 to 20, preferably 1 to 5, and more preferably 1 to 4 carbon atoms; a substituted or unsubstituted alkoxy group having 1 to 20, preferably 1 to 5, and more preferably 1 to 4 carbon atoms; a substituted or unsubstituted fluoroalkoxy group having 1 to 20, preferably 1 to 5, and more preferably 1 to 4 carbon atoms; a substituted or unsubstituted aryloxy group having 6 to 50, preferably 6 to 25, more preferably 6 to 18, and still more preferably 6 to 12 ring carbon atoms; or a cyano group.

Preferably, $R^1$ to $R^8$ in formulae (A-0) and (B-0) each independently represent a group selected from the group consisting of a substituted or unsubstituted alkyl group having 1 to 20 carbon atoms, a substituted or unsubstituted heteroaryl group having 5 to 50 ring atoms, and a halogen atom, with a substituted or unsubstituted alkyl group having 1 to 20 carbon atoms being more preferred.

The subscripts k3, k4, k7, and k8 each independently represent an integer of 0 to 5, preferably an integer of 0 to 2, more preferably 0 or 1, and still more preferably 0;

m2 and m6 each independently represent an integer of 0 to 4, preferably an integer of 0 to 2, more preferably 0 or 1, and still more preferably 0; and n1 and n5 each independently represent an integer of 0 to 3, preferably an integer of 0 to 2, more preferably 0 or 1, and still more preferably 0.

When k3, k4, k7, k8, m2, m6, n1, and n5 are each 0, each benzene ring has no substituent.

When $R^1$ to $R^8$ are each plurality in number, groups $R^1$ to groups $R^8$ may be the same or different.

In an embodiment of the invention, two selected from $R^1$ to $R^4$ are not bonded to each other, thereby failing to form a ring structure.

In another embodiment of the invention, two selected from $R^5$ to $R^8$ in formula (A-0) may be bonded to each other to form a ring structure, and $R^5$ and $R^6$ in formula (B-0) may be bonded to each other to form a ring structure.

Example of the 9,9-diphenyl-9H-fluorene skeleton of formula (A-0) wherein a ring structure is formed include a structure represented by formula (1-a), with a structure represented by formula (2-a) being preferred:

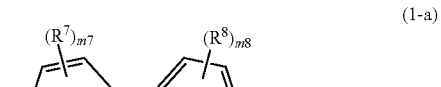

(1-a)

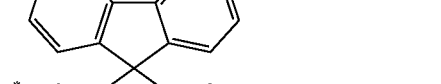

(2-a)

wherein $R^5$ to $R^8$, n5, and m6 are as defined in formula (A-0);

m7 and m8 in formula (1-a) each independently represent an integer of 0 to 4, preferably an integer of 0 to 2, more preferably 0 or 1, and still more preferably 0; and

* represents a bonding site to $L^1$ or the nitrogen atom in formula (A-0).

$R^9$ and $R^{10}$ in formula (B-0) each independently represent a substituted or unsubstituted phenyl group.

The 9,9-diphenyl-9H-fluorene skeleton wherein $R^9$ and $R^{10}$ in formula (B-0) each represent a substituted or unsubstituted phenyl group is preferably represented by formula (1-b):

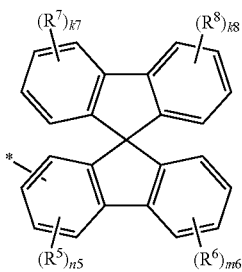

(1-b)

wherein $R^5$, $R^6$, n5, and m6 are as defined in formula (B-0), and $R^7$, $R^8$, k7, and k8 are as defined in formula (A-0).

$R^9$ and $R^{10}$ may be bonded to each other, i.e., a substituent of one of the phenyl groups (phenyl group (I)) may be bonded to a carbon atom or a substituent of the other phenyl group (II), to form a ring structure.

A compound wherein $R^9$ and $R^{10}$ are bonded to each other to form a ring structure is, for example, represented by formula (2-b) and preferably represented by formula (3-b):

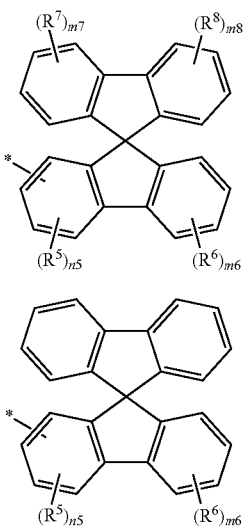

(2-b)

(3-b)

wherein $R^5$, $R^6$, n5, and m6 are as defined in formula (B-0), $R^7$, $R^8$, m7 and m8 are as defined in formula (1-a), and * represents a bonding site to $L^1$ in formula (B-0).

Examples of the alkyl group having 1 to 20 carbon atoms include a methyl group, an ethyl group, a n-propyl group, an isopropyl group, a n-butyl group, an isobutyl group, a s-butyl group, a t-butyl group, a pentyl group (inclusive of isomeric groups), a hexyl group (inclusive of isomeric groups), a heptyl group (inclusive of isomeric groups), an octyl group (inclusive of isomeric groups), a nonyl group (inclusive of isomeric groups), a decyl group (inclusive of isomeric groups), an undecyl group (inclusive of isomeric groups), and a dodecyl group (inclusive of isomeric groups).

Of the above, preferred are a methyl group, an ethyl group, a n-propyl group, an isopropyl group, a n-butyl group, an isobutyl group, a s-butyl group, a t-butyl group, and a pentyl group (inclusive of isomeric groups), with a methyl group, an ethyl group, a n-propyl group, an isopropyl group, a n-butyl group, an isobutyl group, a s-butyl group, and a t-butyl group being more preferred, and a methyl group and a t-butyl group being still more preferred.

Examples of the aryl group having 6 to 50 ring carbon atoms include a phenyl group, a naphthylphenyl group, a biphenylyl group, a terphenylyl group, a biphenylenyl group, a naphthyl group, a phenylnaphthyl group, an acenaphthylenyl, an anthryl group, a benzanthryl group, an aceanthryl group, a phenanthryl group, a benzophenanthryl group, a phenalenyl group, a fluorenyl group, a 9,9-dimethylfluorenyl group, a 7-phenyl-9,9-dimethylfluorenyl group, a pentacenyl group, a picenyl group, a pentaphenyl group, a pyrenyl group, a chrysenyl group, a benzochrysenyl group, a s-indacenyl group, an a s-indacenyl group, a fluoranthenyl group, and a perylenyl group.

Of the above, preferred are a phenyl group, a naphthylphenyl group, a biphenylyl group, a terphenylyl group, a naphthyl group, and a 9,9-dimethylfluorenyl group, with a phenyl group, a biphenylyl group, a naphthyl group, and a 9,9-dimethylfluorenyl group being more preferred, and a phenyl group being still more preferred.

The heterocyclic group having 5 to 50 ring atoms comprises at least one, preferably 1 to 3 hetero atoms which may be the same or different, such as a nitrogen atom, a sulfur atom and an oxygen atom.

Examples of the heterocyclic group include a pyrrolyl group, a furyl group, a thienyl group, a pyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, an indolyl group, an isoindolyl group, a benzofuranyl group, an isobenzofuranyl group, a benzothiophenyl group, an isobenzothiophenyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzisoxazolyl group, a benzisothiazolyl group, a dibenzofuranyl group, a dibenzothiophenyl group, a phenanthridinyl group, an acridinyl group, a phenanthrolinyl group, a phenazinyl group, a phenothiazinyl group, a phenoxazinyl group, and a xanthenyl group.

Of the above, preferred are a furyl group, a thienyl group, a pyridyl group, a pyridazinyl group, a pyrimidinyl group, a pyrazinyl group, a triazinyl group, a benzofuranyl group, a benzothiophenyl group, a dibenzofuranyl group, and a dibenzothiophenyl group, with a benzofuranyl group, a benzothiophenyl group, a dibenzofuranyl group, and a dibenzothiophenyl group being more preferred.

Examples of the halogen atom include a fluorine atom, a chlorine atom, a bromine atom, and an iodine atom, with a fluorine atom being preferred.

Examples of the fluoroalkyl group having 1 to 20 carbon atoms include, for example, those derived from the above alkyl group having 1 to 20 carbon atoms by replacing at least one hydrogen atom, preferably 1 to 7 hydrogen atoms or all hydrogen atoms with a fluorine atom or fluorine atoms.

Preferred examples thereof are a heptafluoropropyl group, a pentafluoroethyl group, a 2,2,2-trifluoroethyl group, and a trifluoromethyl group, with a pentafluoroethyl group, a 2,2,2-trifluoroethyl group, and a trifluoromethyl group being more preferred, and a trifluoromethyl group being still more preferred.

The alkoxy group having 1 to 20 carbon atoms is represented by —OR$^X$, wherein R$^X$ is the above alkyl group having 1 to 20 carbon atoms.

Preferred examples thereof include a t-butoxy group, a propoxy group, an ethoxy group, and a methoxy group, with an ethoxy group and a methoxy group being more preferred, and a methoxy group being still more preferred.

The fluoroalkoxy group having 1 to 20 carbon atoms is represented by —OR$^Y$, wherein R$^Y$ is the above fluoroalkyl group having 1 to 20 carbon atoms.

Preferred examples thereof include a heptafluoropropoxy group, a pentafluoroethoxy group, a 2,2,2-trifluoroethoxy group, and a trifluoromethoxy group, with a pentafluoroethoxy group, a 2,2,2-trifluoroethoxy group, and a trifluoromethoxy group being more preferred, and a trifluoromethoxy group being still more preferred.

The aryloxy group having 6 to 50 ring carbon atoms is represented by —OR$^Z$, wherein R$^Z$ is the above aryl group having 6 to 50 ring carbon atoms.

Preferred examples thereof include a phenyloxy group, 1-naphthyloxy group, 2-naphthyloxy group, a 4-biphenylyloxy group, a p-terphenyl-4-yloxy group, and a p-tolyloxy group, with a phenyloxy group and a 2-naphthyloxy group being more preferred and a phenyloxy group being still more preferred.

L$^0$ to L$^2$ in Formulae (A-0) and (B-0)

In formulae (A-0) and (B-0), L$^0$ to L$^2$ each independently represent a single bond, a substituted or unsubstituted arylene group having 6 to 50, preferably 6 to 24, and more preferably 6 to 12 ring carbon atoms, or a substituted or unsubstituted heteroarylene group having 5 to 50, preferably 5 to 10, more preferably 5 to 8, and still more preferably 5 or 6 ring atoms.

Examples of the arylene group having 6 to 50 ring carbon atoms include divalent groups derived from the aryl group having 6 to 50 ring carbon atoms mentioned above with respect to R$^1$ to R$^8$ of formulae (A-0) and (B-0) by removing one hydrogen atom.

Preferred examples thereof include a terphenyldiyl group (inclusive of isomeric groups), a biphenyldiyl group (inclusive of isomeric groups), and a phenylene group (inclusive of isomeric groups), with a biphenyldiyl group (inclusive of isomeric groups) and a phenylene group (inclusive of isomeric groups) being more preferred, an o-phenylene group, a m-phenylene group, and a p-phenylene group being still more preferred, and a p-phenylene group being further preferred.

The substituted or unsubstituted heteroarylene group having 5 to 50 ring atoms comprises at least one, preferably 1 to 3 hetero atoms which may be the same or different, such as a nitrogen atom, a sulfur atom and an oxygen atom.

Examples the heteroarylene group include divalent groups derived from the heteroaryl group having 5 to 50 ring atoms mentioned above with respect to R$^1$ to R$^8$ of formulae (A-0) and (B-0) by removing one hydrogen atom.

Preferred examples thereof include a furylene group, a thienylene group, a pyridylene group, a pyridazinylene group, a pyrimidinylene group, a pyrazinylene group, a triazinylene group, a benzofuranylene group, a benzothiophenylene group, a dibenzofuranylene group, and a dibenzothiophenylene group, with a benzofuranylene group, a benzothiophenylene group, a dibenzofuranylene group, and a dibenzothiophenylene group being more preferred.

L$^1$ in formula (A-0) is bonded to one of the carbon atoms at 1-, 2-, 3- and 4-positions (carbon atoms *1, *2, *3, and *4) of the following 9,9-diphenyl-9H-fluorene skeleton and preferably bonded to the carbon atom at 2-position (carbon atom *2):

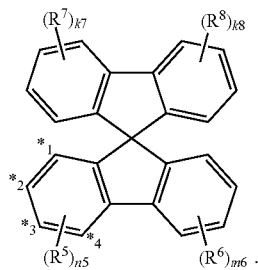

L$^1$ in formula (B-0) is bonded to one of the carbon atoms at 1-, 2-, 3- and 4-positions (carbon atoms *1, *2, *3, and *4) of the following fluorene skeleton having R$^9$ and R$^{10}$ at its 9-position and preferably bonded to the carbon atom at 2-position (carbon atom *2):

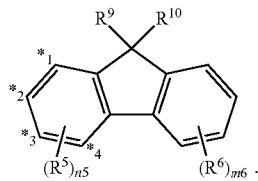

L$^0$ to L$^2$ each preferably represent a single bond or a substituted or unsubstituted arylene group having 6 to 50 ring carbon atoms, more preferably a single bond or a group represented by formula (i) or (ii), still more preferably a single bond or a group represented by formula (i), and further preferably a single bond.

L$^0$ in formula (A-0) or (B-0) is preferably a single bond or a substituted or unsubstituted arylene group having 6 to 50 ring carbon atoms.

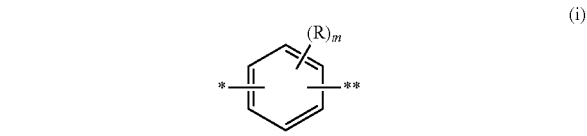

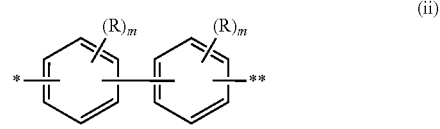

In formula (i) and (ii), * and ** each represent a bonding site.

In the compound (A), one of * and ** is the bonding site to the nitrogen atom in formula (A-0) and the other is the bonding site to Ar or the carbon atom of the benzene ring in the 9,9-diphenyl-9H-fluorene skeleton in formula (A-0).

In the compound (B), one of * and ** is the bonding site to the nitrogen atom in formula (B-0) and the other is the bonding site to Ar or the carbon atom of the benzene ring in the fluorene skeleton in formula (B-0).

In formula (i) and (ii), each R and preferred examples thereof are independently the same as those described with respect to $R^1$ in formulae (A-0) and (B-0). Each R is a substituent which is bonded to the carbon atom of each benzene ring in formula (i) and (ii).

In an embodiment of the invention, when more than one R occurs, groups R may be the same or different. In another embodiment of the invention, when more than one R occurs, two selected from groups R may be bonded to each other to form a ring structure.

Examples of formula (i) wherein a ring structure is formed are shown below:

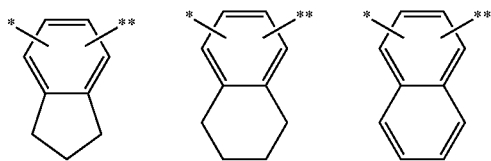

wherein * and ** are as defined in formula (i).

Examples of formula (ii) wherein a ring structure is formed are shown below:

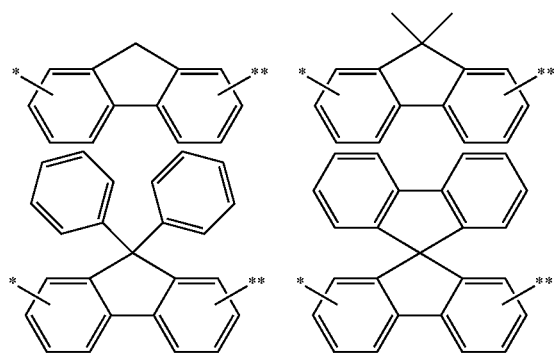

wherein * and ** are as defined in formula (ii).

In formula (i) and (ii), each m independently represents an integer of 0 to 4, preferably an integer of 0 to 2, more preferably 0 or 1, and still more preferably 0.

When m is 0, each benzene ring has no substituent.

The group represented by formula (i) is preferably represented by formula (i-a), and the group represented by formula (ii) is preferably represented by formula (ii-a):

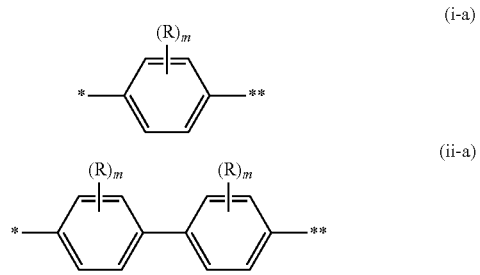

wherein R, m, *, and ** are as defined in formulae (i) and (ii).

In the compound (A) in an aspect of the invention, $L^2$ in formula (A-0) is preferably a substituted or unsubstituted arylene group having 6 to 50 ring carbon atoms or a substituted or unsubstituted heteroarylene group having 5 to 50 ring atoms.

In the compound (A) in an aspect of the invention, $L^1$ in formula (A-0) is preferably a substituted or unsubstituted arylene group having 6 to 50 ring carbon atoms or a substituted or unsubstituted heteroarylene group having 5 to 50 ring atoms, which are more preferred when $L^0$ is a single bond.

Ar in Formulae (A-0) and (B-0)

In formulae (A-0) and (B-0), Ar represents a substituted or unsubstituted aryl group having 6 to 50, preferably 6 to 25, more preferably 6 to 18, and still more preferably 6 to 12 ring carbon atoms or a substituted or unsubstituted heteroaryl group having 5 to 50, preferably 5 to 10, more preferably 5 to 8, and still more preferably 5 or 6 ring atoms.

The examples of the aryl group having 6 to 50 ring carbon atoms and the heteroaryl group having 5 to 50 ring atoms are the same as those described with respect to $R^1$ to $R^8$ in formulae (A-0) and (B-0).

When the compound (A) or (B) in an aspect of the invention is used as a material for a second hole transporting layer of an organic EL device which comprises a two-layered hole transporting layer having a first hole transporting layer (anode side) and a second hole transporting layer (light emitting layer side), Ar in formula (A-0) or (B-0) is preferably a heteroaryl group having 5 to 50 ring atoms in view of emission efficiency and preferably an aryl group having 6 to 50 ring carbon atoms in view of low voltage drive.

When the compound (A) or (B) in an aspect of the invention is used as a material for a first hole transporting layer of an organic EL device which comprises a two-layered hole transporting layer having a first hole transporting layer (anode side) and a second hole transporting layer (light emitting layer side), Ar in formula (A-0) or (B-0) is preferably a heteroaryl group having 5 to 50 ring atoms and more preferably a group represented by any of formulae (h), (i") and (j") described below, in view of emission efficiency.

In an embodiment of the invention, Ar in formula (A-0) is preferably a group represented by any of formulae (a) to (k), more preferably a group represented by any of formulae (a) to (j), and still more preferably a group represented by any of formulae (b) to (j); and Ar in formula (B-0) is preferably a group represented by any of formulae (a) to (k) and more preferably a group represented by any of formulae (b), (c), and (f) to (j):

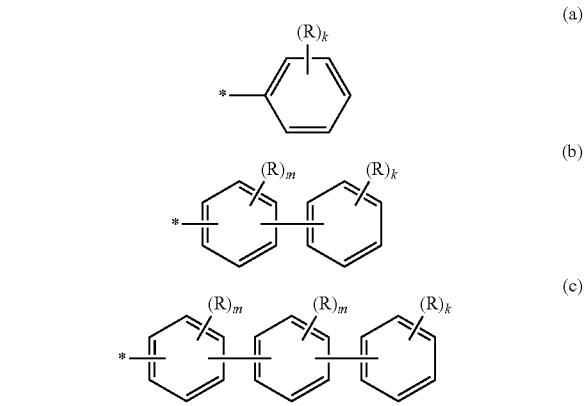

-continued (d) 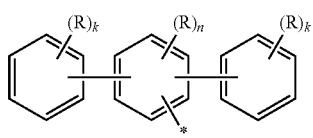

(e) 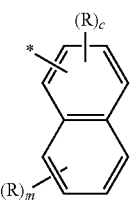

(f) 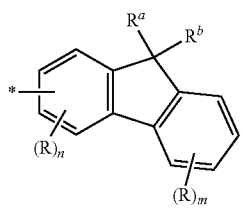

(g) 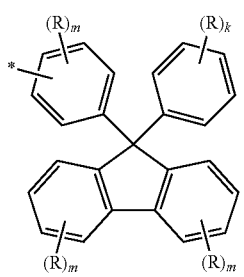

(h) 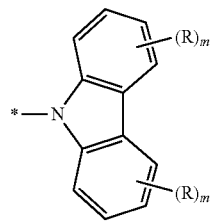

(i) 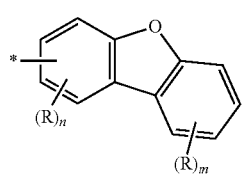

(j) 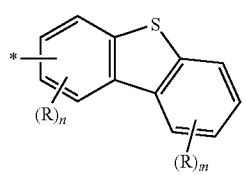

-continued (k) 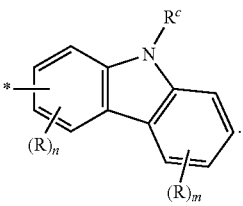

In formulae (a) to (k), examples R, $R^a$, and $R^b$ and preferred examples thereof are each independently the same as those described with respect to $R^1$ in formulae (A-0) and (B-0). R is a substituent which is bonded to a carbon atom of each benzene ring in formulae (a) to (k).

$R^a$ and $R^b$ in formula (f) are each preferably selected from a hydrogen atom, a substituted or unsubstituted alkyl group having 1 to 20, preferably 1 to 8, and more preferably 1 to 3 carbon atoms, and a substituted or unsubstituted aryl group having 6 to 50, preferably 6 to 25, more preferably 6 to 18, and still more preferably 6 to 12 ring carbon atoms.

$R^c$ in formula (k) represents a hydrogen atom, a substituted or unsubstituted alkyl group having 1 to 20 carbon atoms, a substituted or unsubstituted aryl group having 6 to 50 ring carbon atoms, or a substituted or unsubstituted heteroaryl group having 5 to 50 ring atoms. These groups are the same as those described with respect to $R^1$ in formulae (A-0) and (B-0).

$R^c$ is preferably a substituted or unsubstituted alkyl group having 1 to 20 carbon atoms or a substituted or unsubstituted aryl group having 6 to 50 ring carbon atoms and more preferably a substituted or unsubstituted aryl group having 6 to 50 ring carbon atoms.

When more than one R occurs, groups R may be the same or different, and two selected from groups R may be bonded to each other to form a ring structure.

In formula (f), two selected from groups R, $R^a$, and $R^b$ may be bonded to each other to form a ring structure.

In formulae (a) to (k), each k independently represents an integer of 0 to 5, preferably an integer of 0 to 2, more preferably 0 or 1, and still more preferably 0.

Each m independently represents an integer of 0 to 4, preferably an integer of 0 to 2, more preferably 0 or 1, and still more preferably 0.

Each n independently represents an integer of 0 to 3, preferably an integer of 0 to 2, more preferably 0 or 1, and still more preferably 0

When k, m, and n are each 0, each benzene ring has no substituent.

* represents a bonding site, for example, a bonding site to $L^2$ or the nitrogen atom in formulae (A-0) and (B-0).

In view of emission efficiency, the group represented by formula (i) is preferably represented by formula (i') or (i") and more preferably represented by formula (i"):

(i') 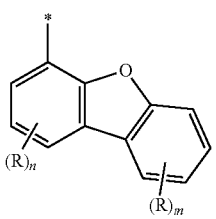

-continued

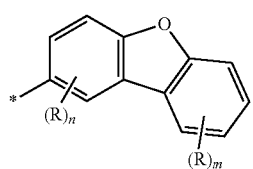
(i″)

wherein R, n, and m are as defined in formula (i).

In view of emission efficiency, the group represented by formula (j) is preferably represented by formula (j') or (j″) and more preferably represented by formula (j″):

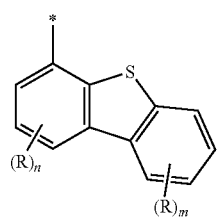
(j')

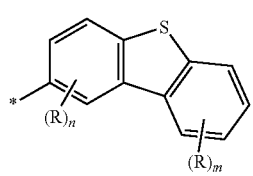
(j″)

wherein R, n, and m are as defined in formula (j).

In an embodiment of the invention, of the above groups for Ar, the group represented by formula (b) is preferably represented by formula (b-1) or (b-2), the group represented by formula (c) is preferably represented by formula (c-1) or (c-2), and the group represented by formula (d) is preferably represented by formula (d-1):

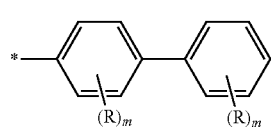
(b-1)

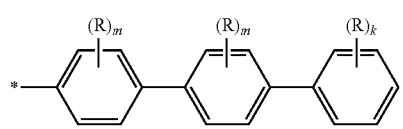
(c-1)

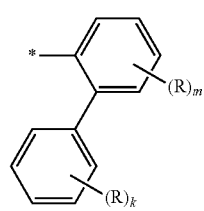
(b-2)

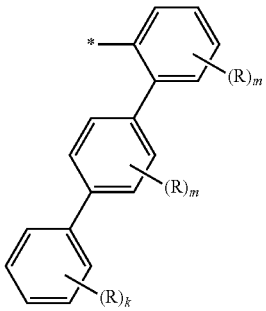
(c-2)

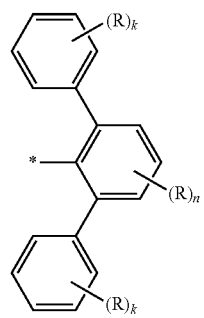
(d-1)

wherein R, k, m, n, and * are as defined in formulae (a) to (k).

In an embodiment of the invention, the group represented by formula (f) for Ar is preferably represented by formula (f-1) or (f-2):

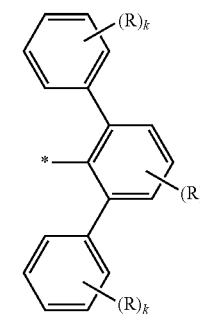
(f-1)

(f-2)

wherein, R, k, m, n, and * are as defined in formulae (a) to (k).

In formula (f-1) or (f-2), when more than one R occurs, groups R may be the same or different, and two selected from groups R may be bonded to each other to form a ring structure. Example of the group represented by formula (f-1) wherein a ring structure is formed includes the following group represented by formula (f-3):

(f-3)

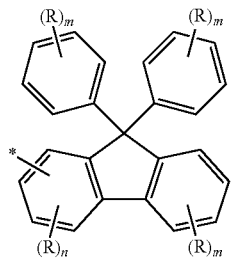

wherein R, m, n, and * are as defined in formulae (a) to (k).

The group -L$^2$-Ar is preferably represented by any of the following formulae:

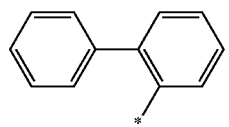
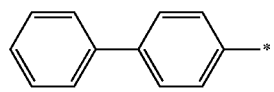

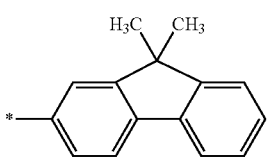

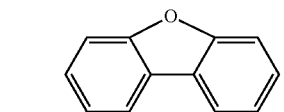

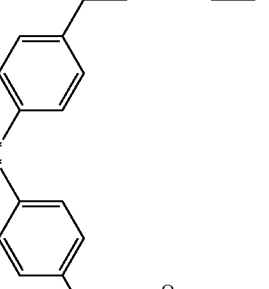

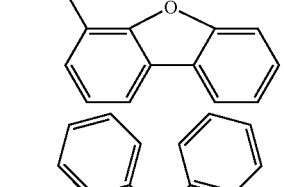

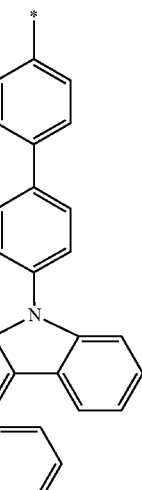

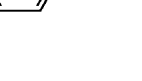

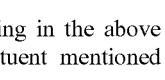

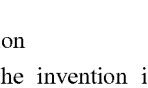

wherein * is a bonding site to the nitrogen atom and R$^c$ is the same as R$^e$ in formula (k).

Each hydrogen atom on the benzene ring in the above groups may be replaced with the substituent mentioned above but preferably not replaced.

Compound (A) in an Aspect of the Invention

The compound (A) in an aspect of the invention is preferably a compound represented by formula (A-1) (also referred to as "compound (A-1)"):

(A-1)

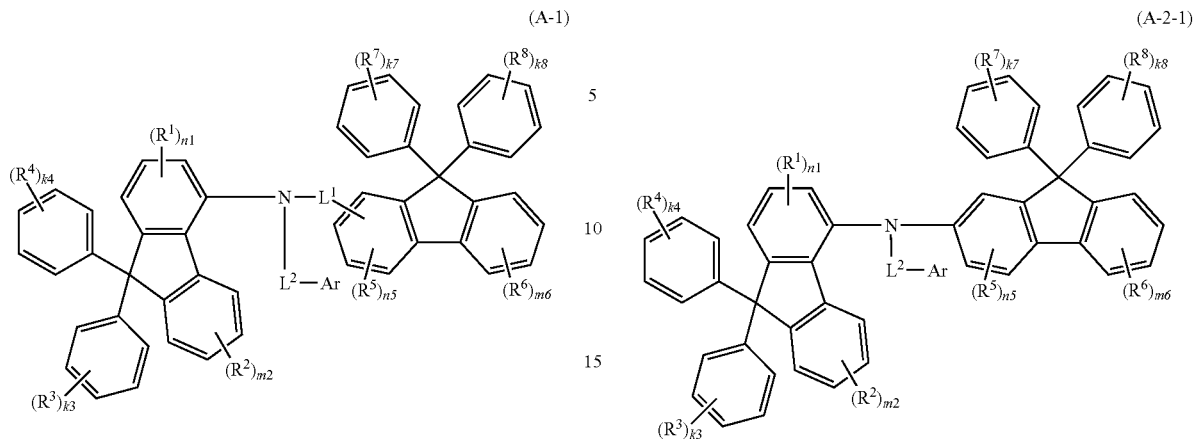

(A-2-1)

wherein $R^1$ to $R^8$, n1, m2, k3, k4, n5, m6, k7, k8, $L^1$, $L^2$, and Ar are as defined in formula (A-0).

In the compound (A-1), $L^2$ in formula (A-1) is preferably a substituted or unsubstituted arylene group having 6 to 50 ring carbon atoms or a substituted or unsubstituted heteroarylene group having 5 to 50 ring atoms.

In the compound (A-1), $L^1$ in formula (A-1) is preferably a substituted or unsubstituted arylene group having 6 to 50 ring carbon atoms or a substituted or unsubstituted heteroarylene group having 5 to 50 ring atoms.

In another embodiment, the compound (A) is preferably a compound represented by formula (A-2) (also referred to as "compound (A-2)"):

wherein $R^1$ to $R^8$, n1, m2, k3, k4, n5, m6, k7, k8, $L^2$, and Ar are as defined in formula (A-0).

In the compound (A-2-1), $L^2$ in formula (A-2-1) is preferably a substituted or unsubstituted arylene group having 6 to 50 ring carbon atoms or a substituted or unsubstituted heteroarylene group having 5 to 50 ring atoms.

In another embodiment, the compound (A) is preferably a compound represented by formula (A-3) (also referred to as "compound (A-3)"):

(A-2)

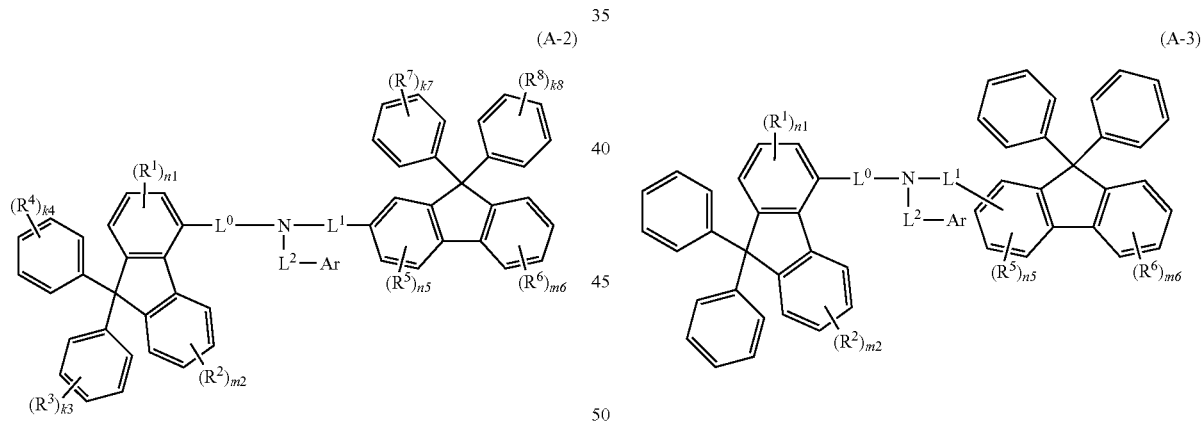

(A-3)

wherein $R^1$ to $R^8$, n1, m2, k3, k4, n5, m6, k7, k8, $L^0$ to $L^2$, and Ar are as defined in formula (A-0).

In the compound (A-2), $L^2$ in formula (A-2) is preferably a substituted or unsubstituted arylene group having 6 to 50 ring carbon atoms or a substituted or unsubstituted heteroarylene group having 5 to 50 ring atoms.

In the compound (A-2), $L^1$ in formula (A-2) is preferably a substituted or unsubstituted arylene group having 6 to 50 ring carbon atoms or a substituted or unsubstituted heteroarylene group having 5 to 50 ring atoms, which are more preferred when $L^0$ is a single bond.

Of the compound (A-2) in an embodiment of the invention, a compound represented by formula (A-2-1) (also referred to as "compound (A-2-1)") is more preferred:

wherein $R^1$, $R^2$, $R^5$, $R^6$, n1, m2, n5, m6, $L^0$ to $L^2$, and Ar are as defined in formula (A-0).

In the compound (A-3), $L^2$ in formula (A-3) is preferably a substituted or unsubstituted arylene group having 6 to 50 ring carbon atoms or a substituted or unsubstituted heteroarylene group having 5 to 50 ring atoms.

In the compound (A-3), $L^1$ in formula (A-3) is preferably a substituted or unsubstituted arylene group having 6 to 50 ring carbon atoms or a substituted or unsubstituted heteroarylene group having 5 to 50 ring atoms, which are more preferred when $L^0$ is a single bond.

In another embodiment, the compound (A) is preferably a compound represented by formula (A-4) (also referred to as "compound (A-4)"):

(A-4)

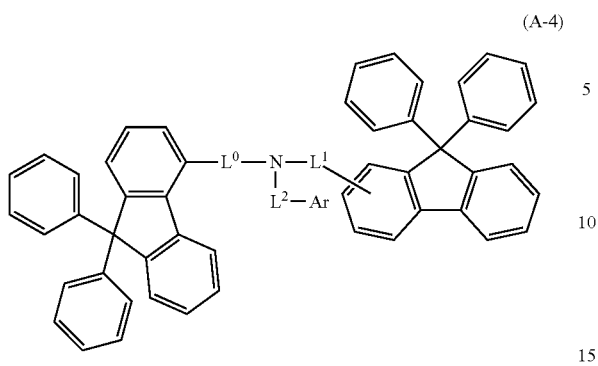

wherein L⁰ to L², and Ar are as defined in formula (A-0).

In the compound (A-4), $L^2$ in formula (A-4) is preferably a substituted or unsubstituted arylene group having 6 to 50 ring carbon atoms or a substituted or unsubstituted heteroarylene group having 5 to 50 ring atoms.

In the compound (A-4), $L^1$ in formula (A-4) is preferably a substituted or unsubstituted arylene group having 6 to 50 ring carbon atoms or a substituted or unsubstituted heteroarylene group having 5 to 50 ring atoms, which are more preferred when $L^0$ is a single bond.

Examples of the compound (A) in an aspect of the invention are shown below, although not limited thereto.

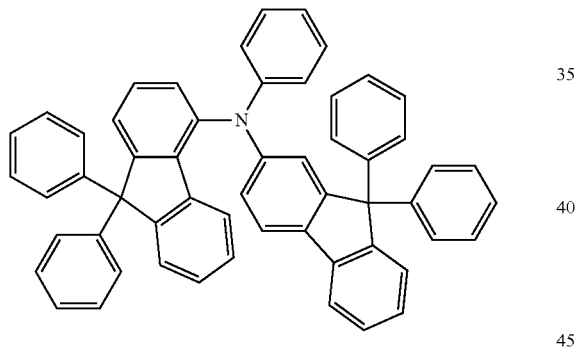

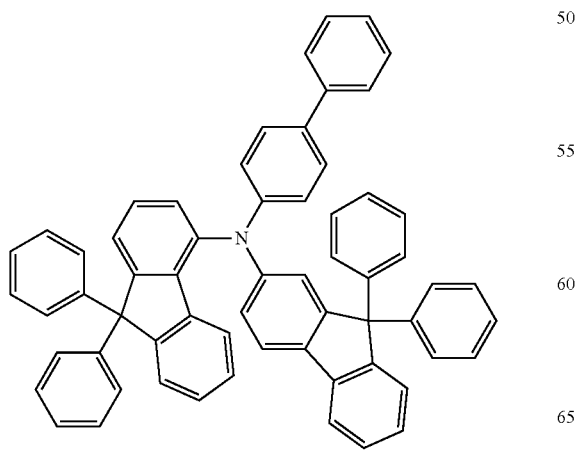

-continued

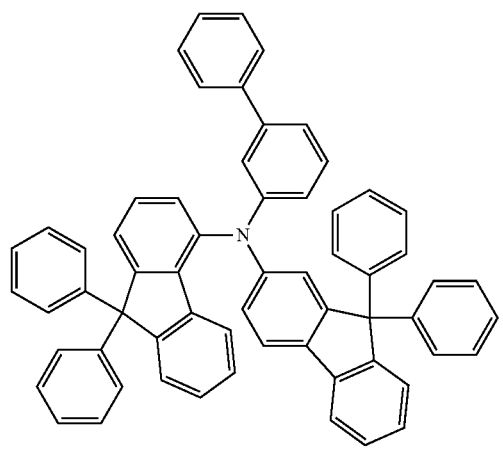

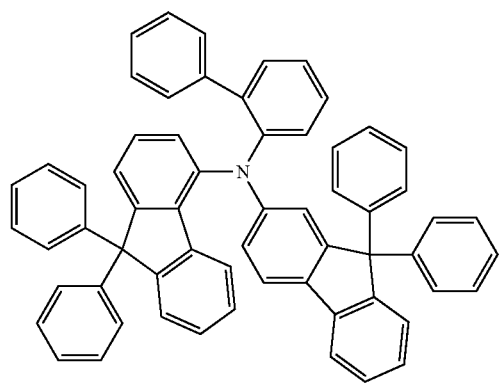

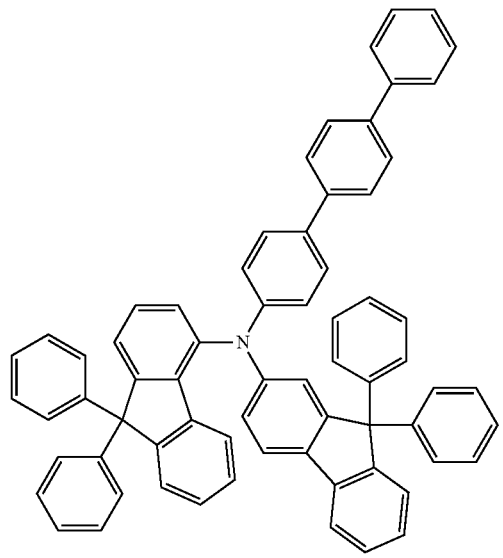

-continued
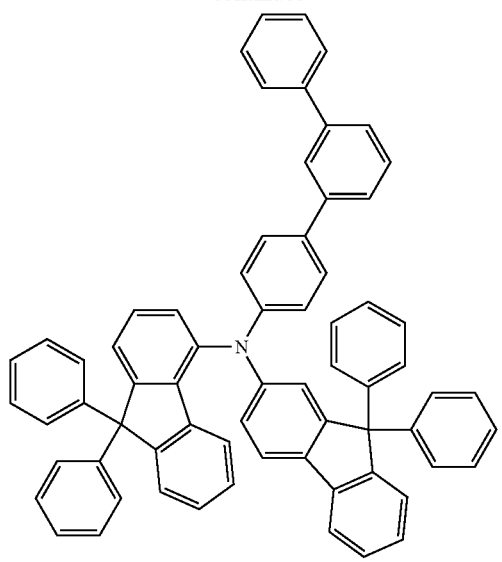
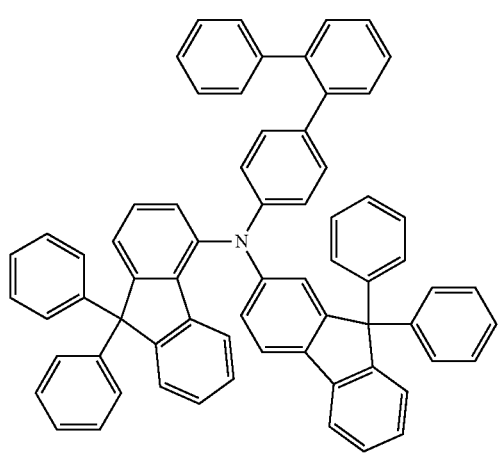
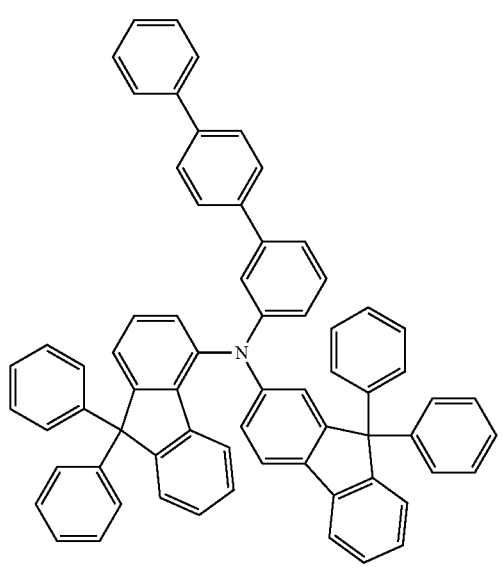
-continued
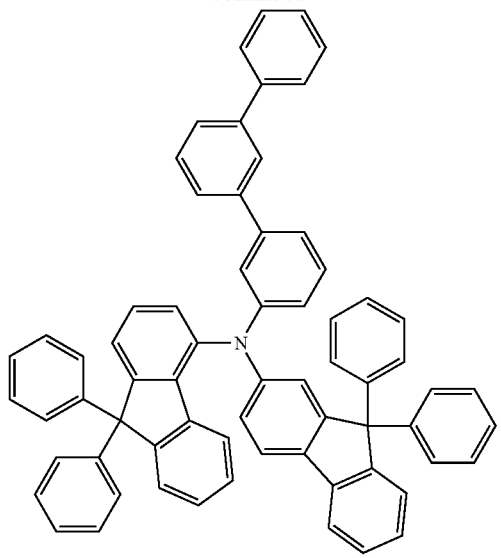
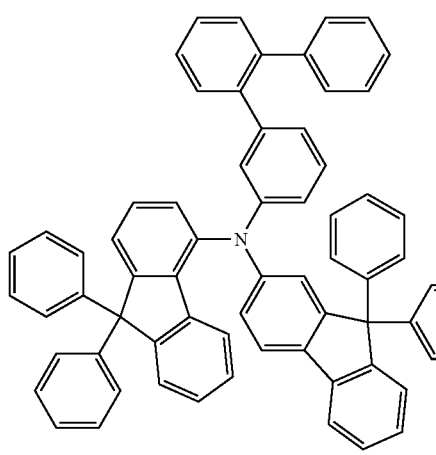
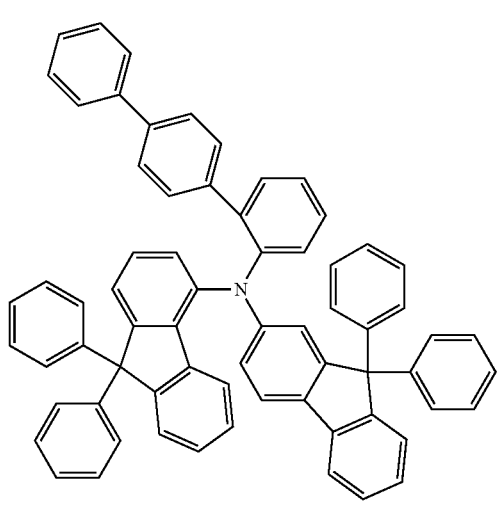

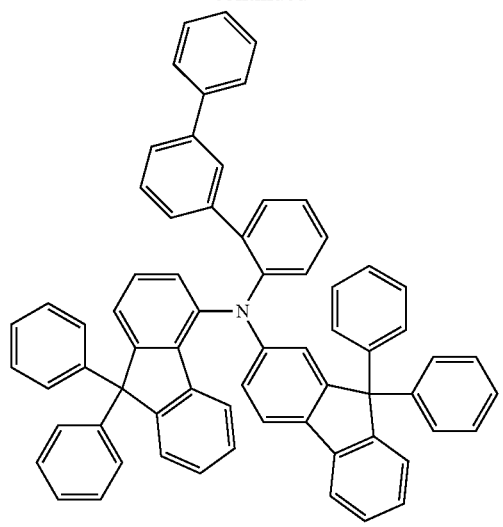
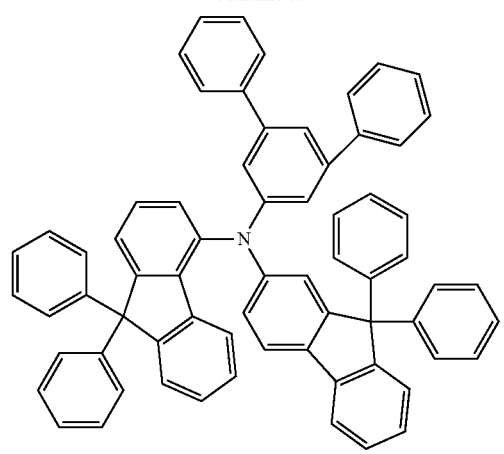
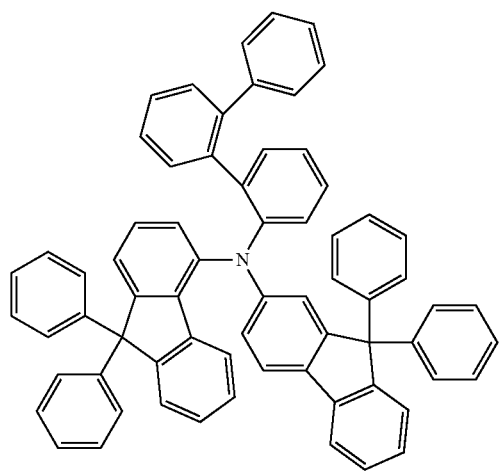
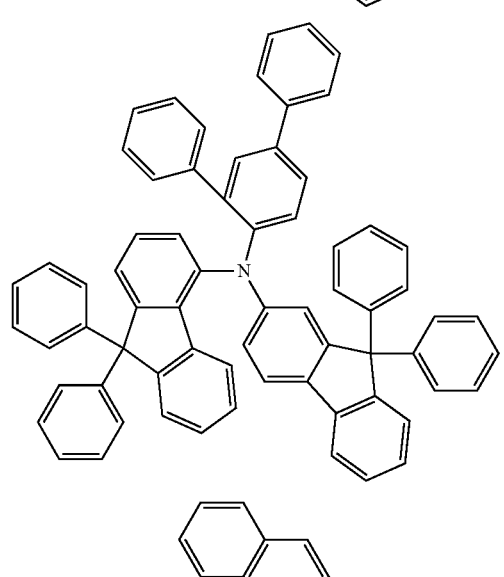
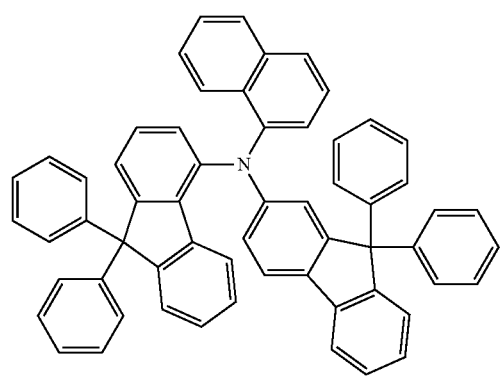
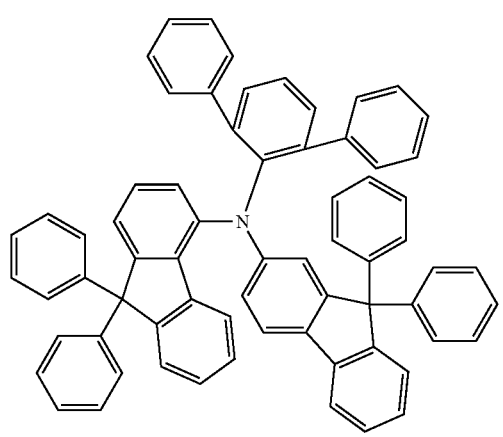
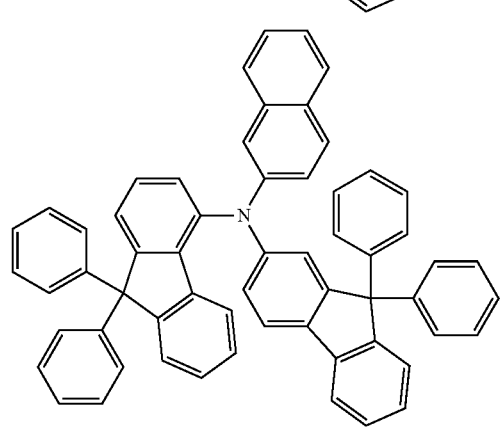

-continued
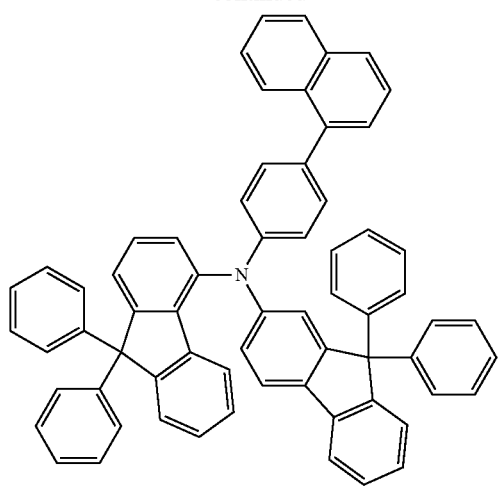
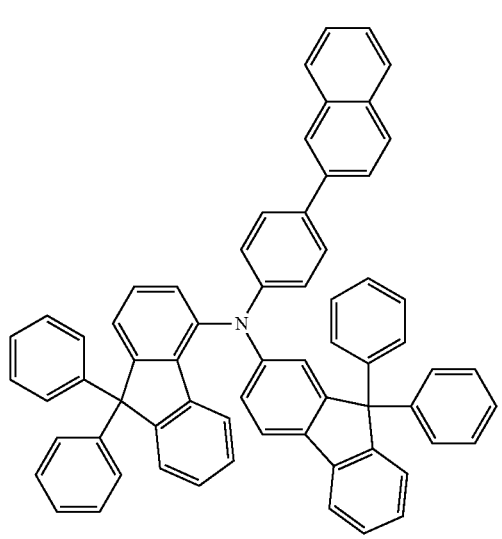
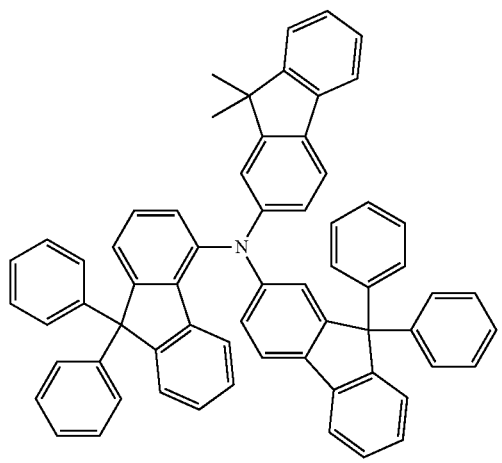
-continued
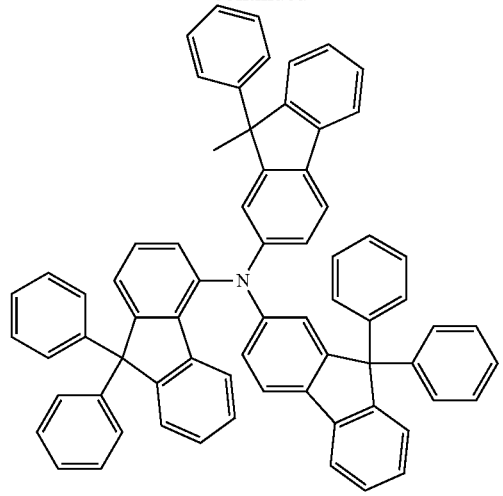
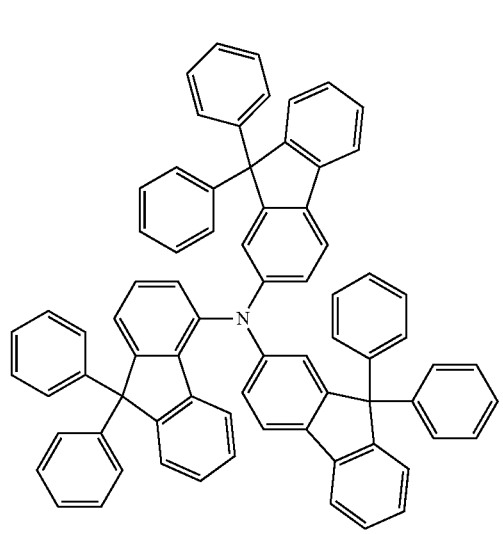
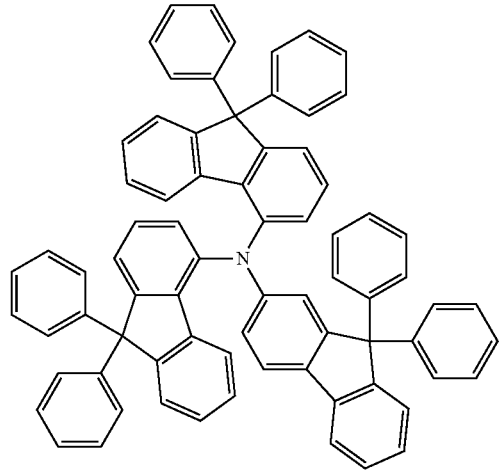

29
-continued
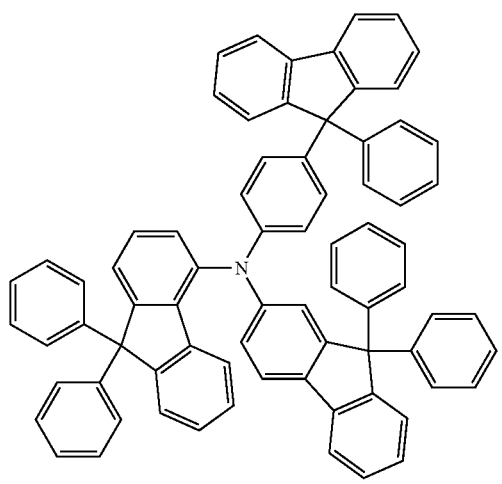
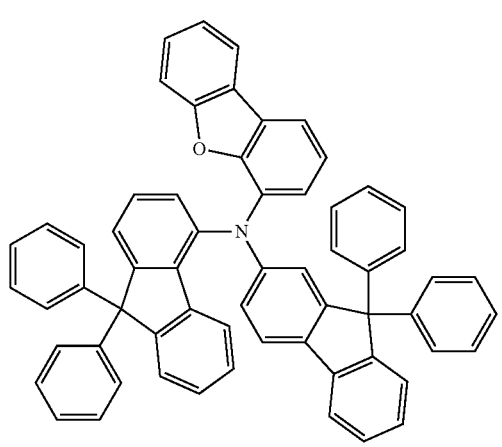
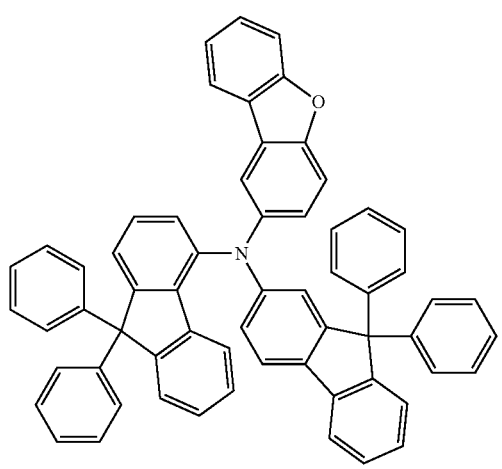
30
-continued
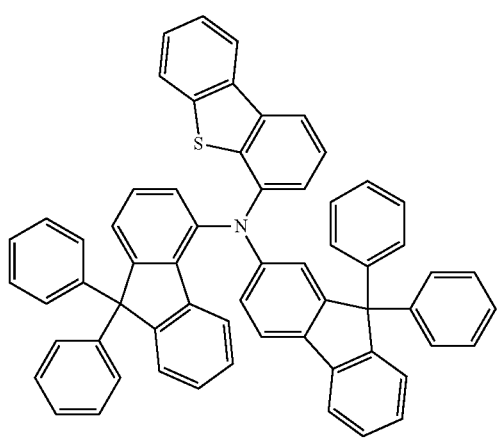
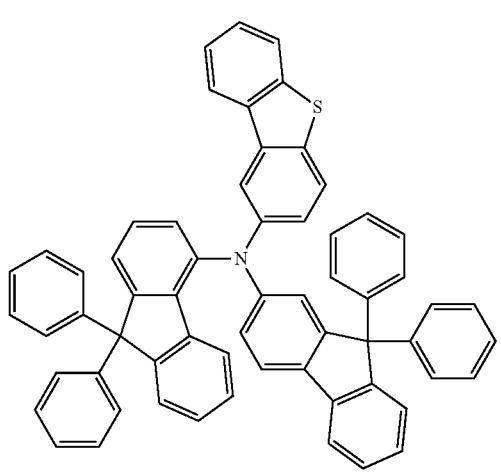
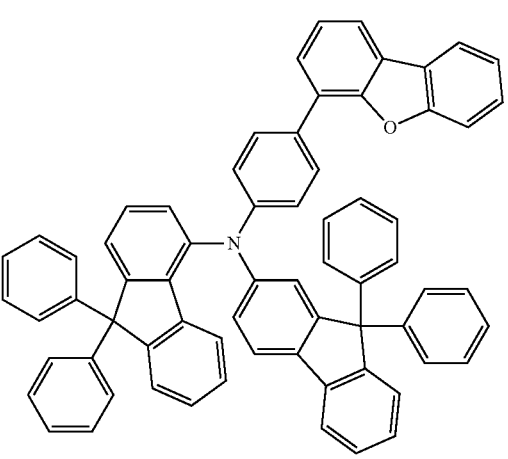

31
-continued
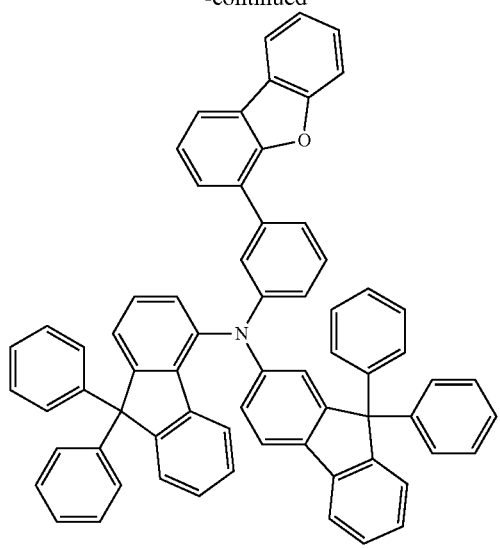
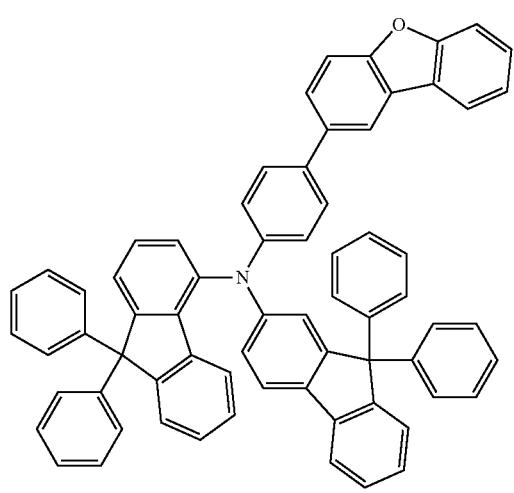
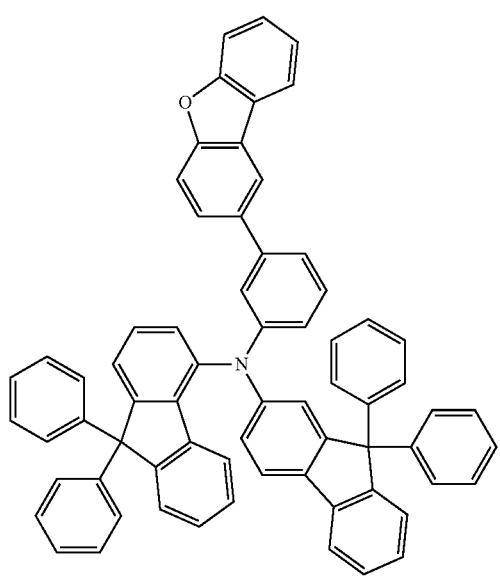
32
-continued
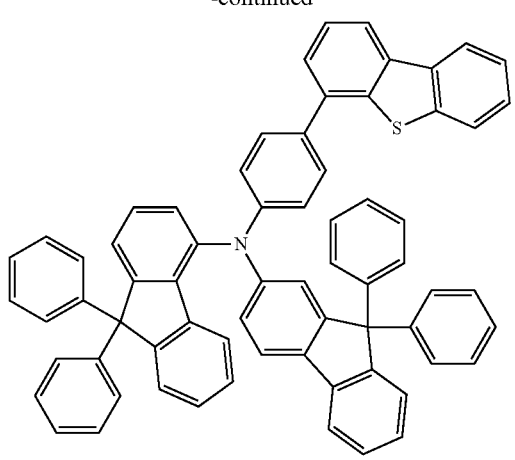
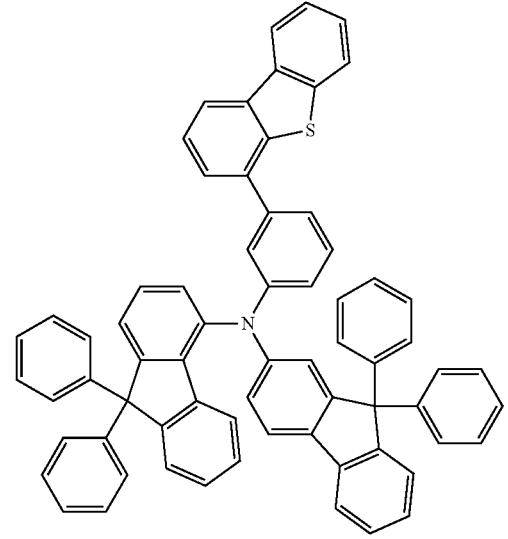
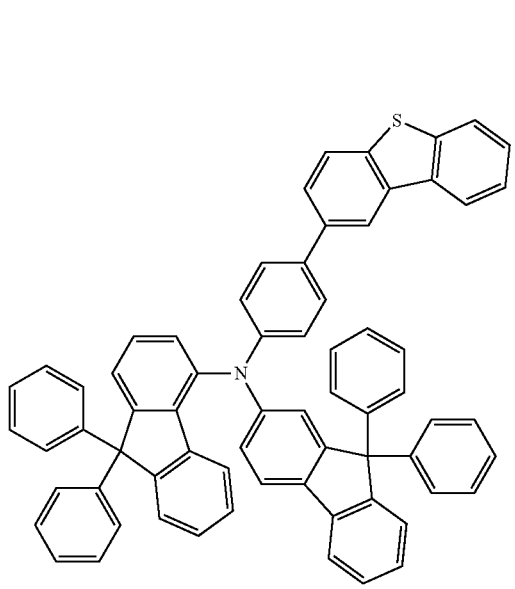

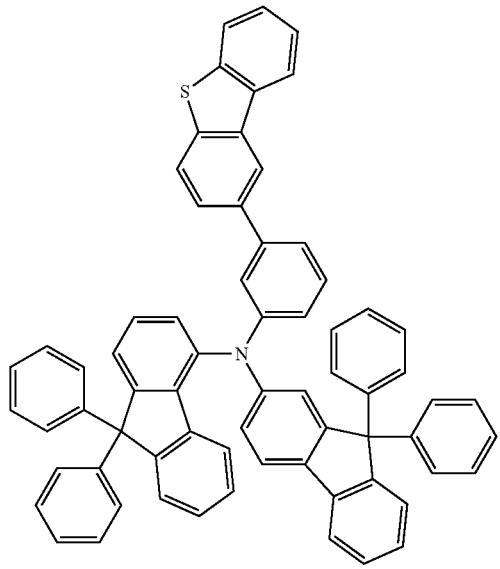
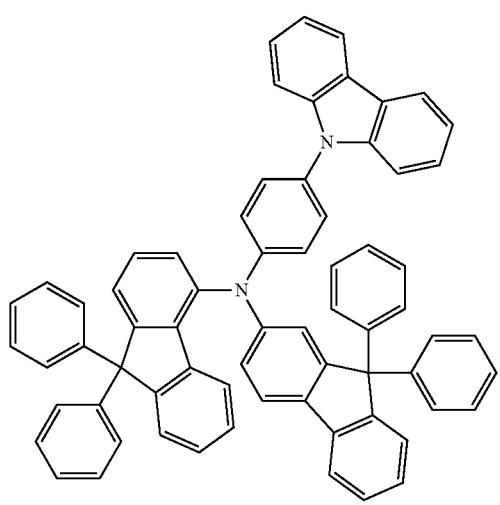
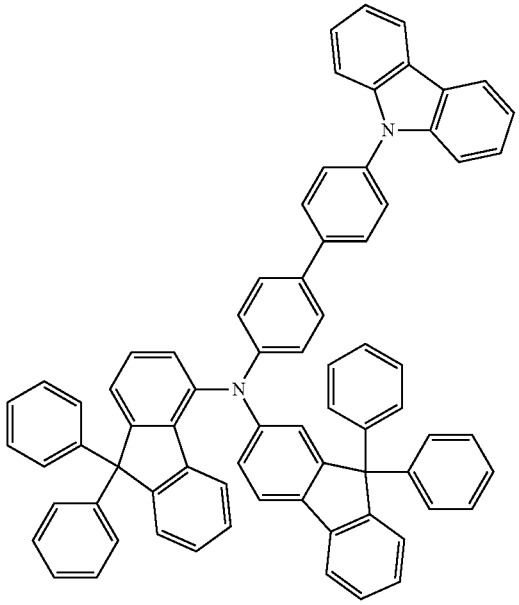
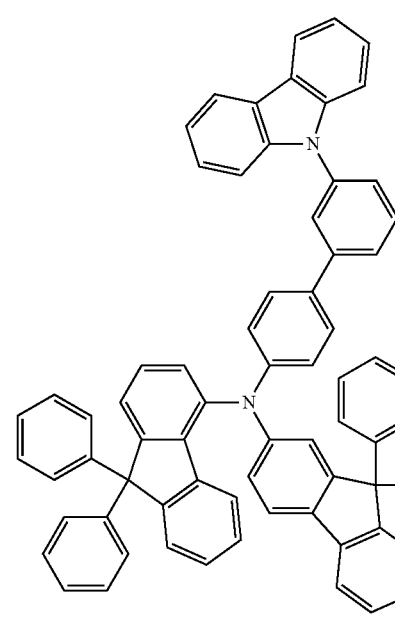
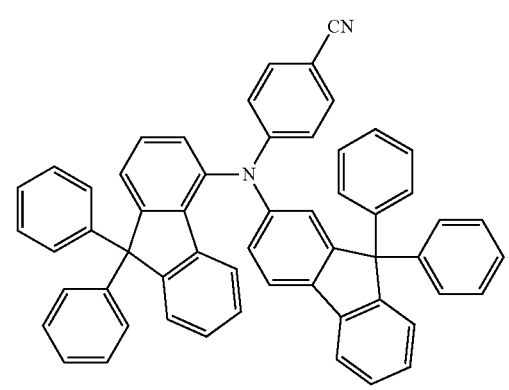

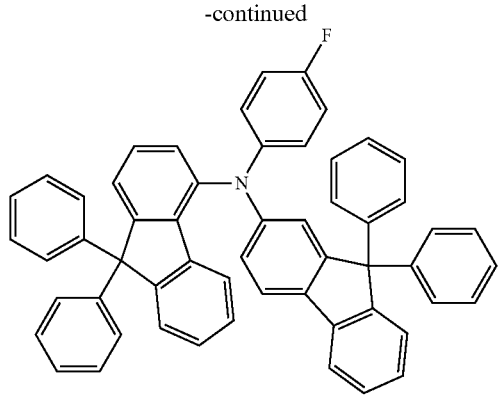
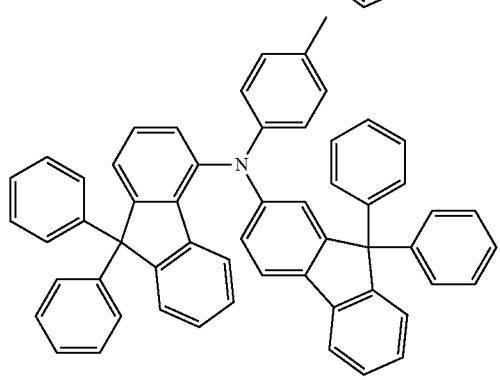
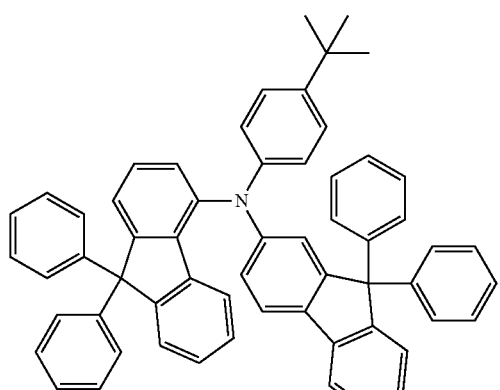
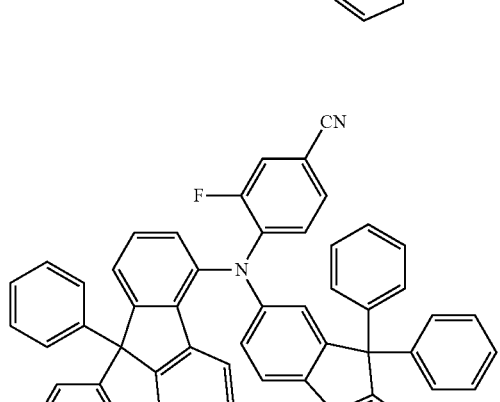
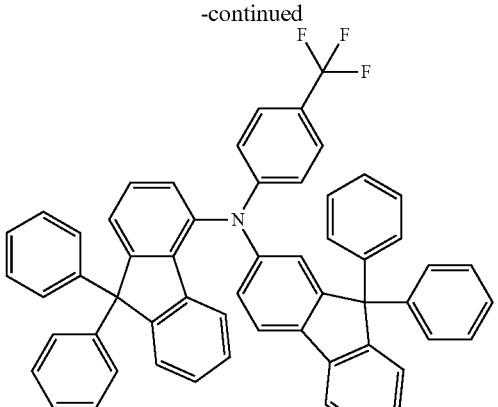
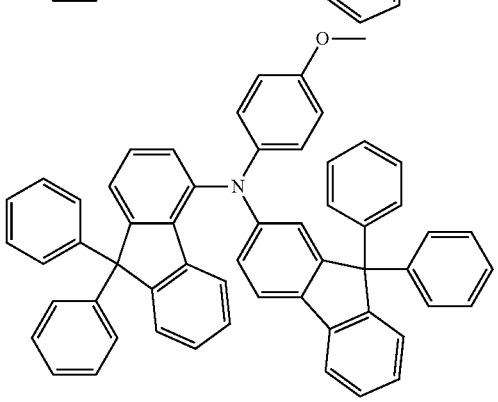
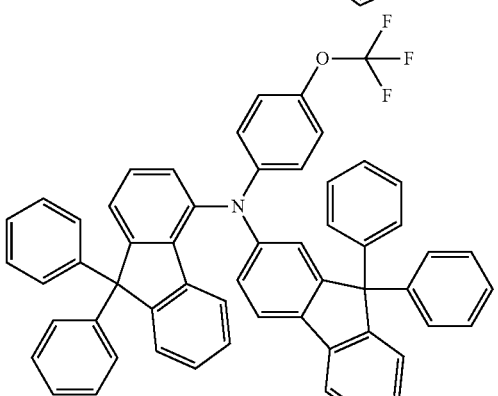
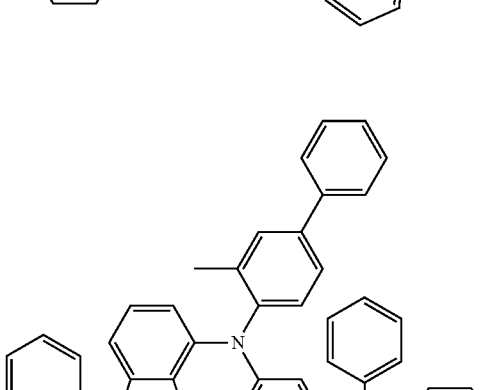

37
-continued
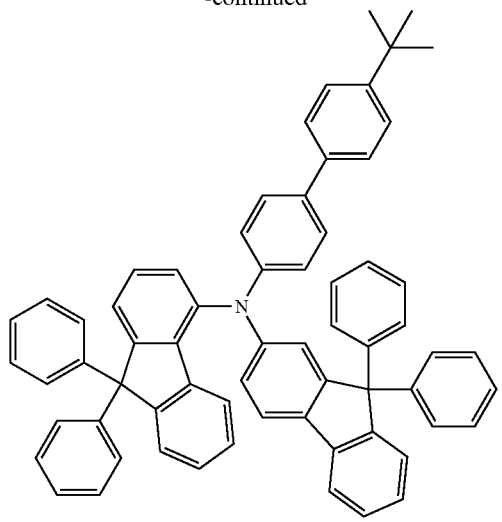
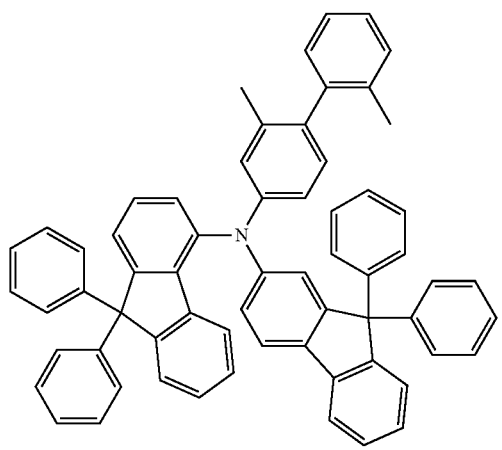
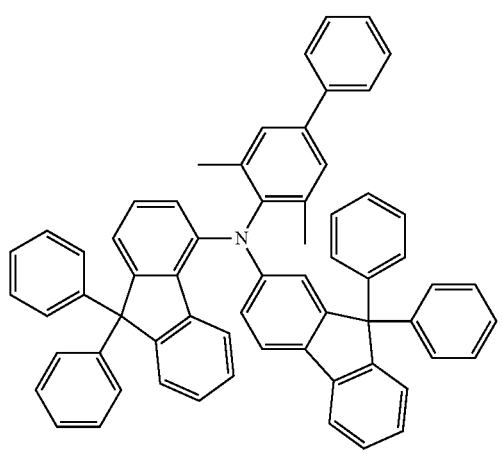
38
-continued
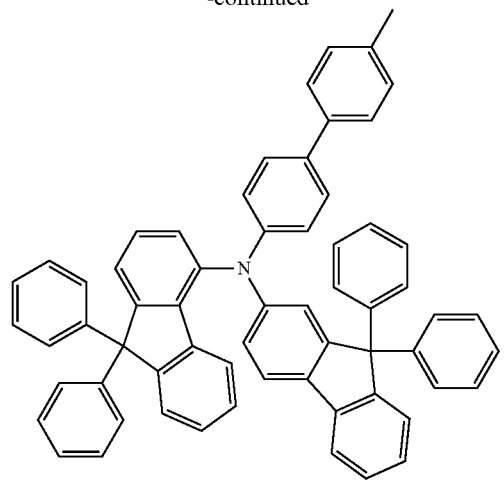
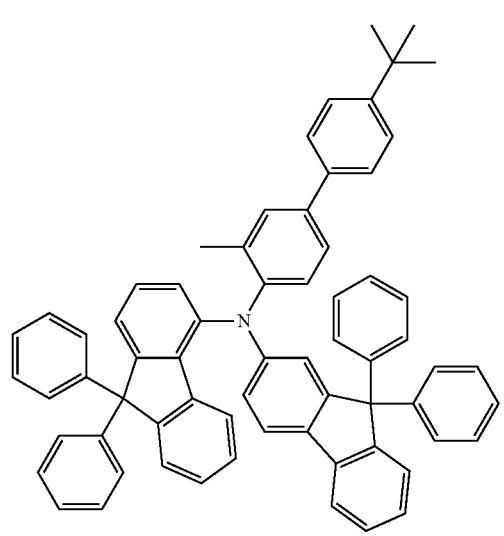
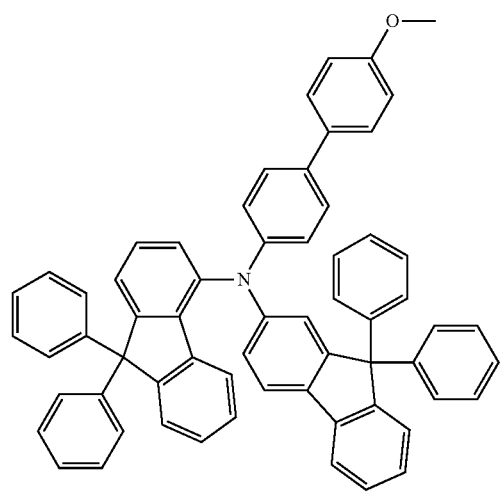

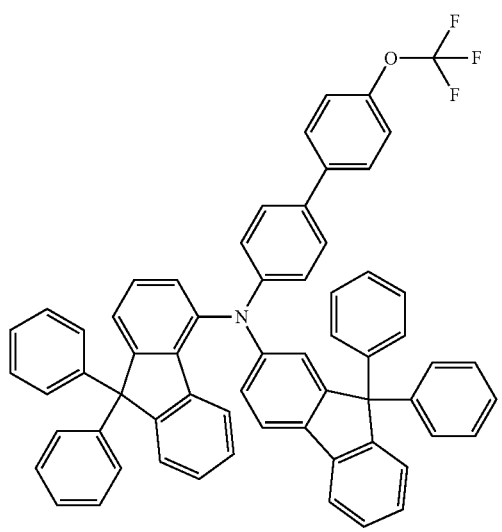
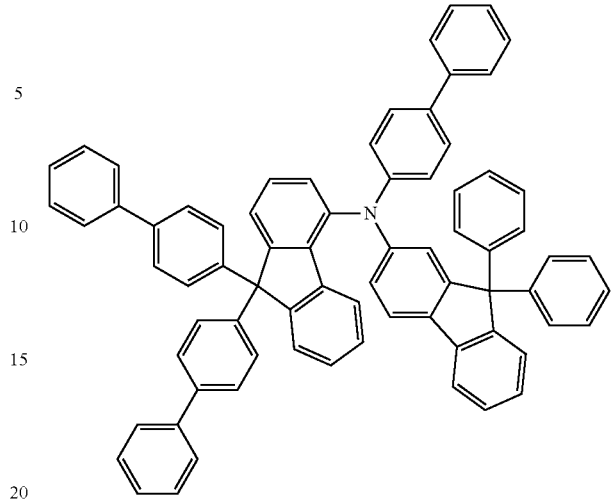
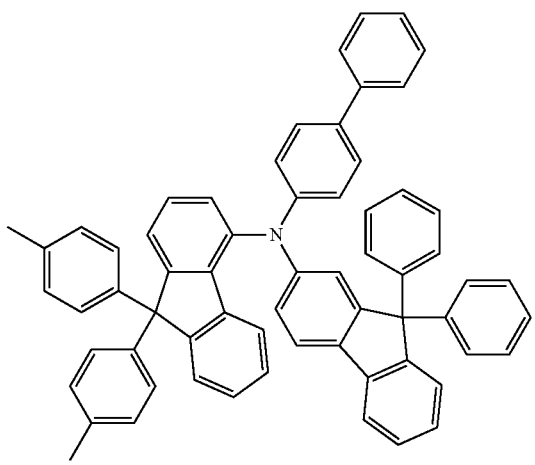
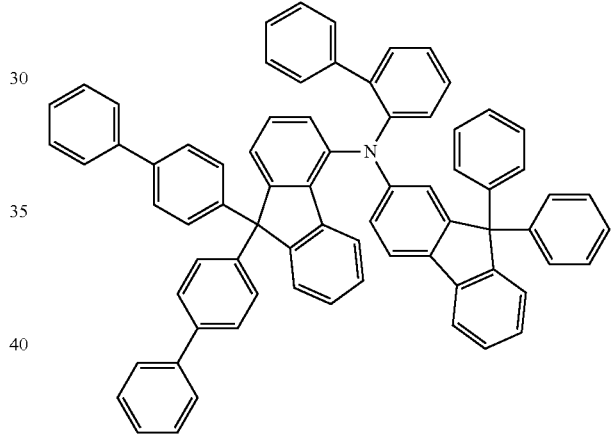
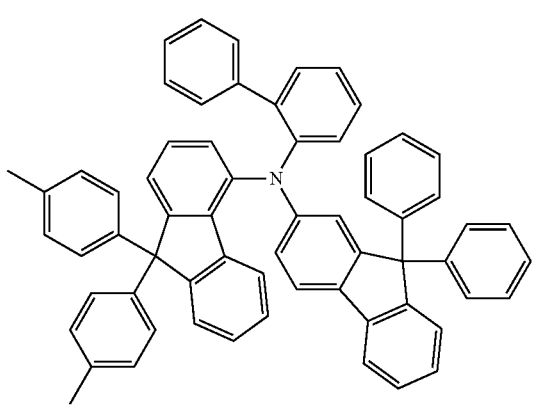
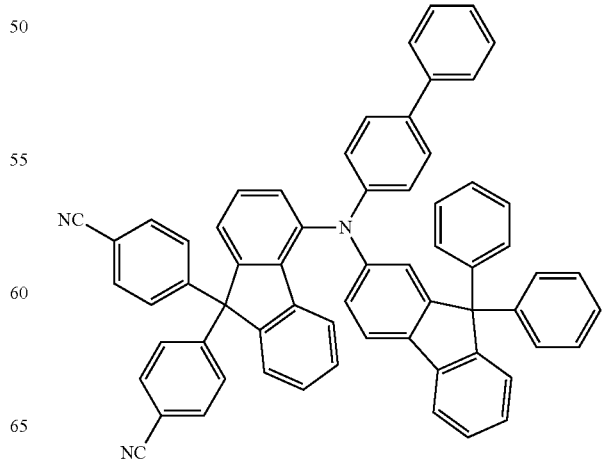

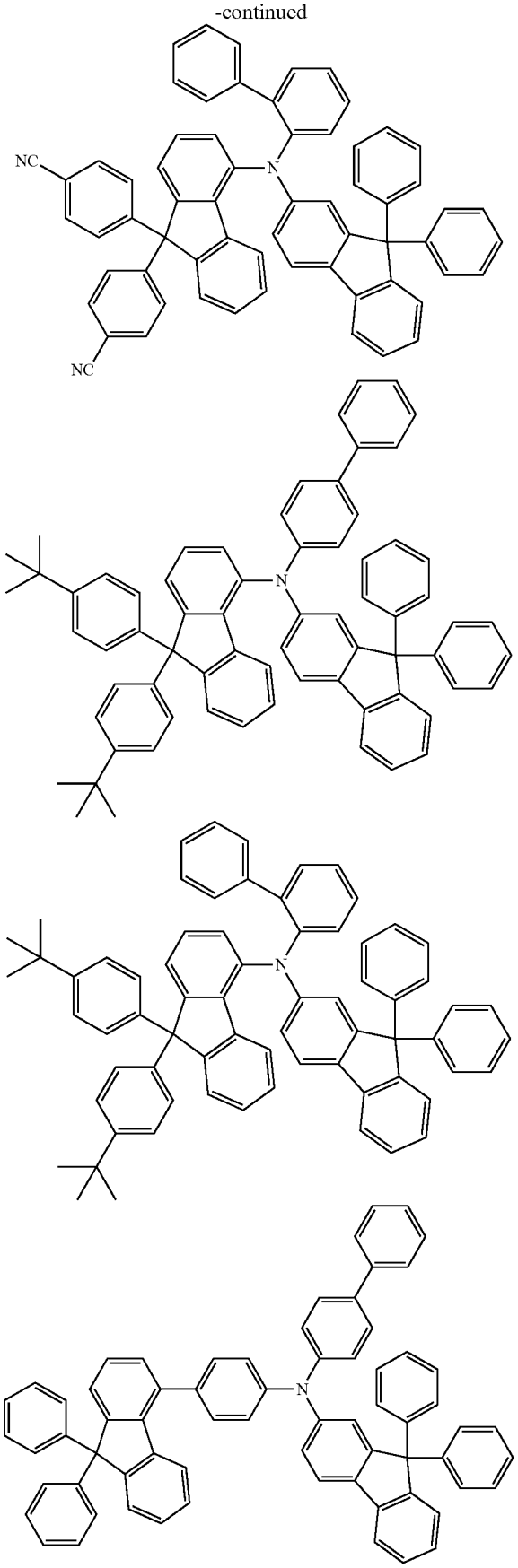
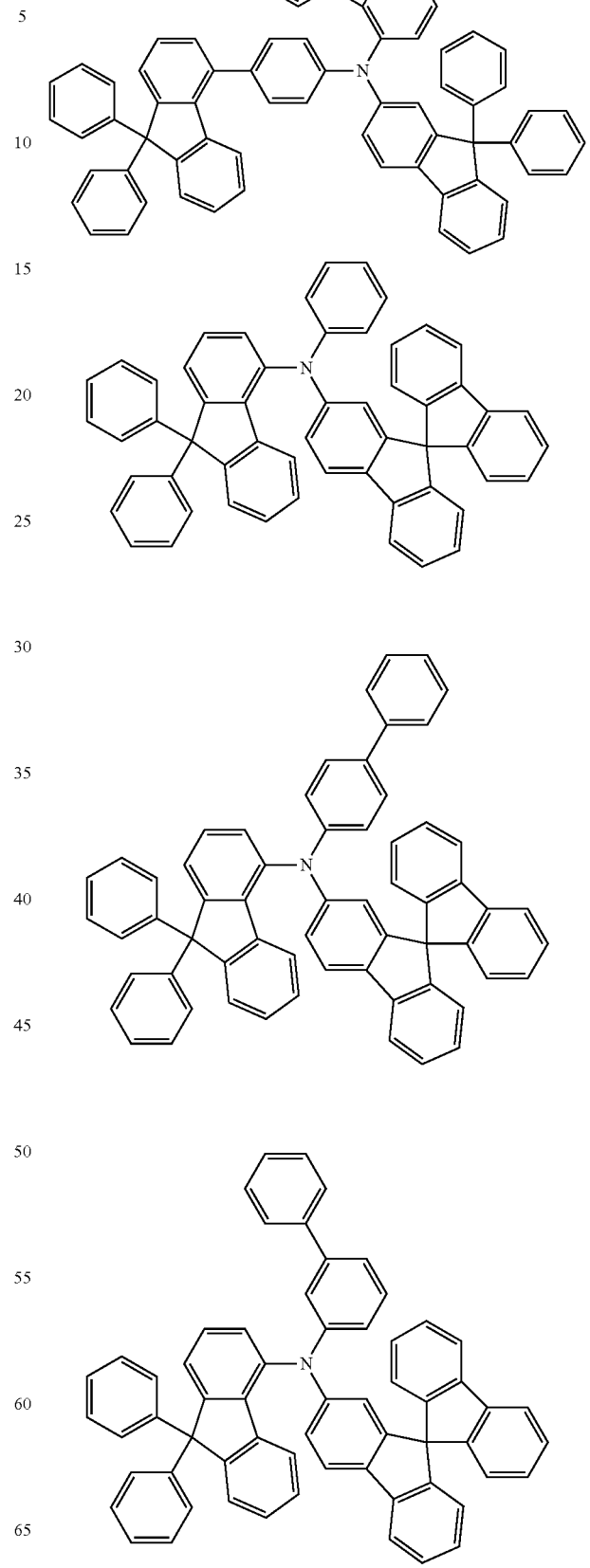

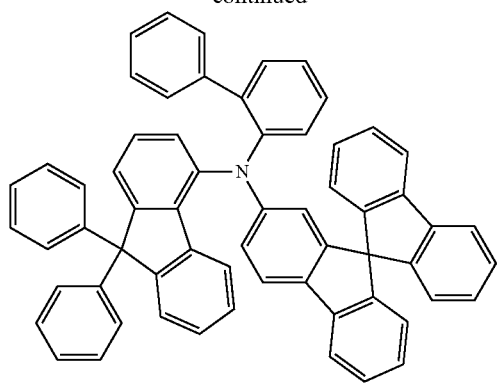
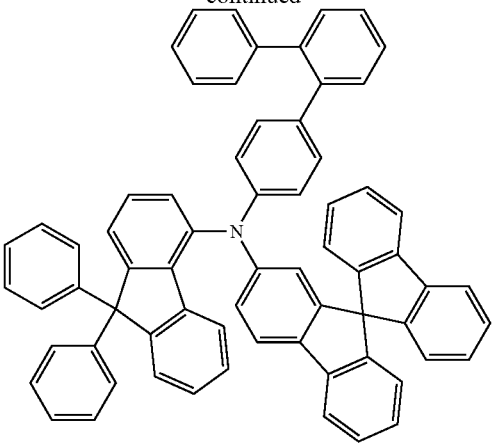
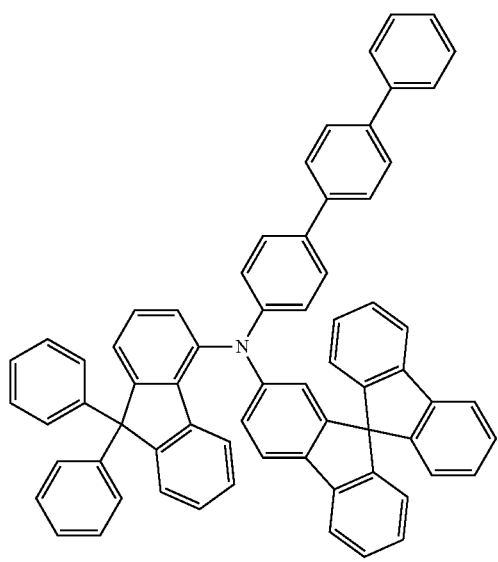
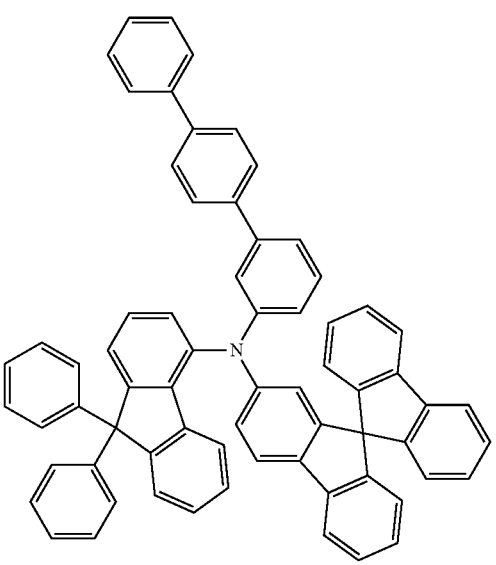
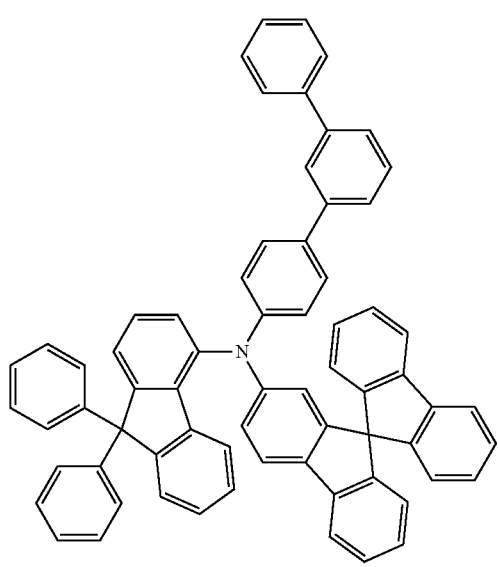
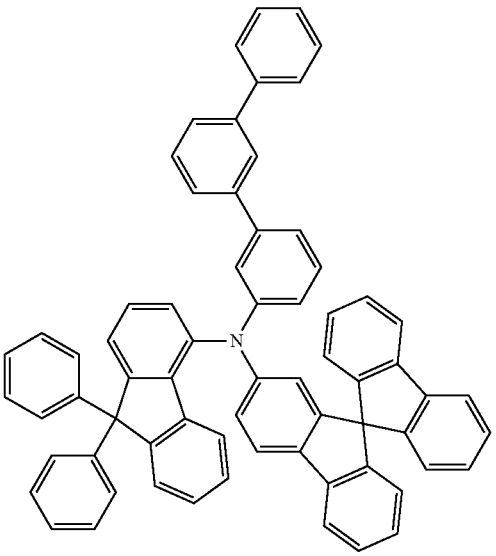

-continued
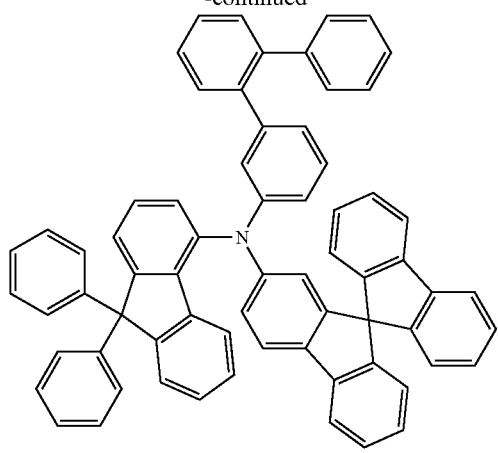
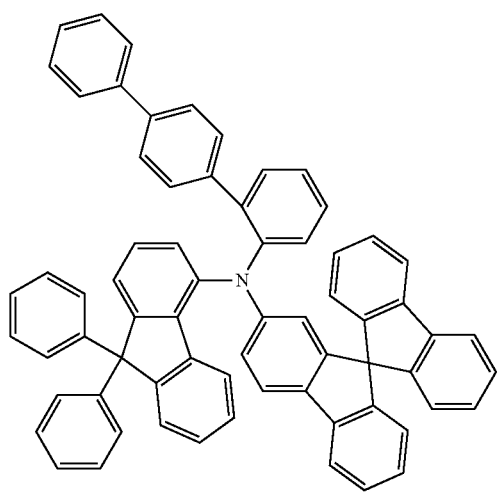
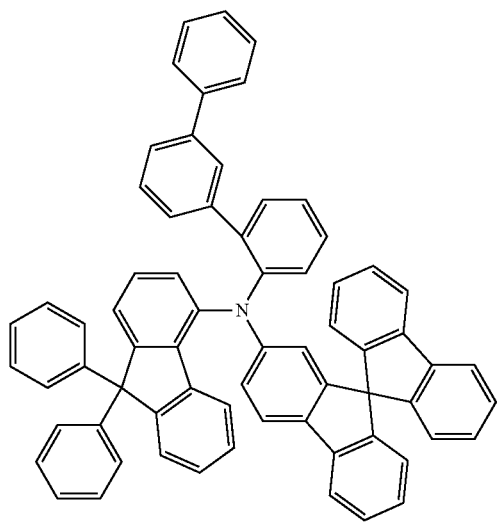
-continued
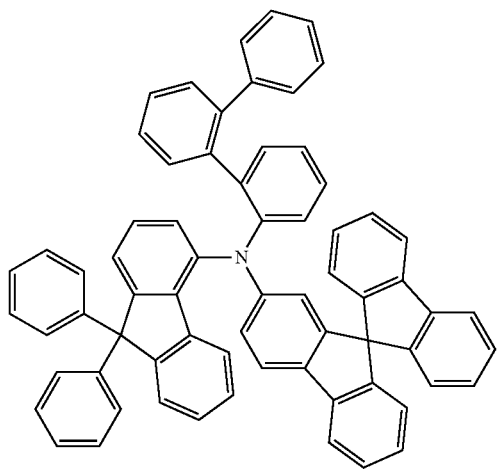
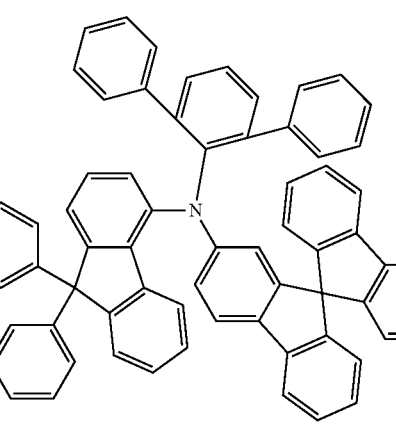
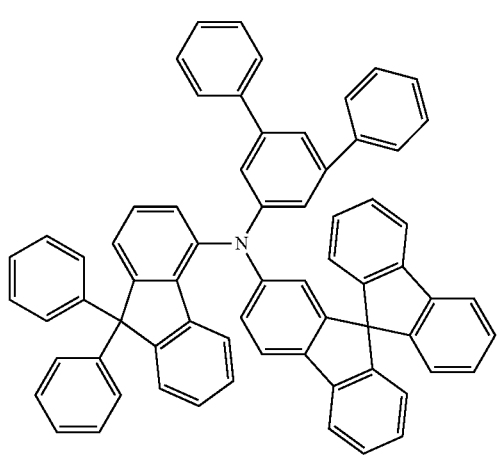

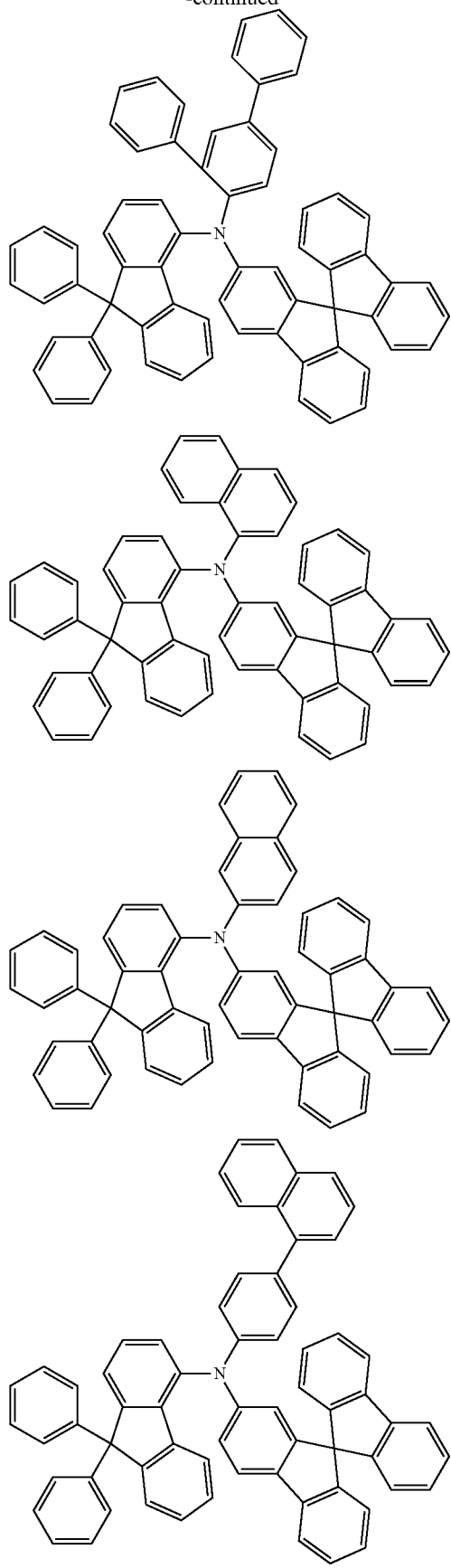
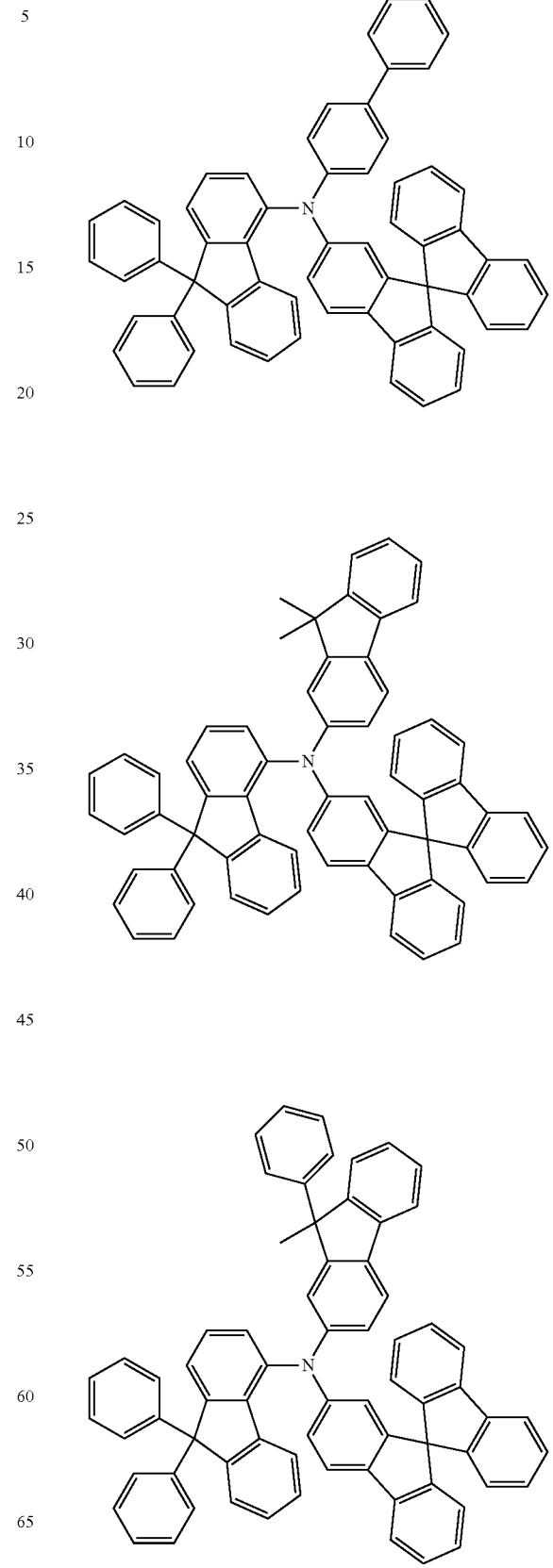

49
-continued
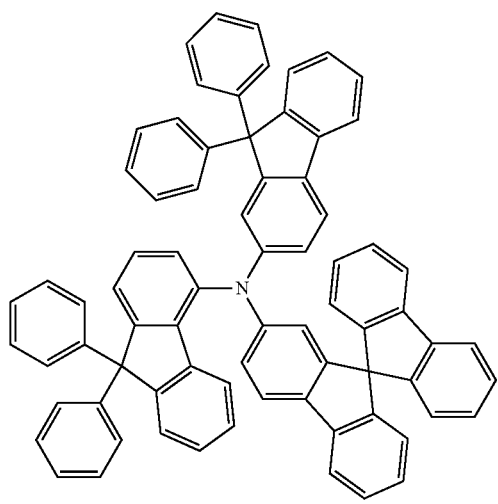
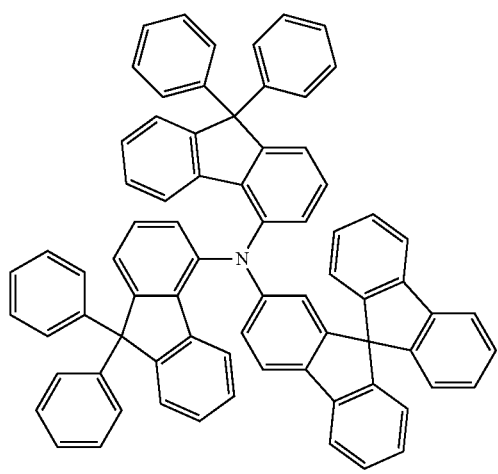
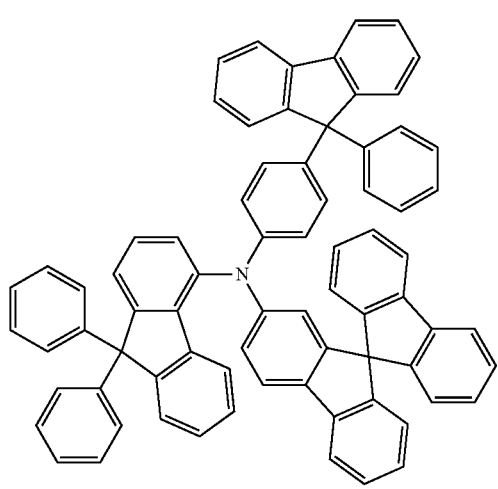
50
-continued
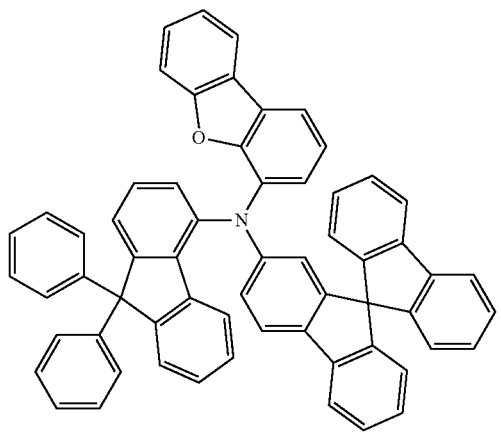
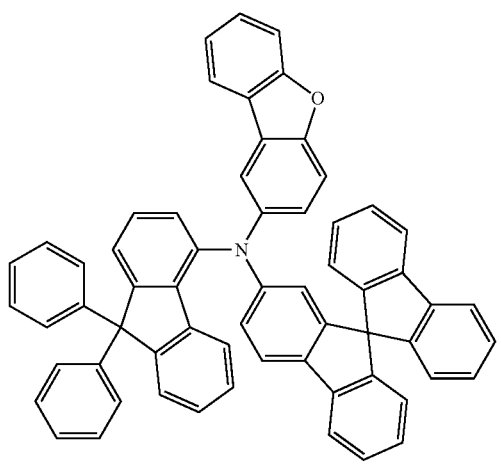
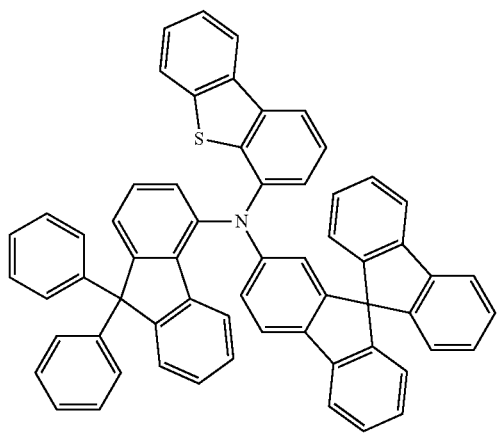

51
-continued
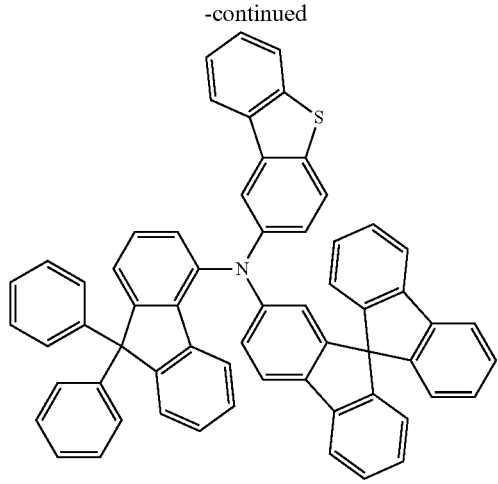
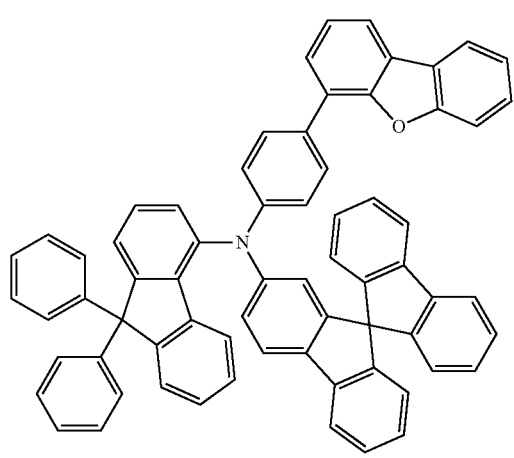
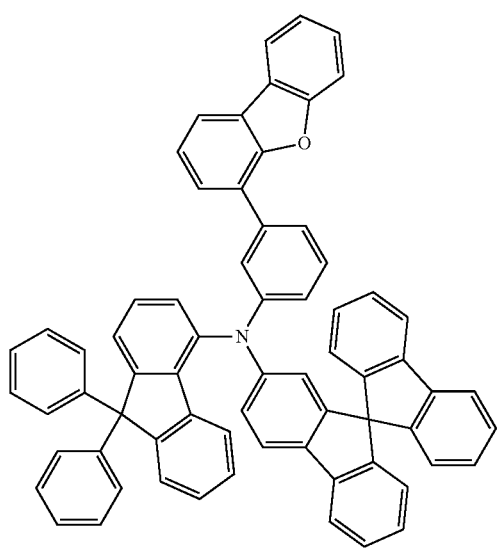
52
-continued
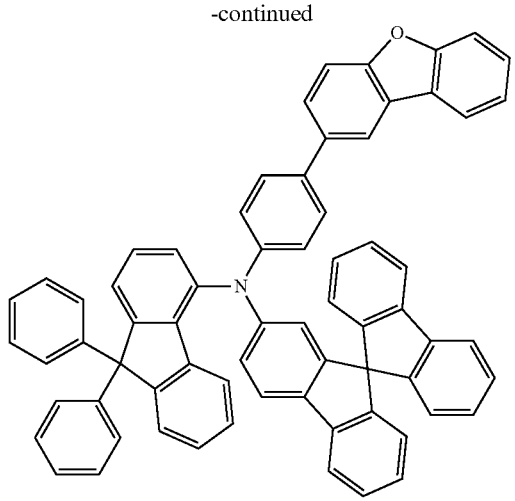
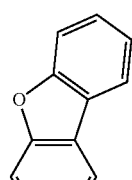
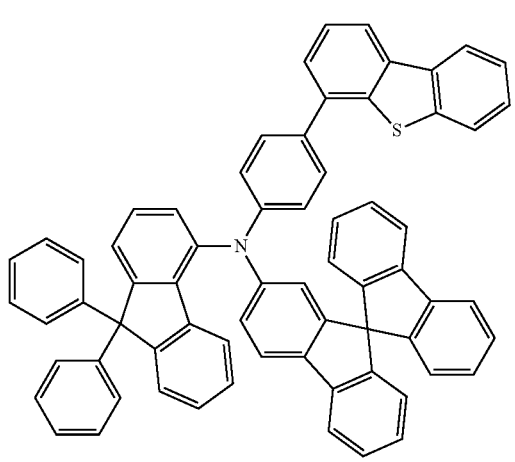

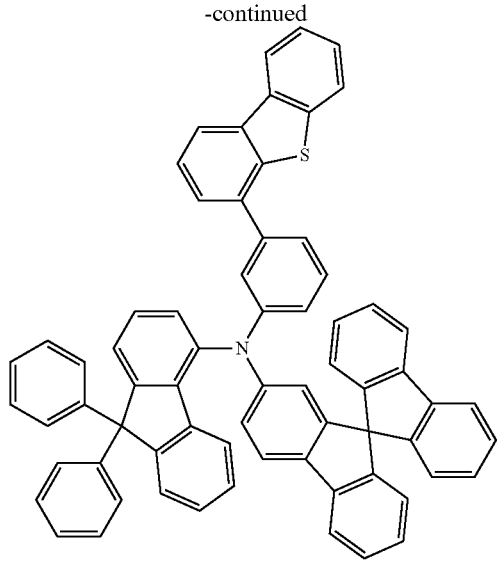
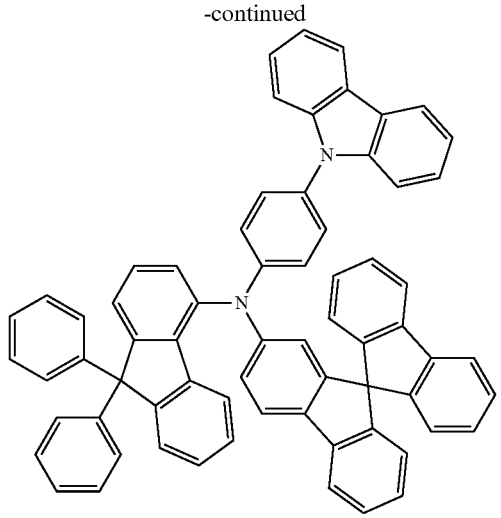
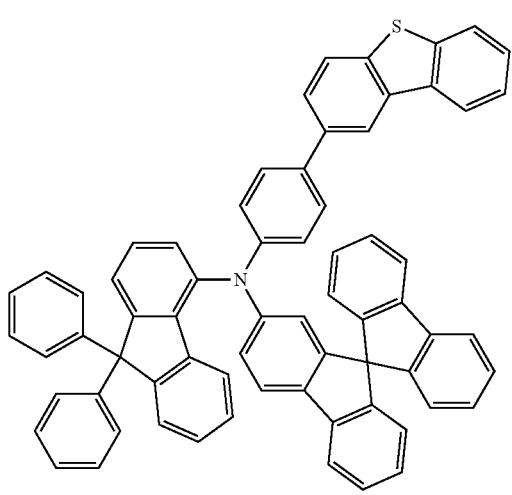
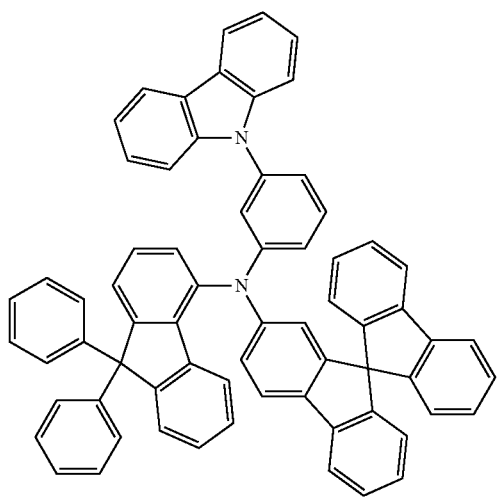
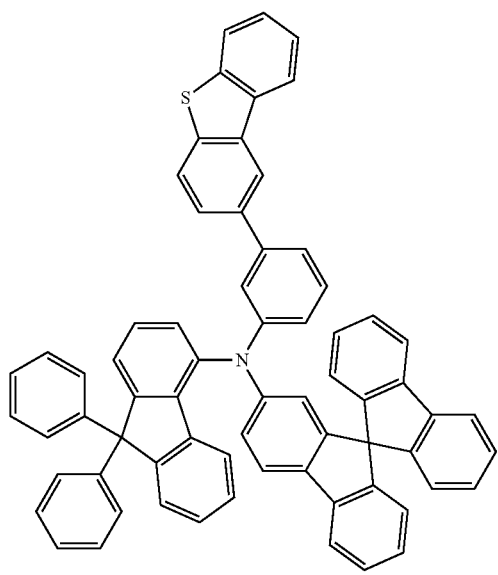
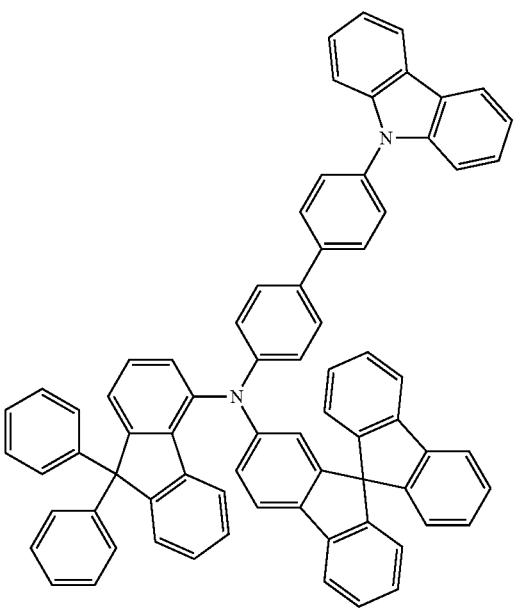

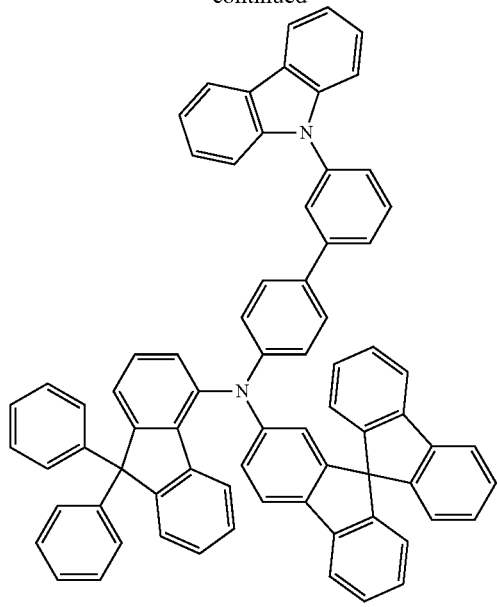
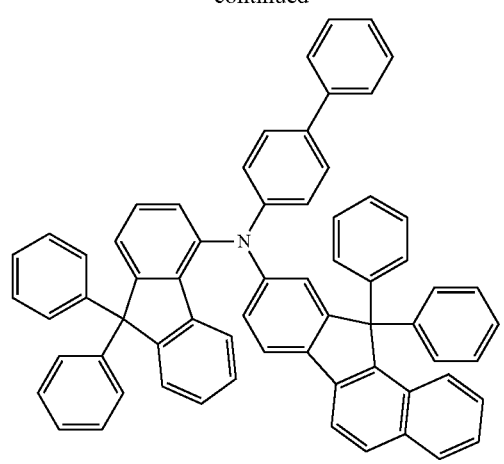
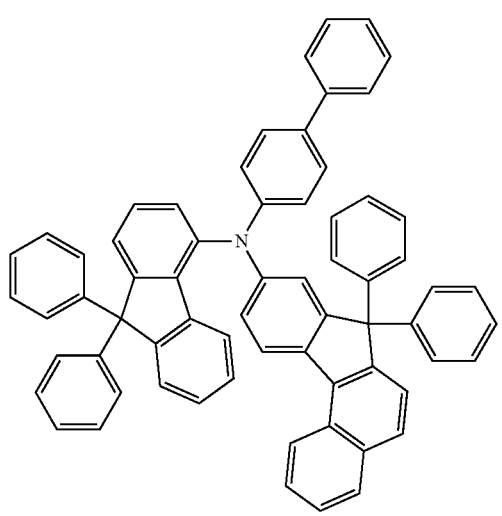
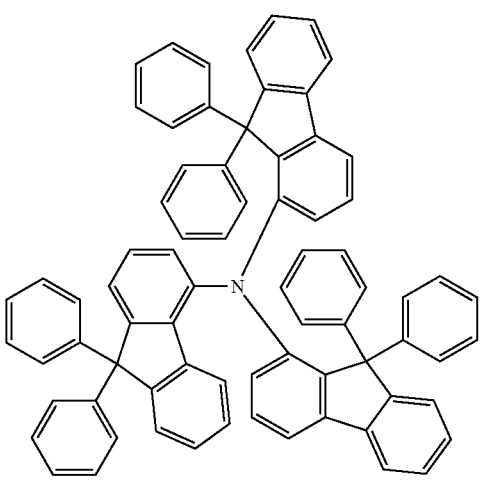
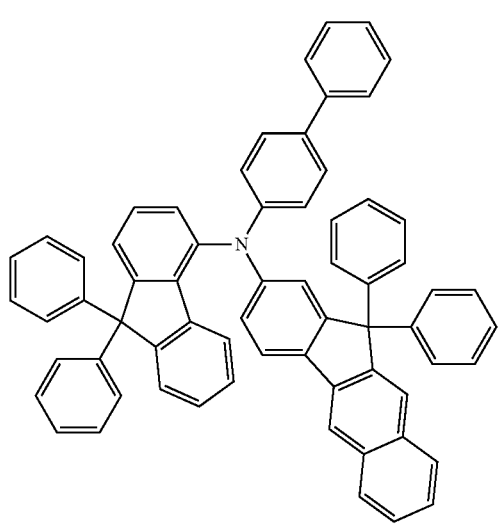
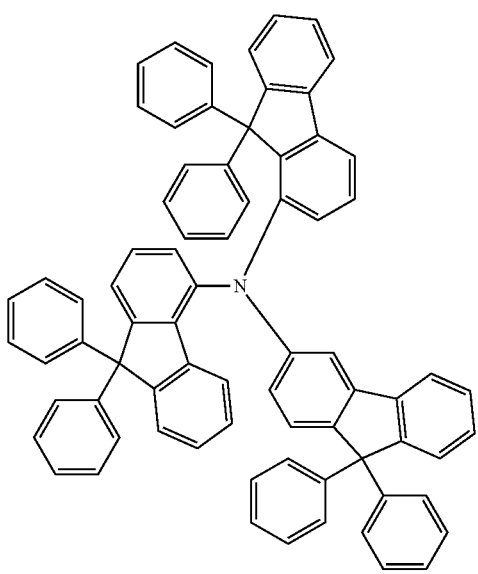

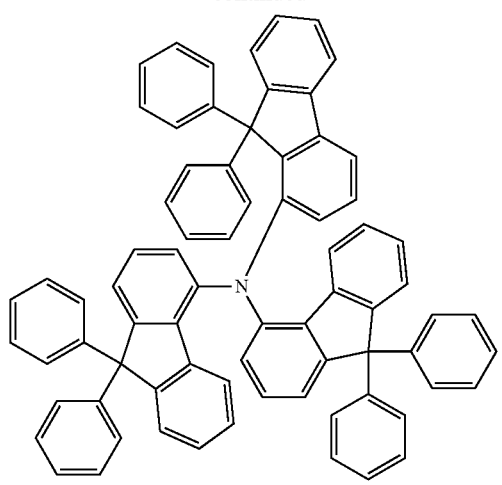
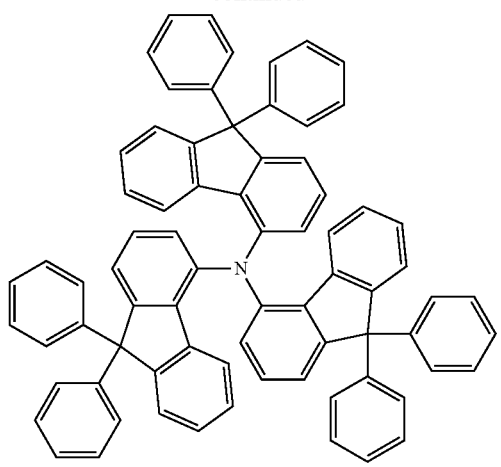
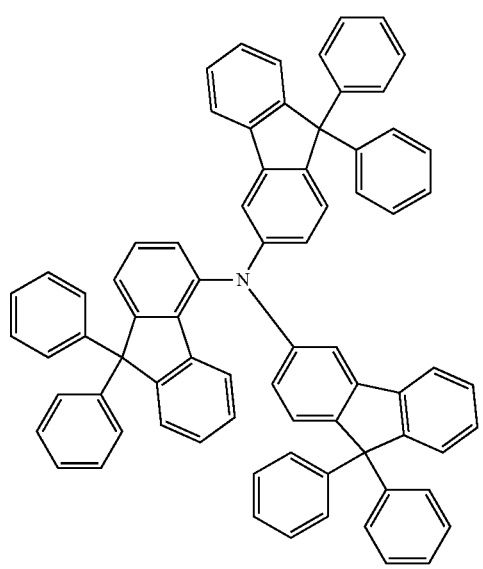
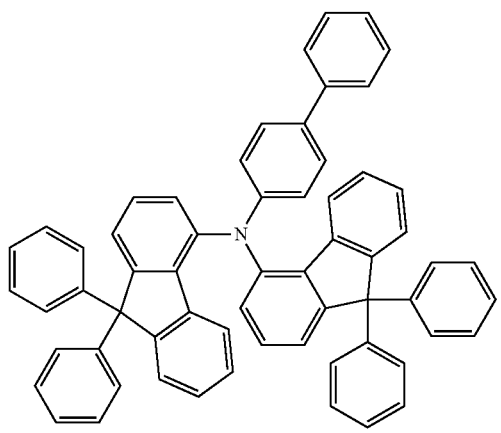
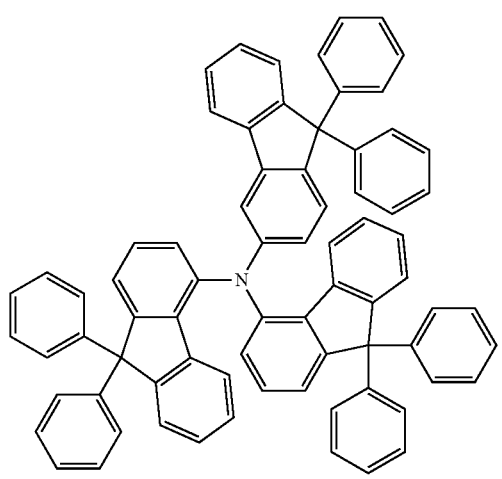
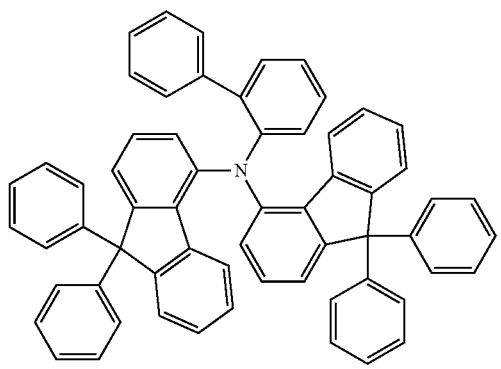

-continued
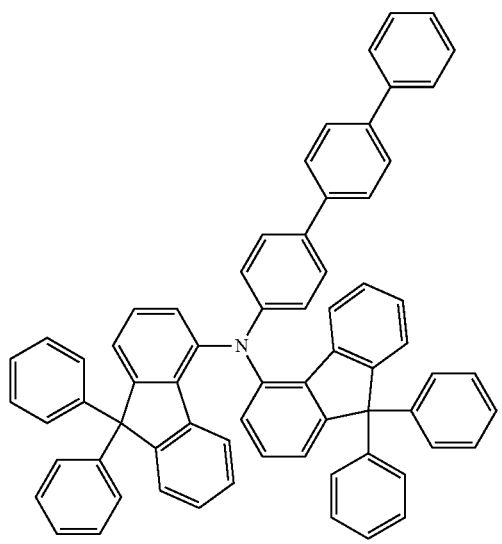
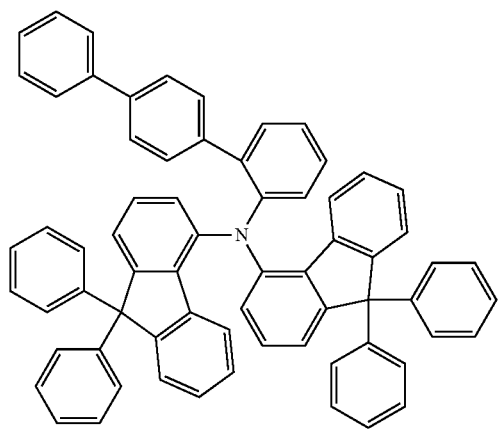
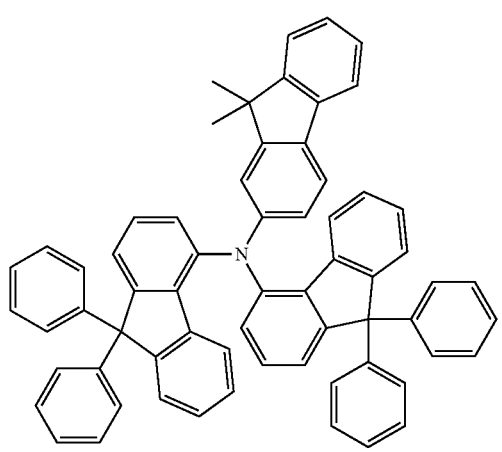
-continued
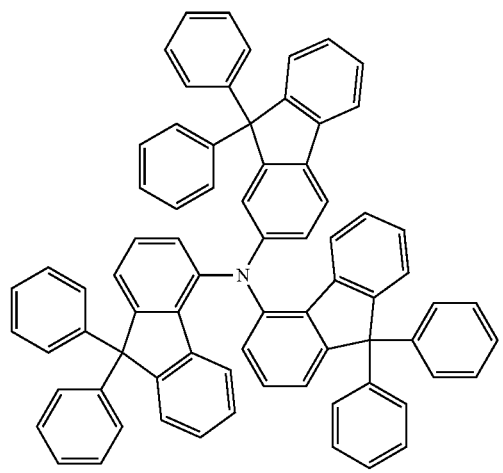
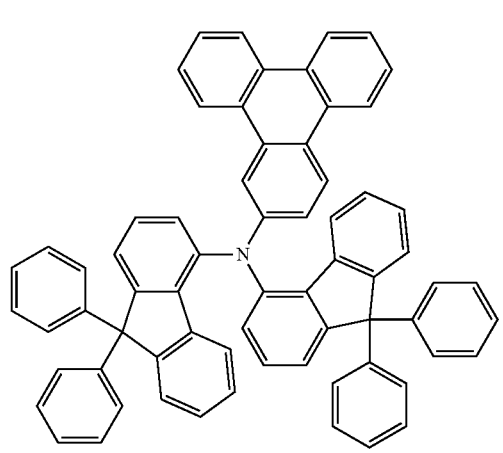
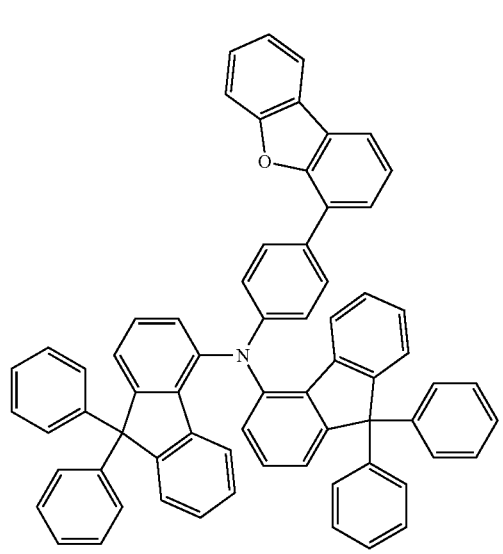

61
-continued
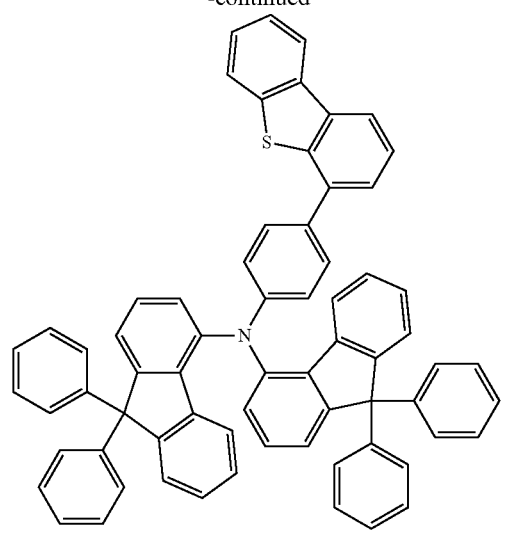
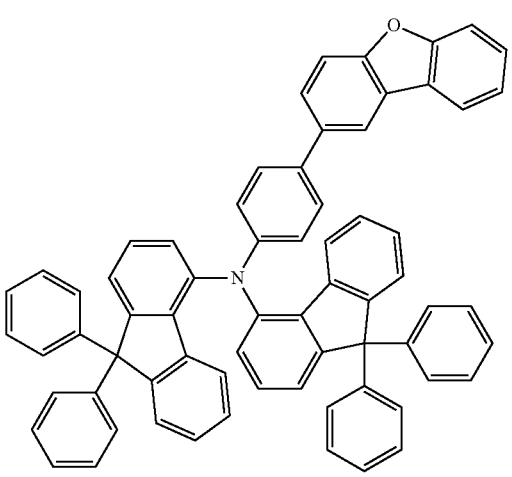
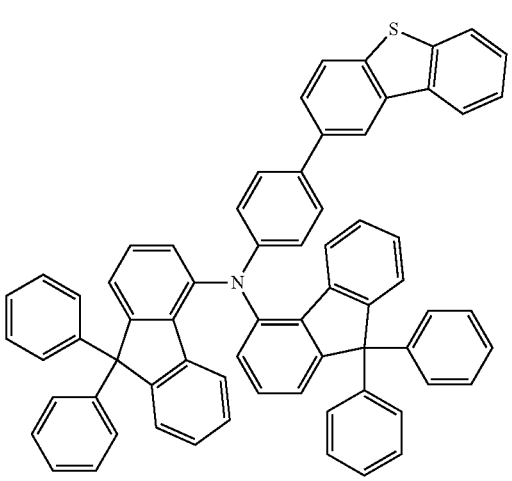
62
-continued
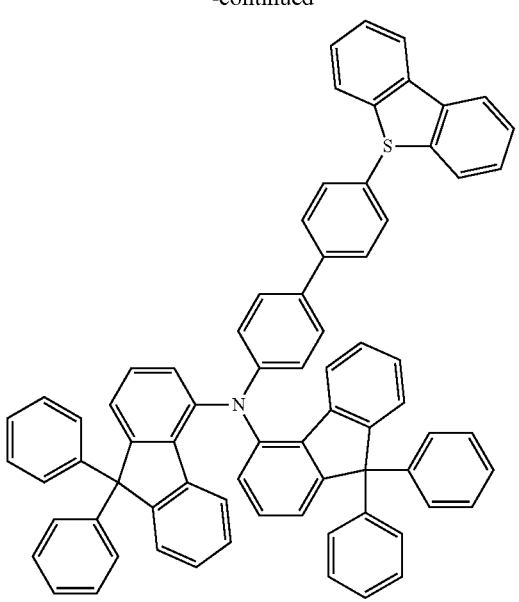
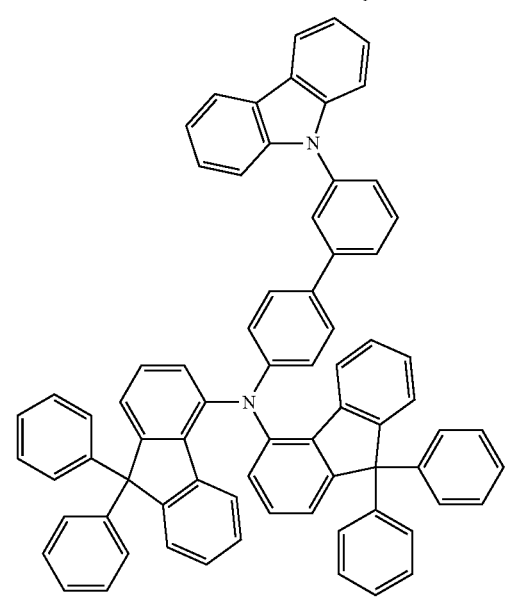
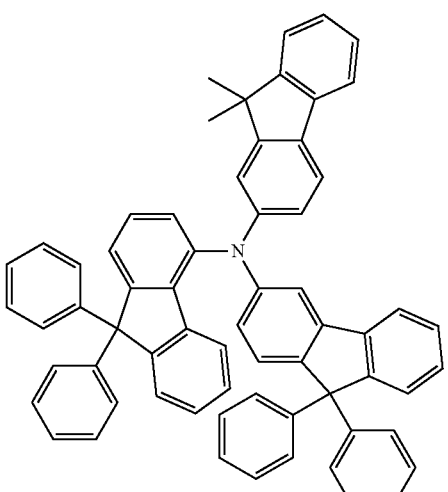

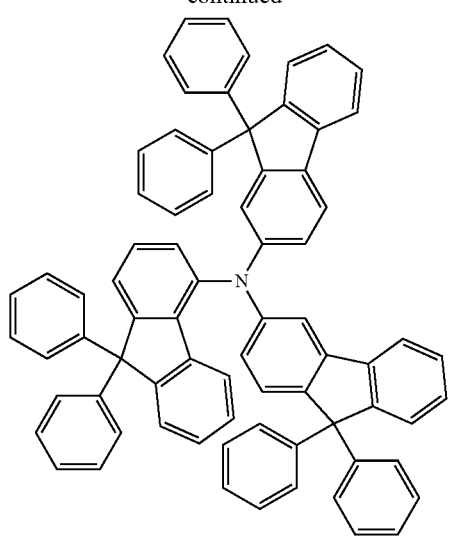
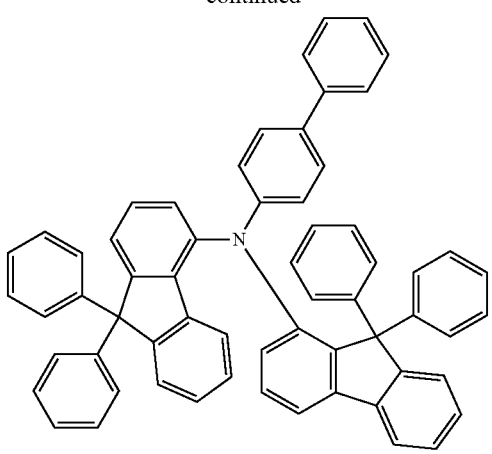
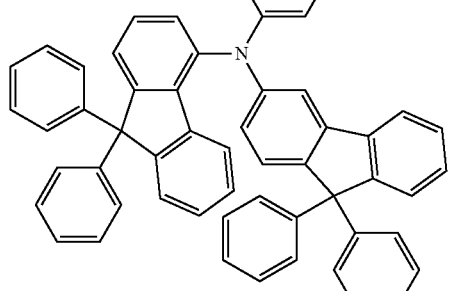
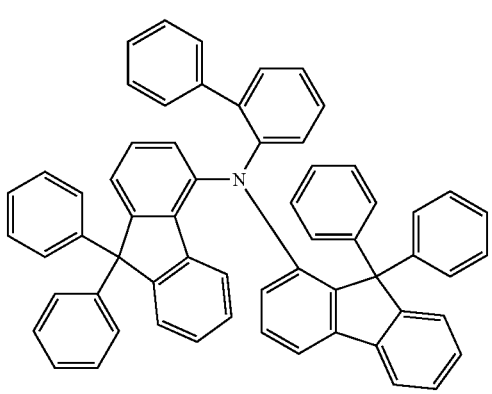
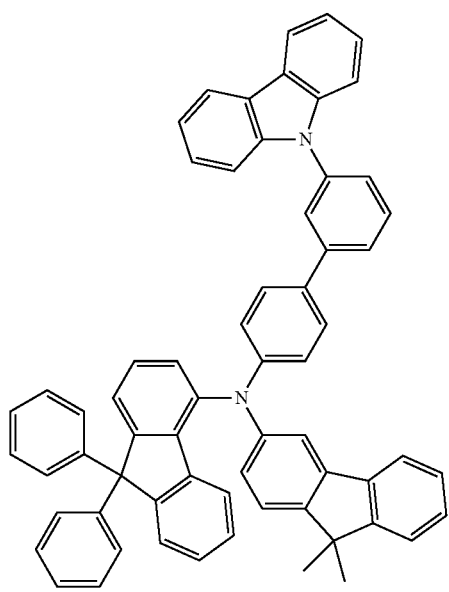
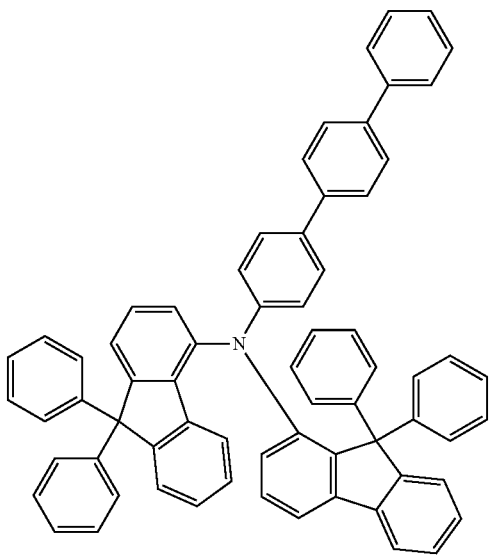

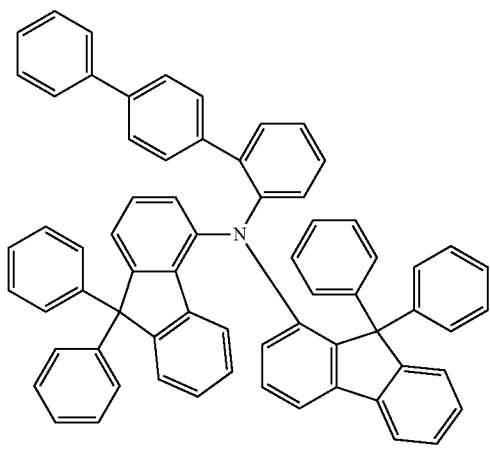
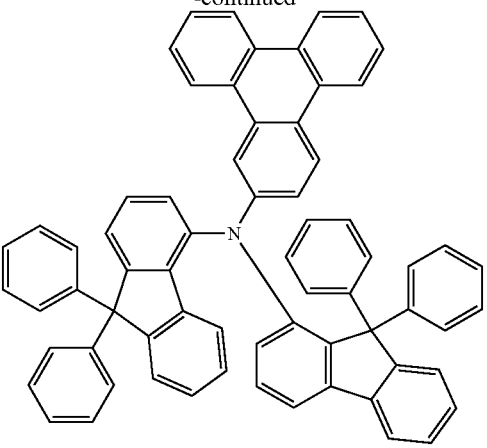
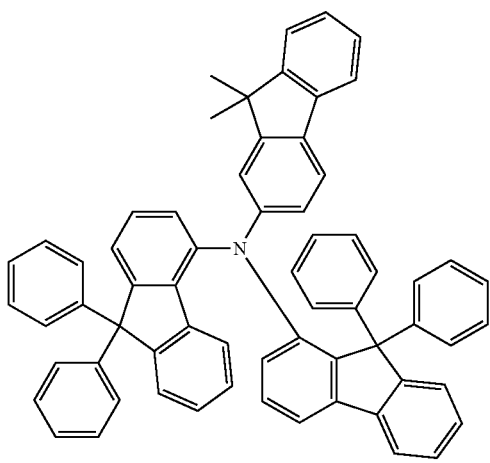
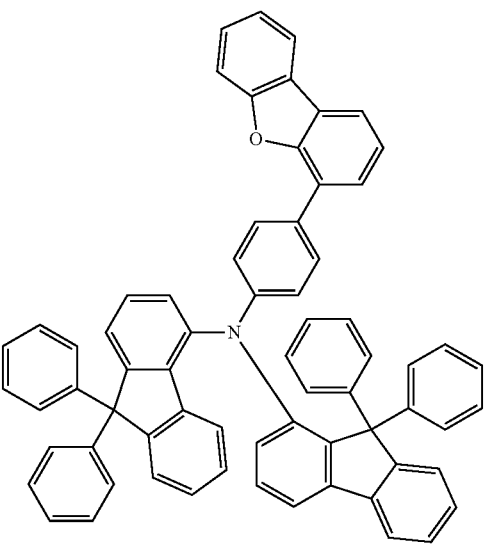
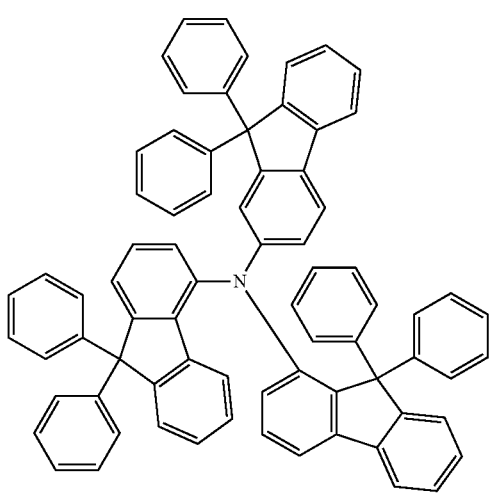
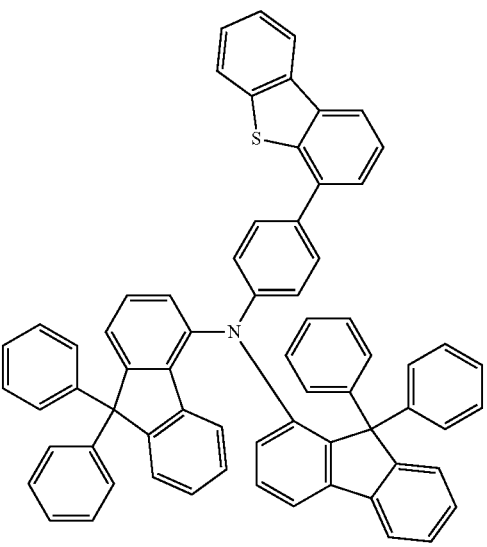

-continued
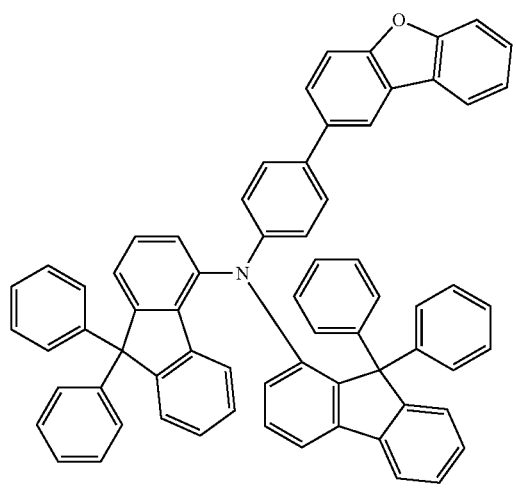
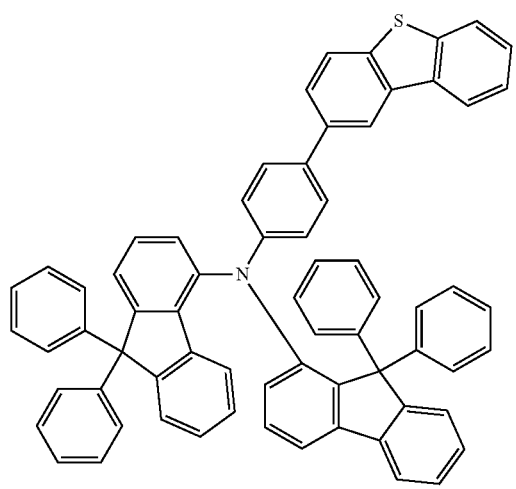
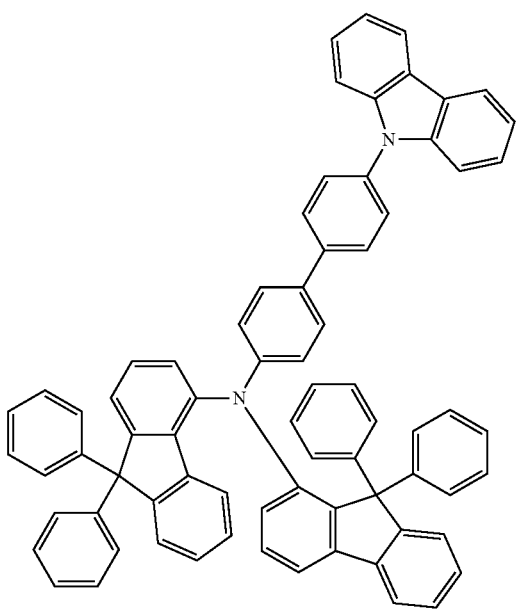
-continued
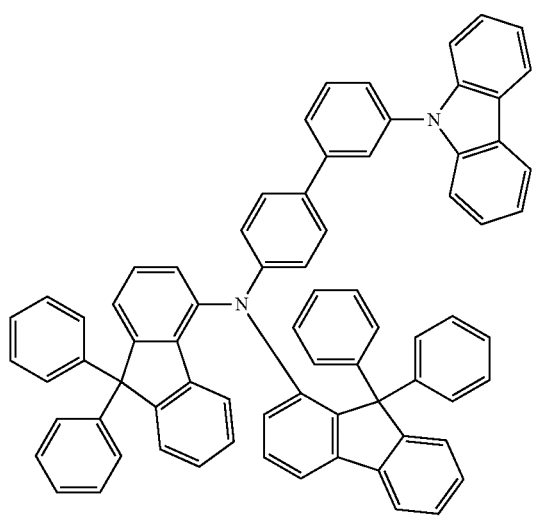
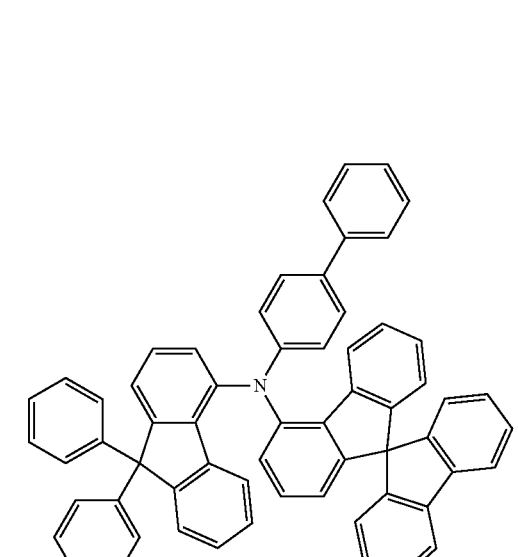
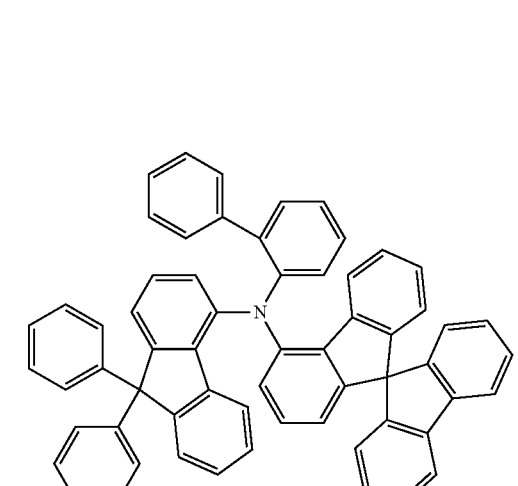

69
-continued
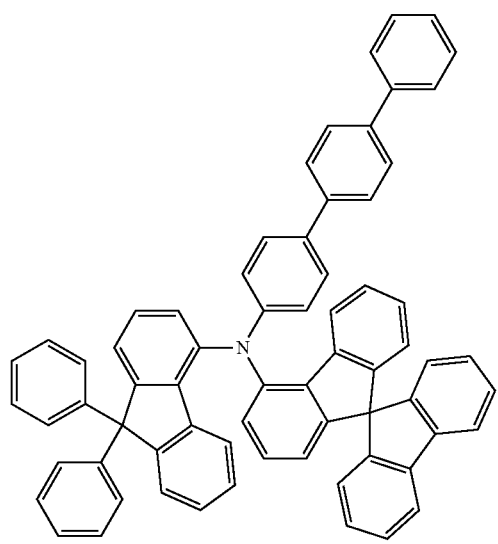
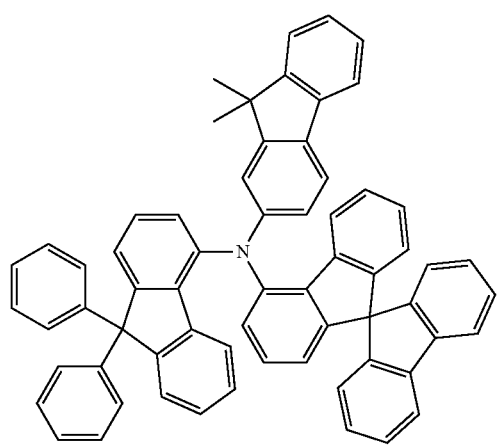
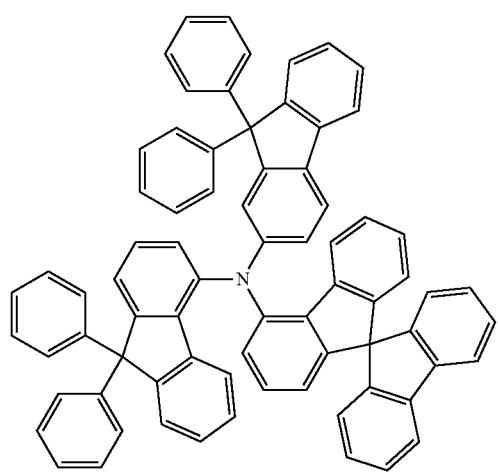
70
-continued
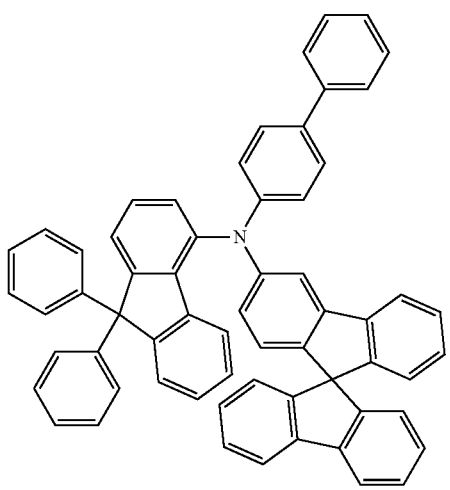
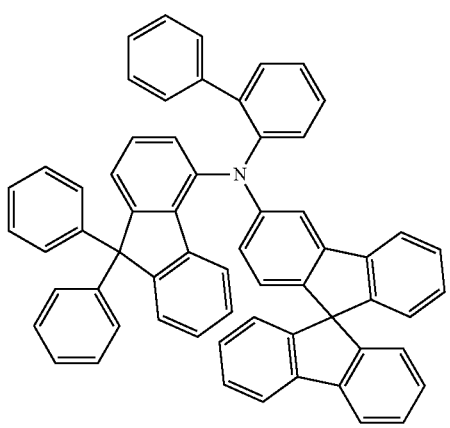
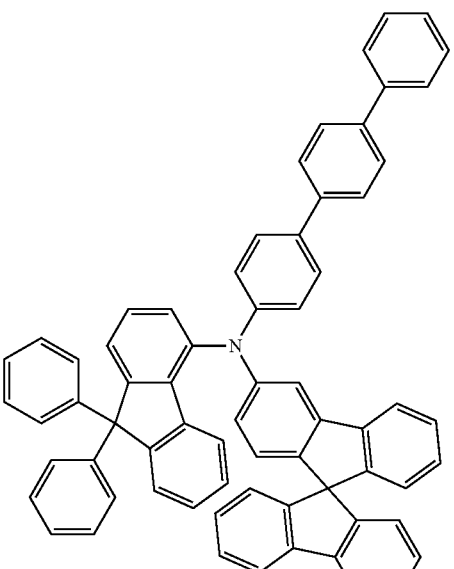

71
-continued
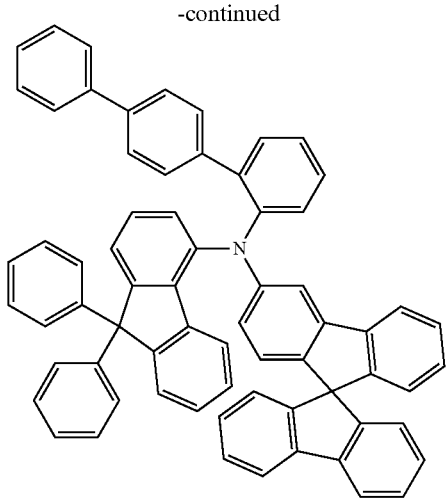
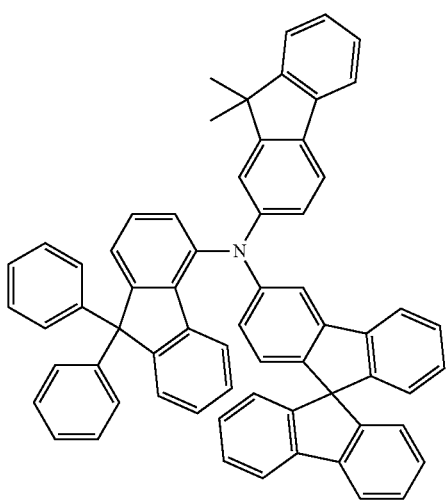
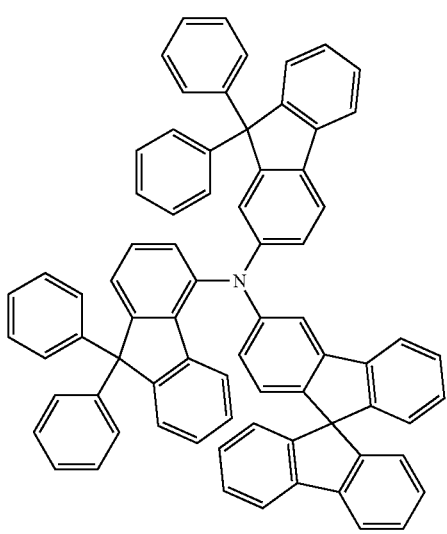
72
-continued
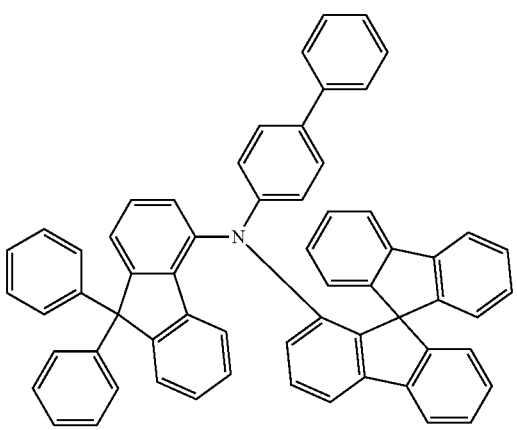
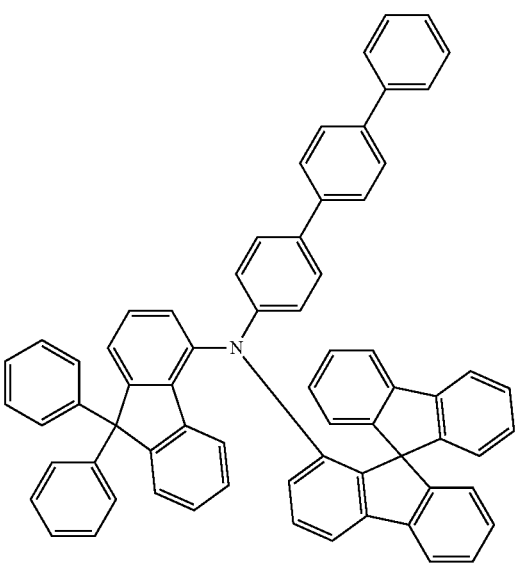

73
-continued
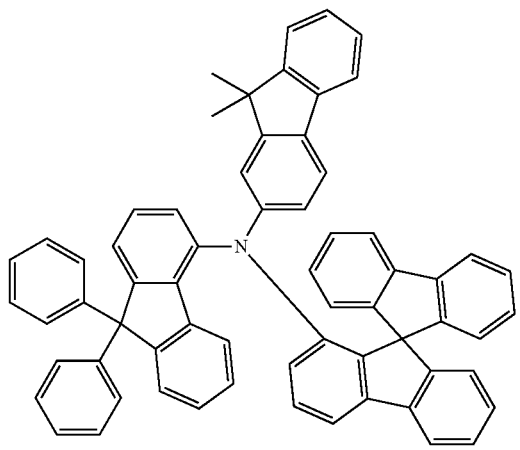
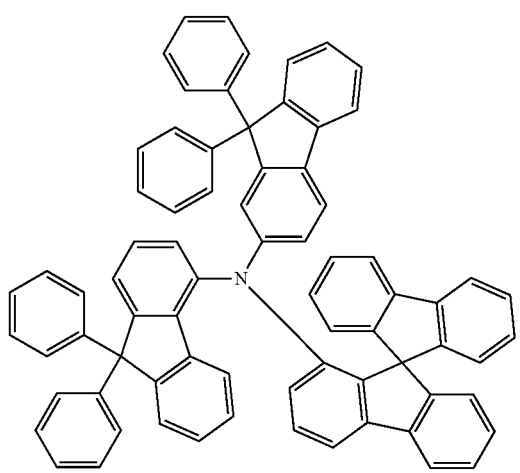
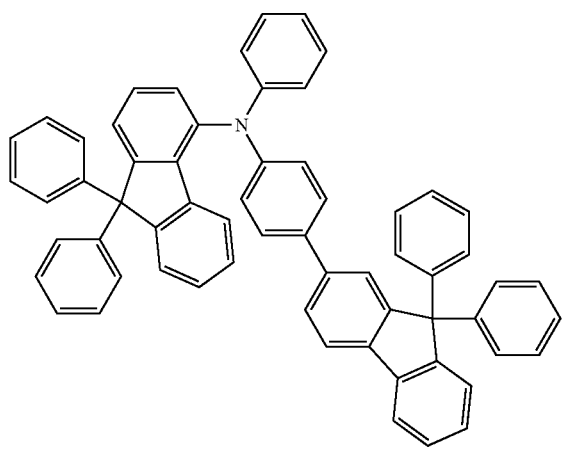
74
-continued
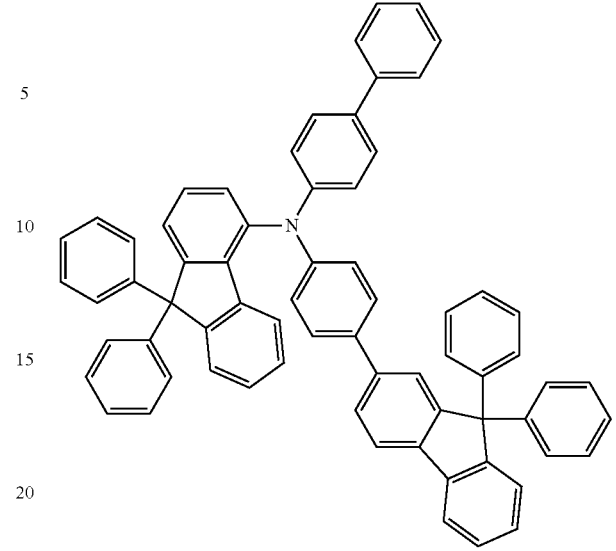
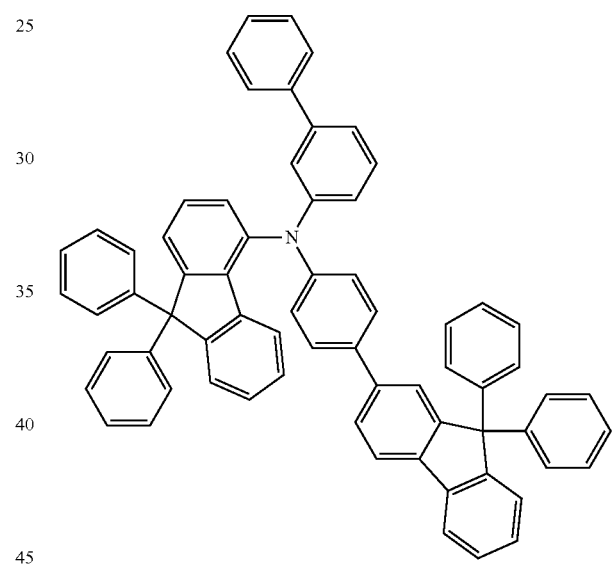
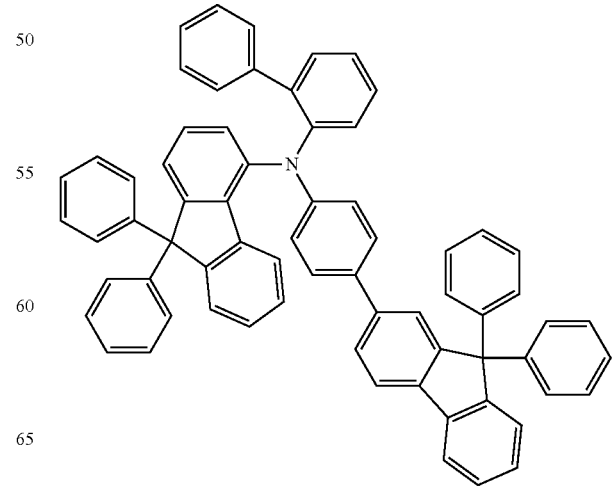

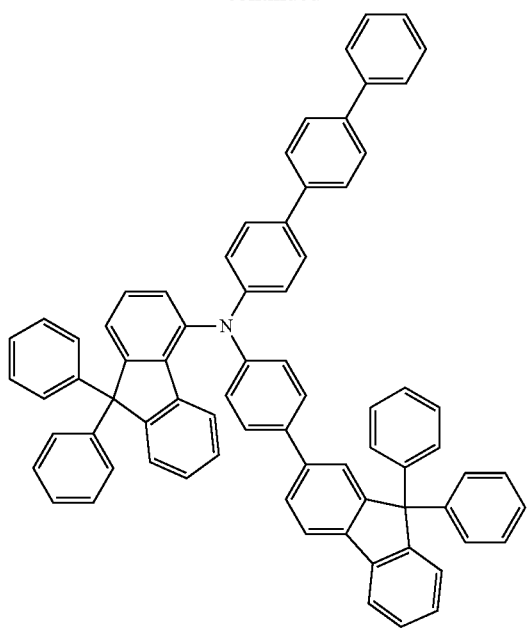
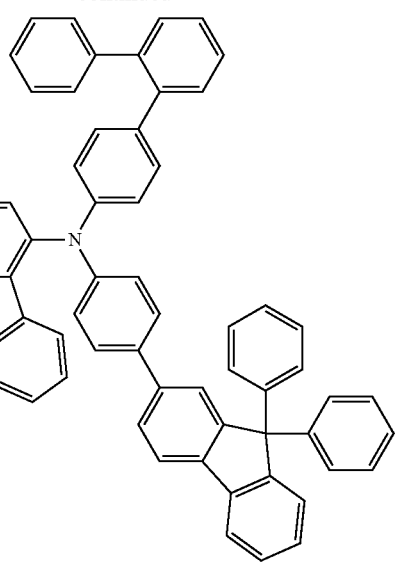
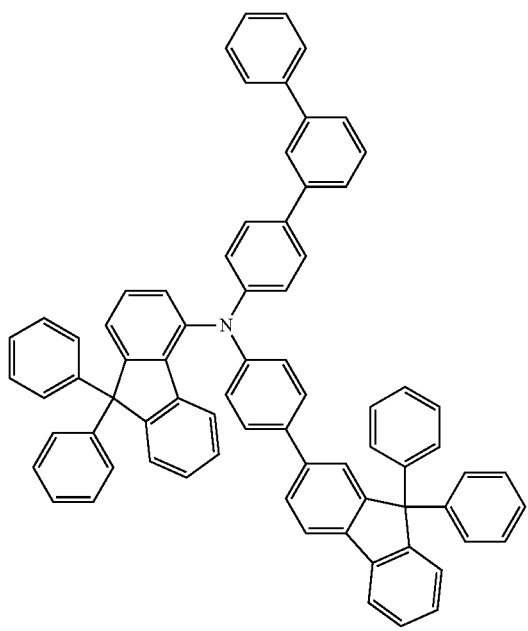
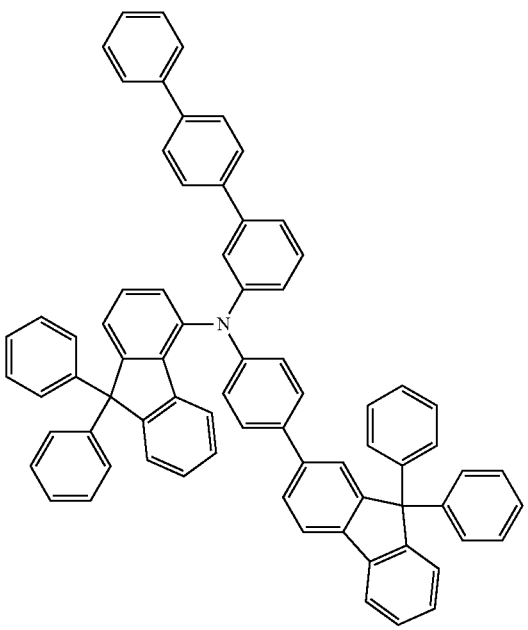

-continued
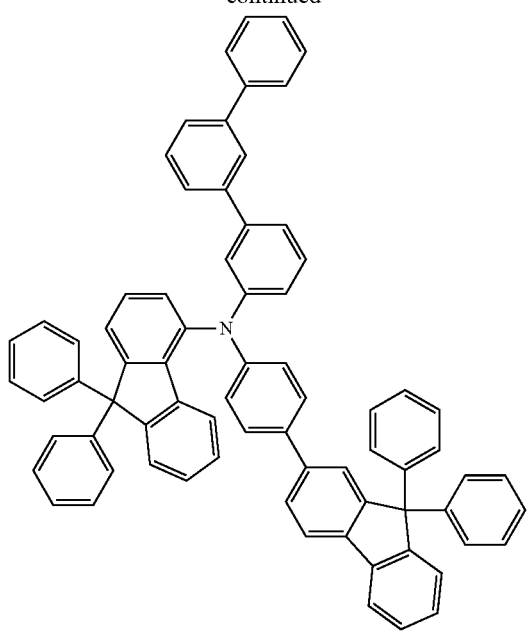
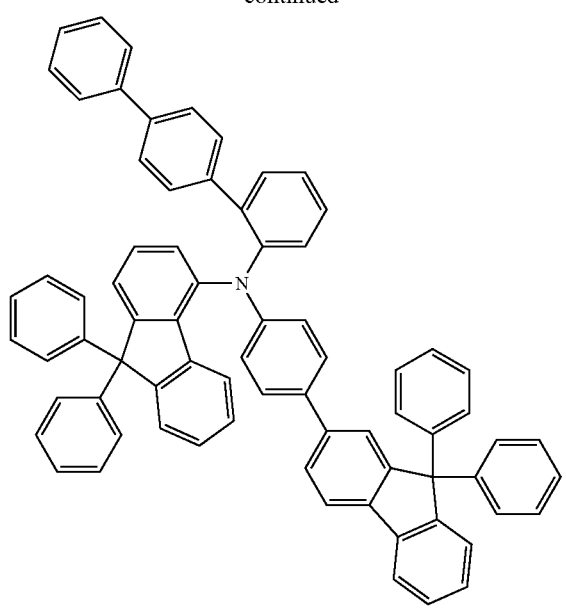
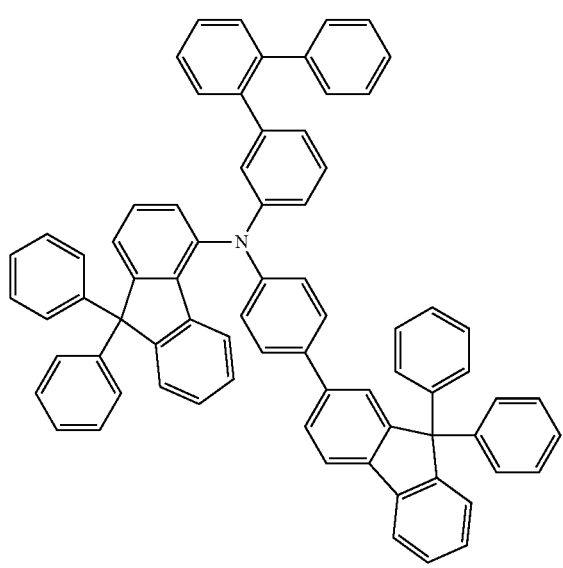

-continued
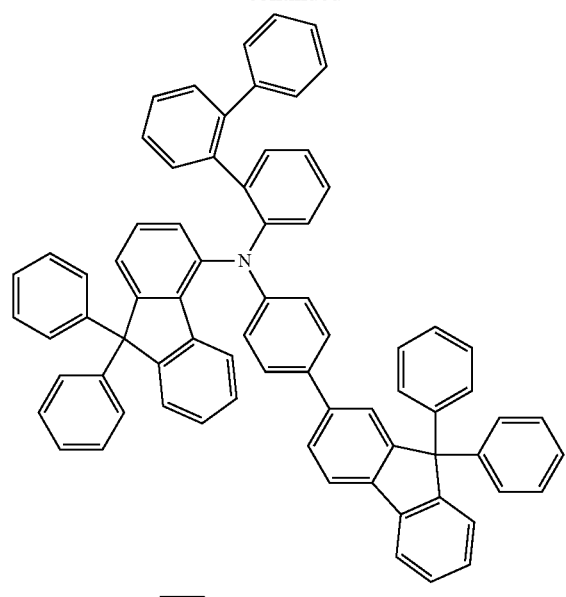
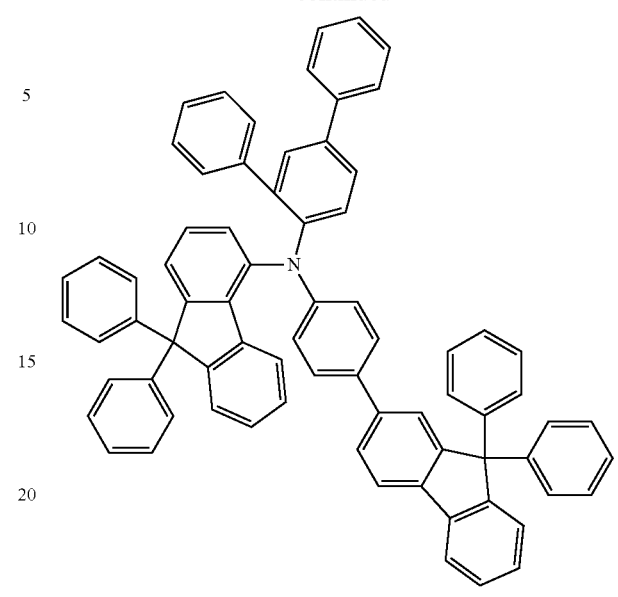
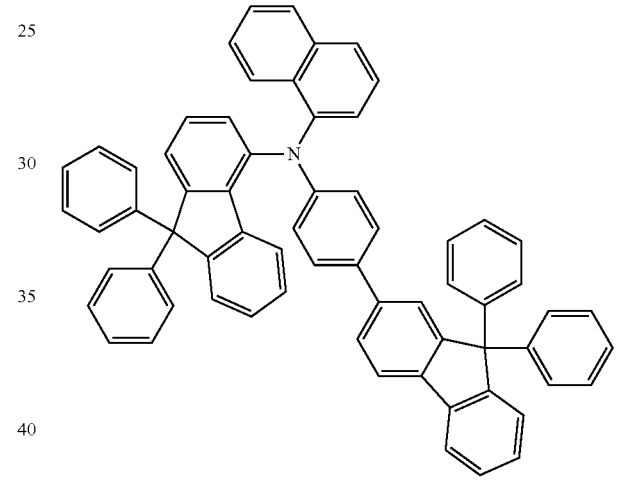
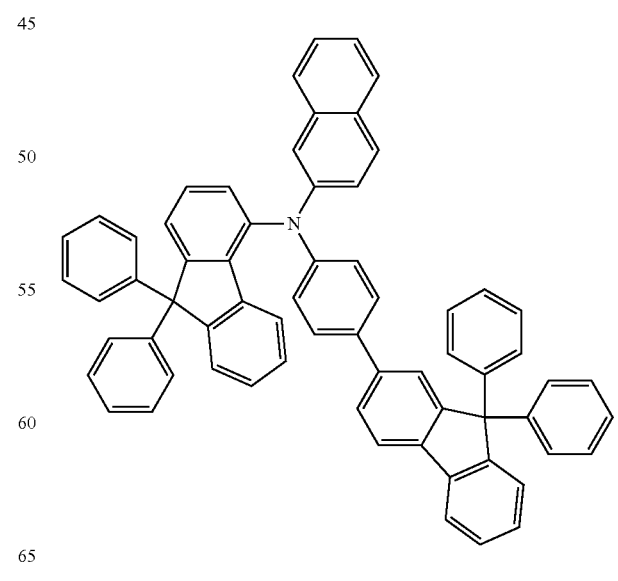

-continued
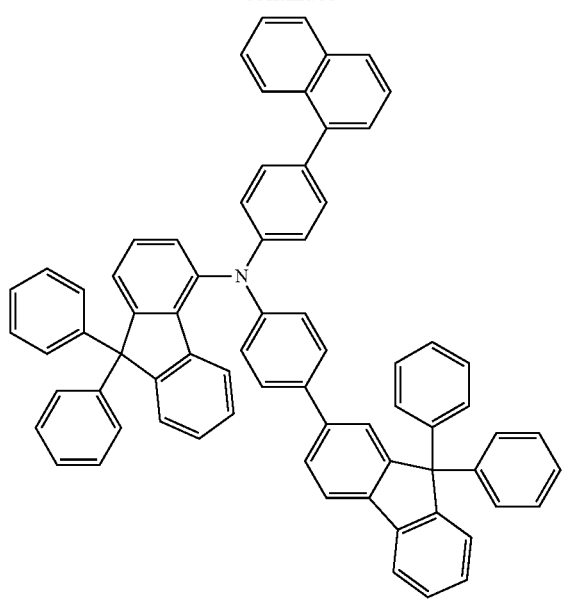
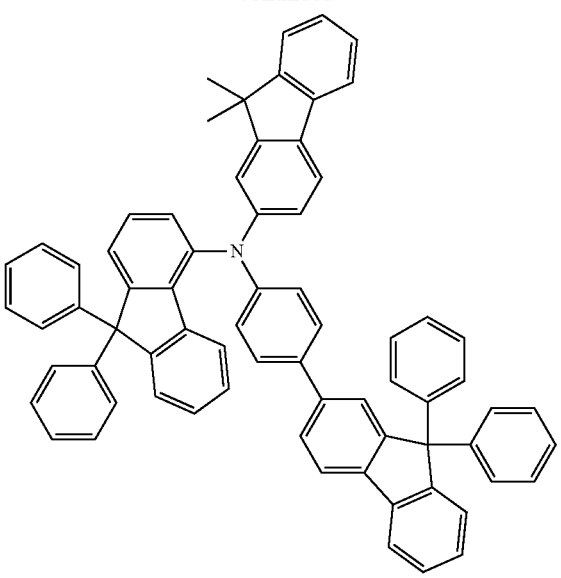
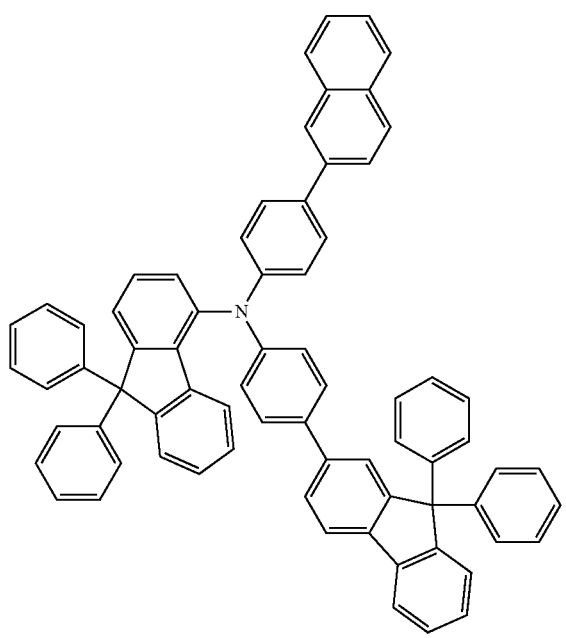
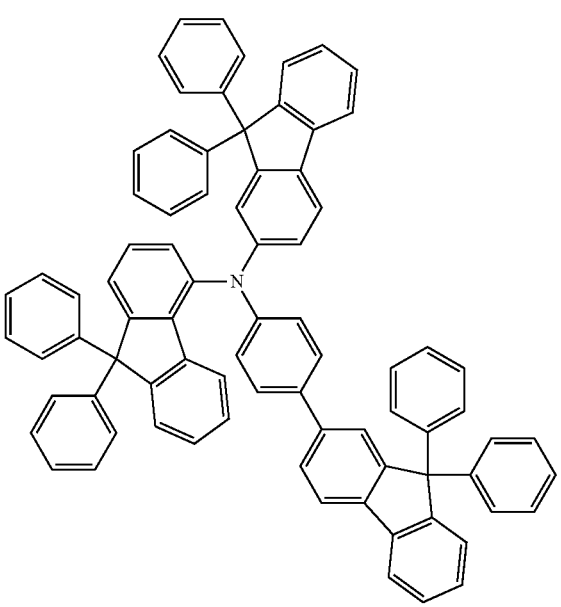

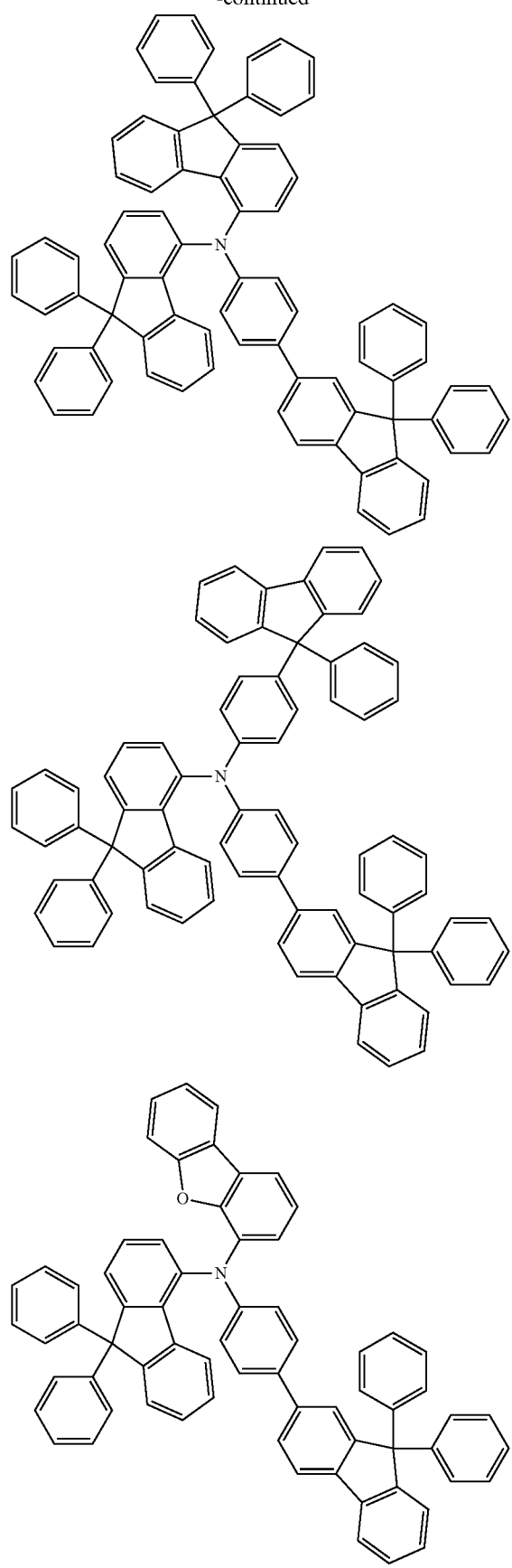
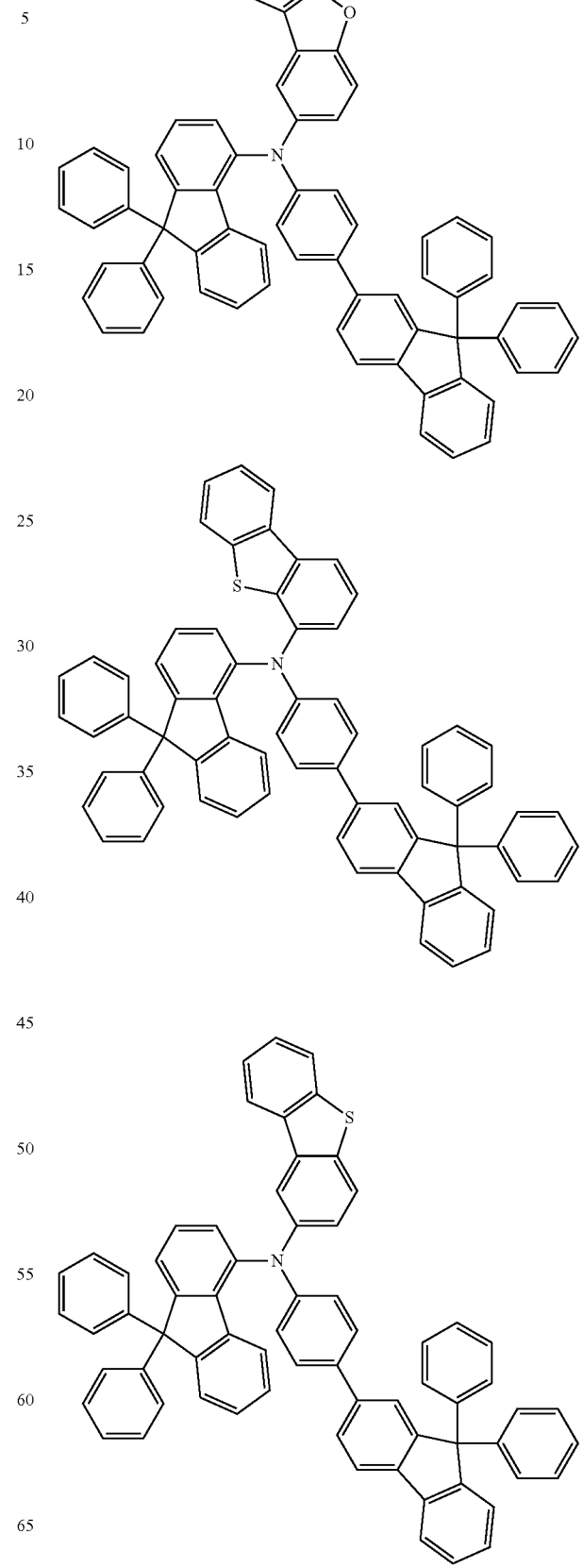

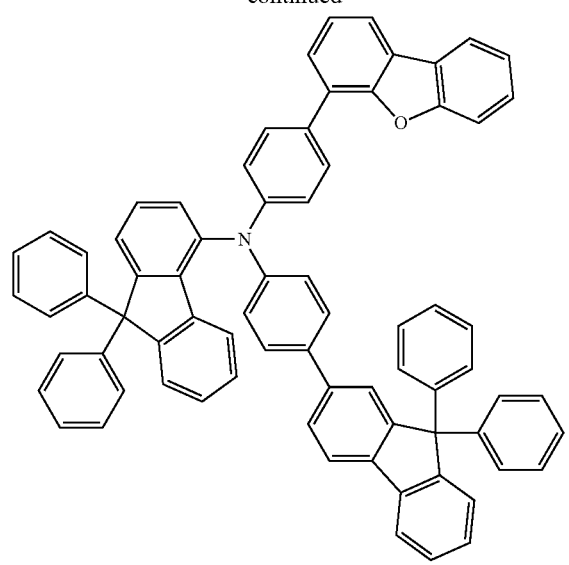
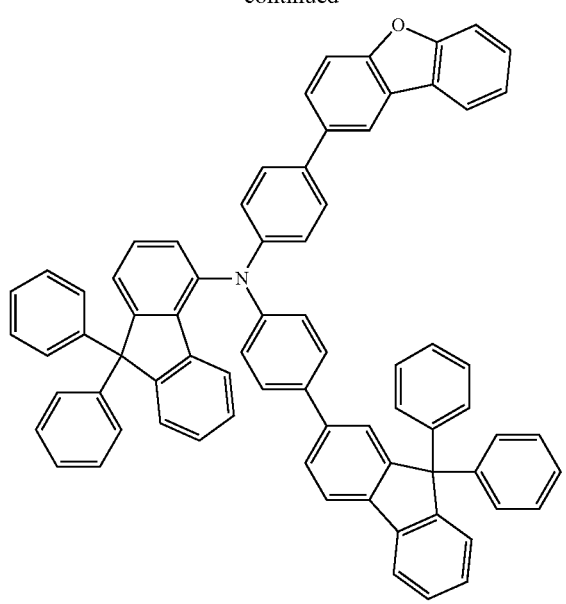
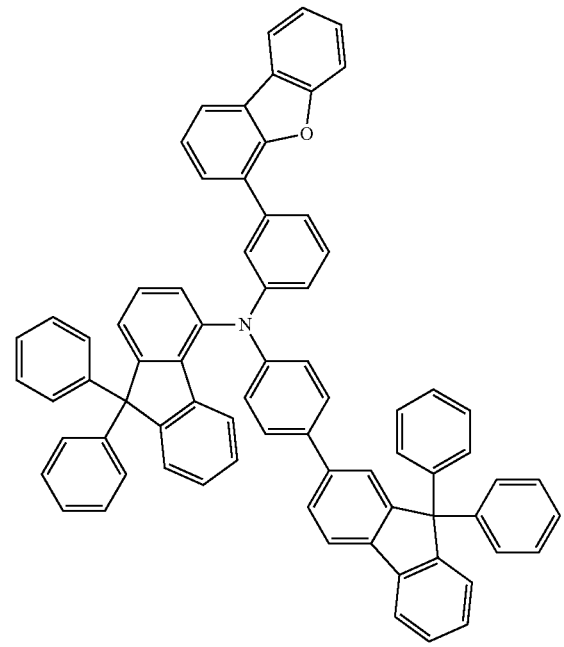
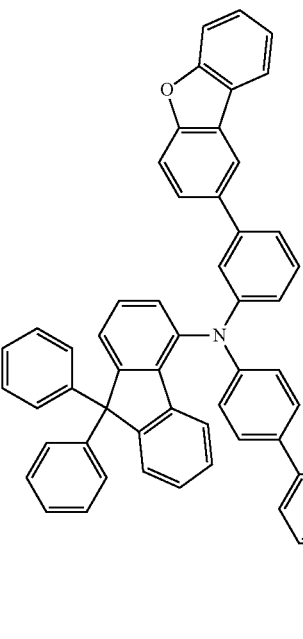

87
-continued
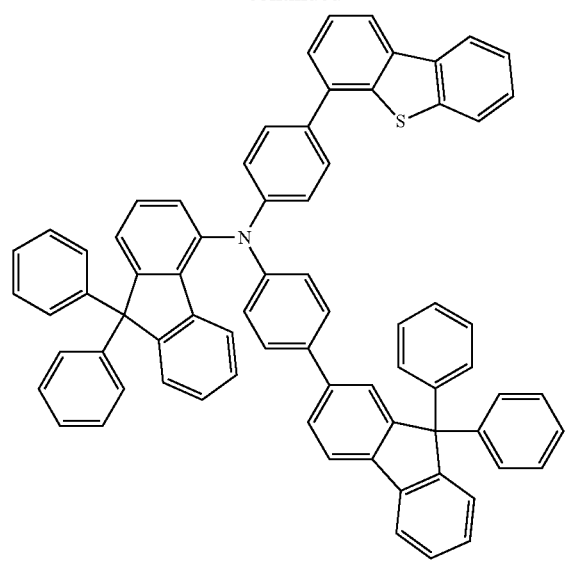
88
-continued
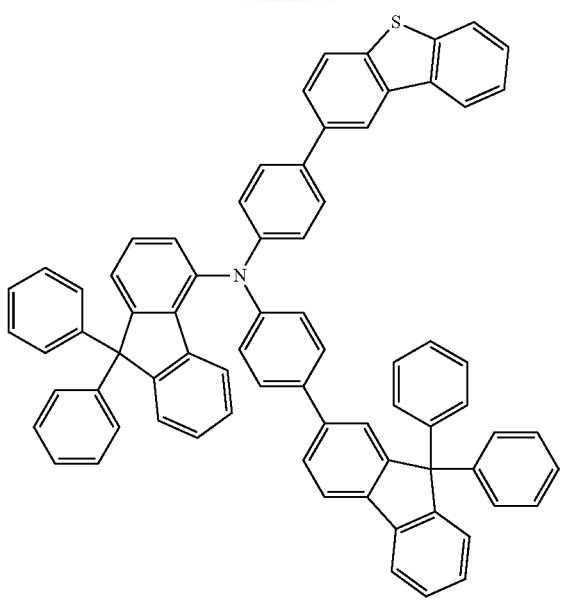

89
-continued
90
-continued
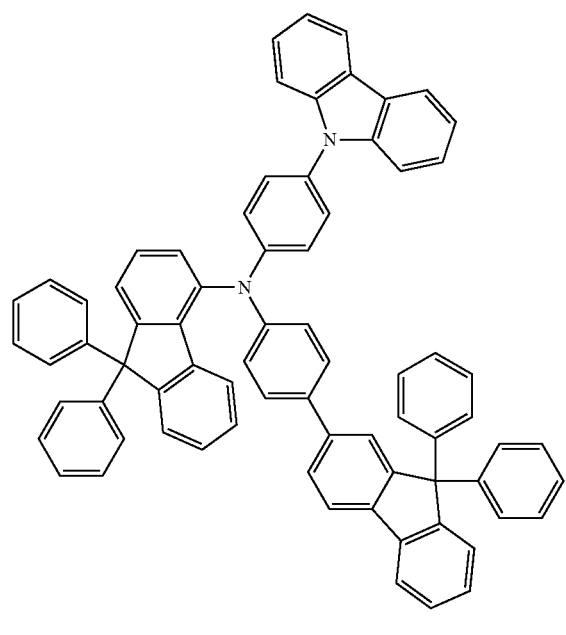
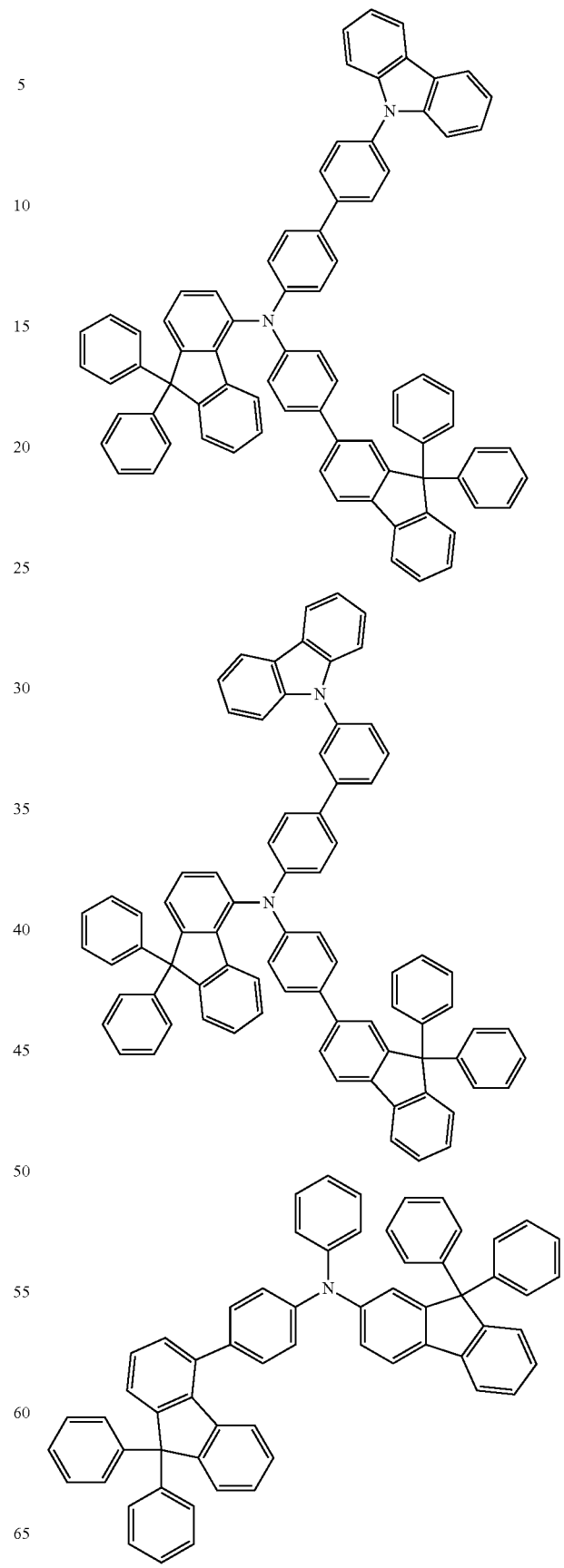

91
-continued
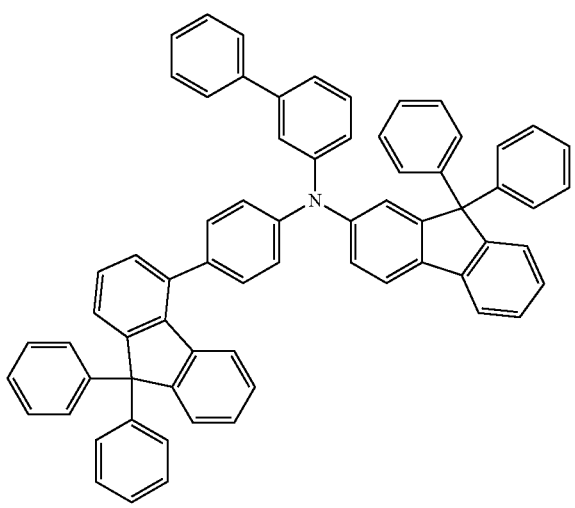
92
-continued
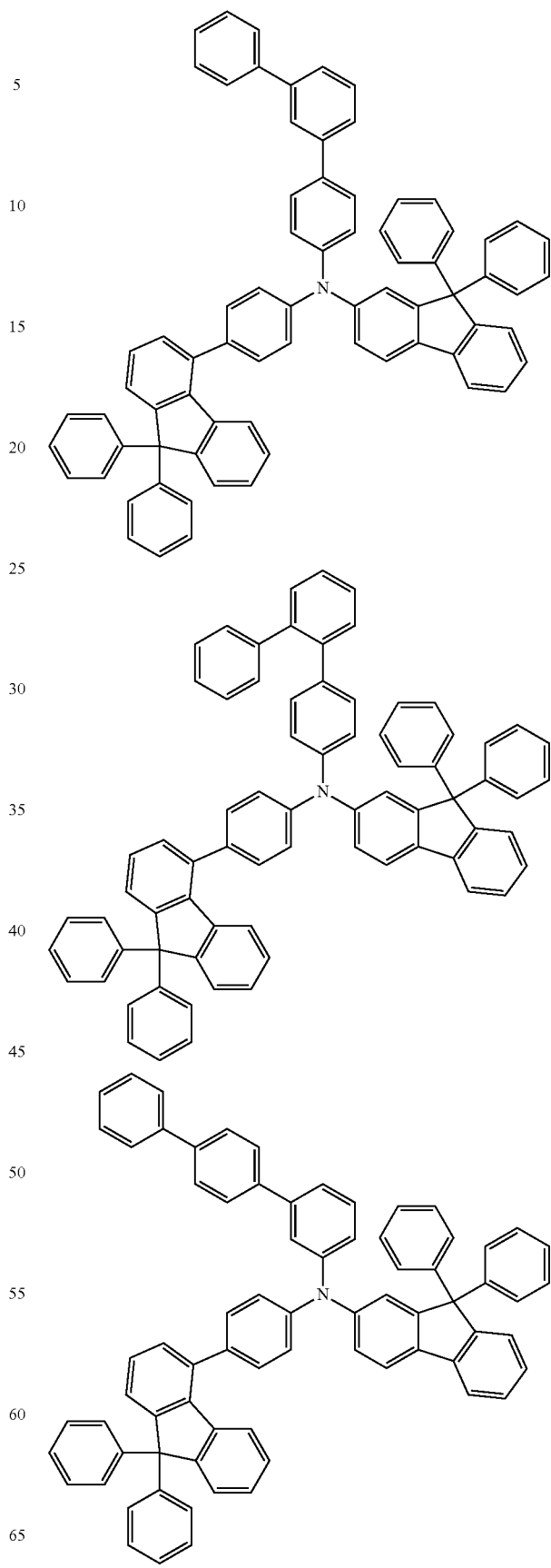

93
-continued
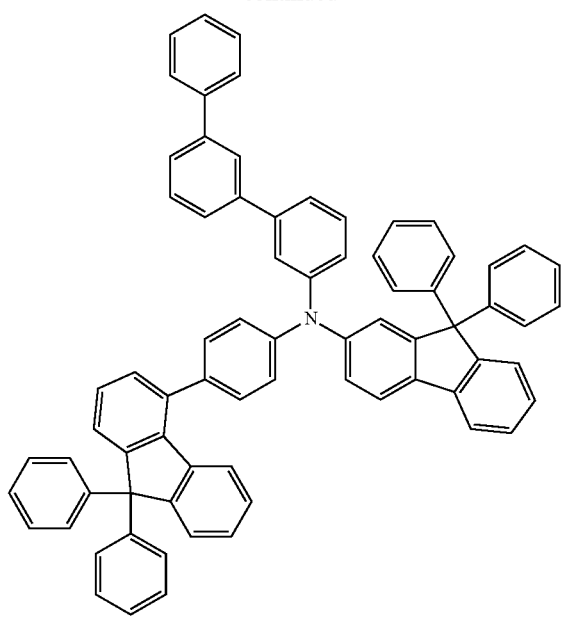
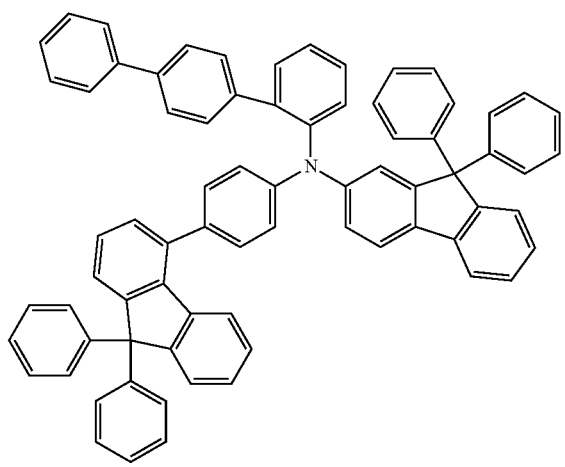
94
-continued
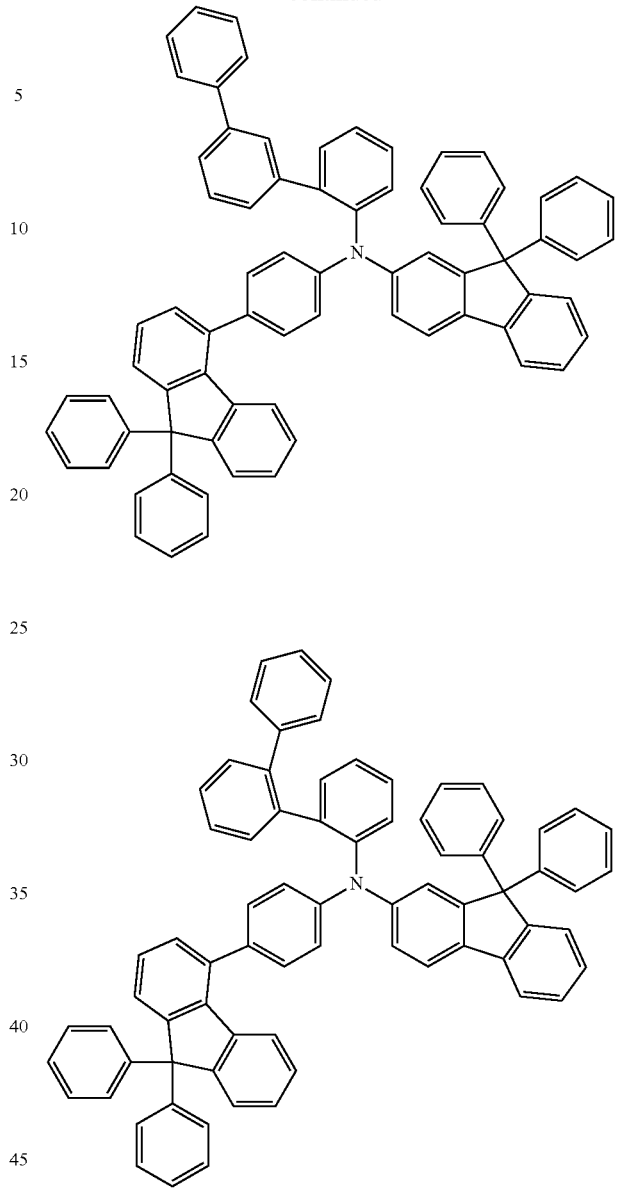
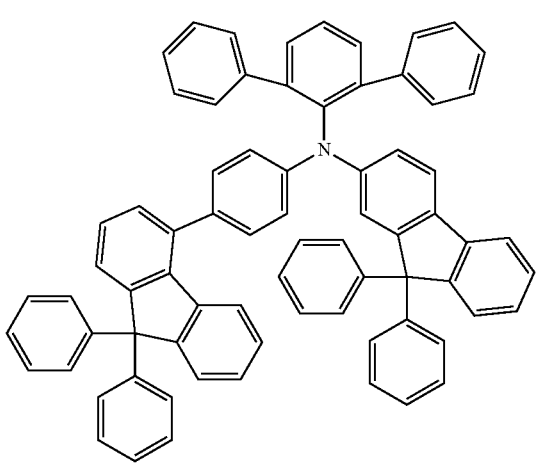

95
-continued
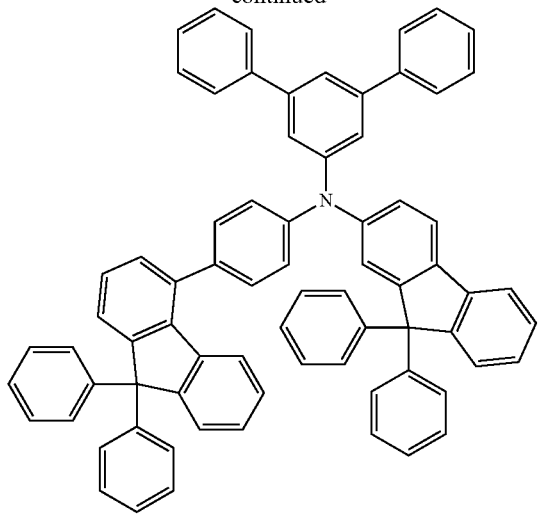
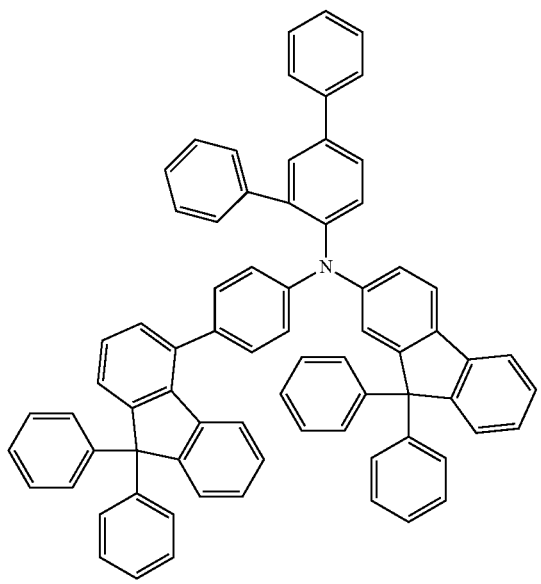
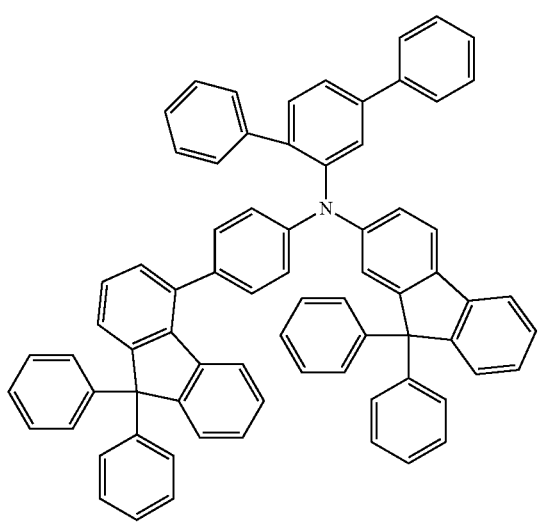
96
-continued
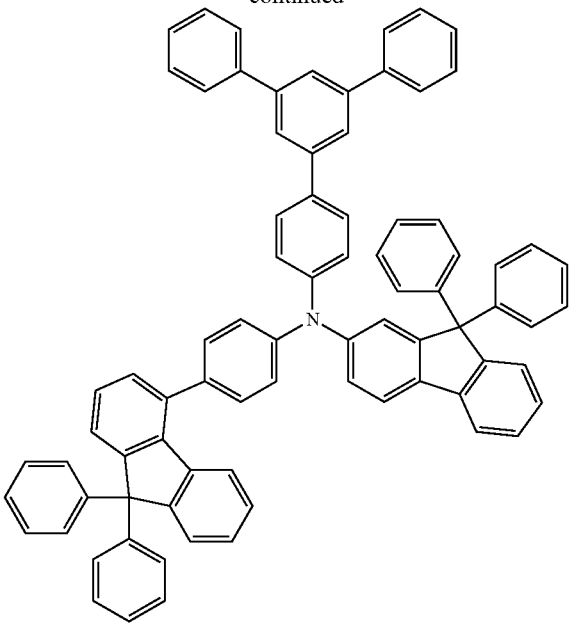
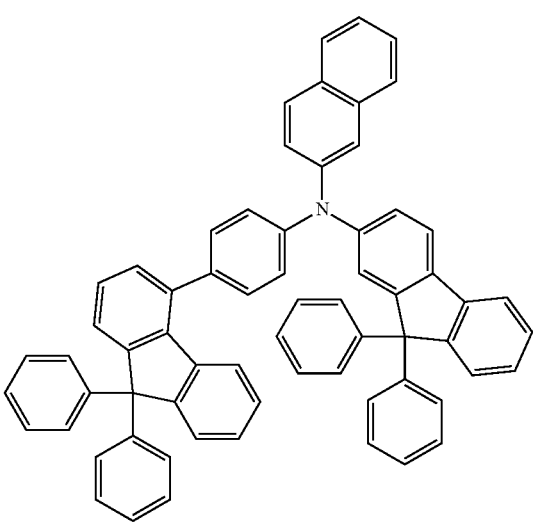

97
-continued
98
-continued
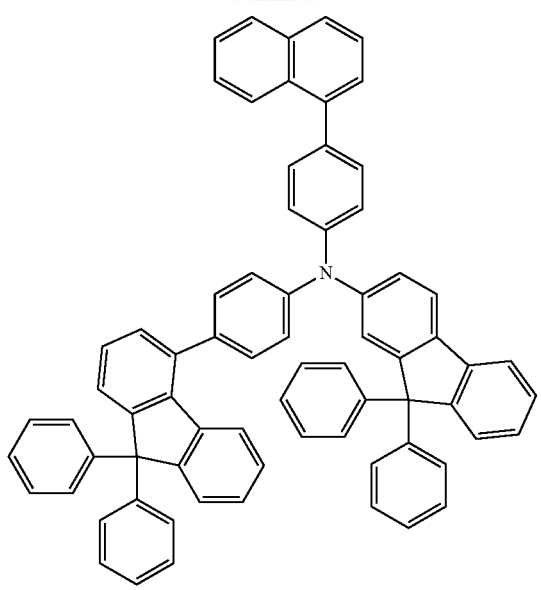
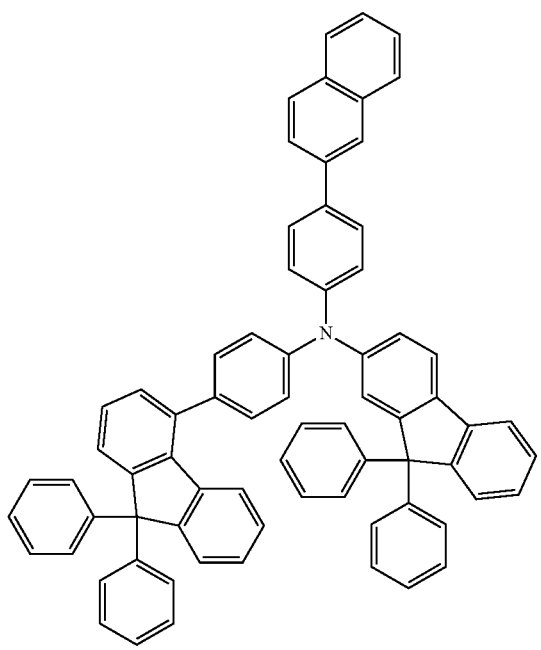
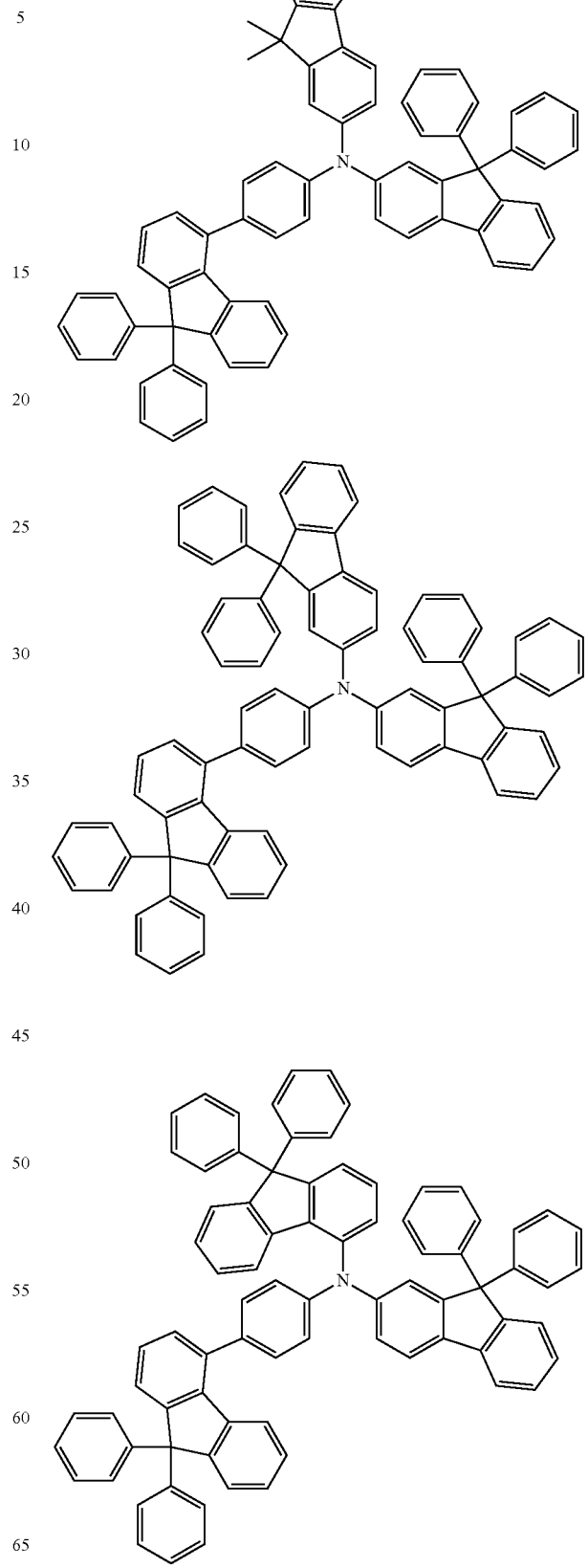

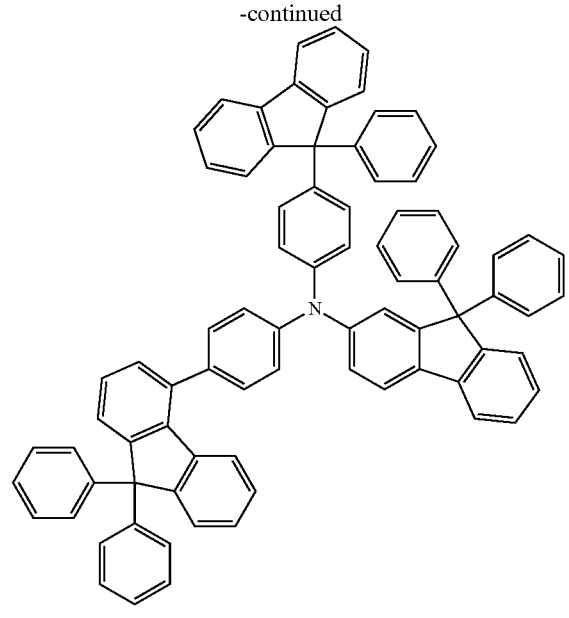
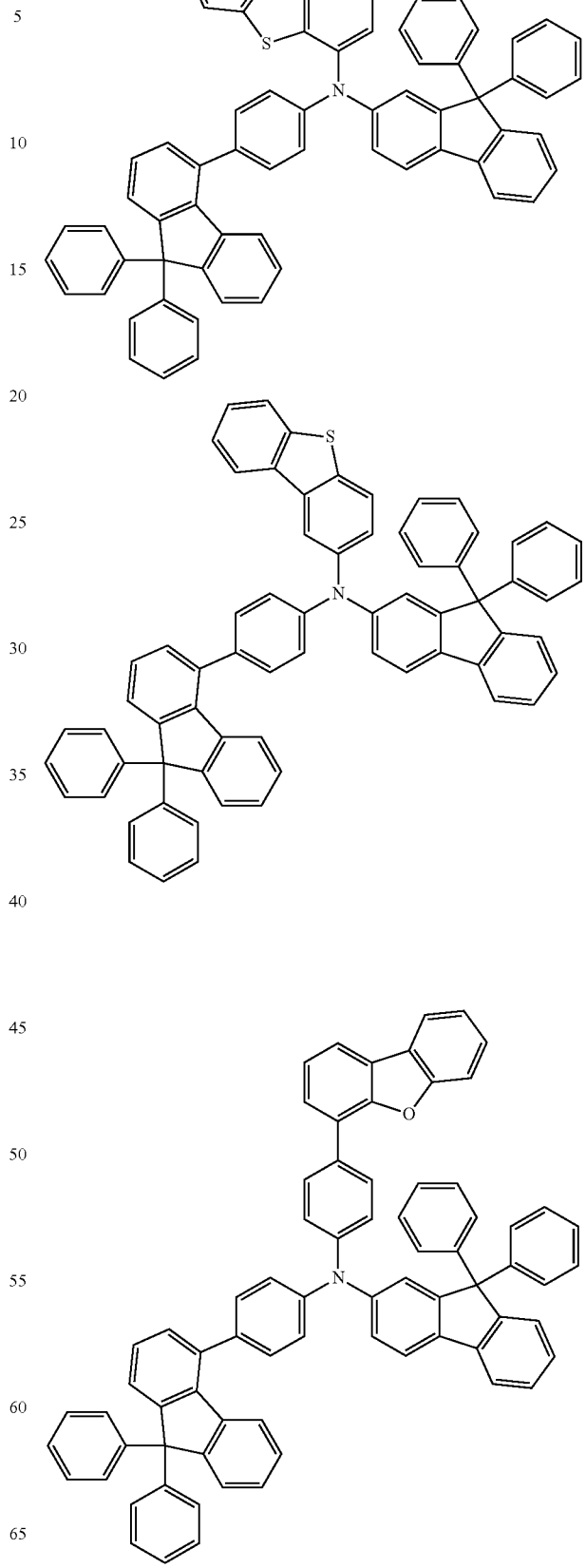

101
-continued
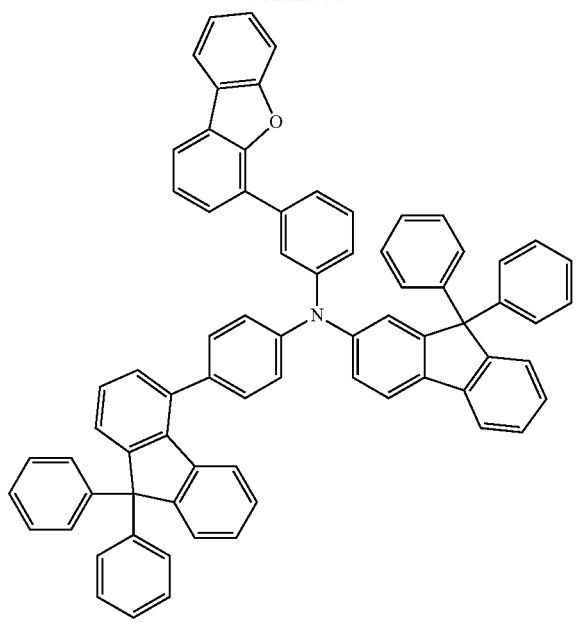
102
-continued
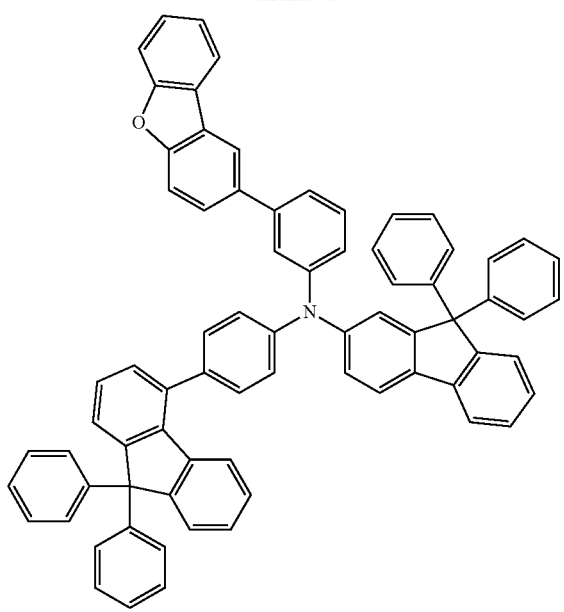
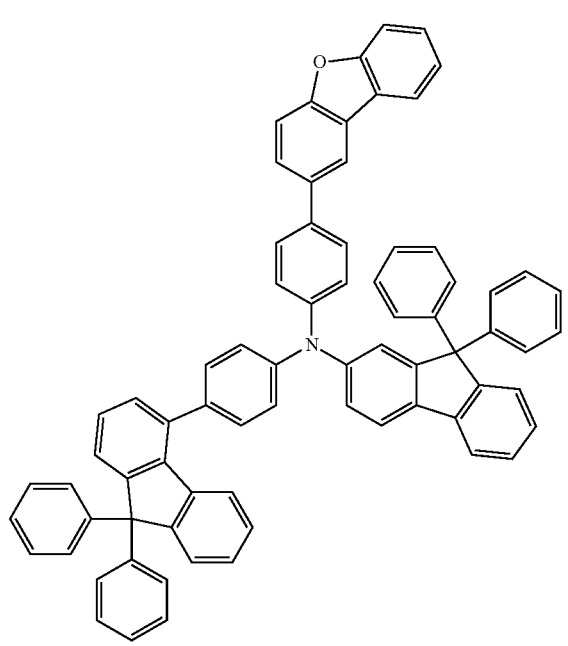
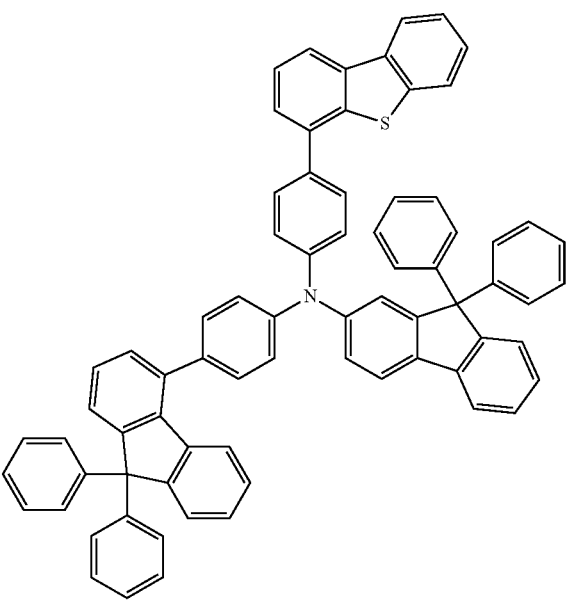

103
-continued
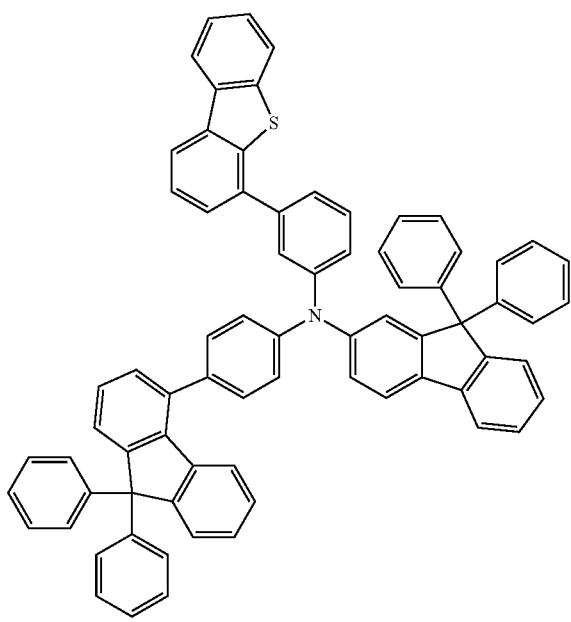
104
-continued
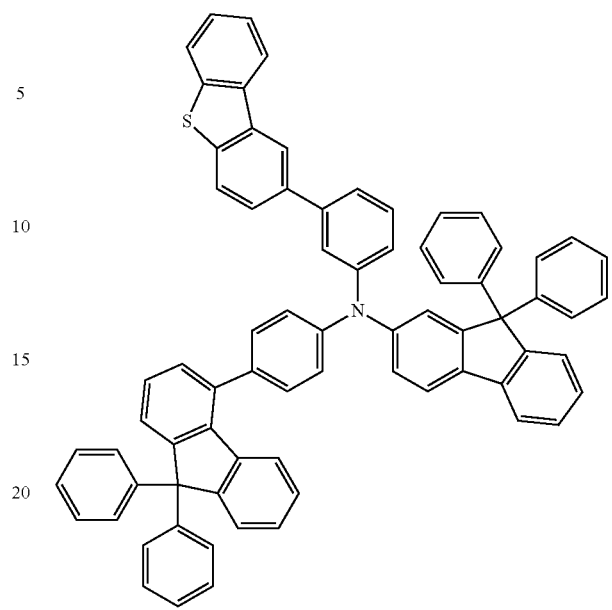
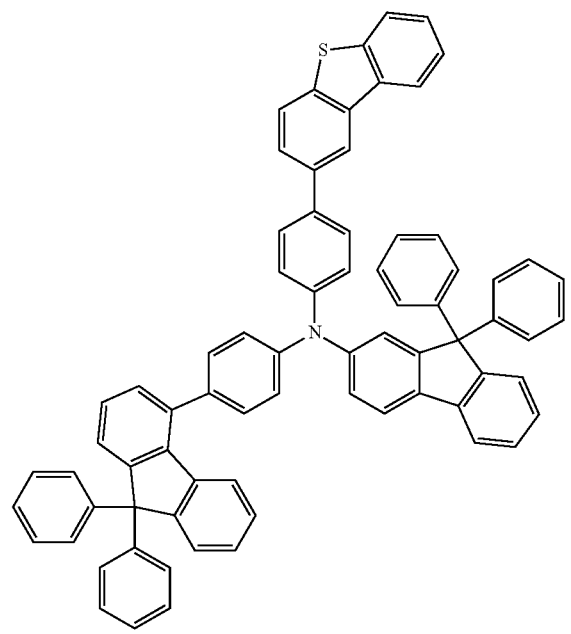
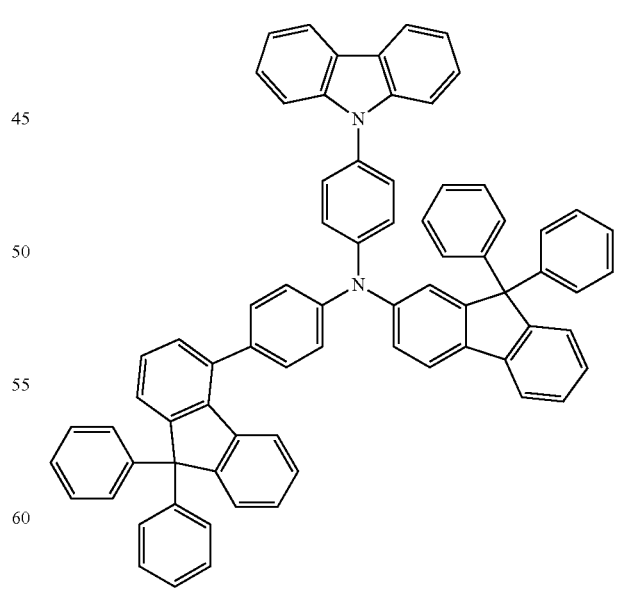

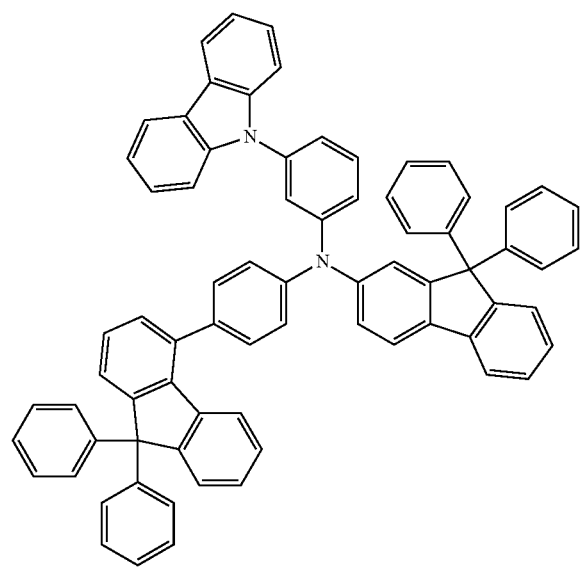
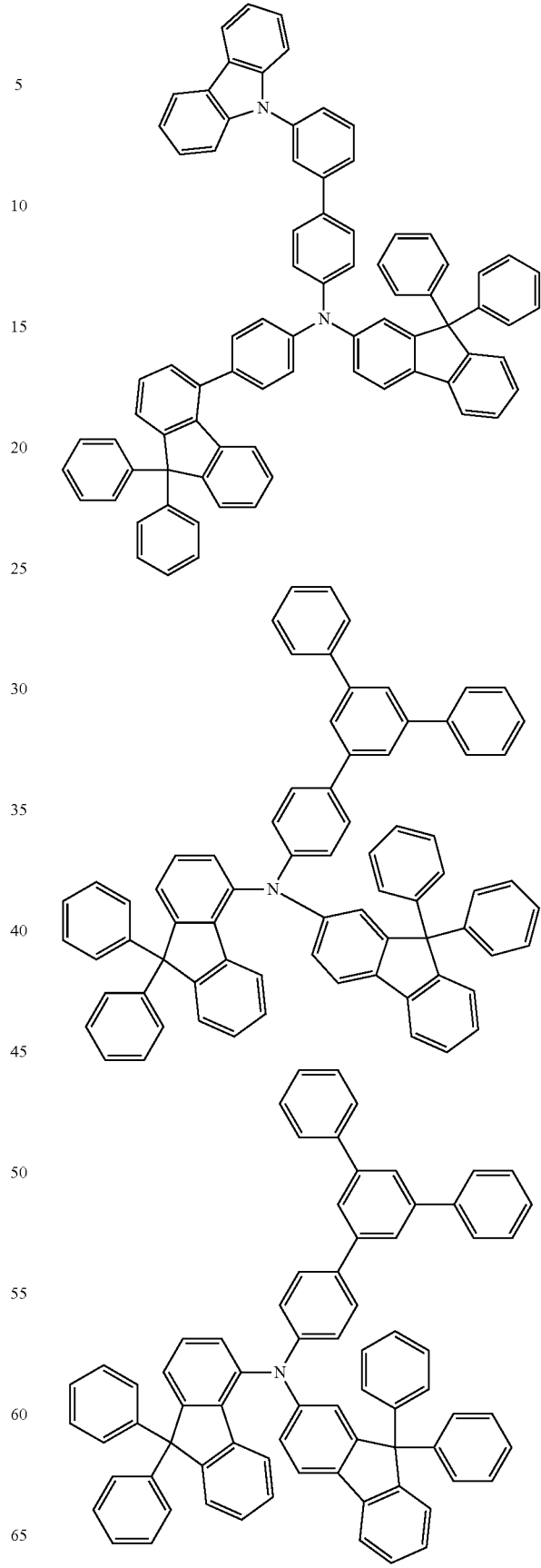

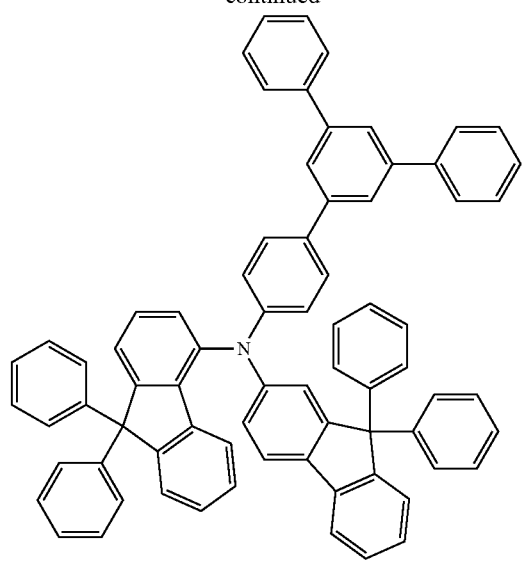
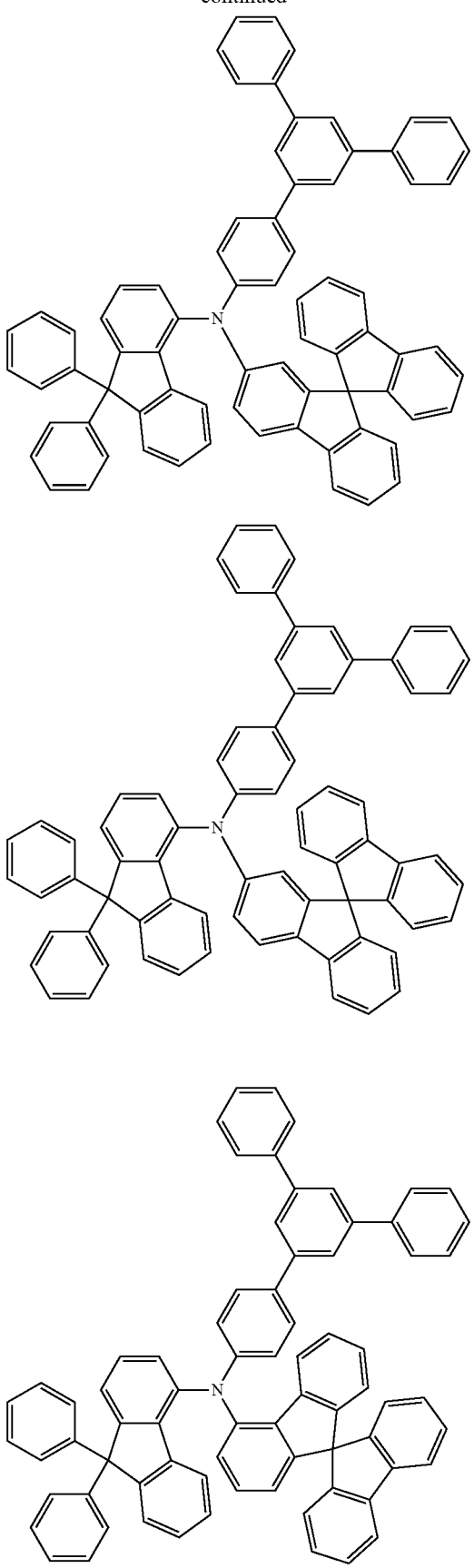

109
-continued
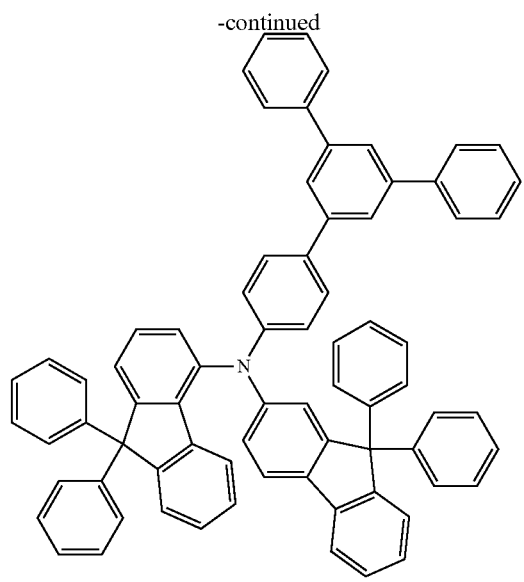
110
-continued
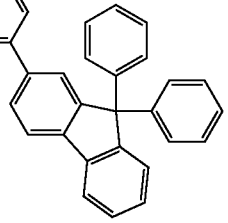
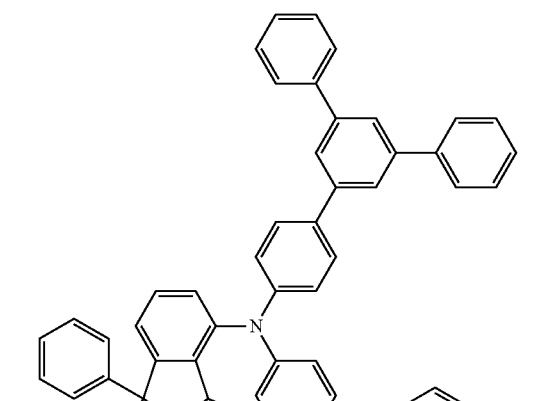
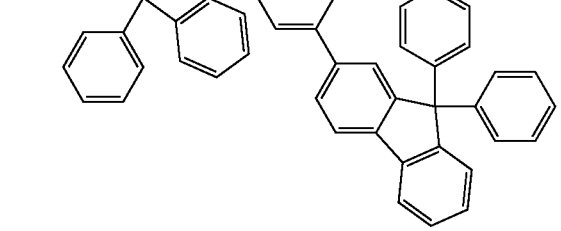

111
-continued
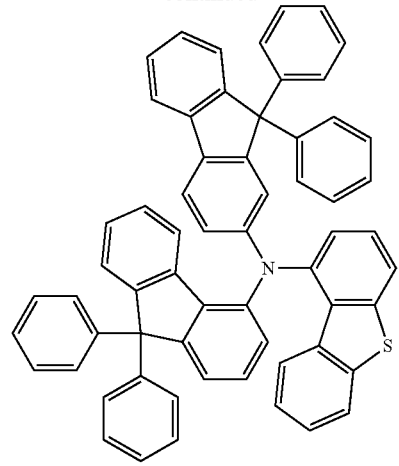
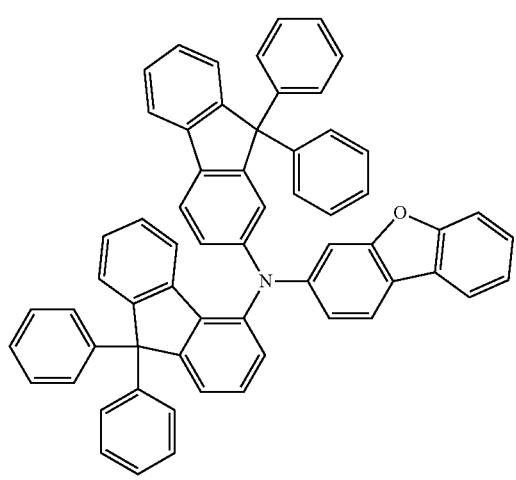
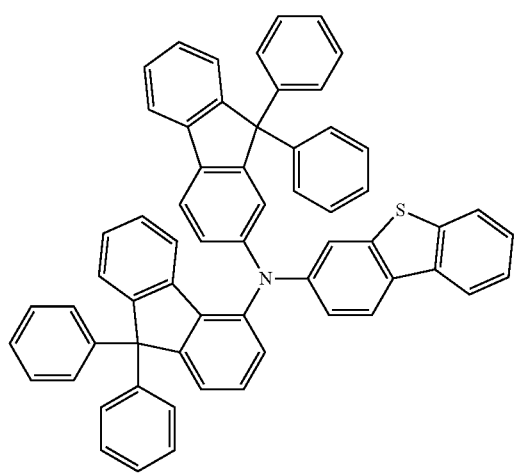
112
-continued
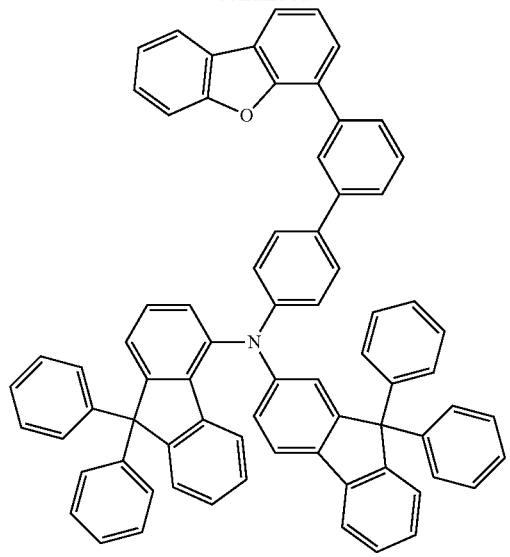
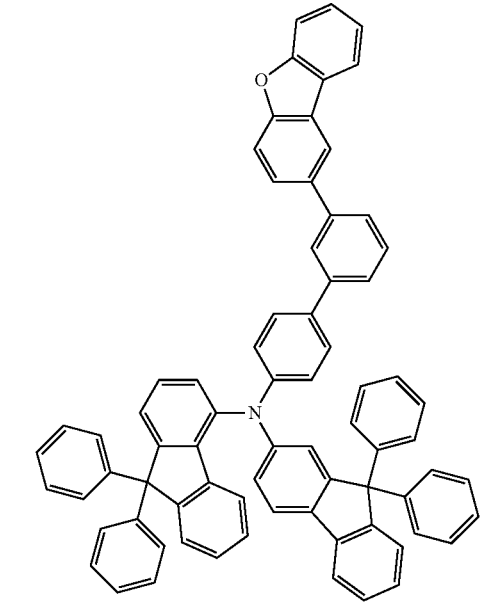 [SMILES: c1ccc(C2(c3ccccc3)c3ccccc3-c3ccc(N(c4ccc(-c5cccc(-c6ccc7sc8ccccc8c7c6)c5)cc4)c4cccc5c4-c4ccccc4C5(c4ccccc4)c4ccccc4)cc32)cc1]
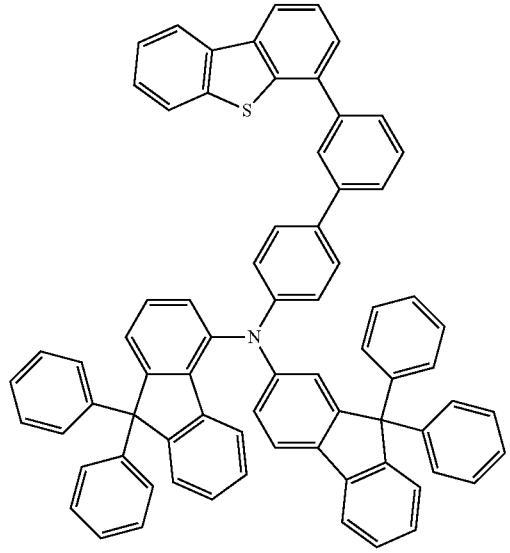

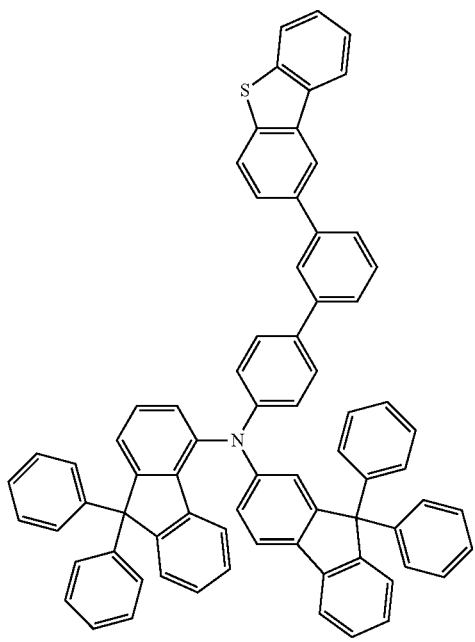
Of the above, the compound (A) is preferably any of the following compounds (H-A1) to (H-A18):
(H-A1)
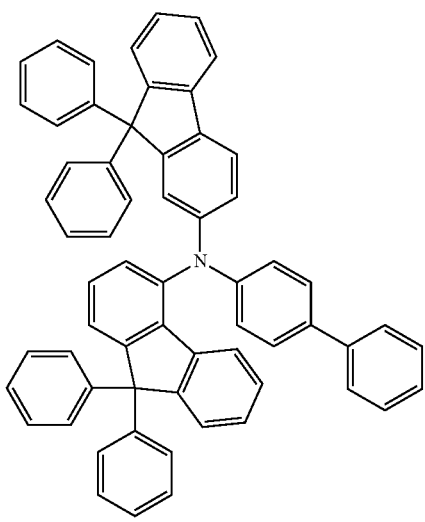
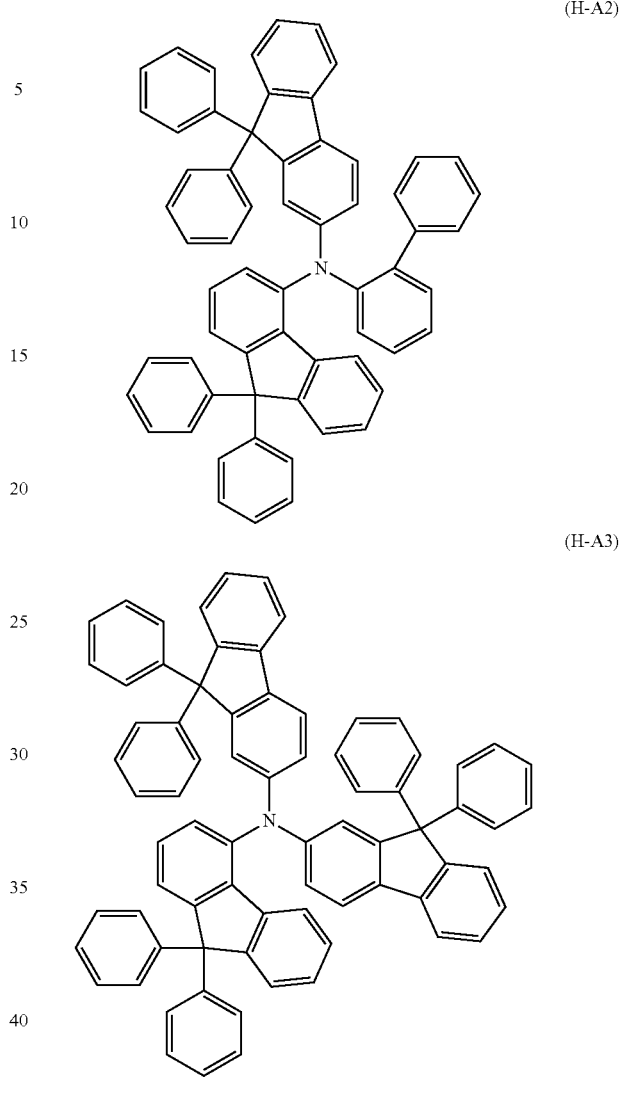
(H-A4)
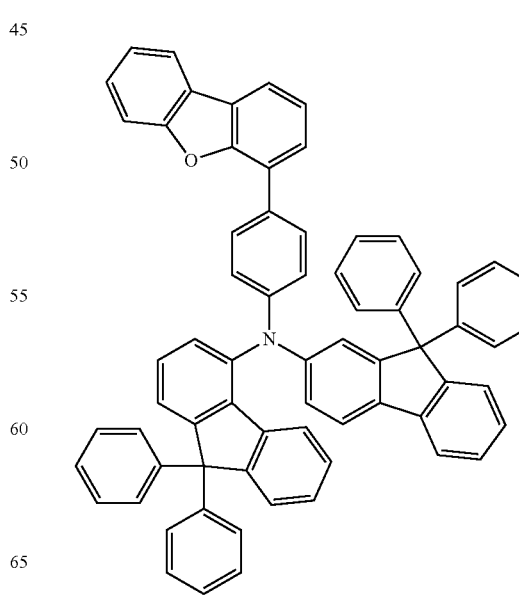

(H-A5)
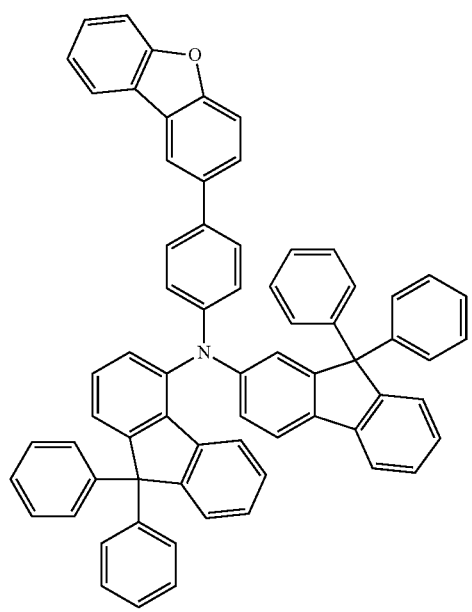
(H-A6)
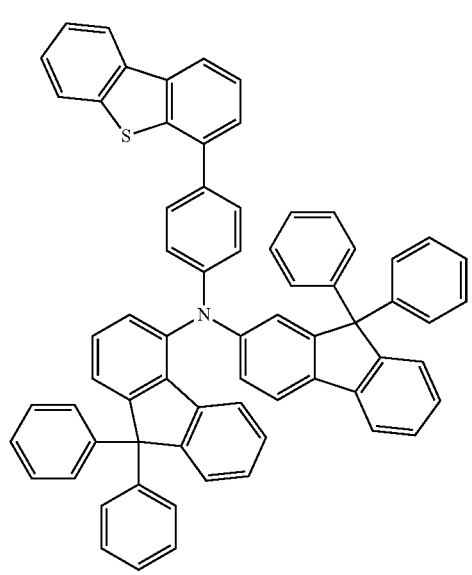
(H-A7)
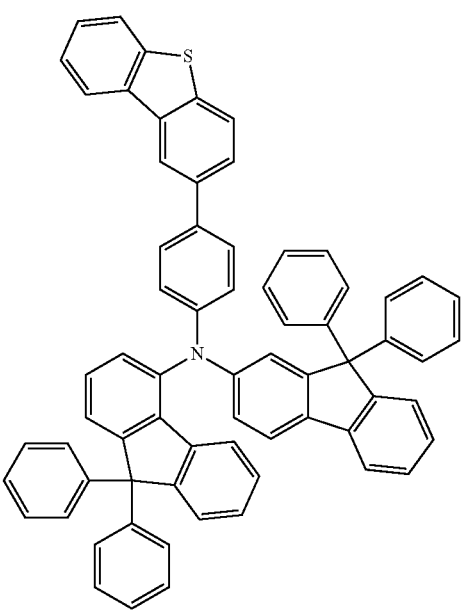
(H-A8)
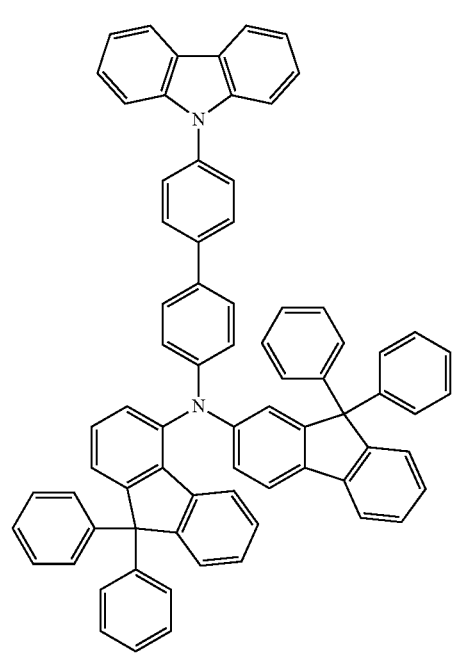

(H-A9)
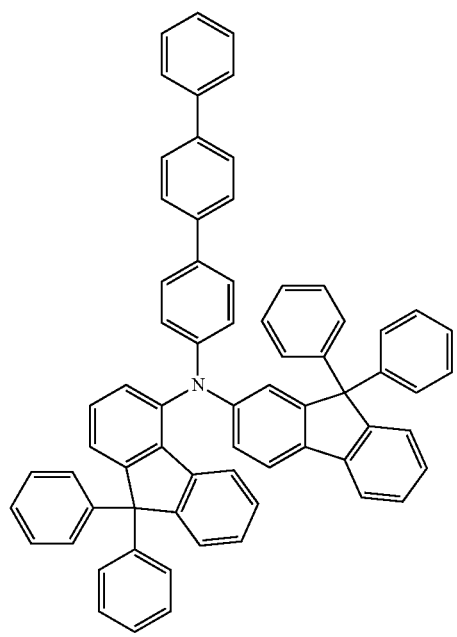
(H-A10)
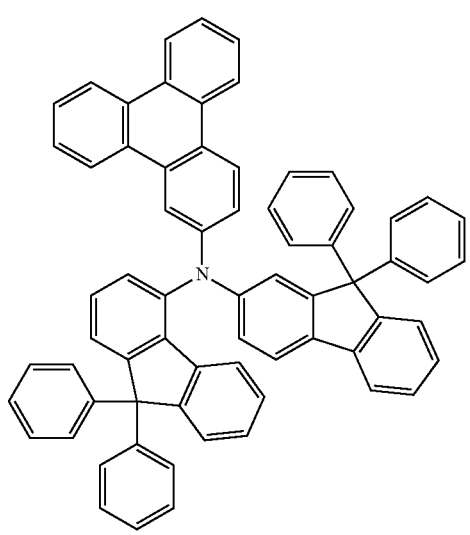
(H-A11)
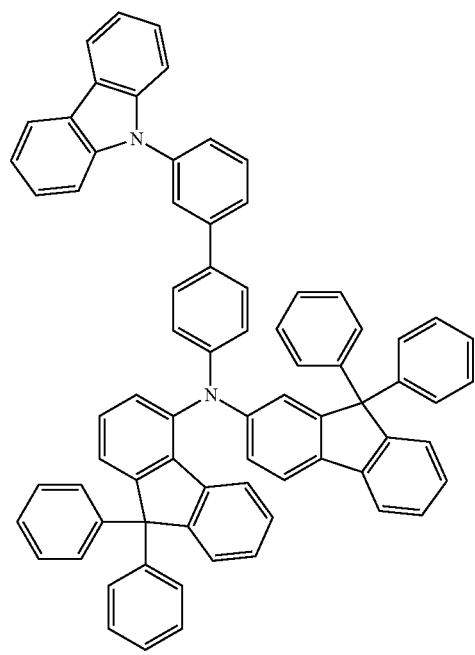
(H-A12)
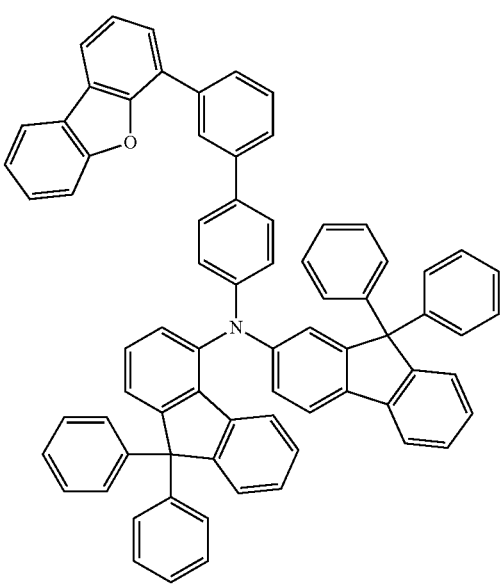

(H-A13)
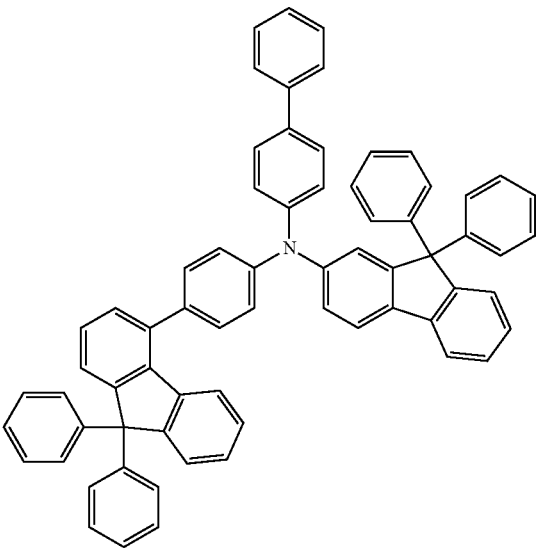
(H-A14)
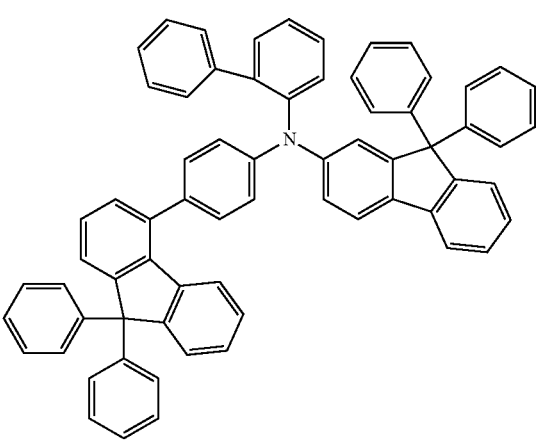
(H-A15)
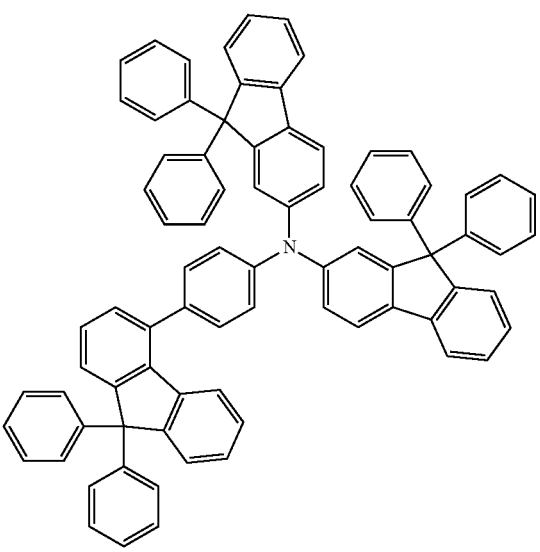
(H-A16)
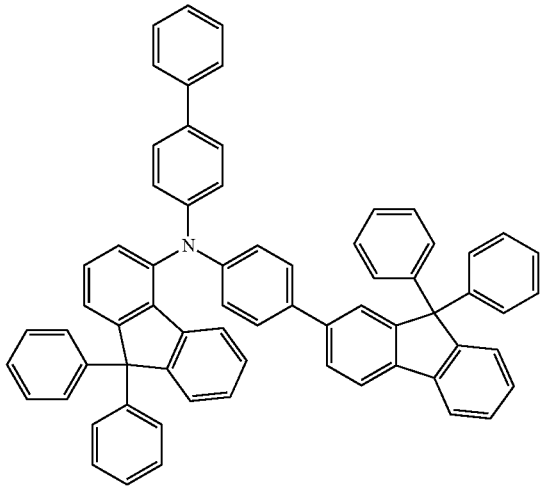
(H-A17)
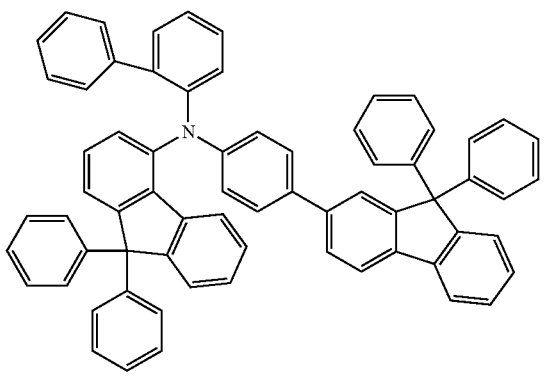
(H-A18)
Compound (B) in an Aspect of the Invention
The compound (B) in an aspect of the invention is preferably a compound represented by formula (B-0-1) (also referred to as "compound (B-0)"):

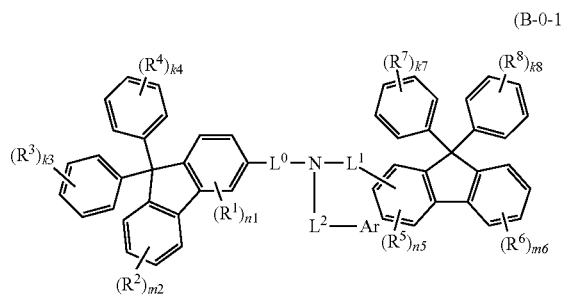

(B-0-1)

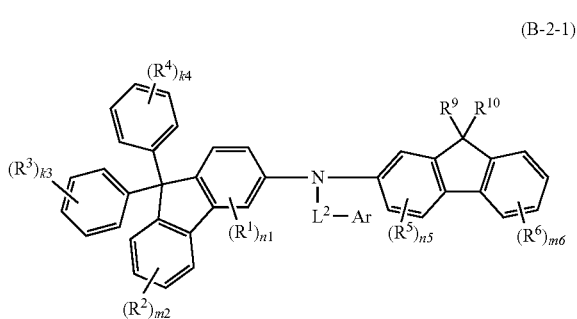

(B-2-1)

wherein $R^1$ to $R^6$, n1, m2, k3, k4, n5, m6, $L^0$ to $L^2$, and Ar are as defined in formula (B-0) and $R^7$, $R^8$, k7, and k8 are as defined in formula (A-0).

In another embodiment, the compound (B) is preferably a compound represented by formula (B-1) (also referred to as "compound (B-1)"):

wherein $R^1$ to $R^6$, $R^9$, $R^{10}$, n1, m2, k3, k4, n5, m6, $L^2$, and Ar are as defined in formula (B-0).

In another embodiment, the compound (B) is preferably a compound represented by formula (B-3) (also referred to as "compound (B-3)"):

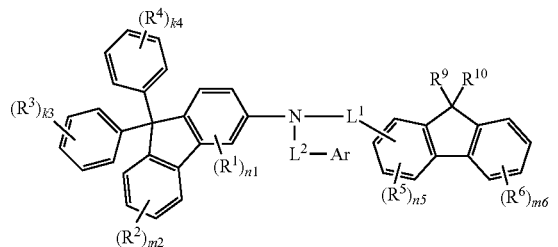

(B-1)

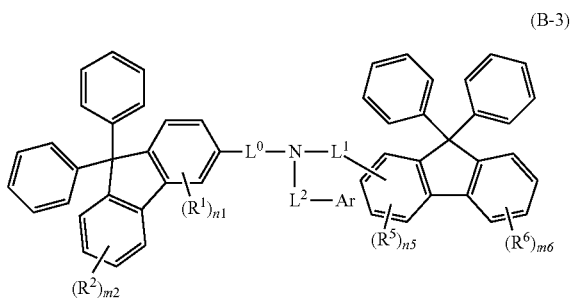

(B-3)

wherein $R^1$ to $R^6$, $R^9$, $R^{10}$, n1, m2, k3, k4, n5, m6, $L^1$, $L^2$, and Ar are as defined in formula (B-0).

In another embodiment, the compound (B) is preferably a compound represented by formula (B-2) (also referred to as "compound (B-2)"):

wherein $R^1$, $R^2$, $R^5$, $R^6$, n1, m2, n5, m6, $L^0$ to $L^2$, and Ar are as defined in formula (B-0).

In another embodiment, the compound (B) is preferably a compound represented by formula (B-4) (also referred to as "compound (B-4)"):

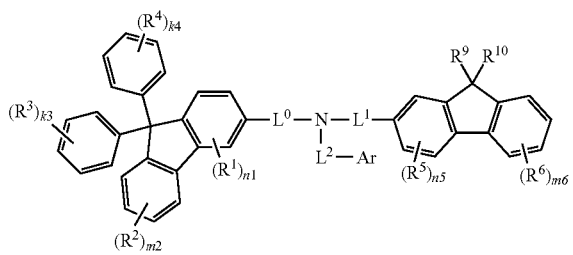

(B-2)

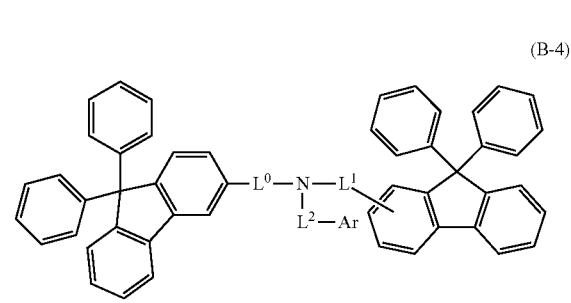

(B-4)

wherein $R^1$ to $R^6$, $R^9$, $R^{10}$, n1, m2, k3, k4, n5, m6, $L^0$ to $L^2$, and Ar are as defined in formula (B-0).

Of the compound (B-2) in an embodiment of the invention, a compound represented by formula (B-2-1) (also referred to as "compound (B-2-1)") is more preferred:

wherein $L^0$ to $L^2$, and Ar are as defined in formula (B-0).

Examples of the compound (B) in an aspect of the invention are shown below, although not limited thereto.

123
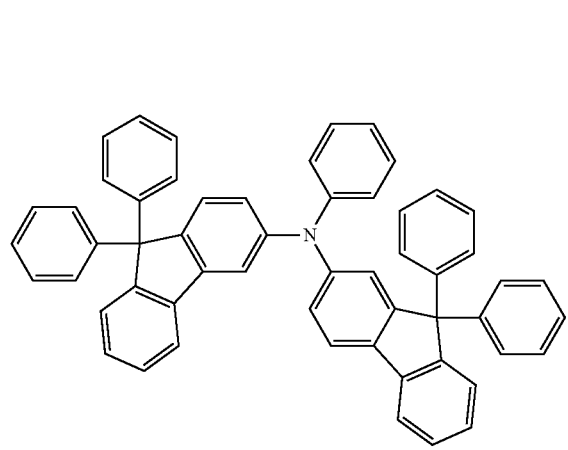
124
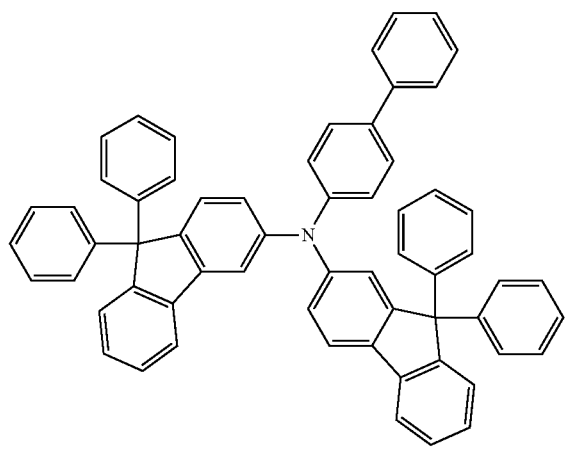
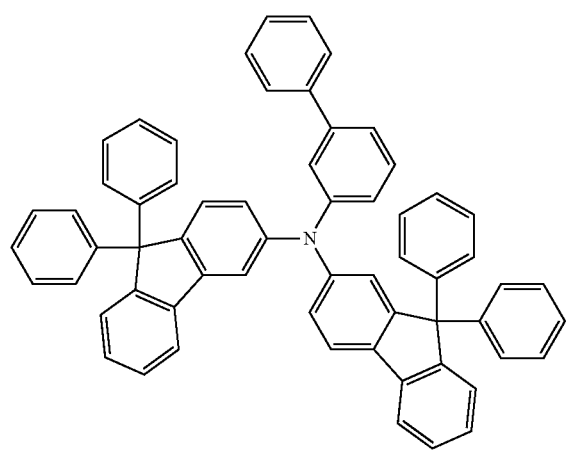
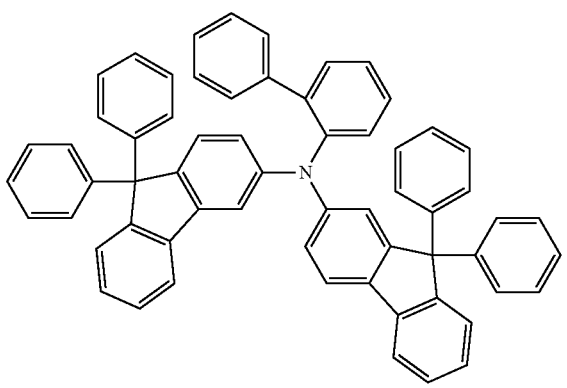
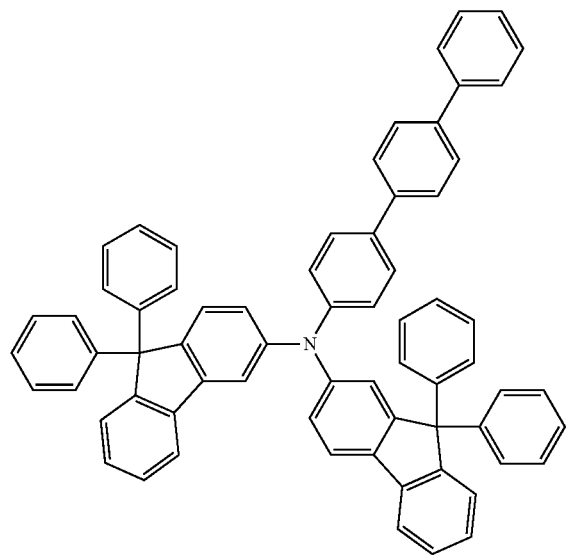
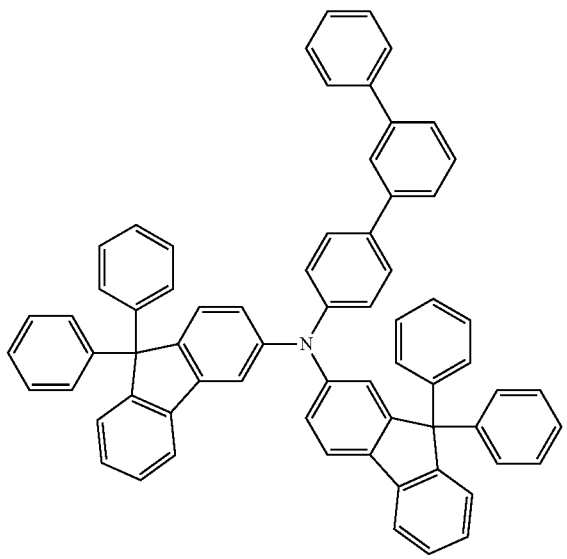

-continued
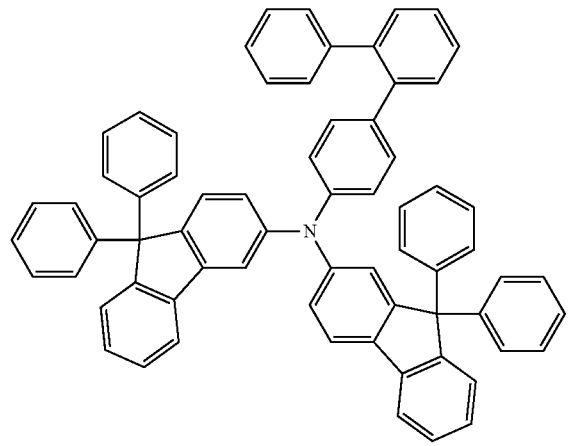
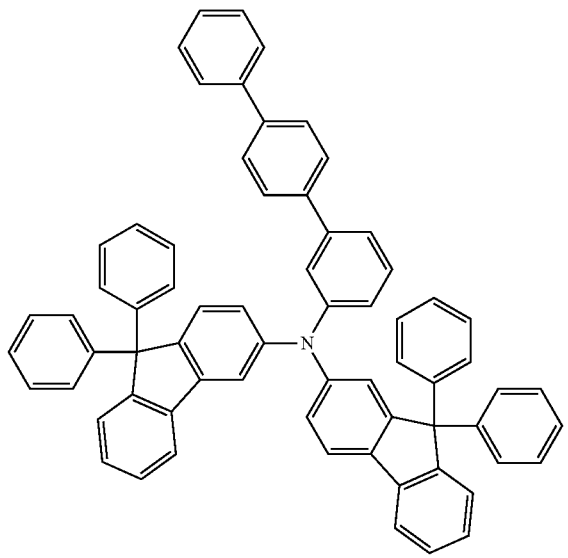
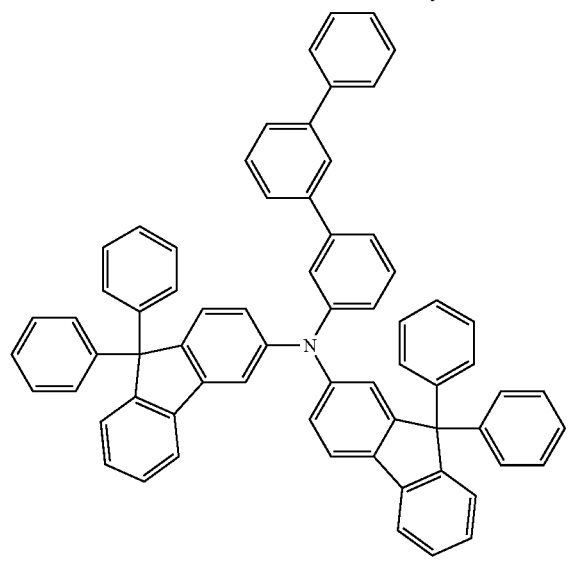
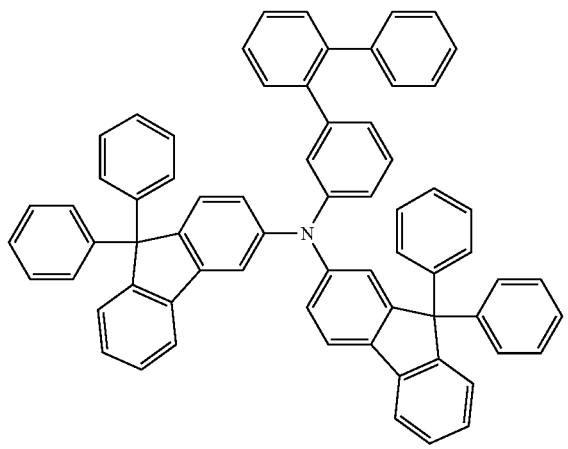
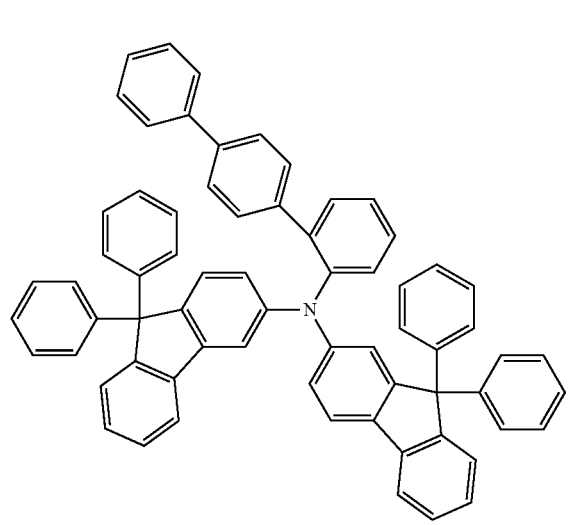
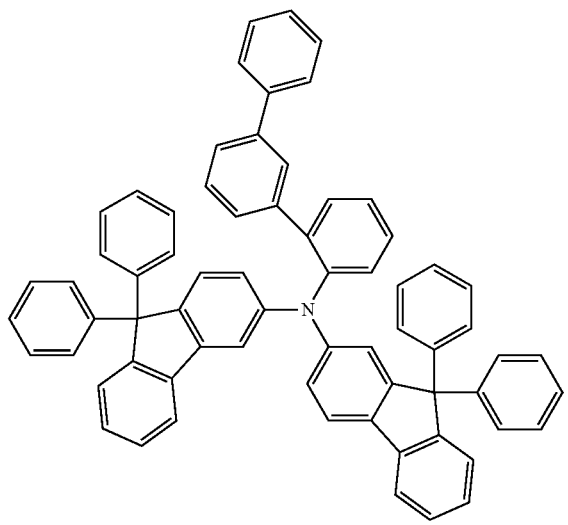

-continued
| 127 | 128 |
|---|---|
| 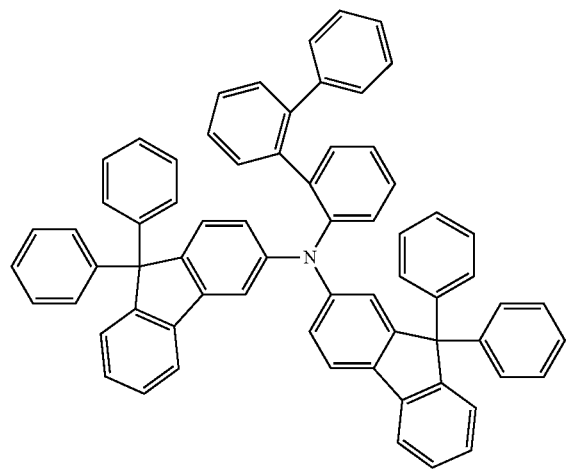 | 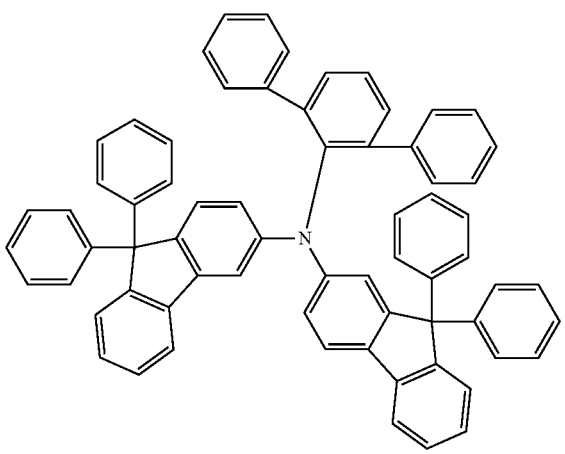 |
| 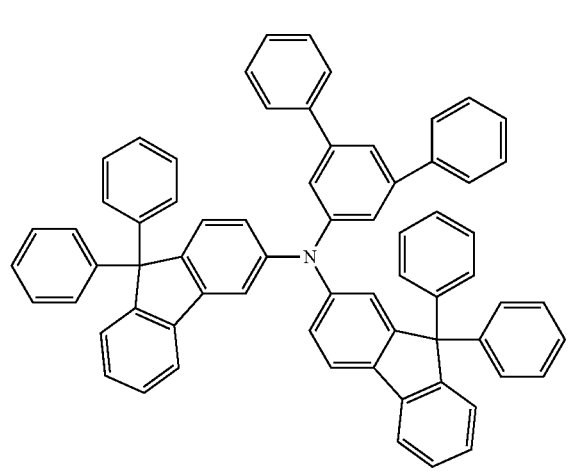 | 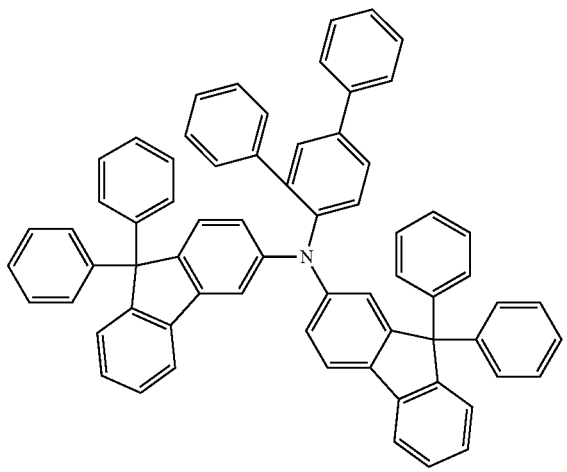 |
| 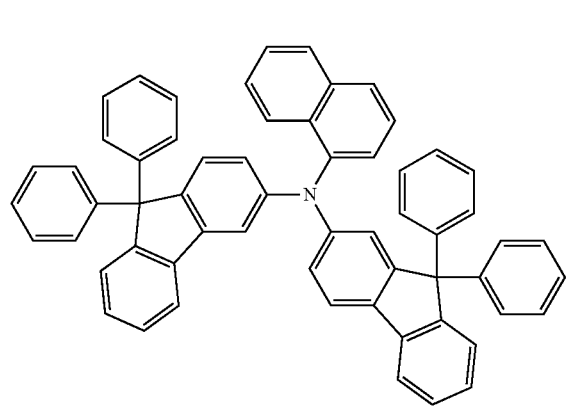 | 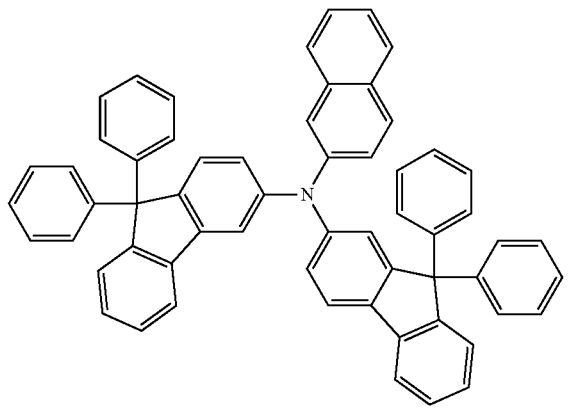 |

129
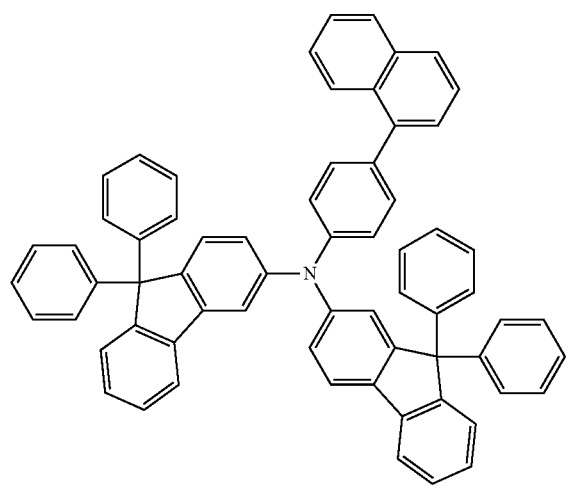
130
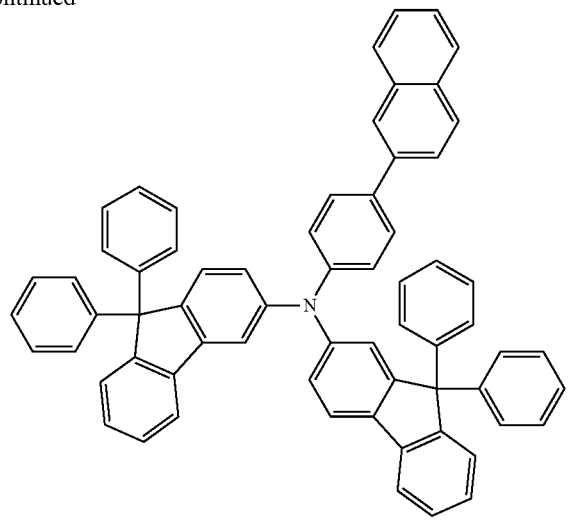
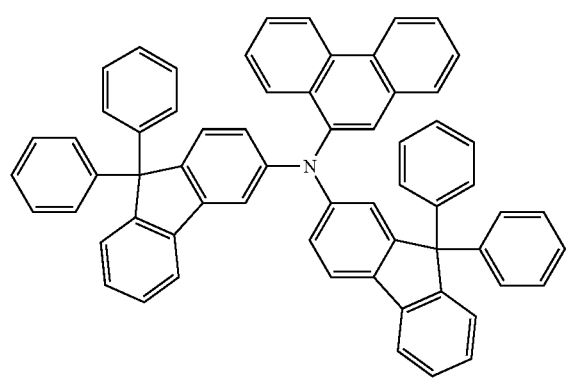
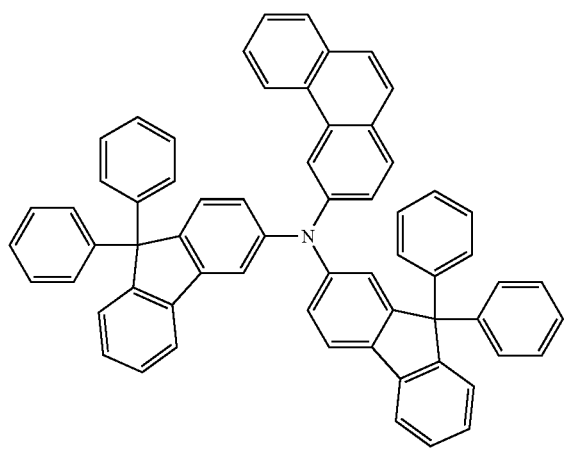
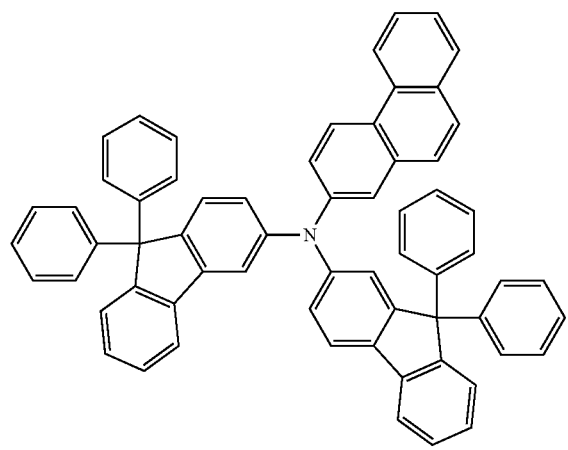
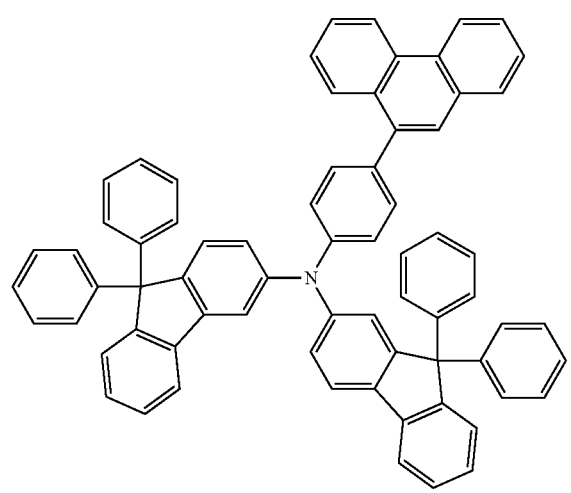

-continued
131
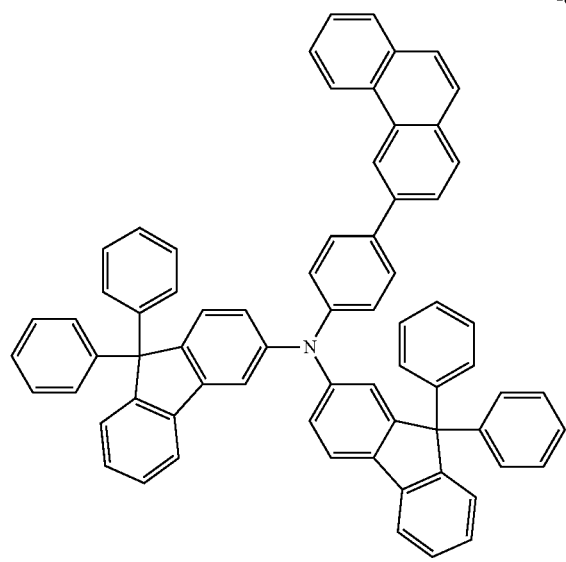
132
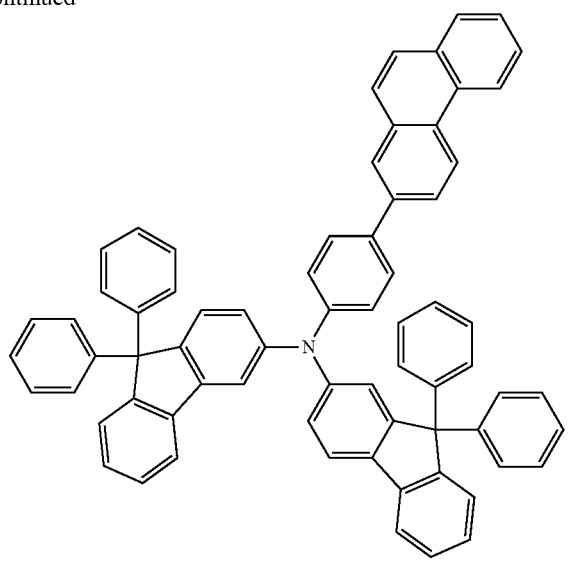
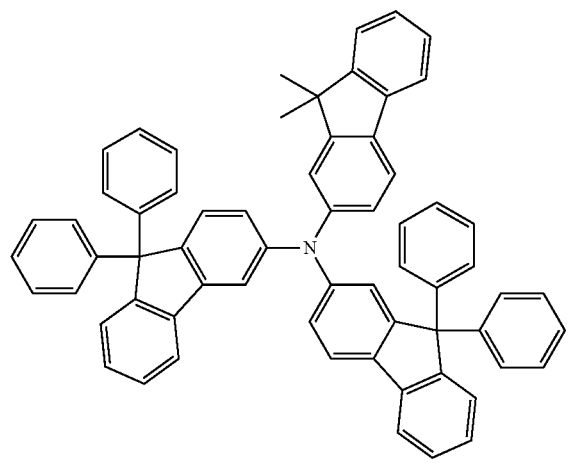
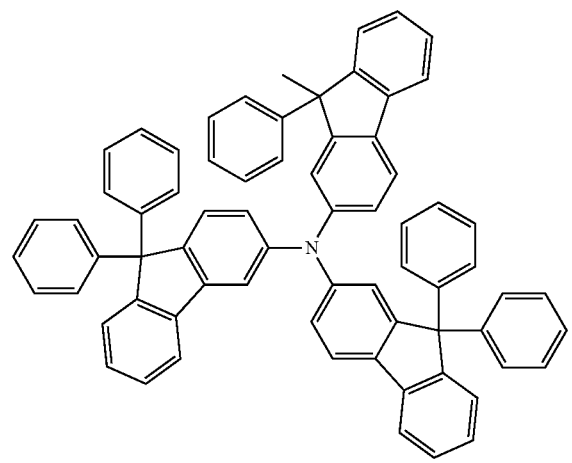
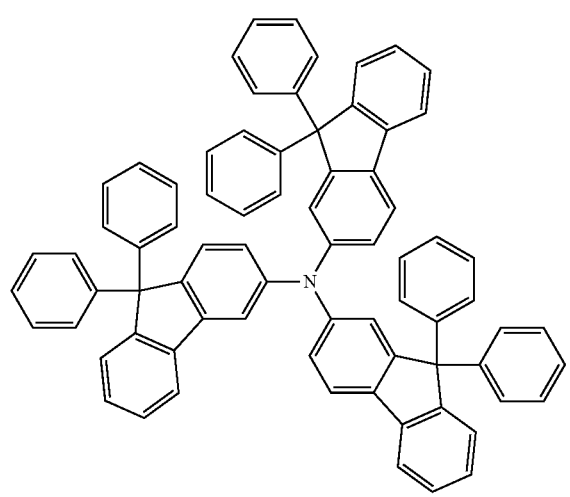
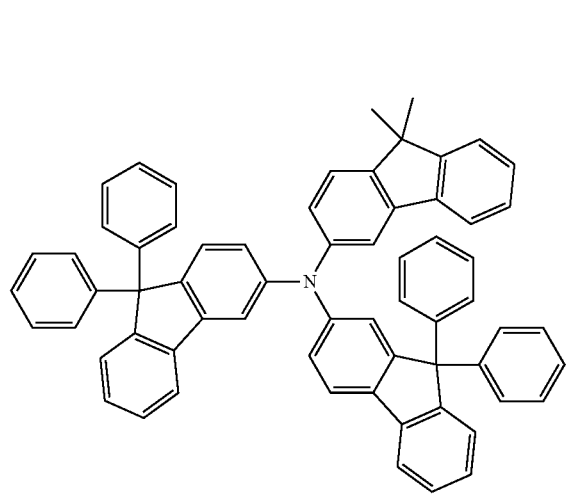

-continued
133
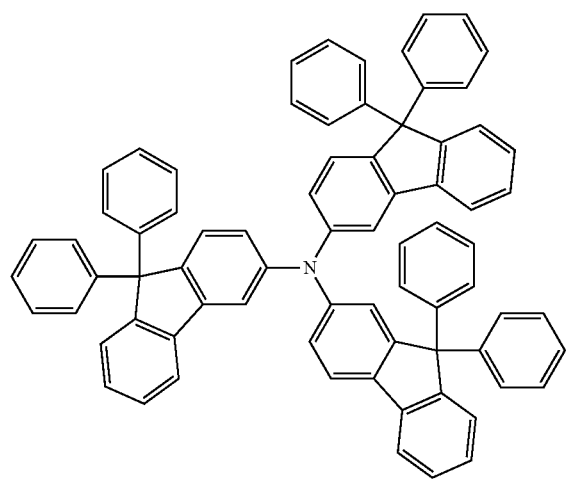
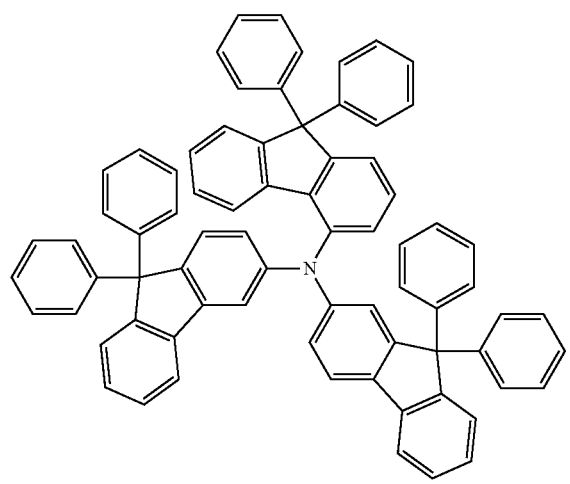
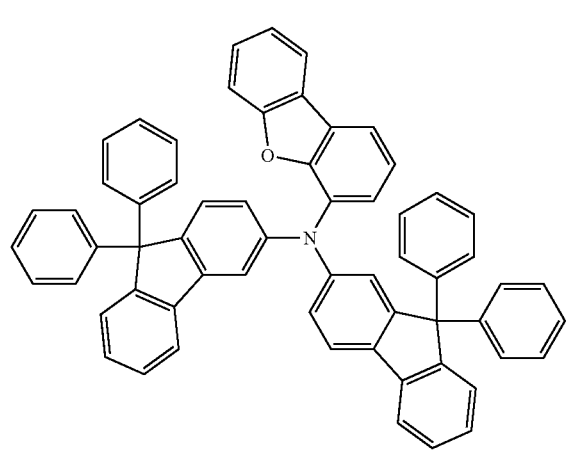
134
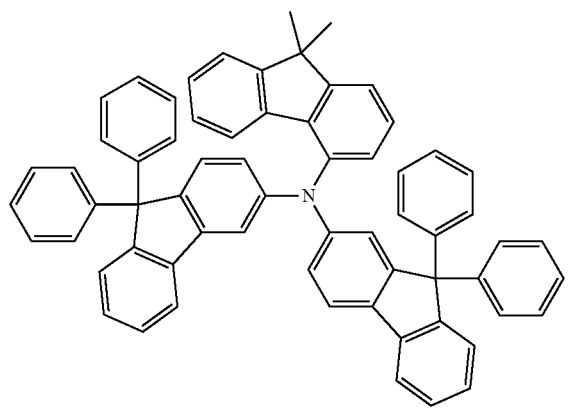
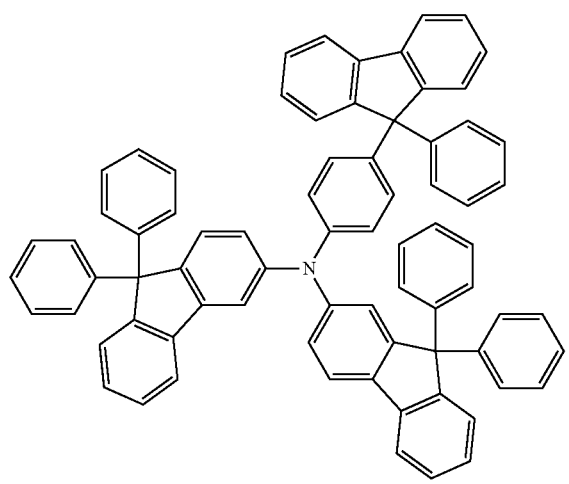
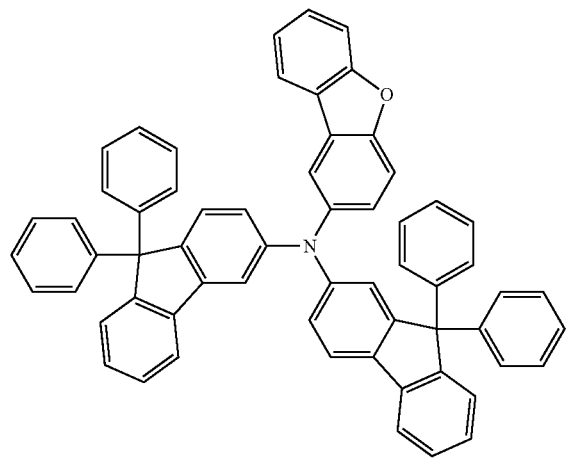

-continued
| 135 | 136 |
|---|---|
| 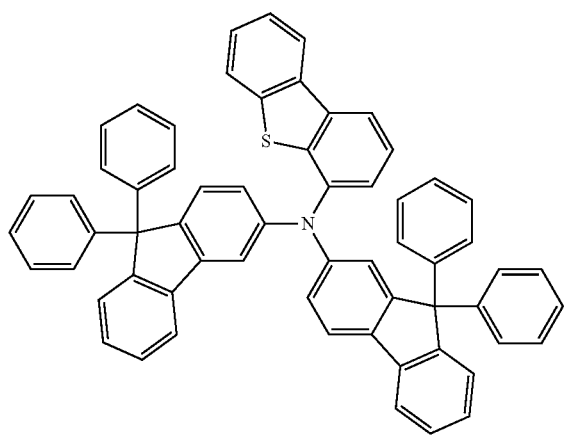 | 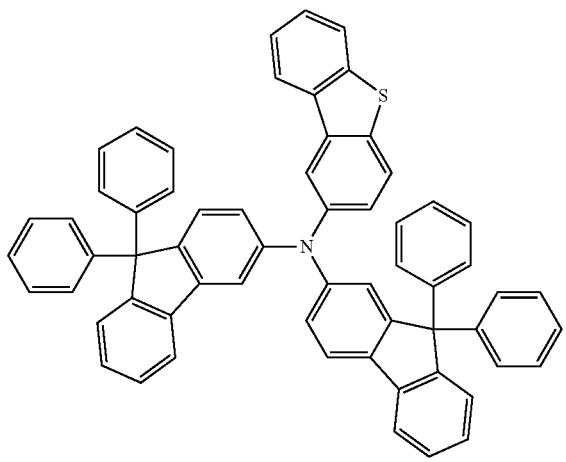 |
| 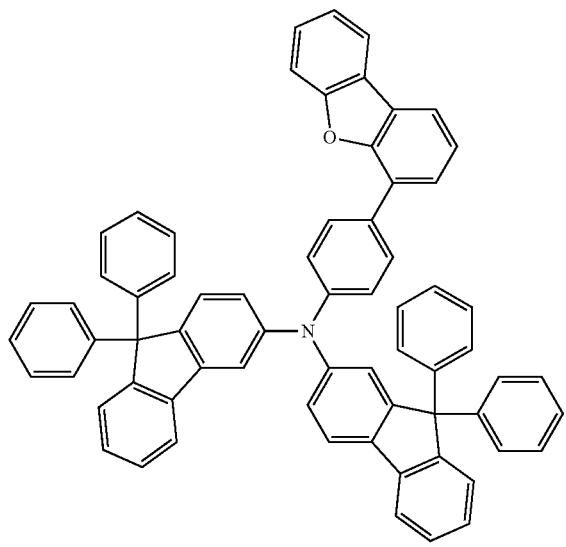 | 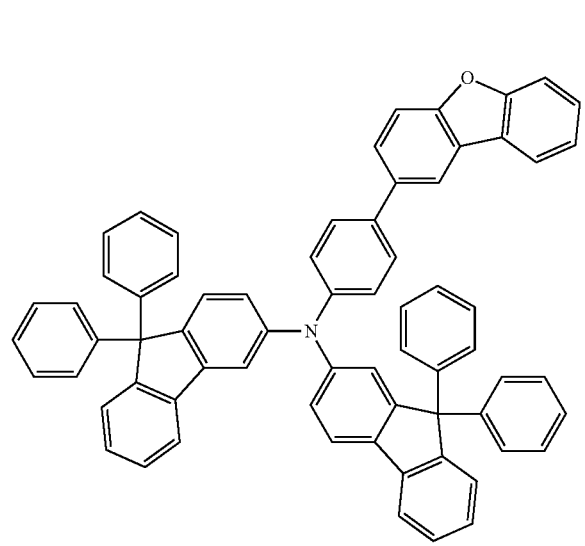 |
| 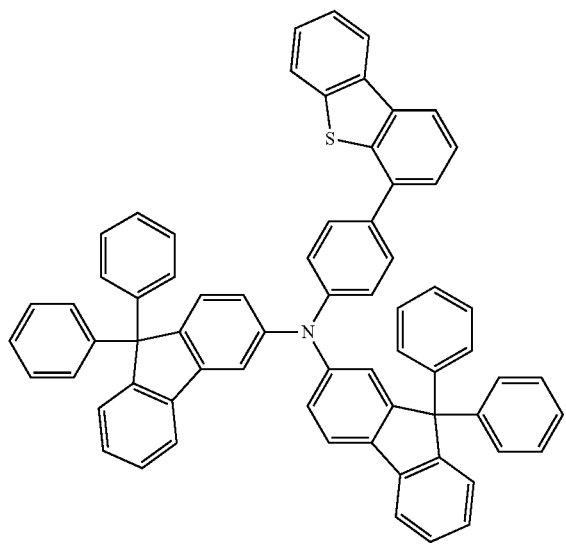 | 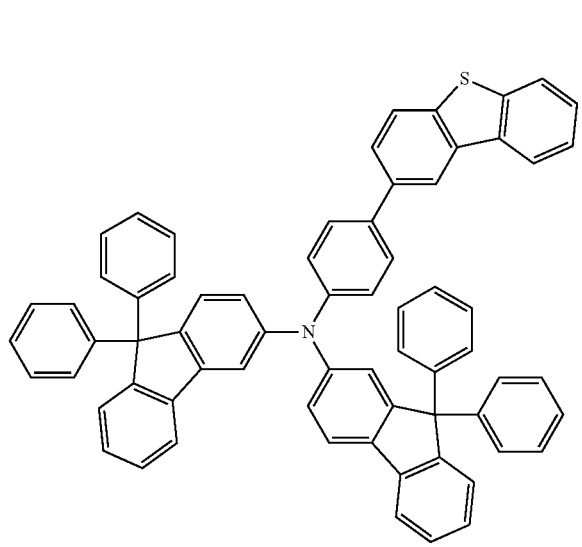 |

137
138
-continued
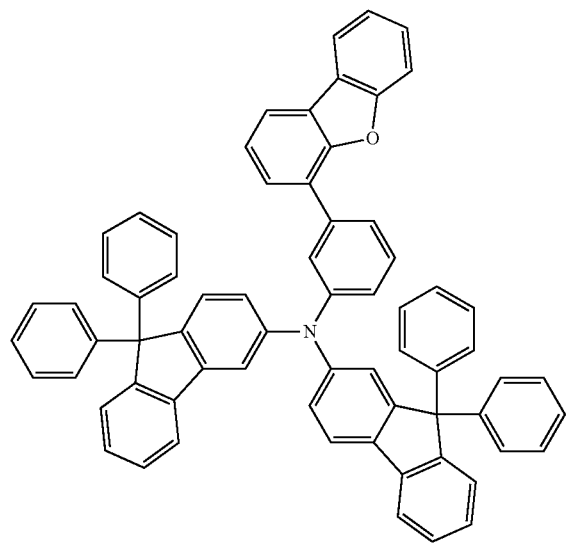
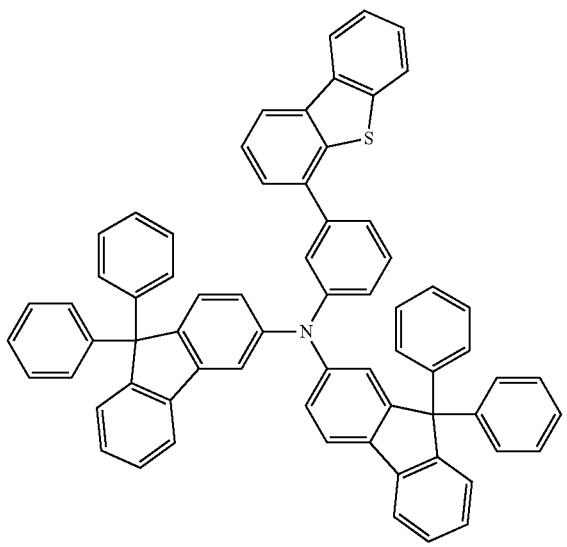
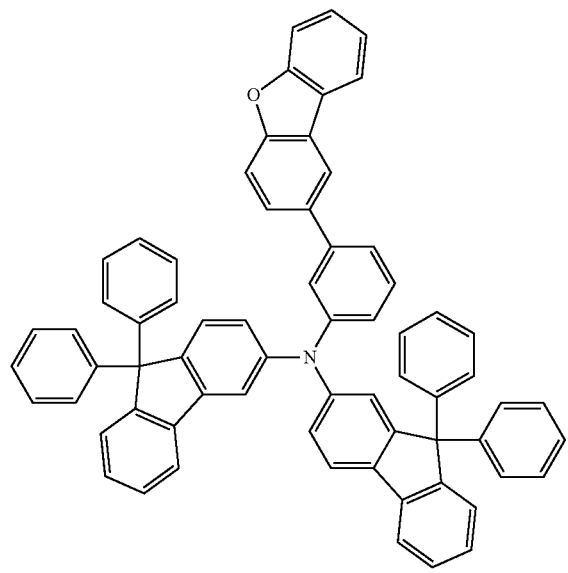
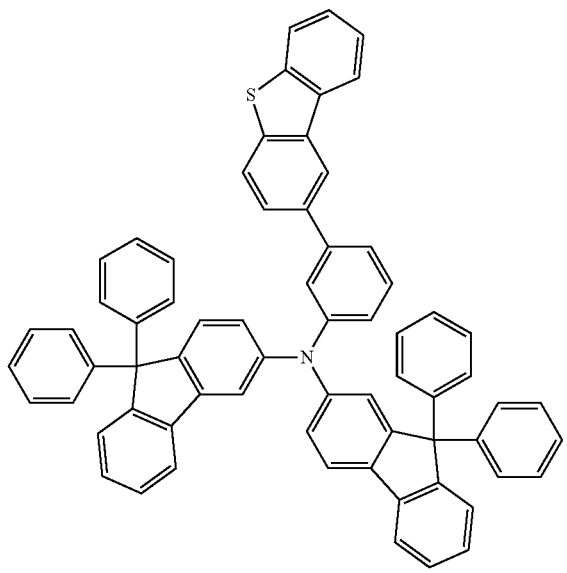
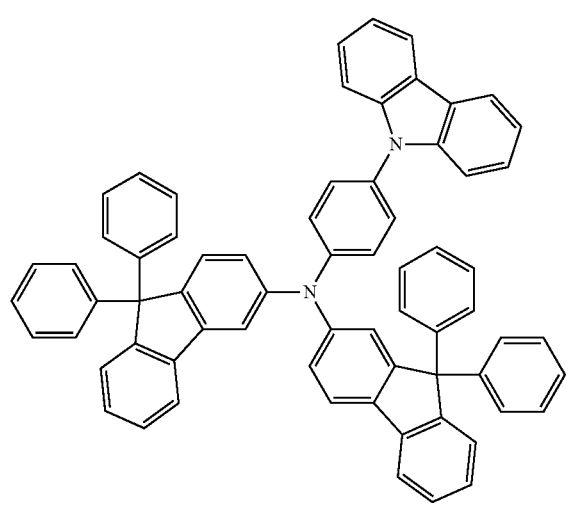
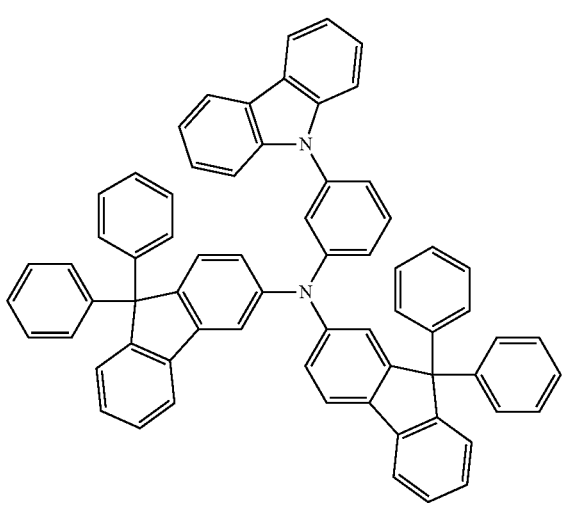

-continued
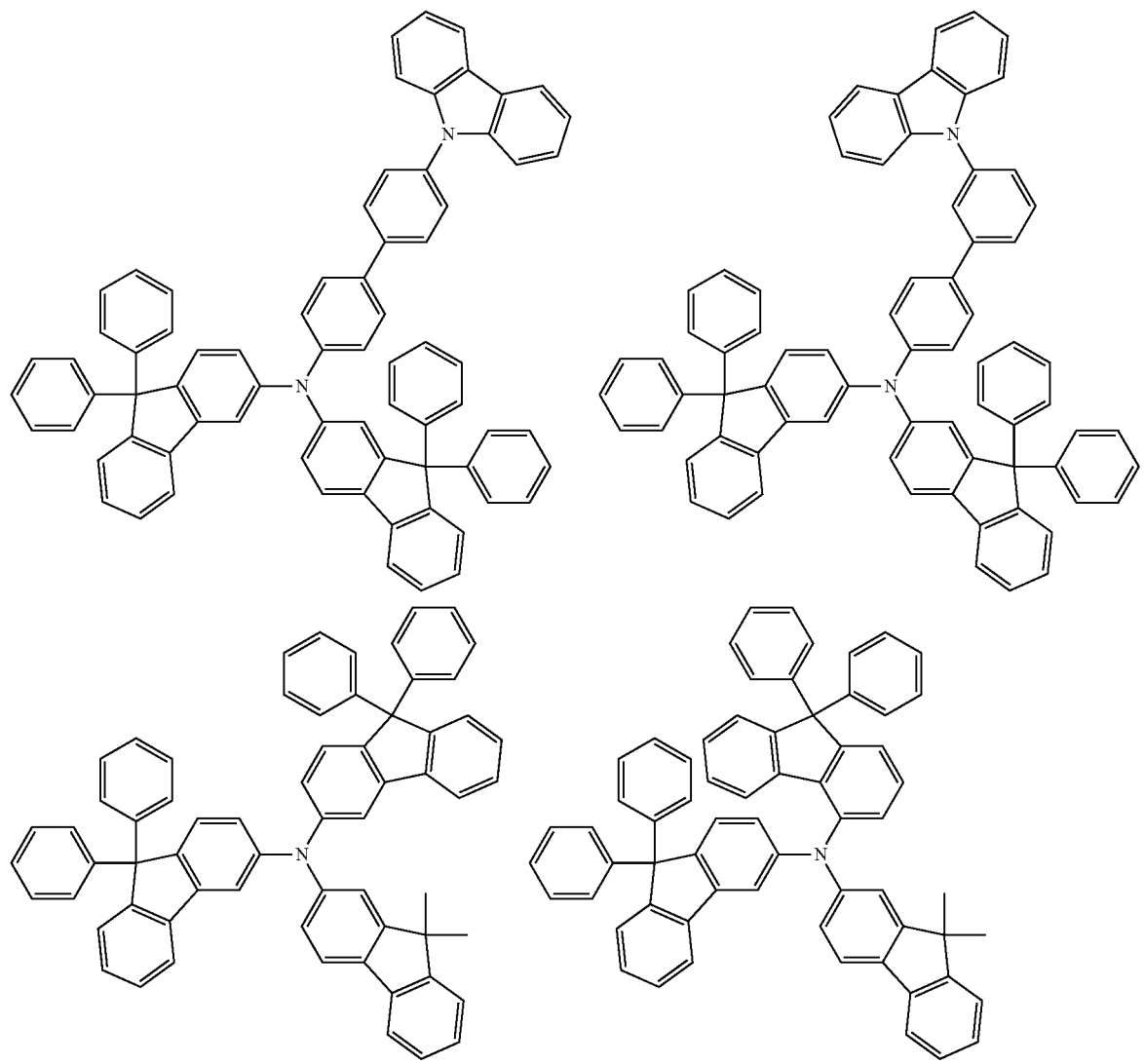
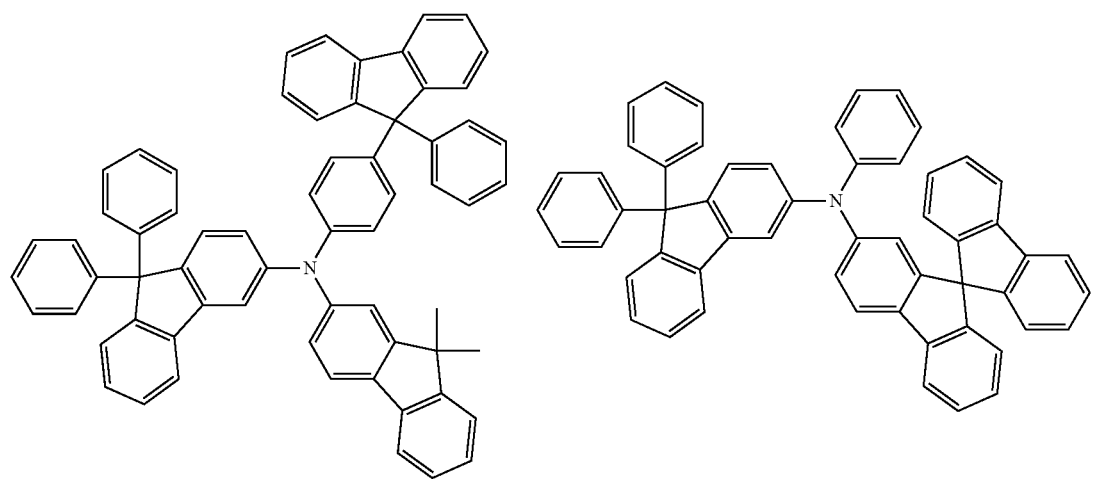

141 142
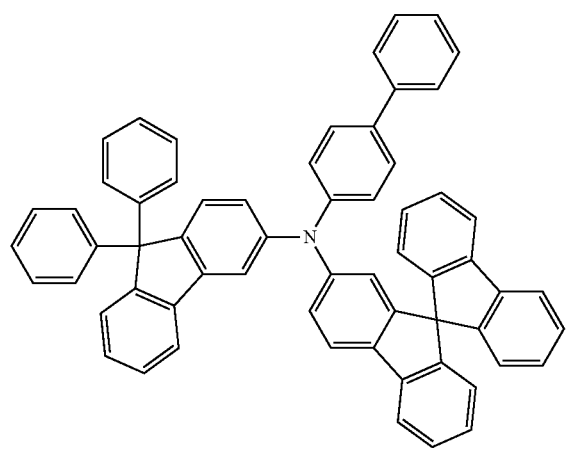
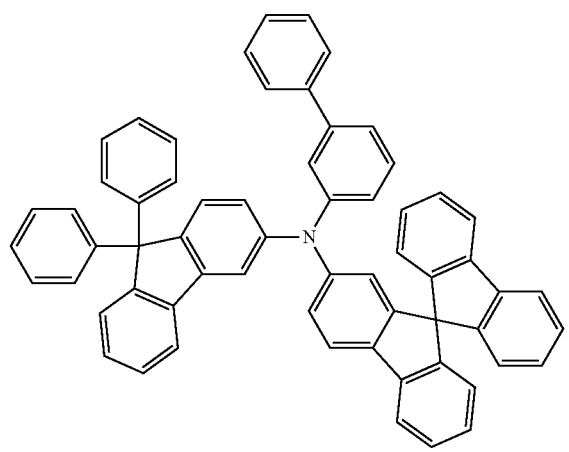
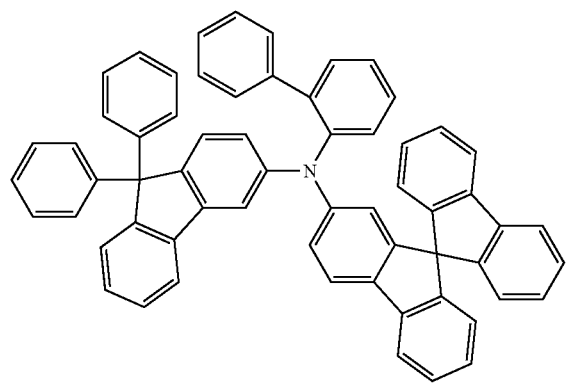
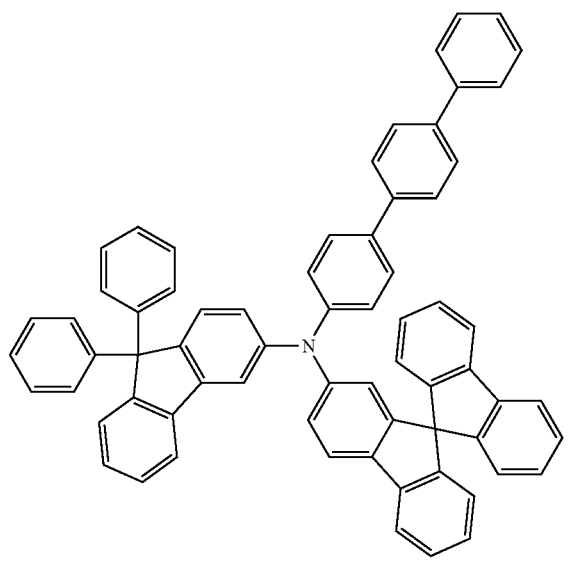
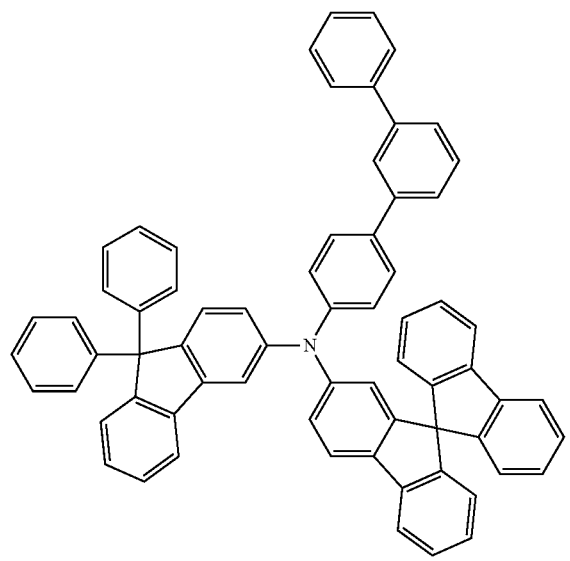
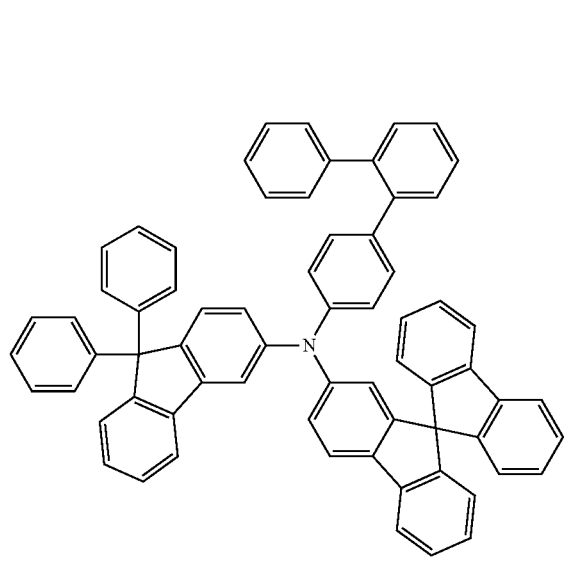

143
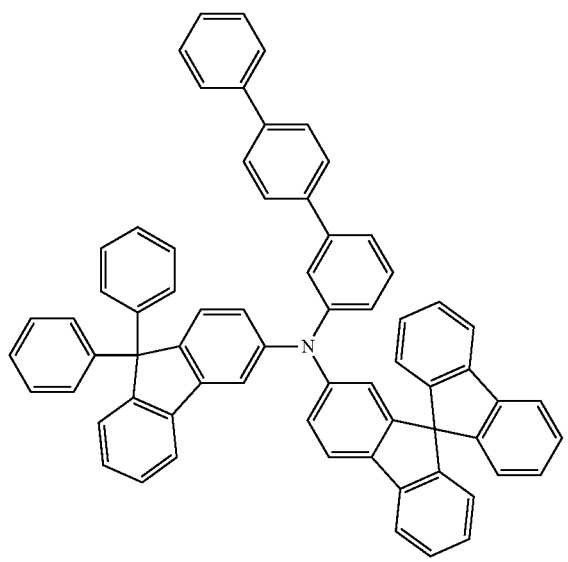
-continued
144
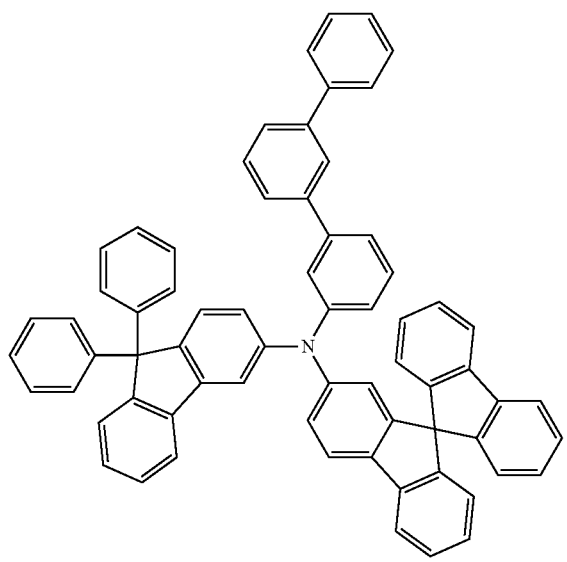
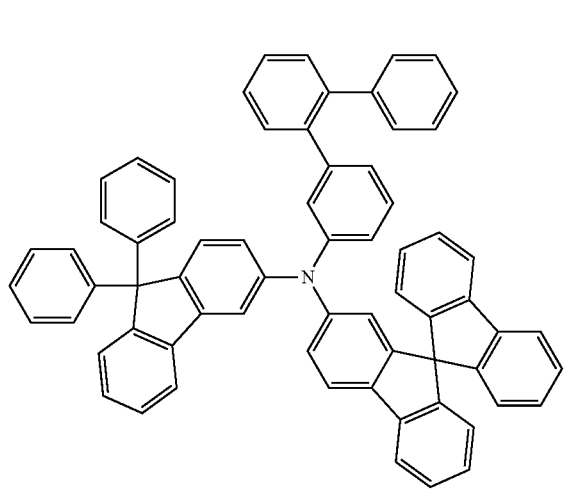
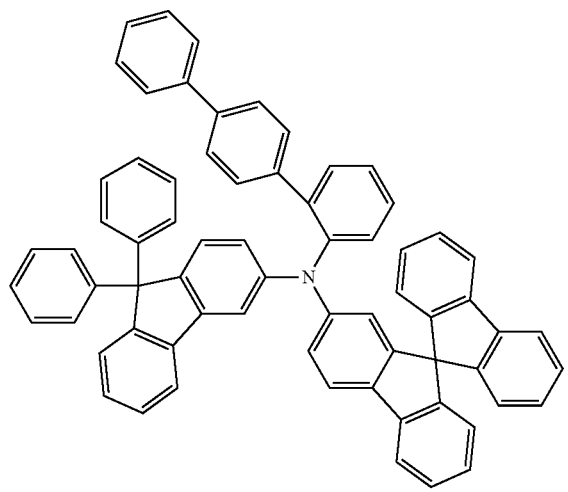
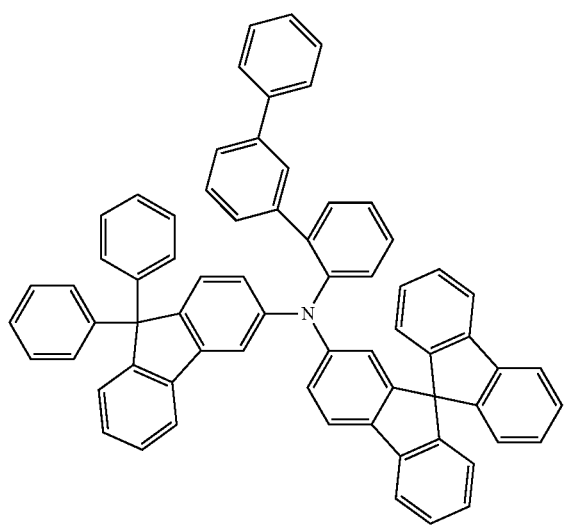
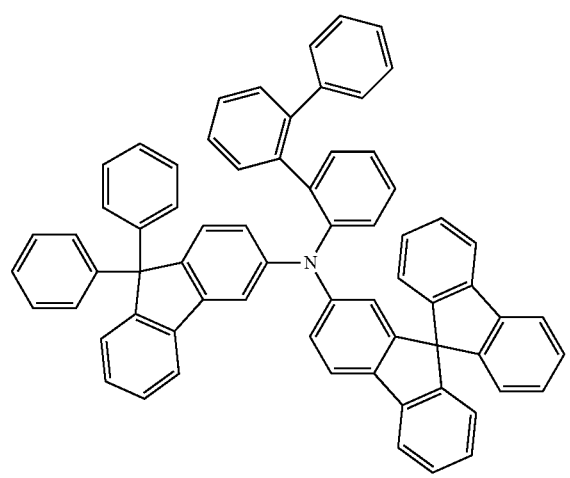

145
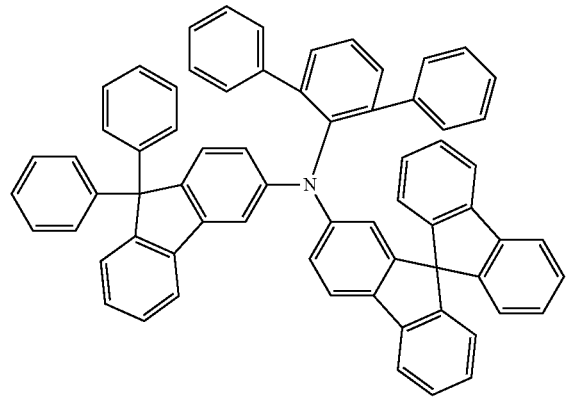
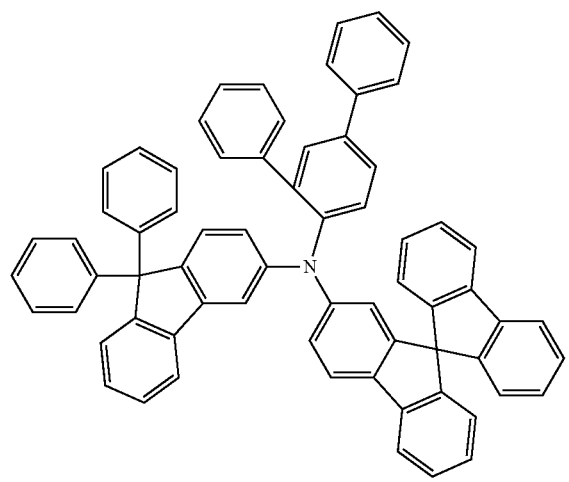
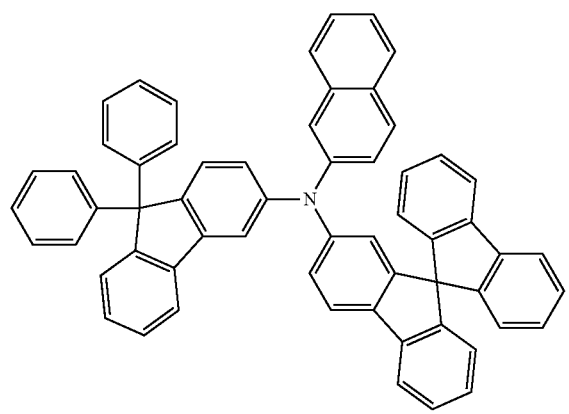
146
-continued
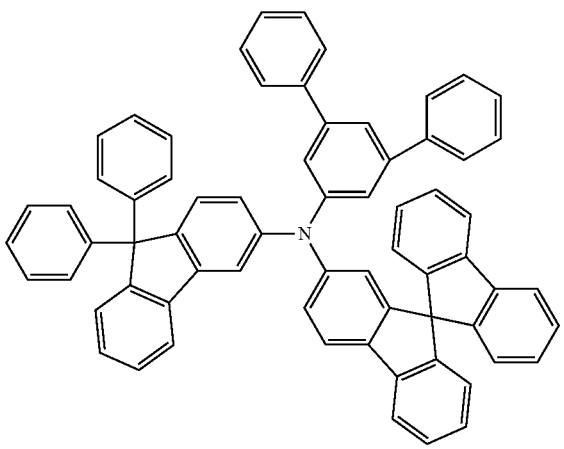
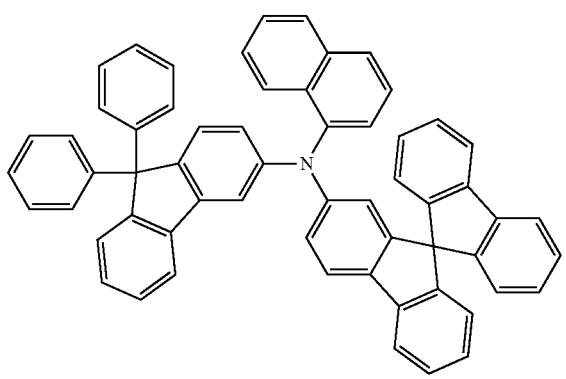
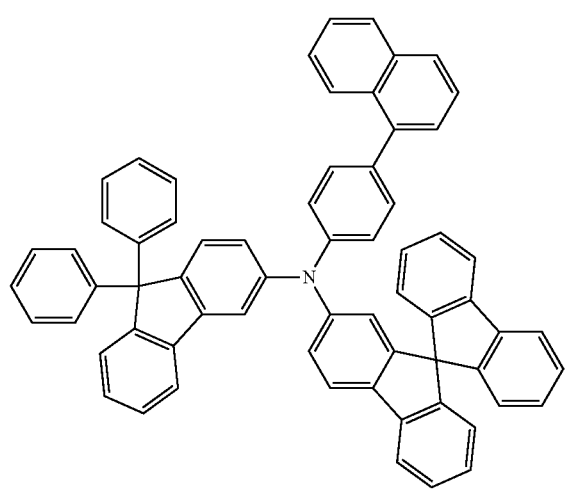

-continued
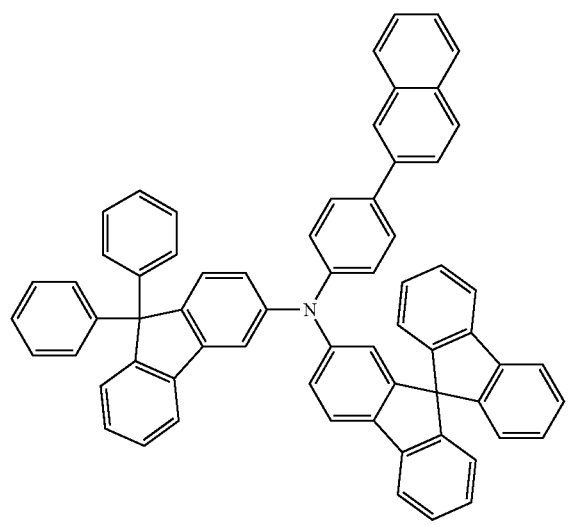
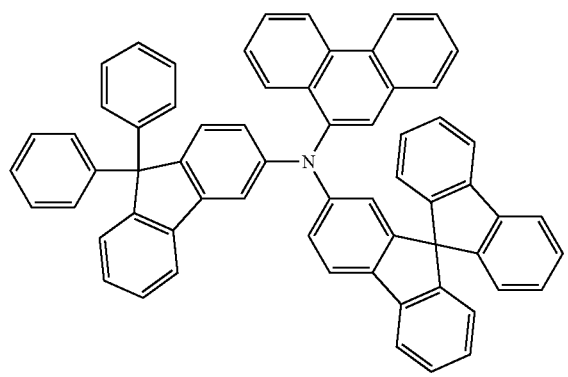
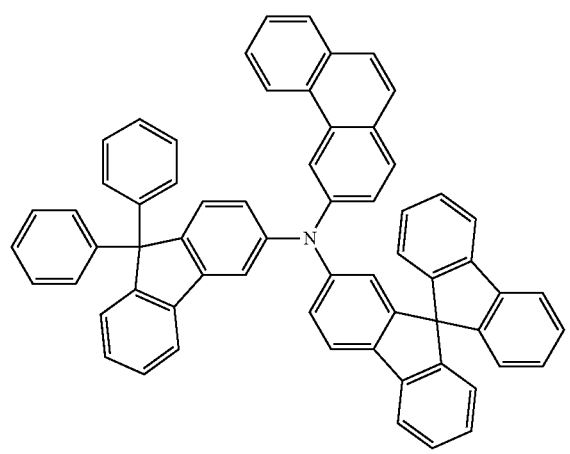
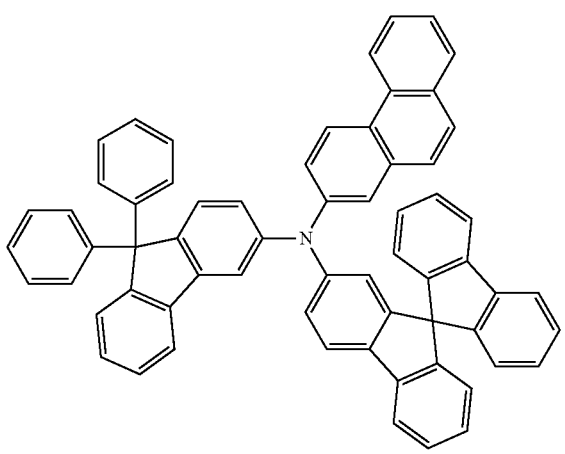
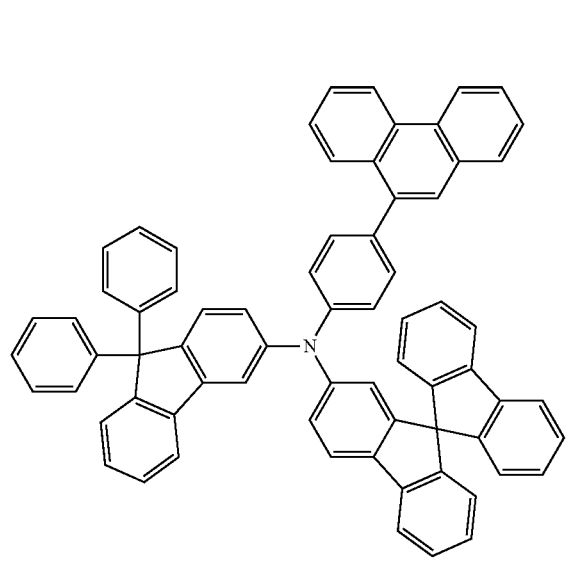
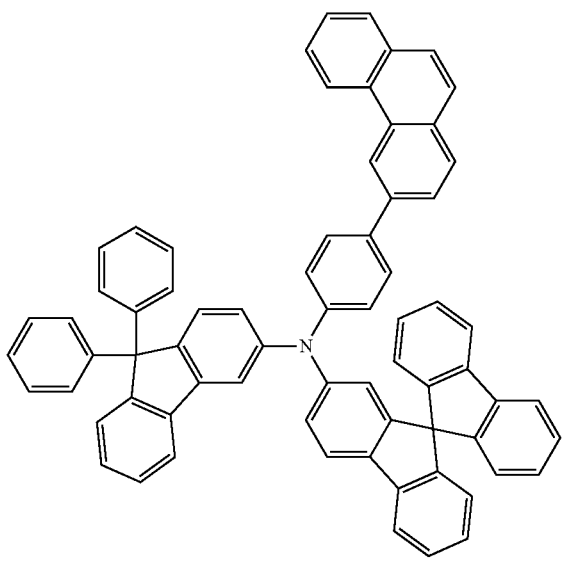

-continued
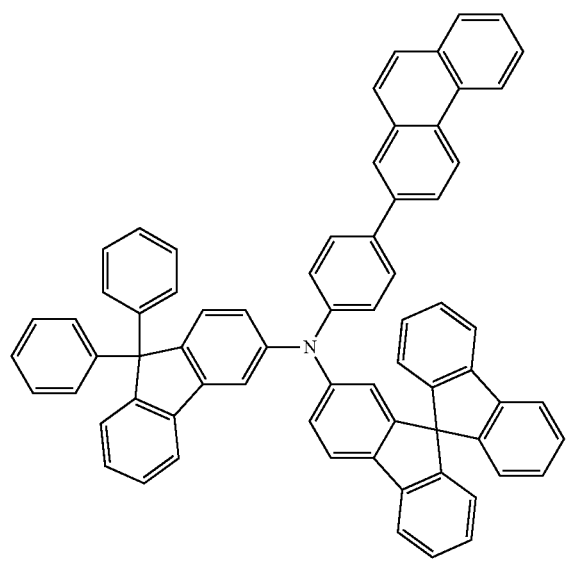
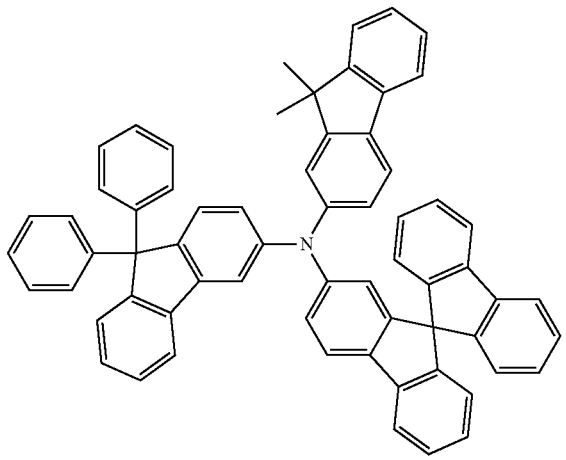
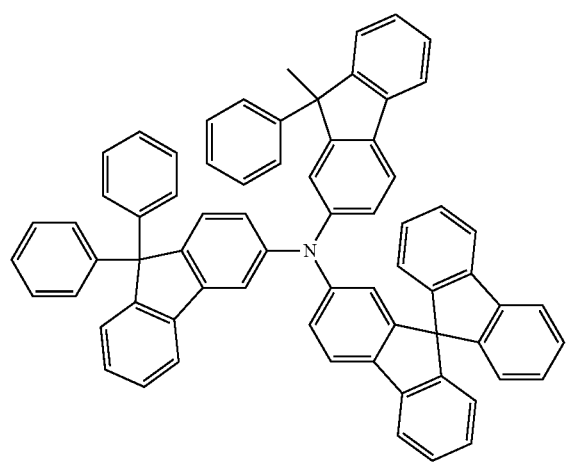
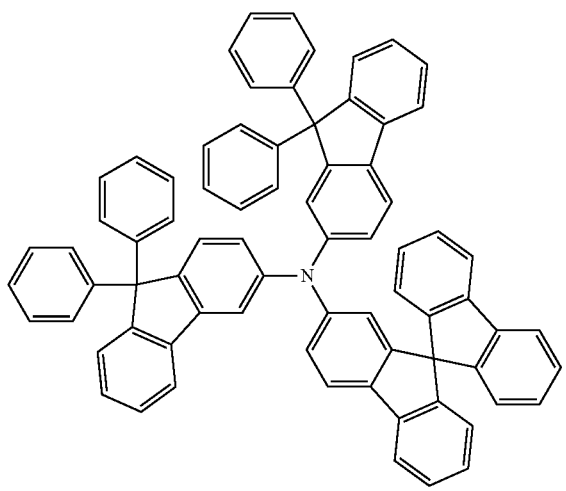
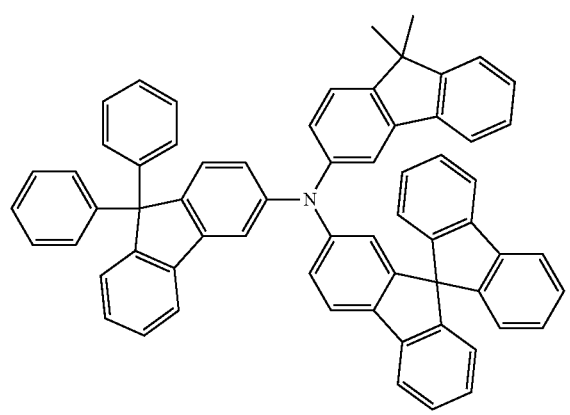
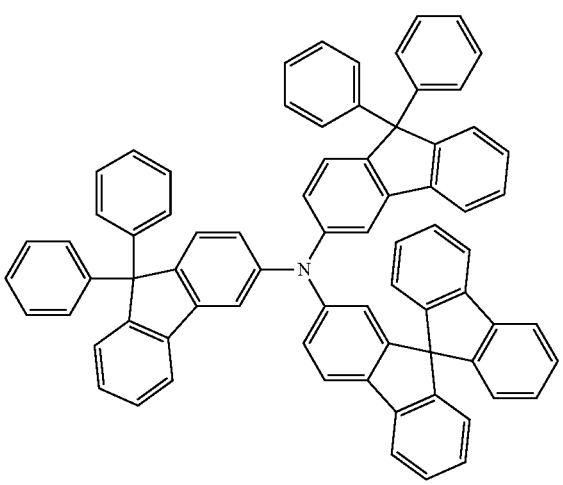

151
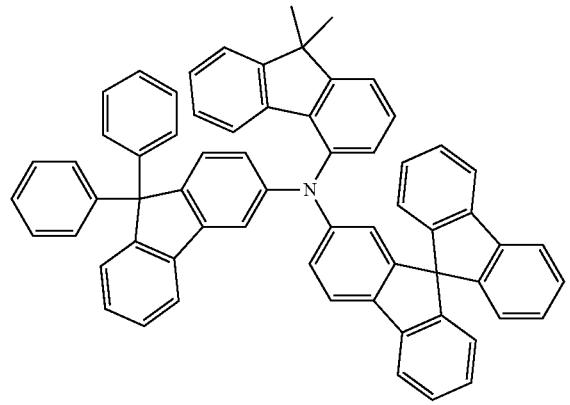
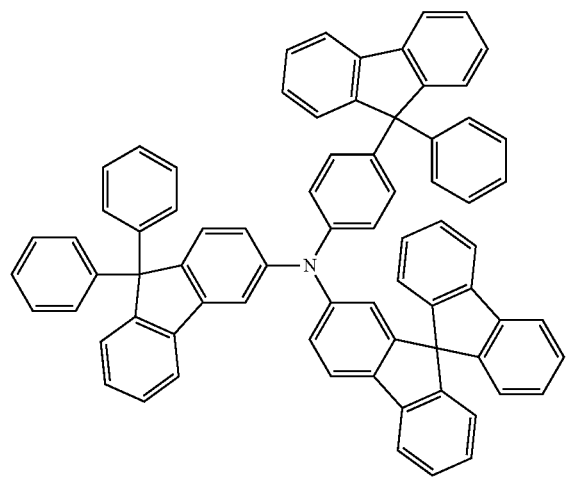
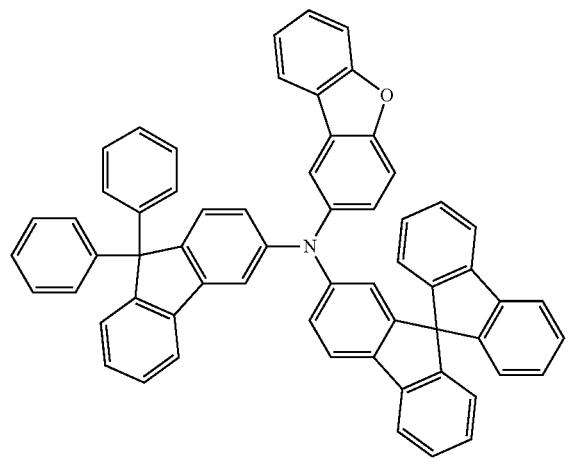
152
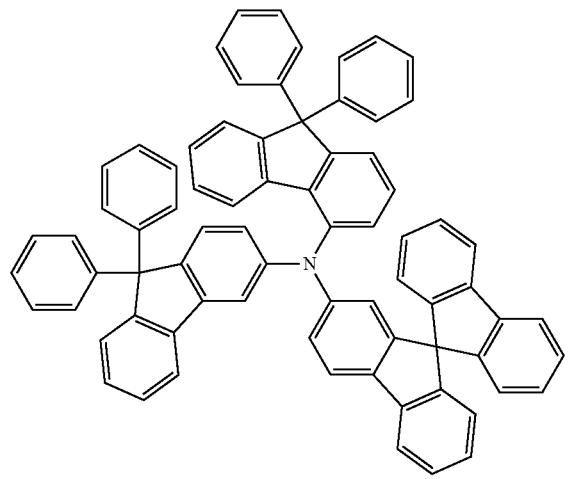
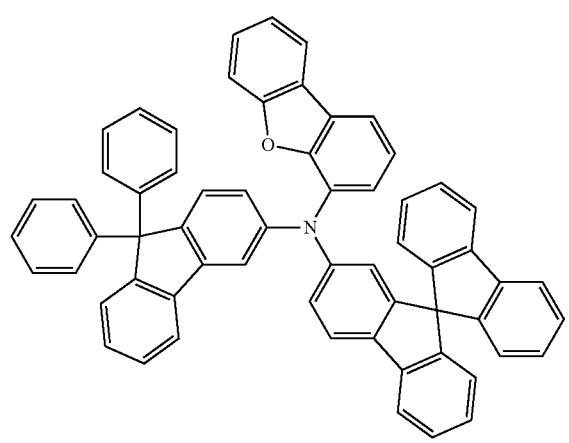
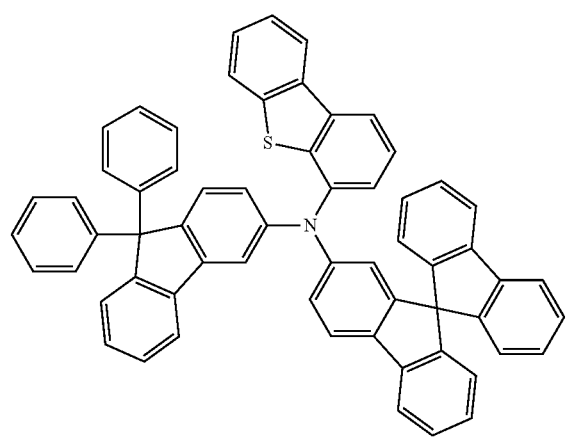

153
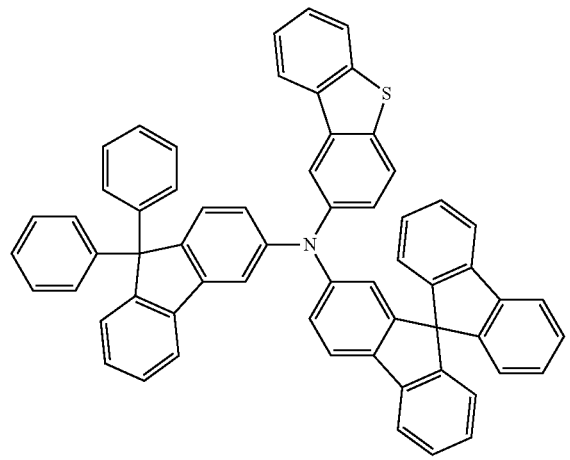
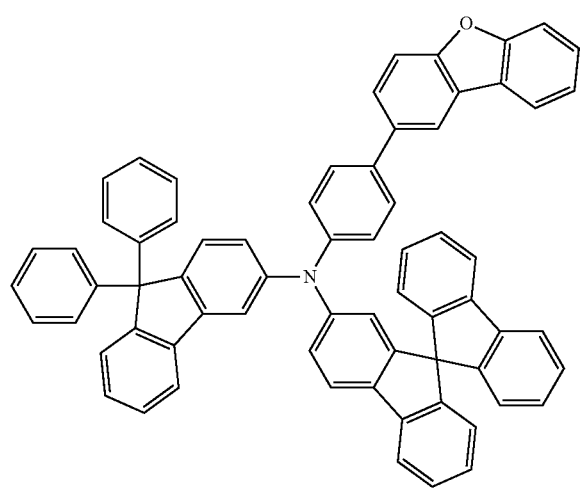
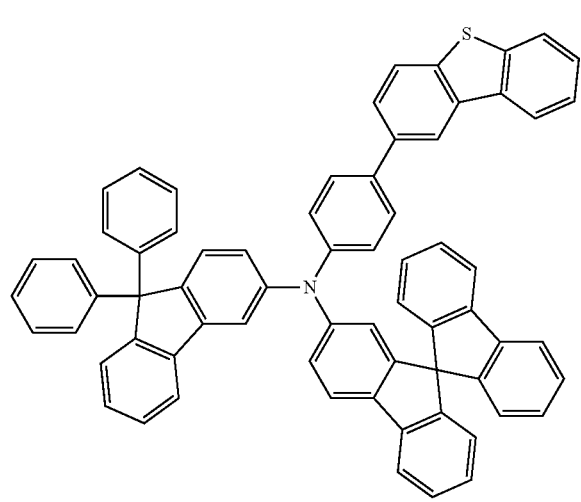
154
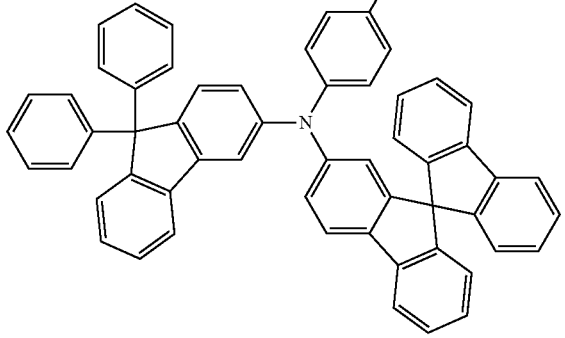
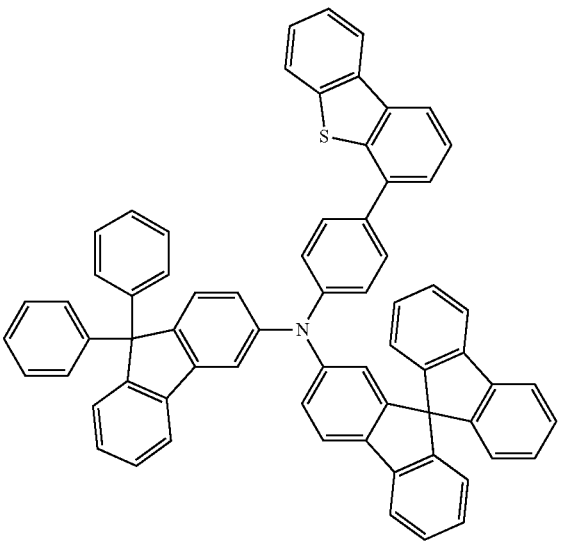
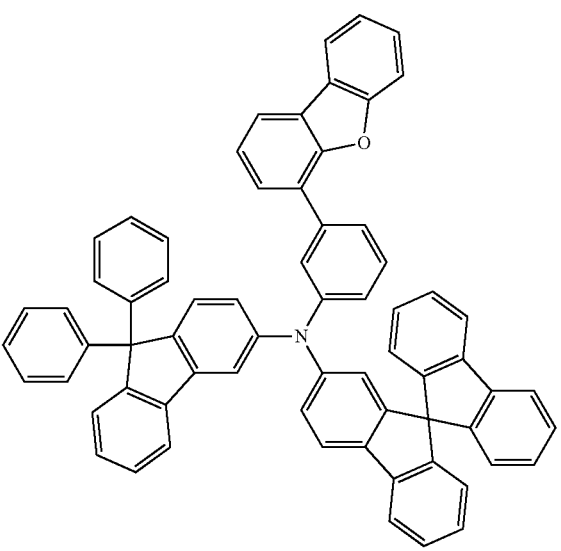

155
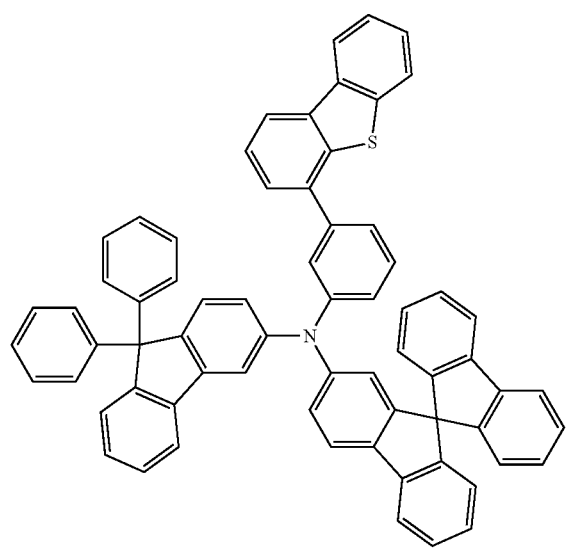
156
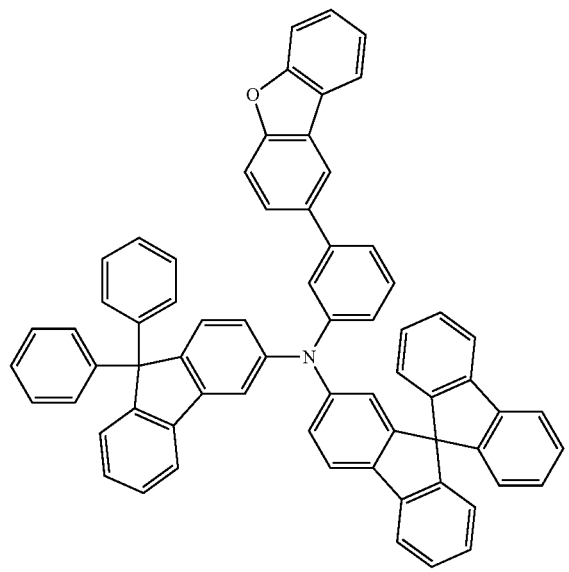
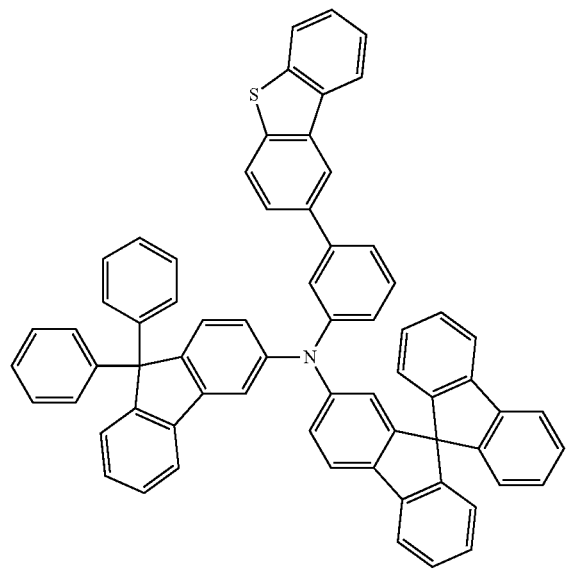
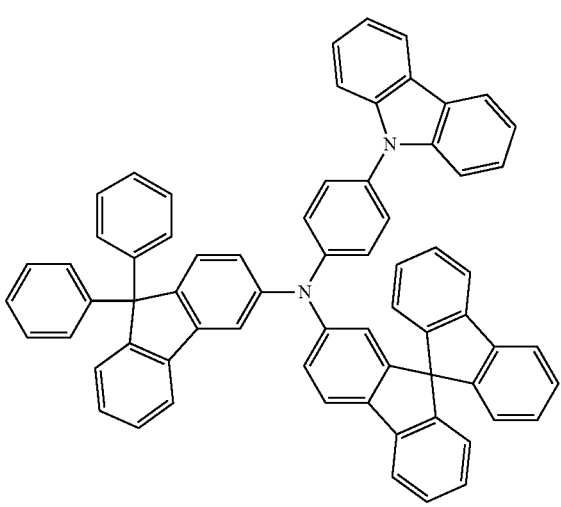

-continued
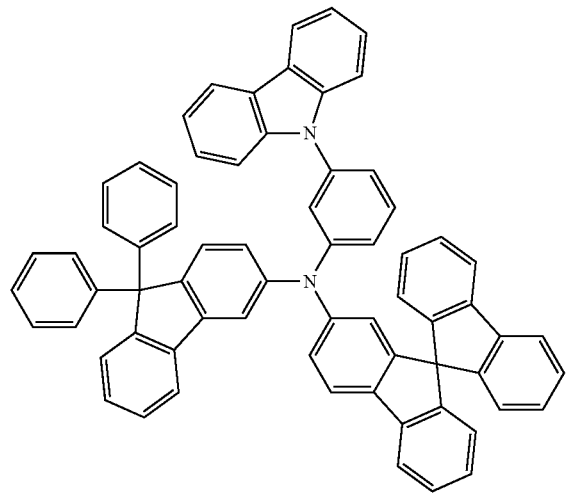
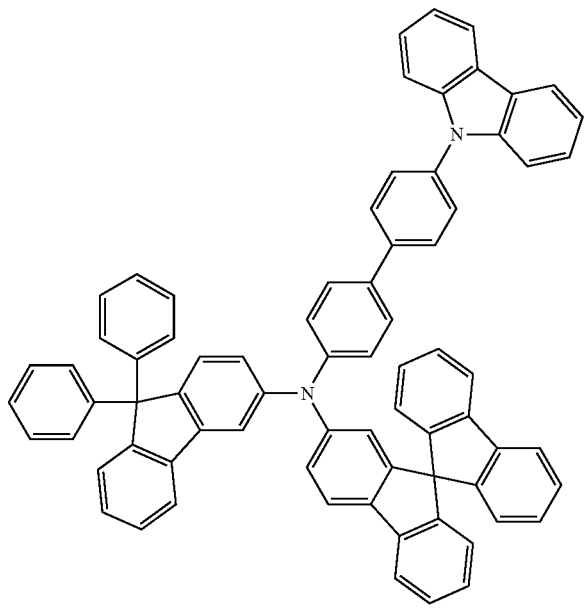
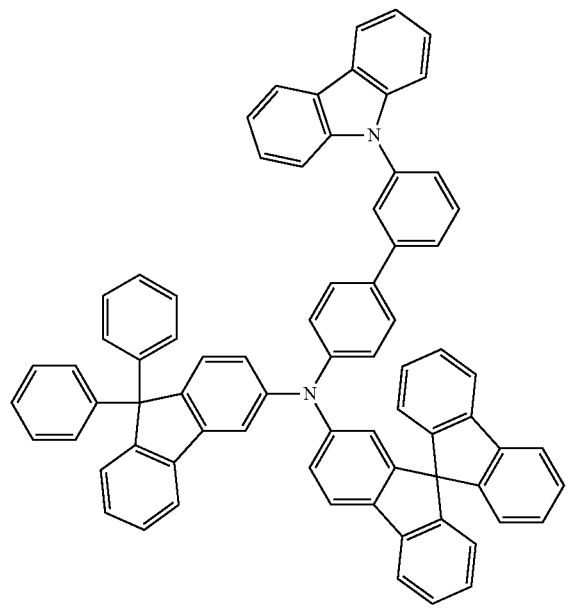
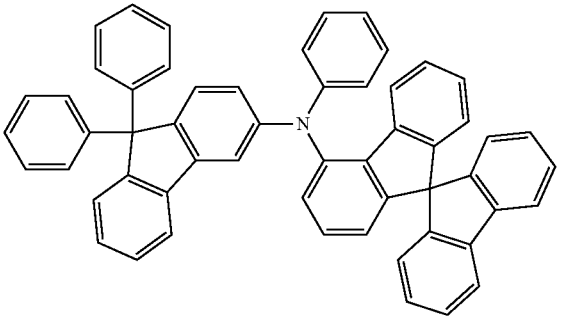
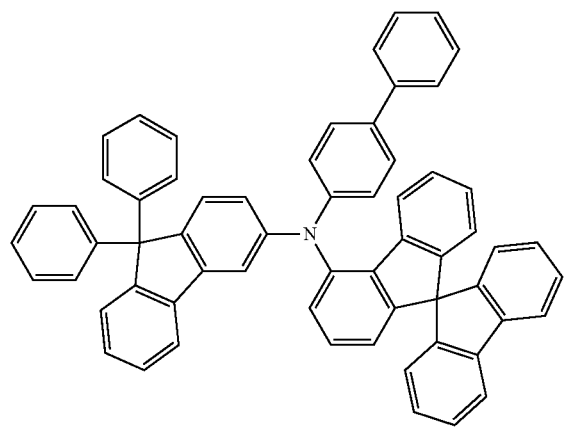
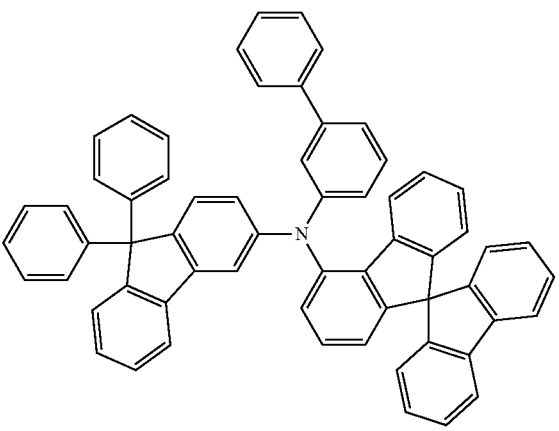

-continued
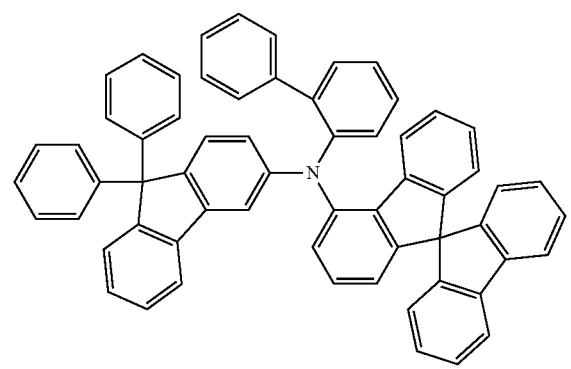
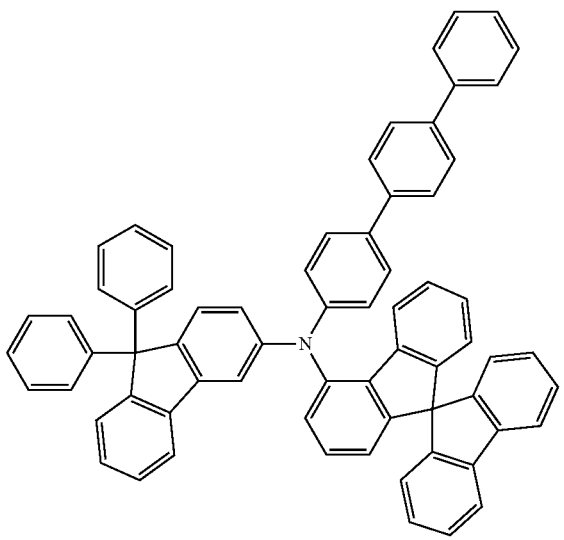
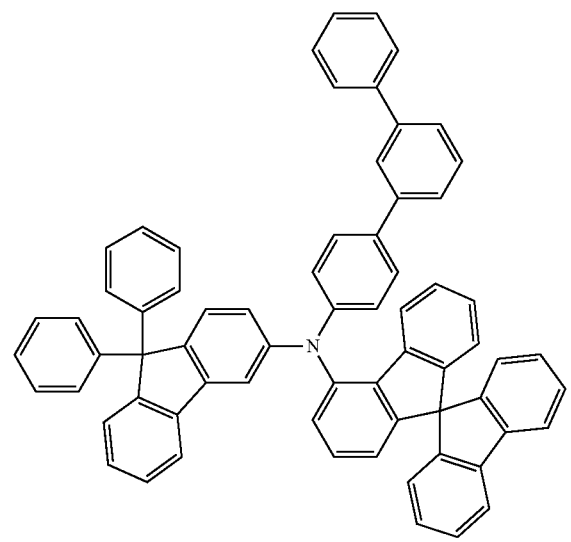
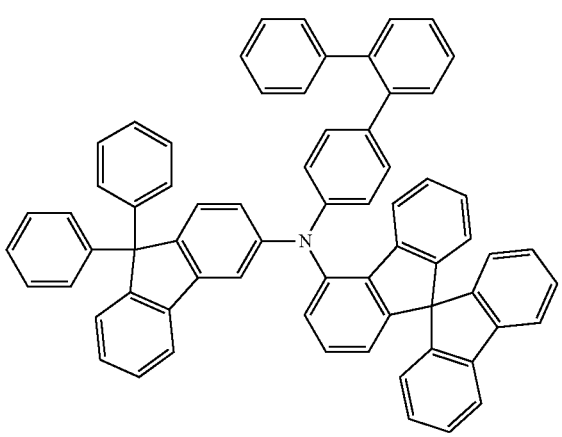
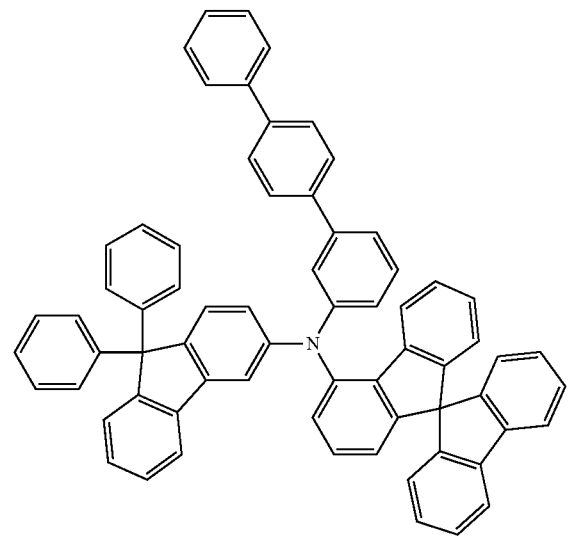
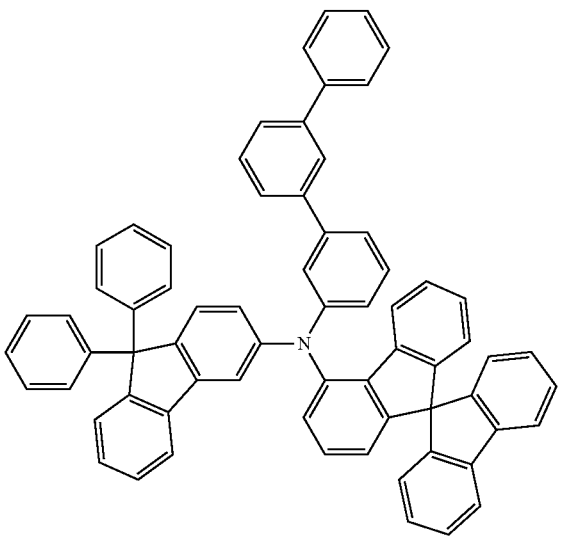

161
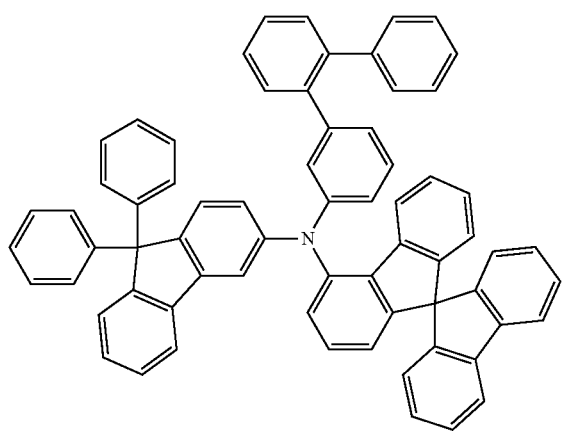
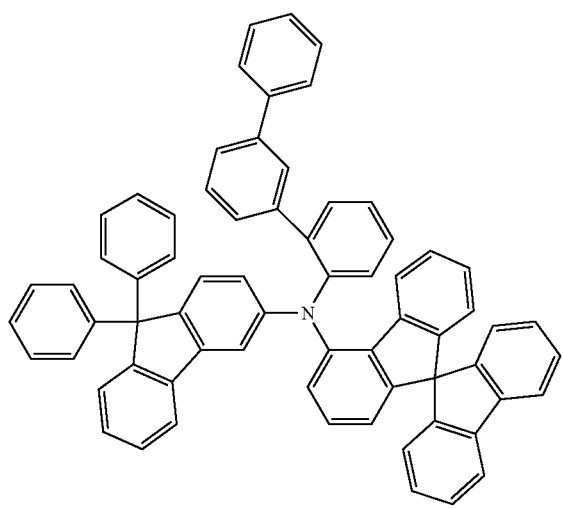
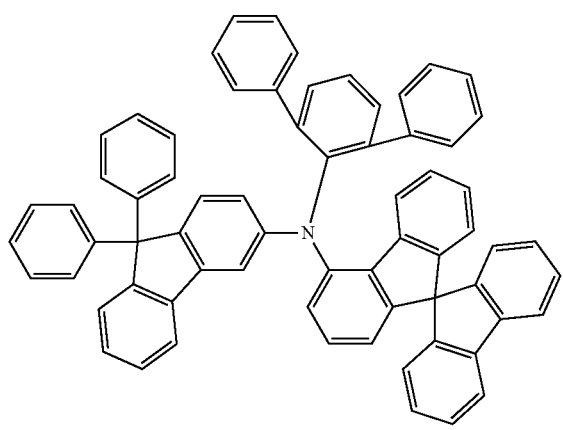
162
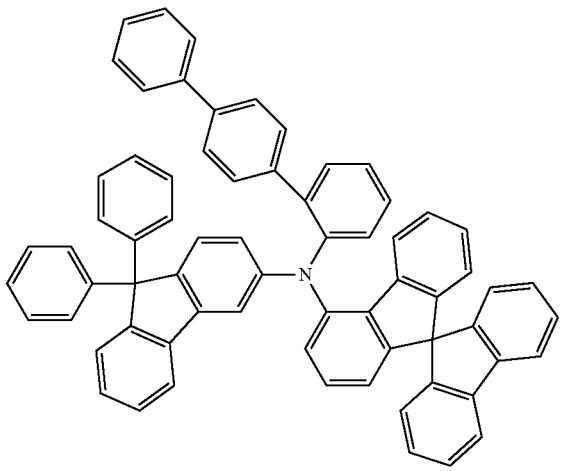
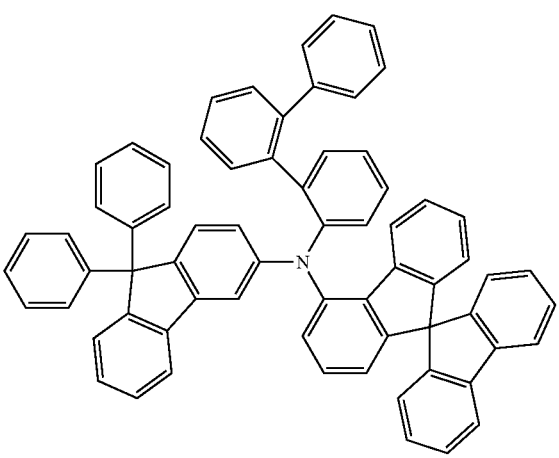
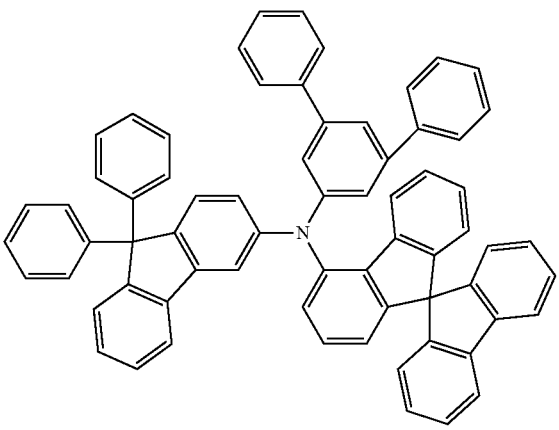

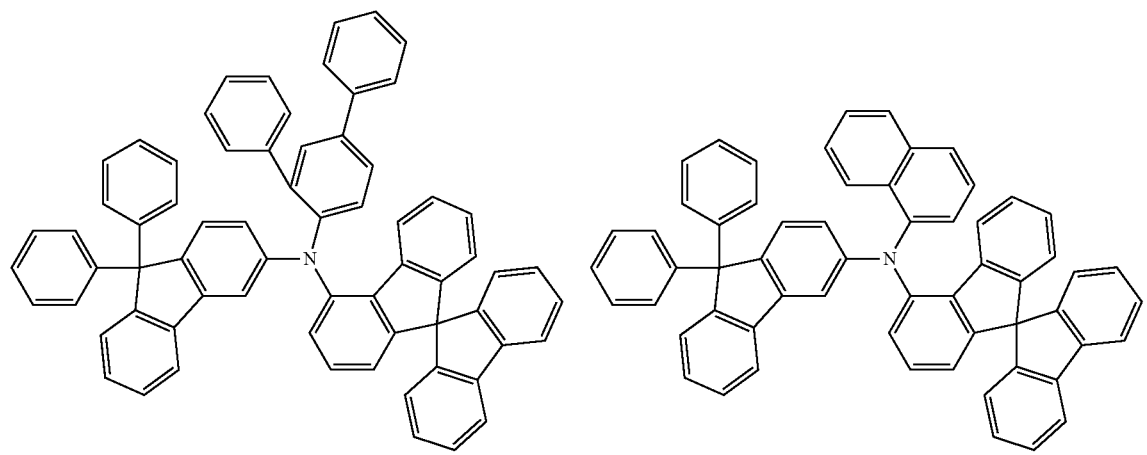
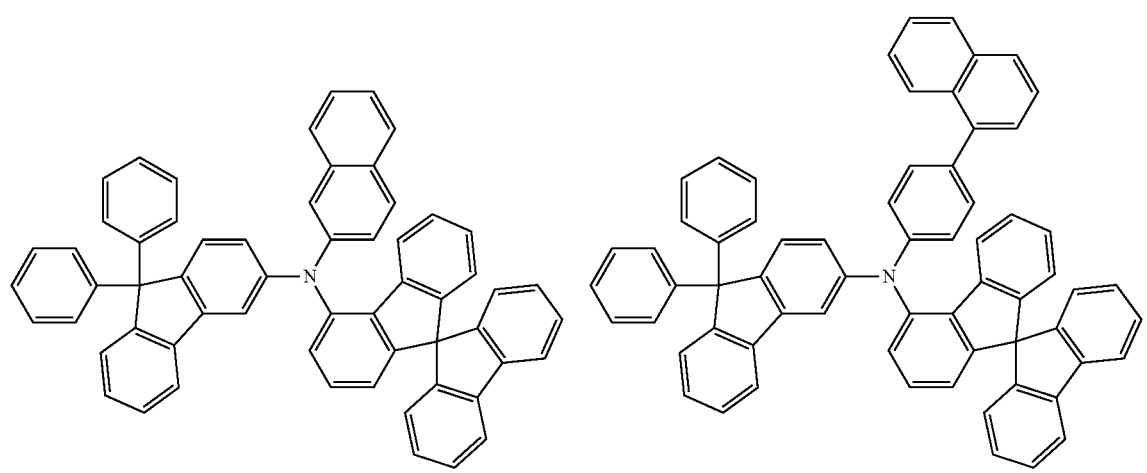
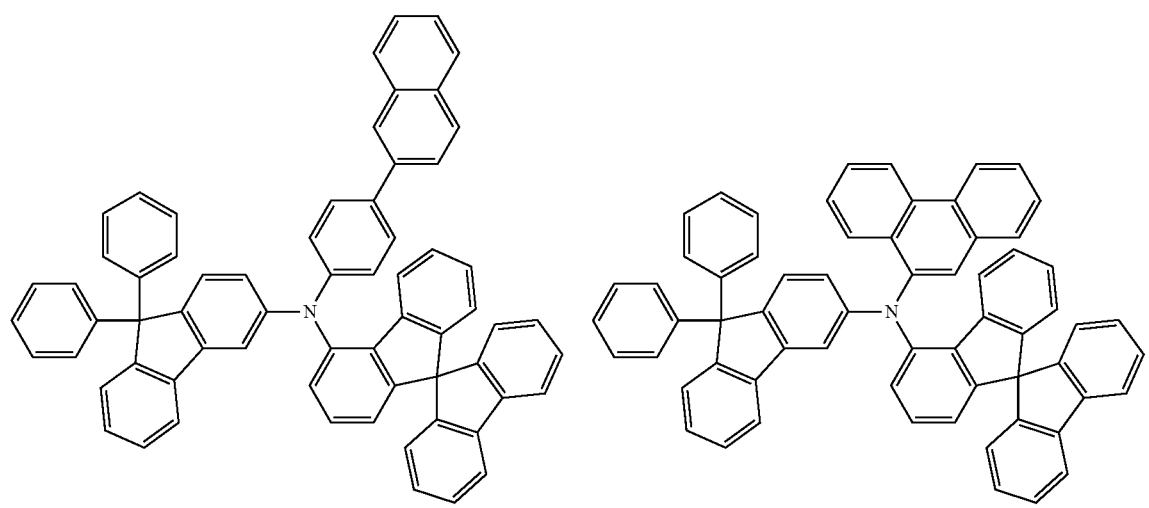

-continued
165
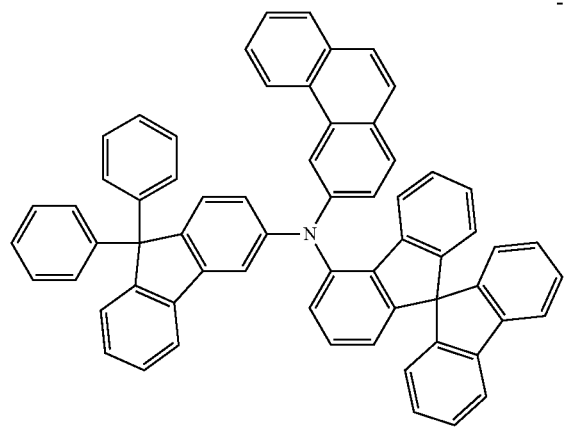
166
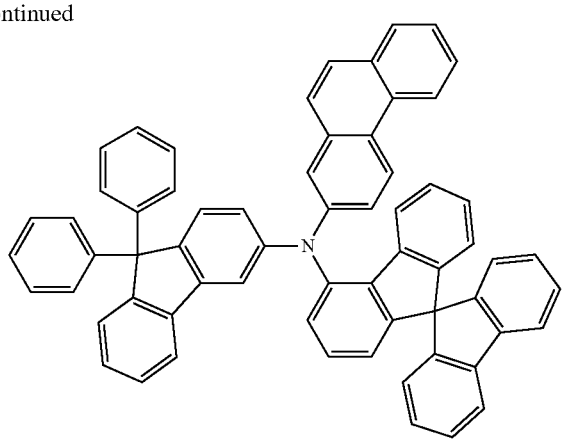
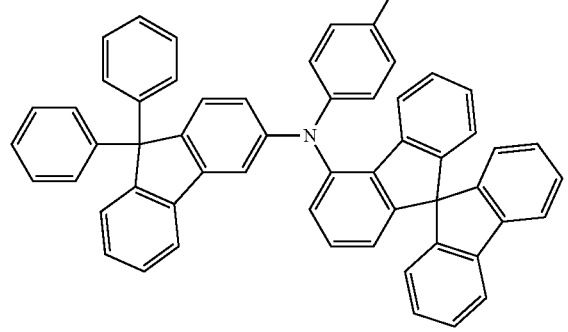
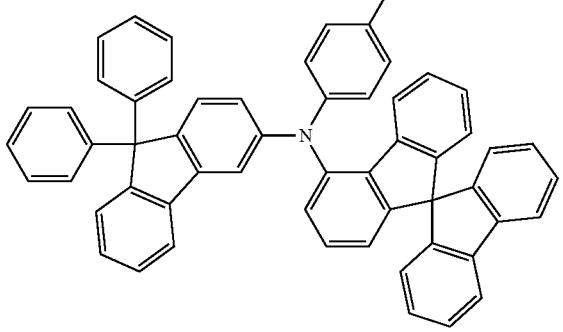
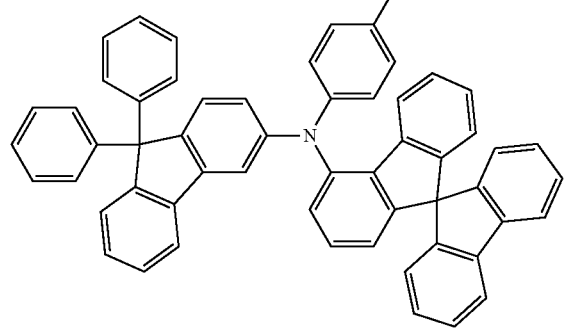
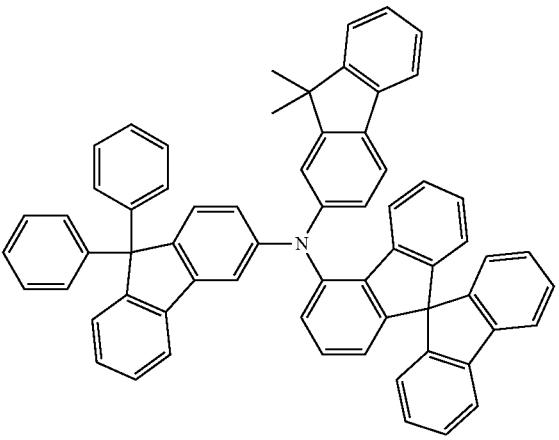

-continued
| 167 | 168 |
|---|---|
| 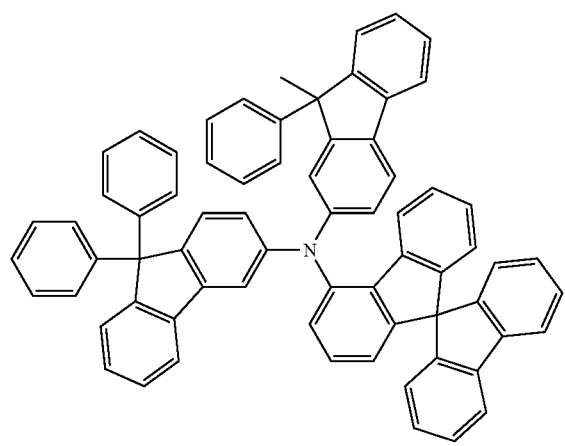 | 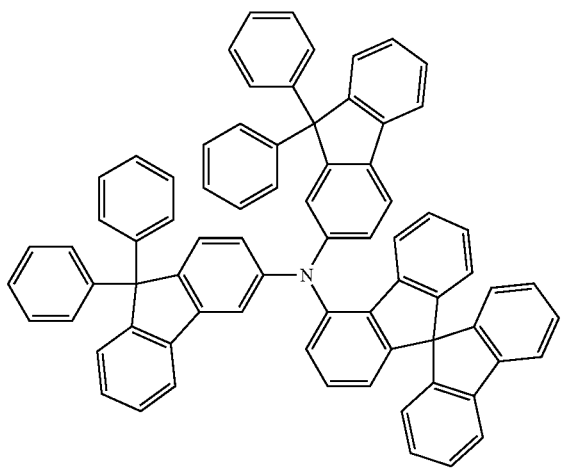 |
| 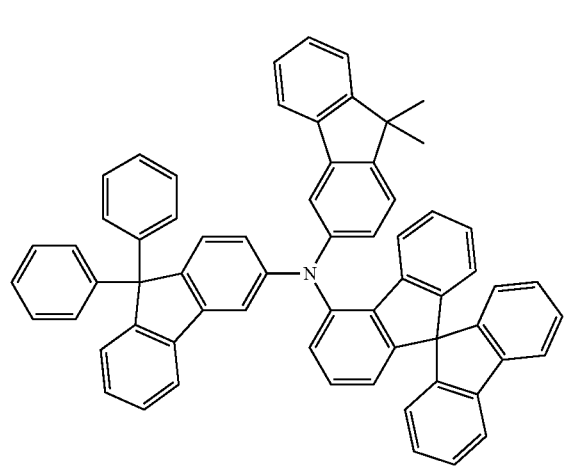 | 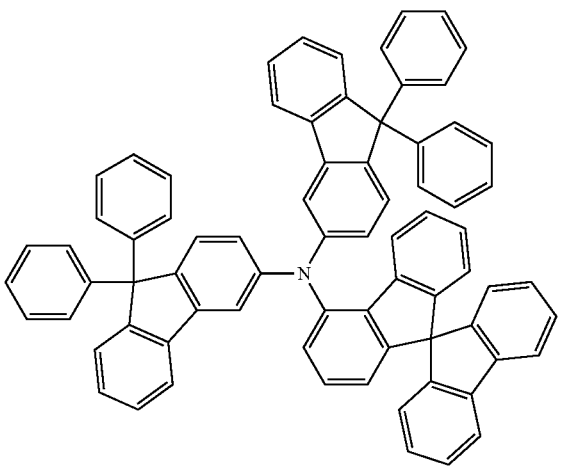 |
| 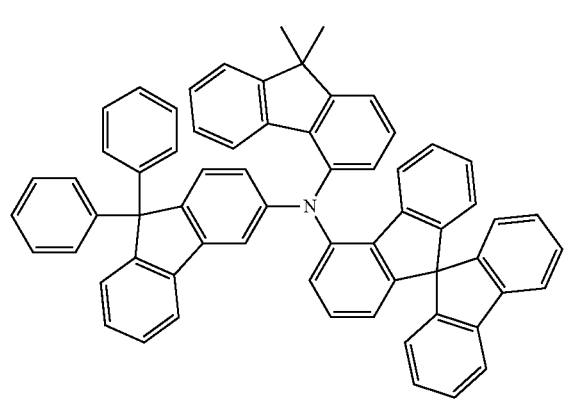 | 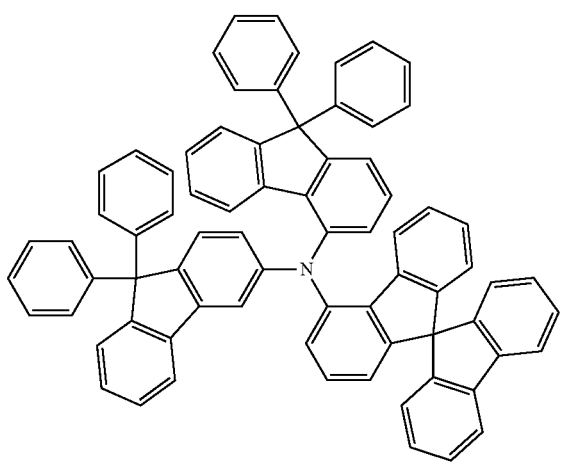 |

-continued
| 169 | 170 |
|---|---|
| 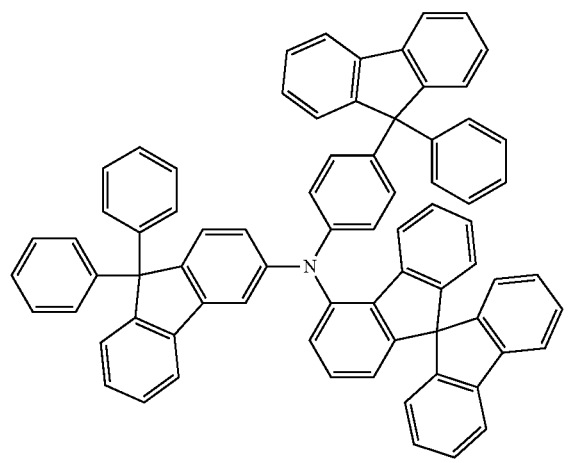 | 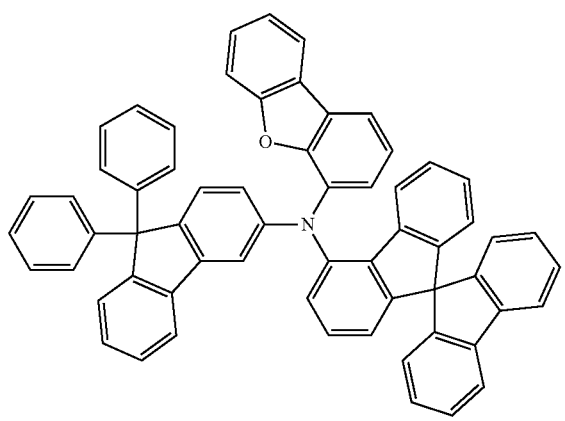 |
| 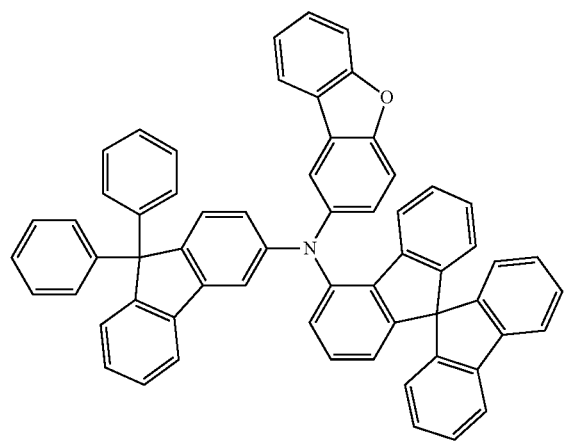 | 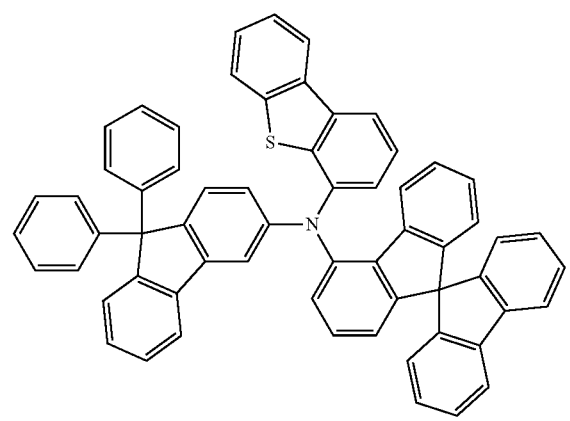 |
| 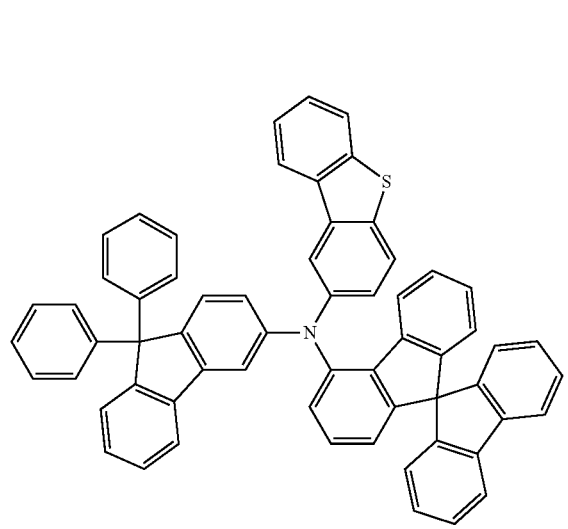 | 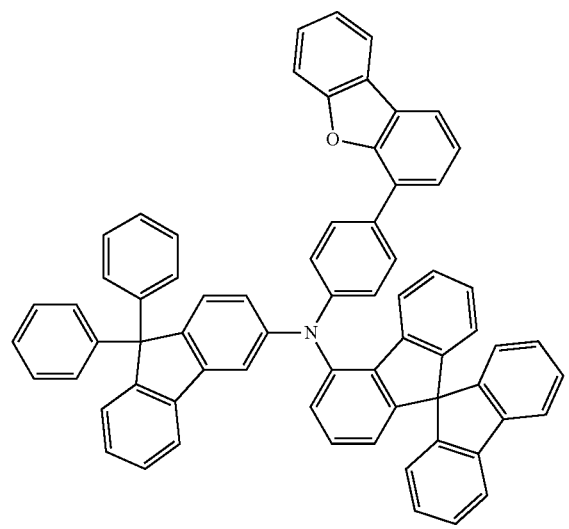 |

-continued
171
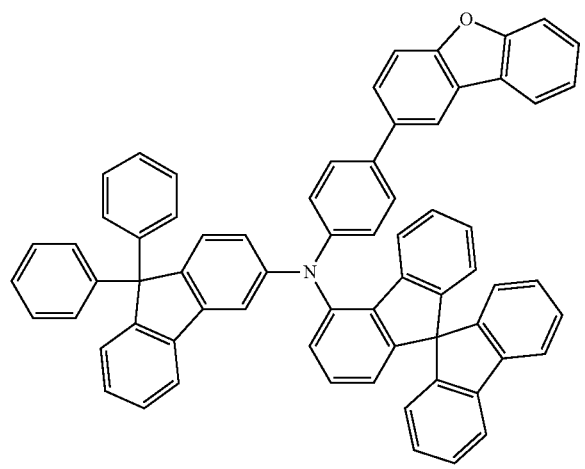
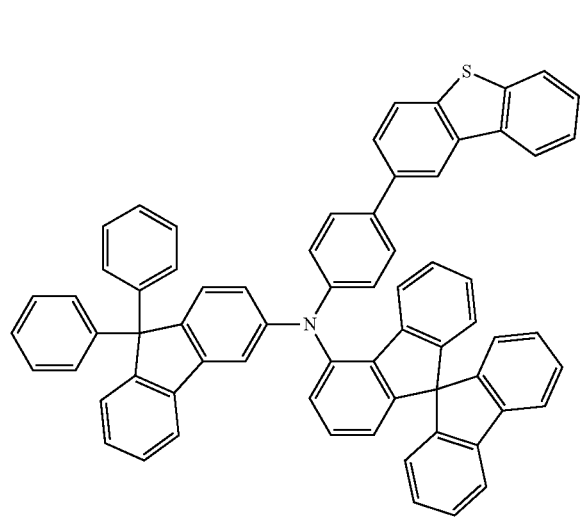
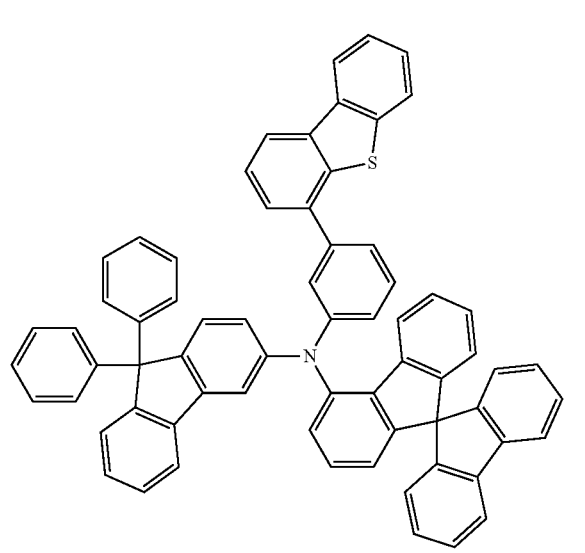
172
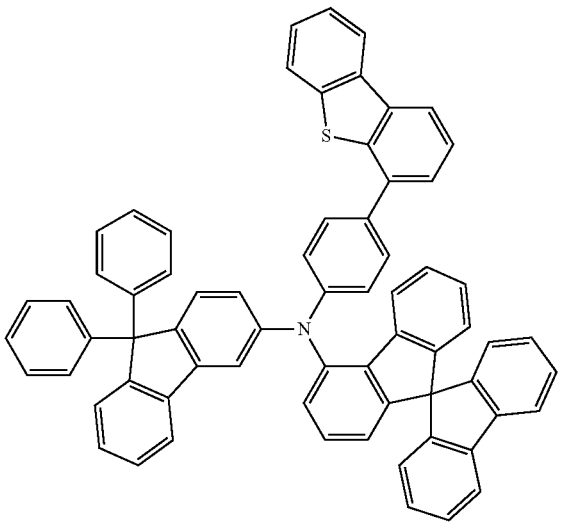
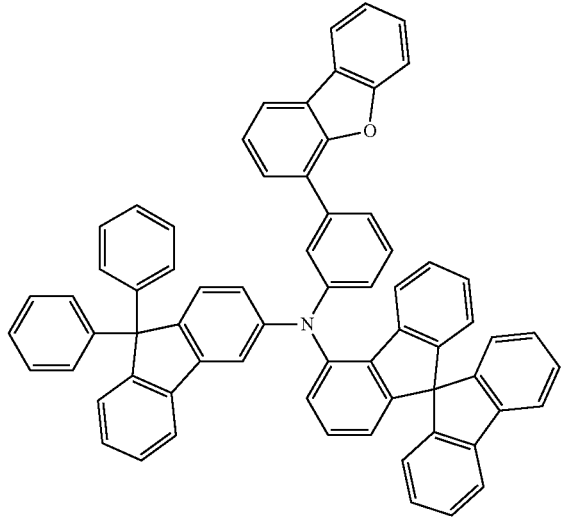
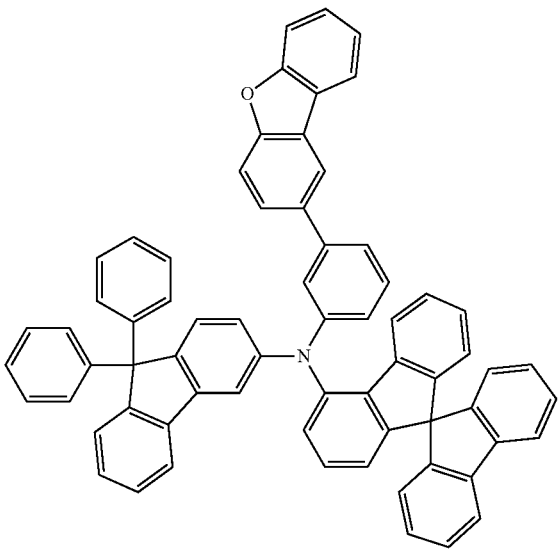

-continued
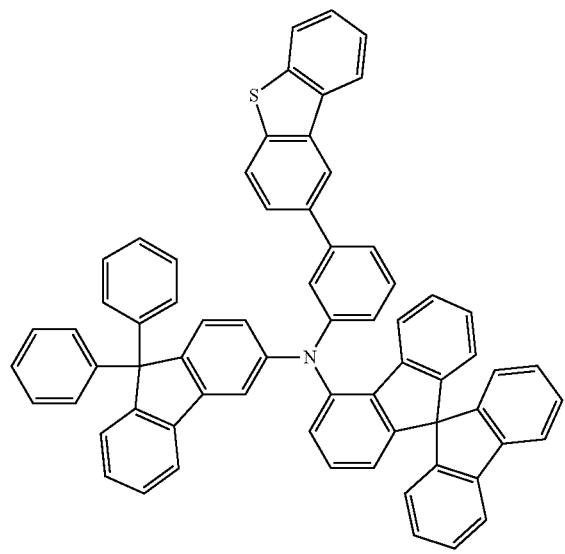
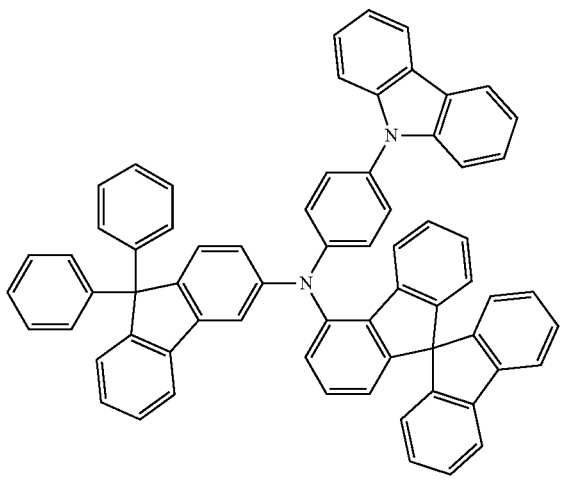
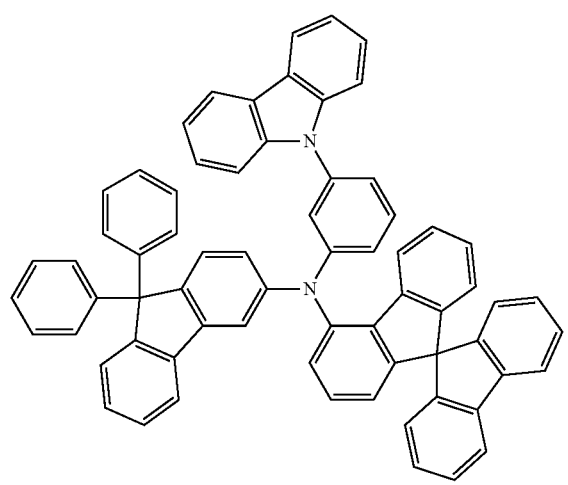
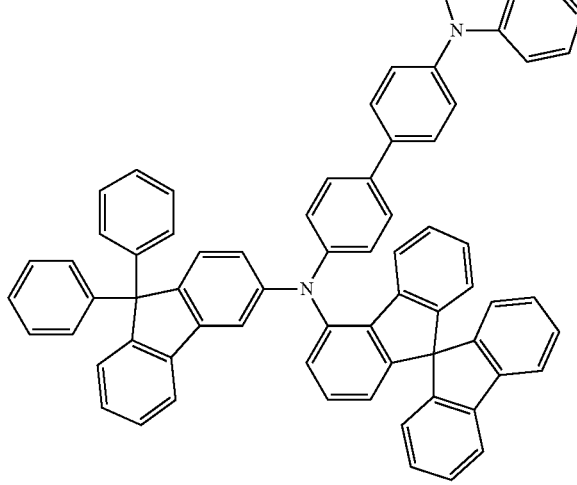
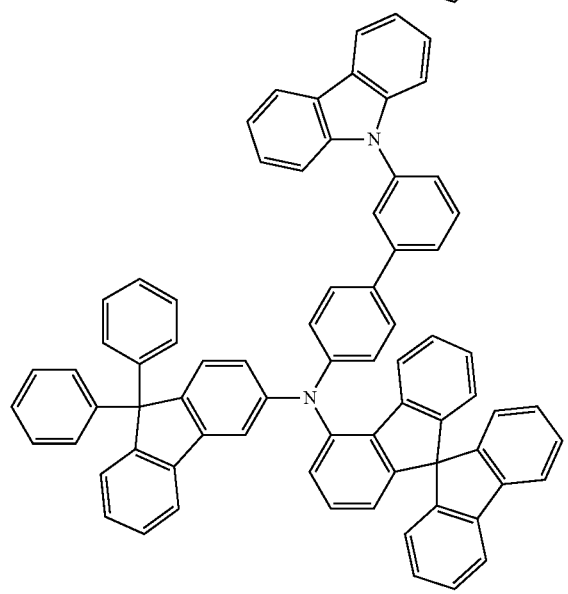
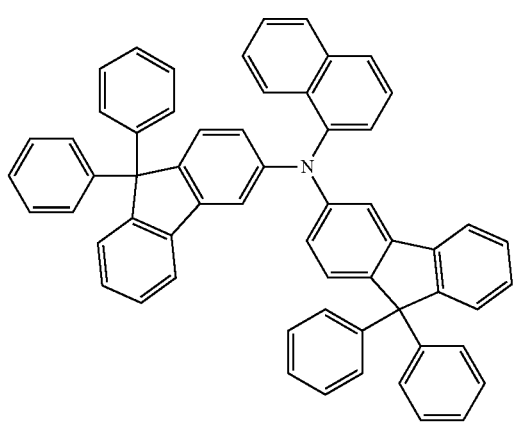

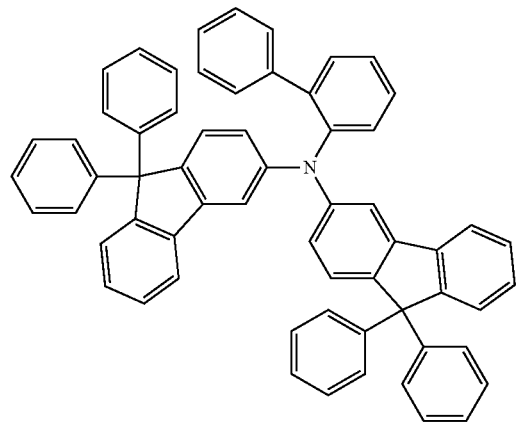
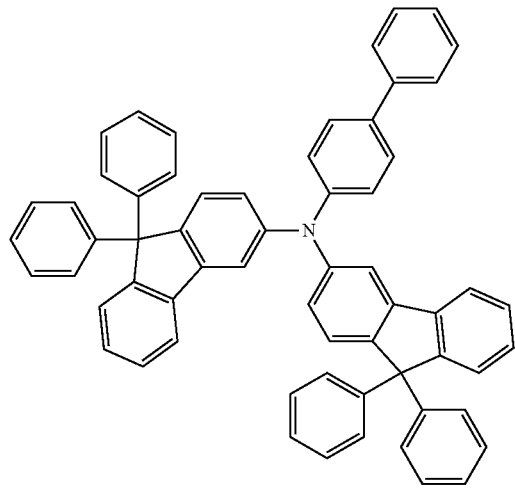
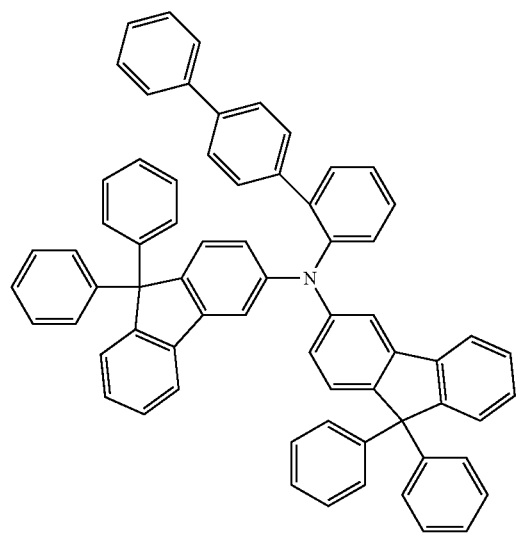
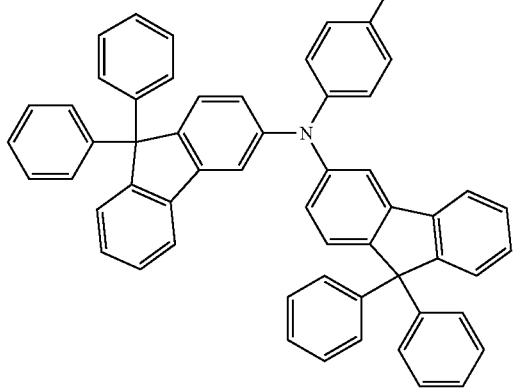
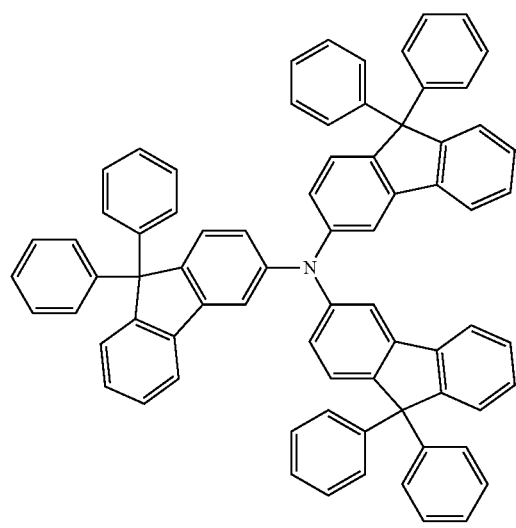
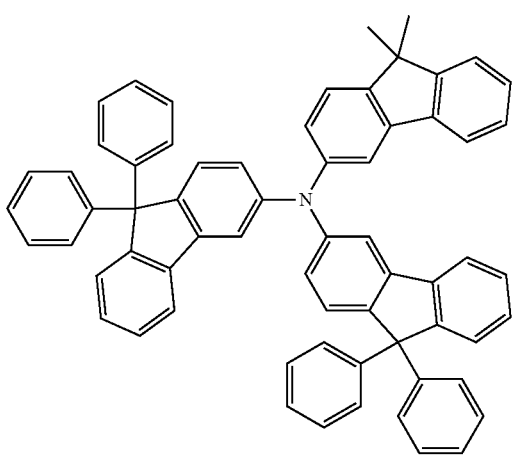

-continued
177
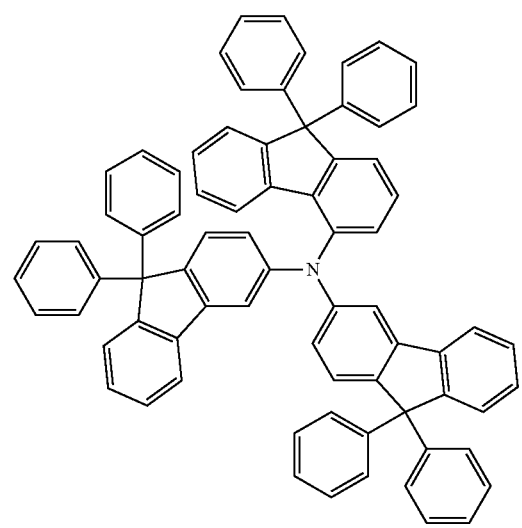
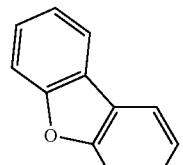
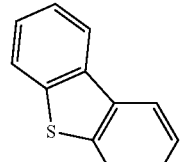
178
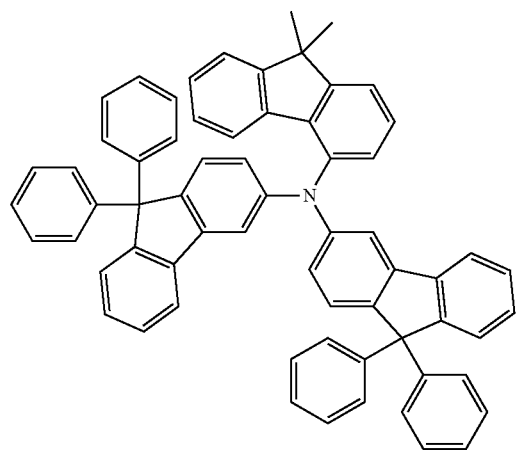
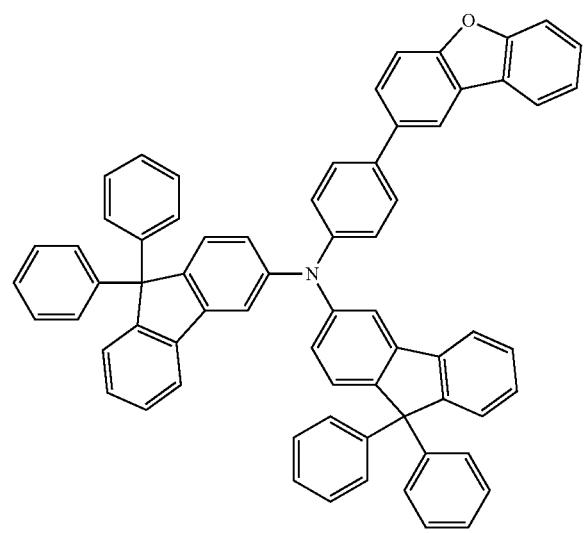
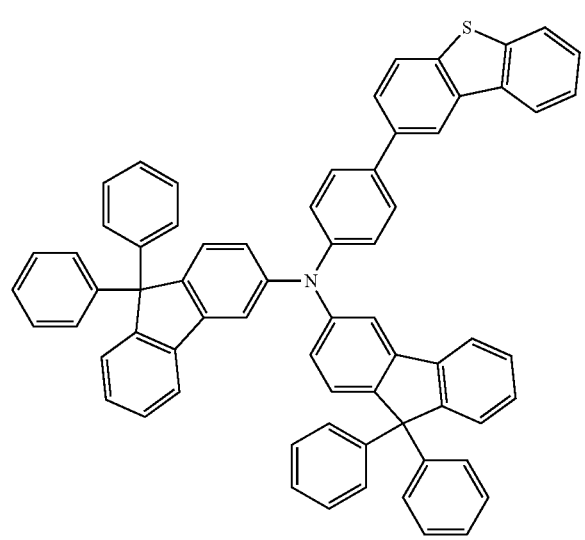

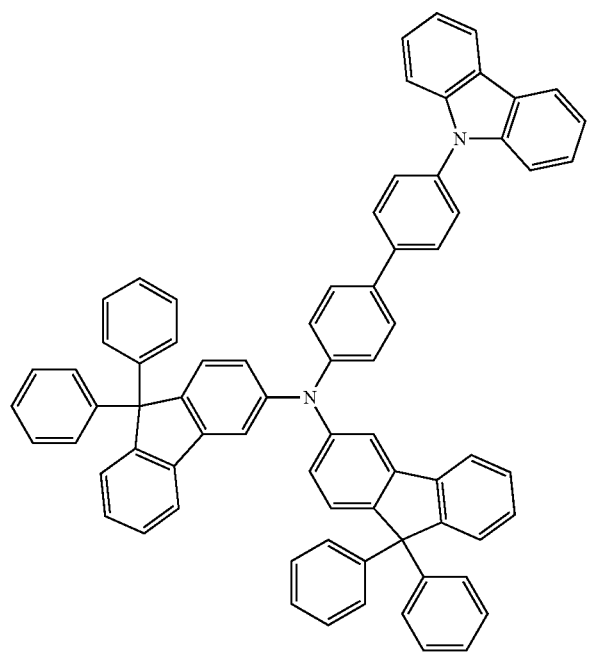
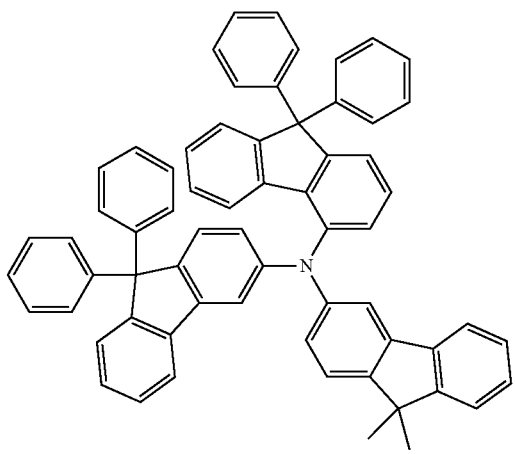
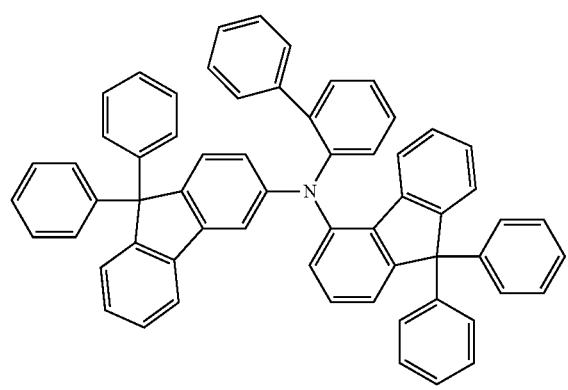
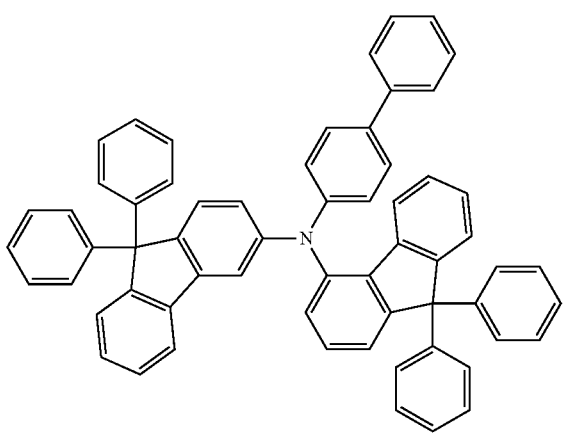
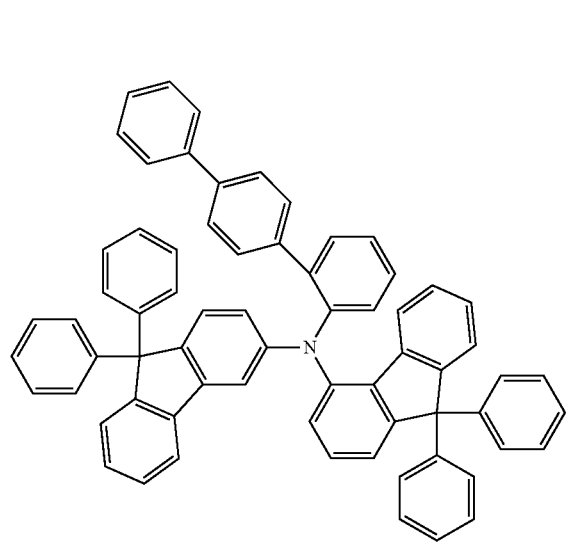
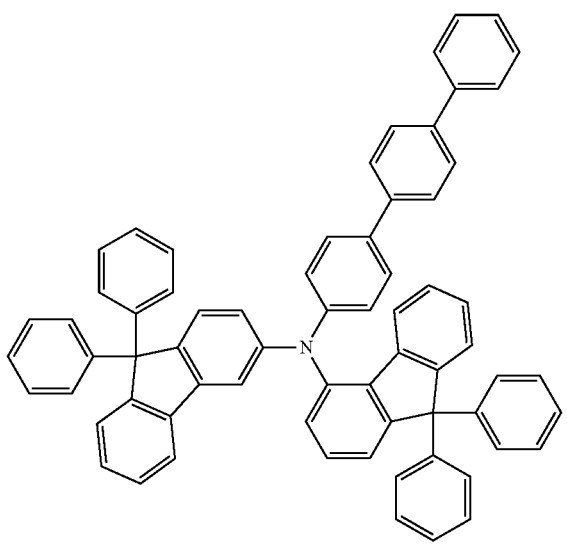

181
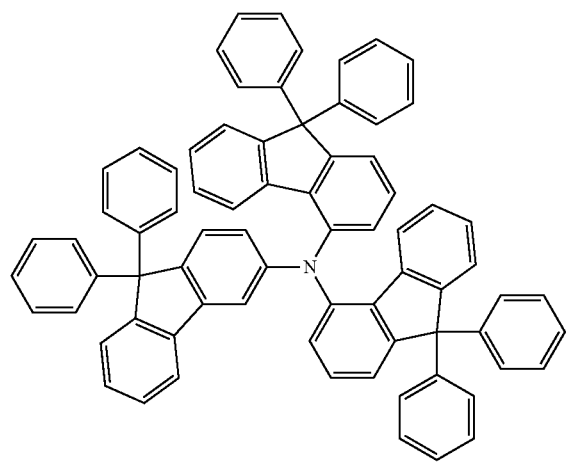
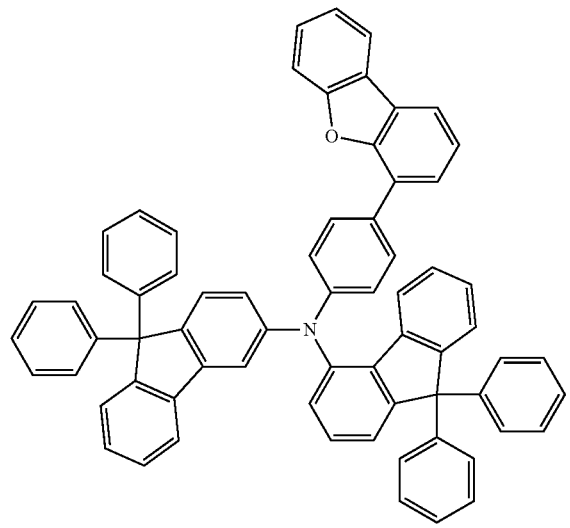
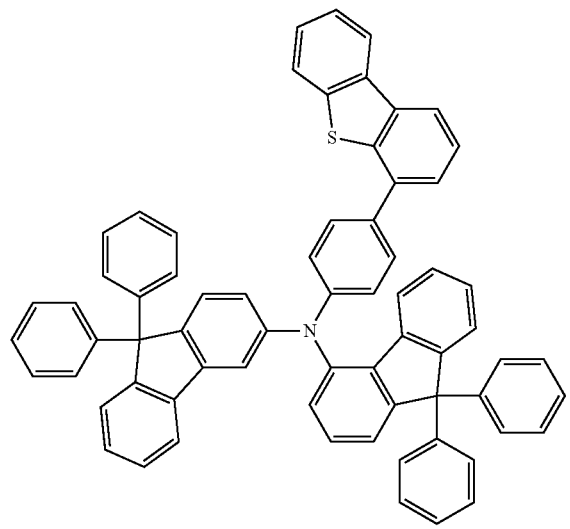
182
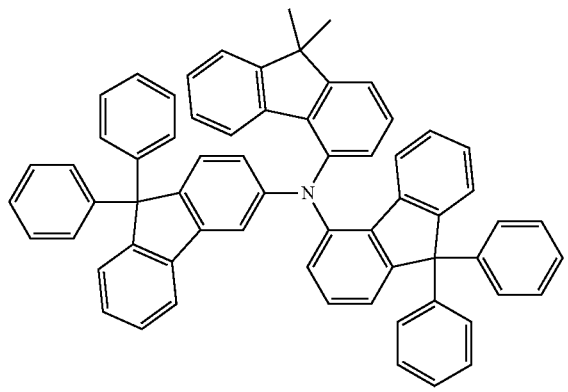
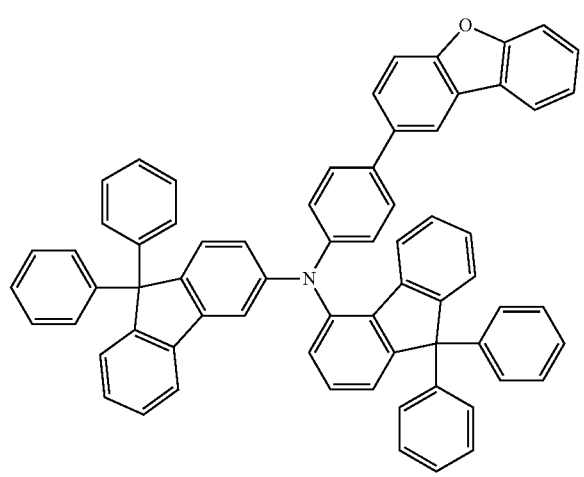
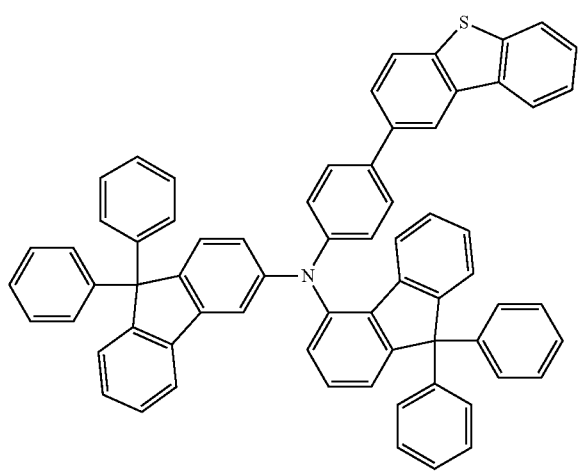

183
184
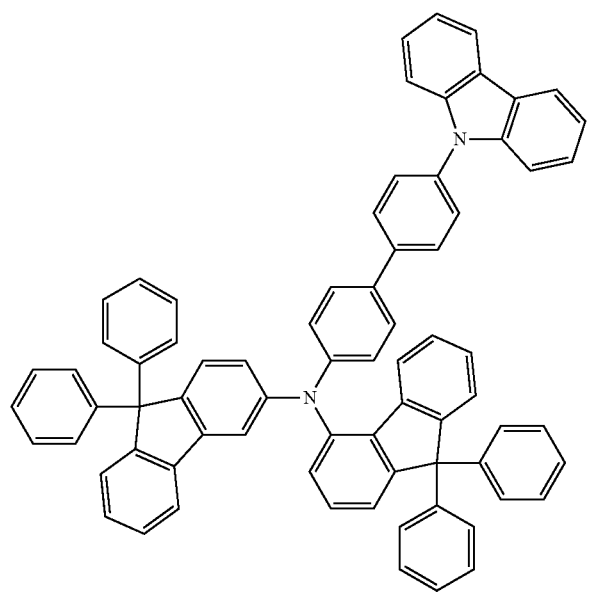
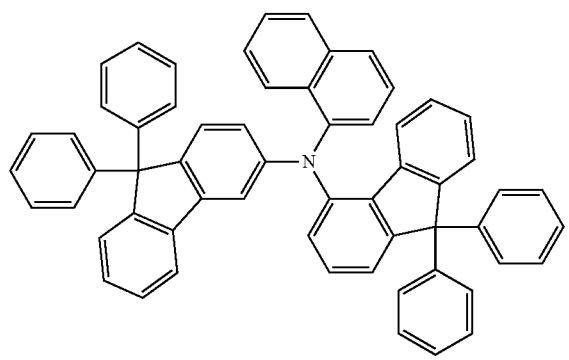
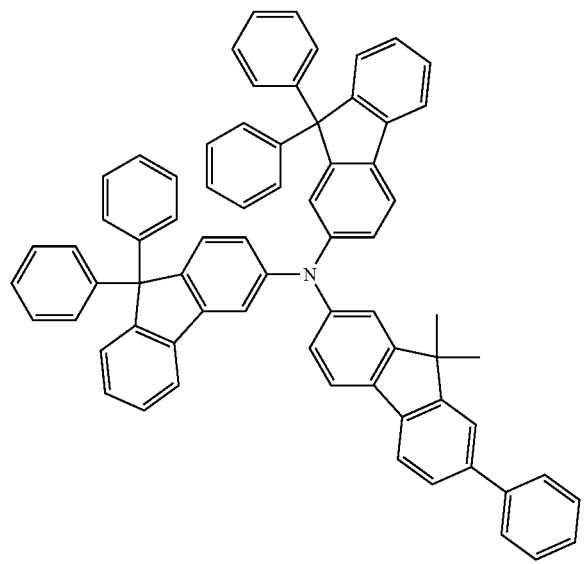
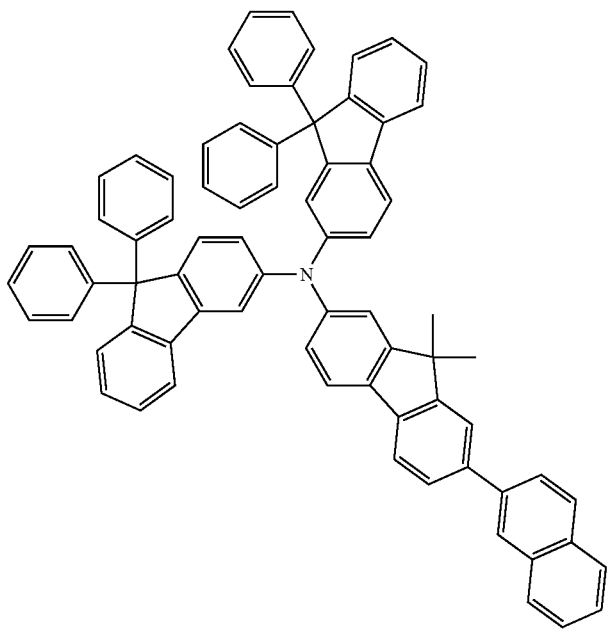

-continued
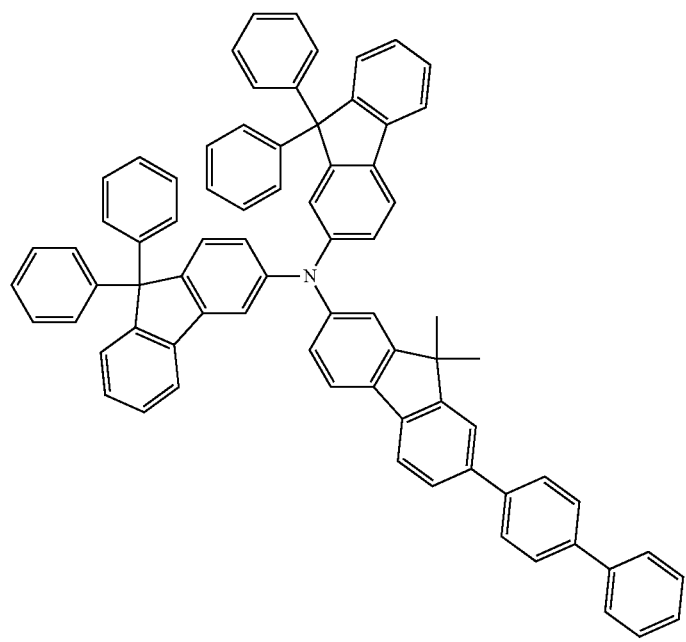
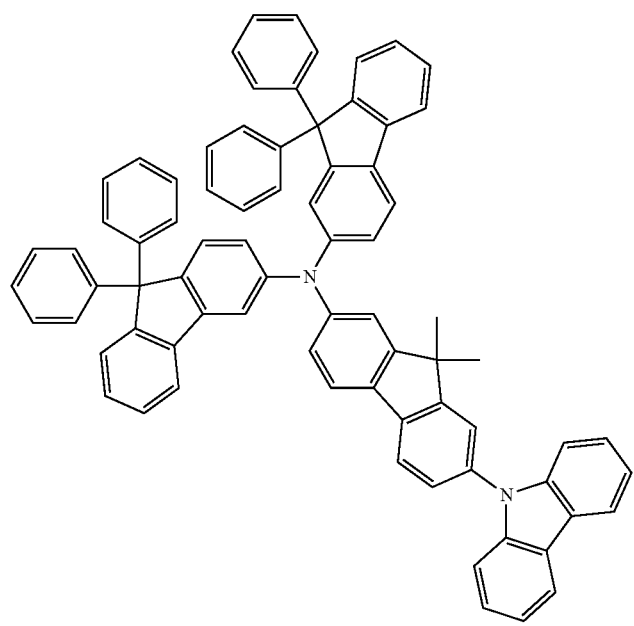
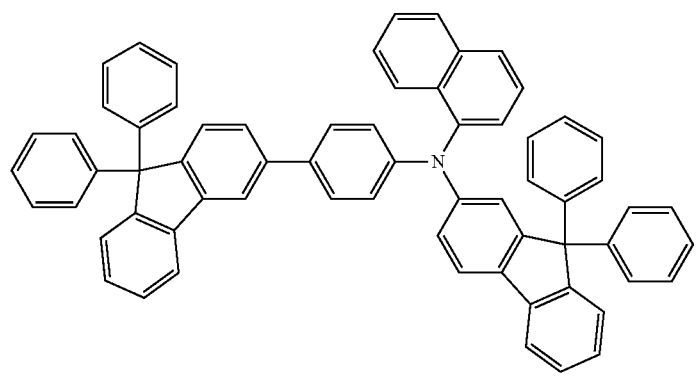

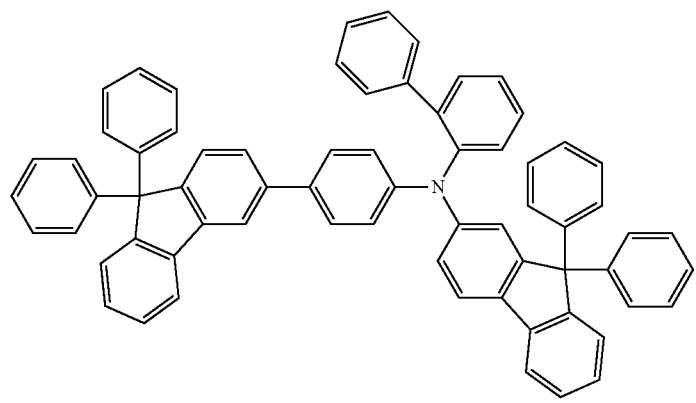
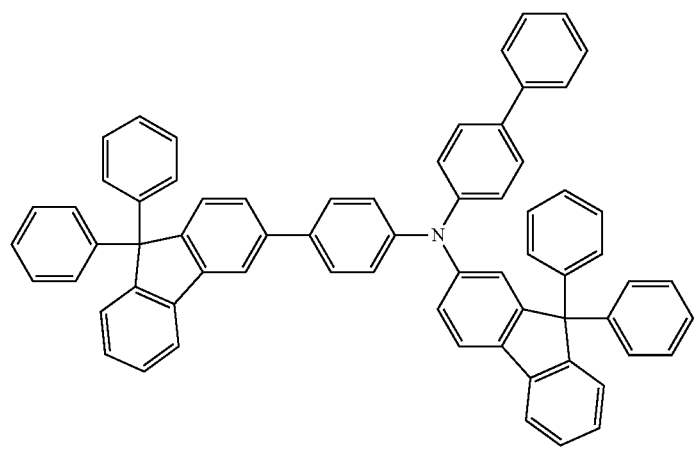
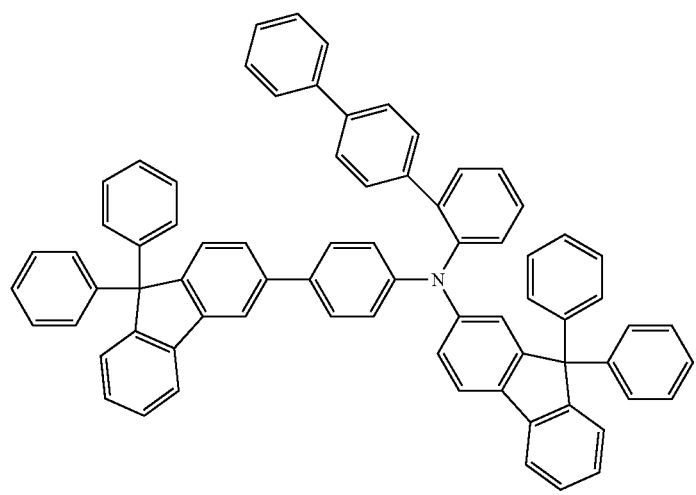

-continued
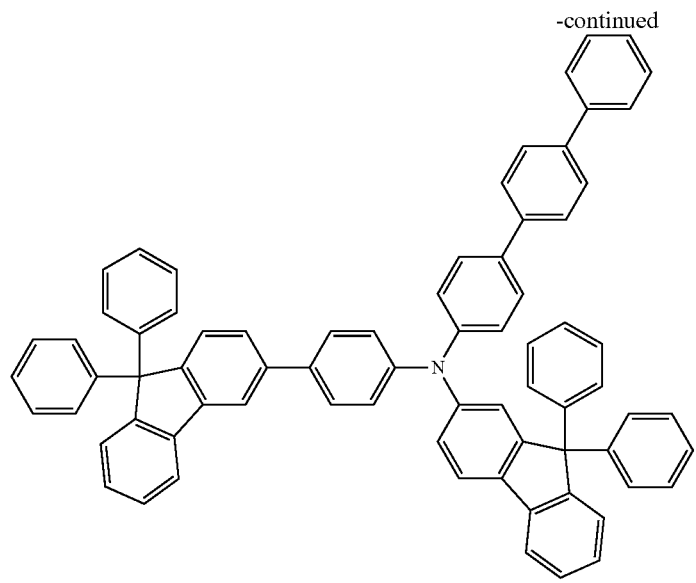
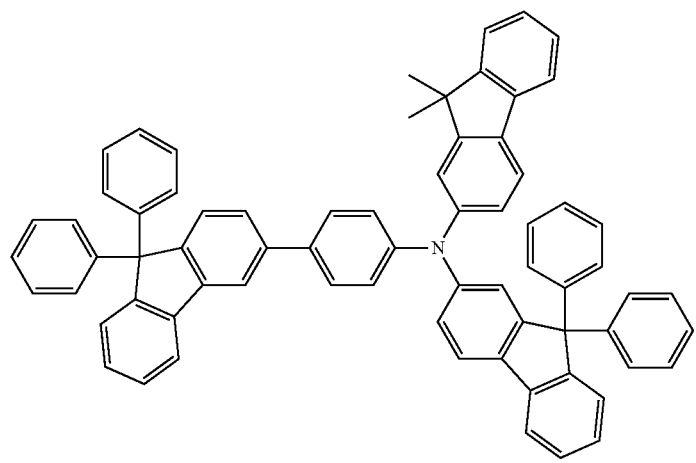
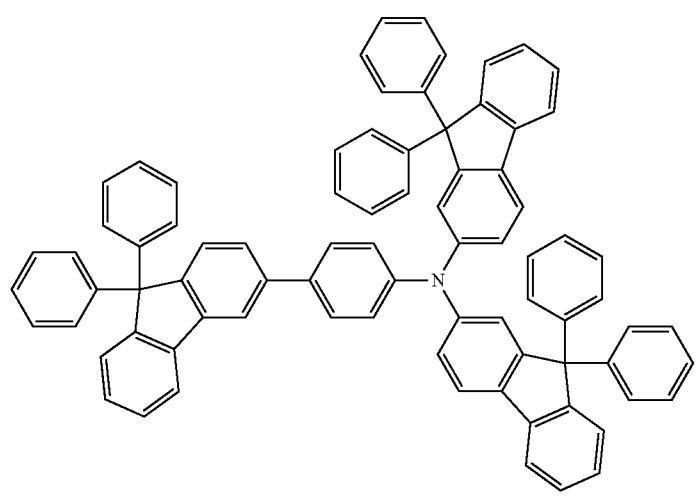

-continued
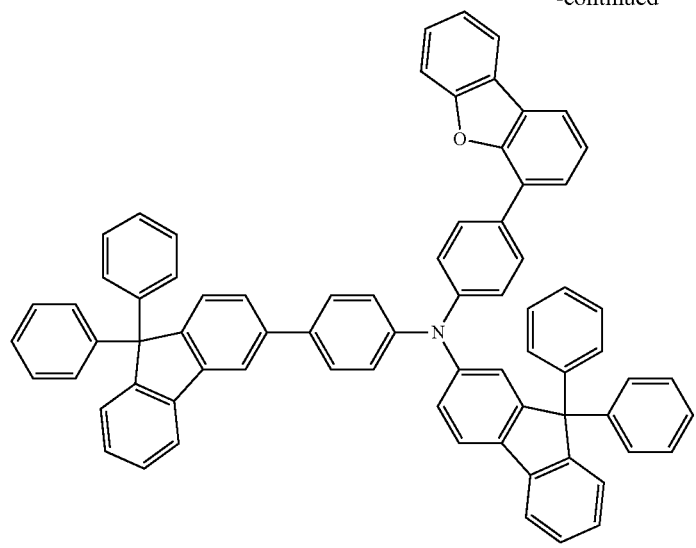
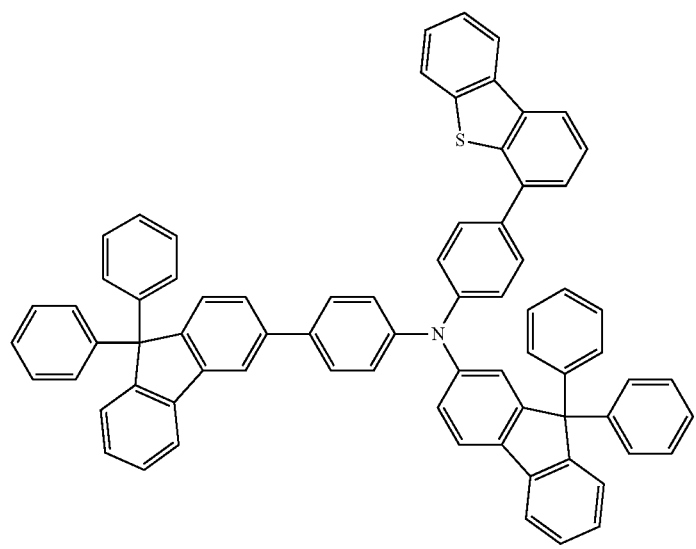
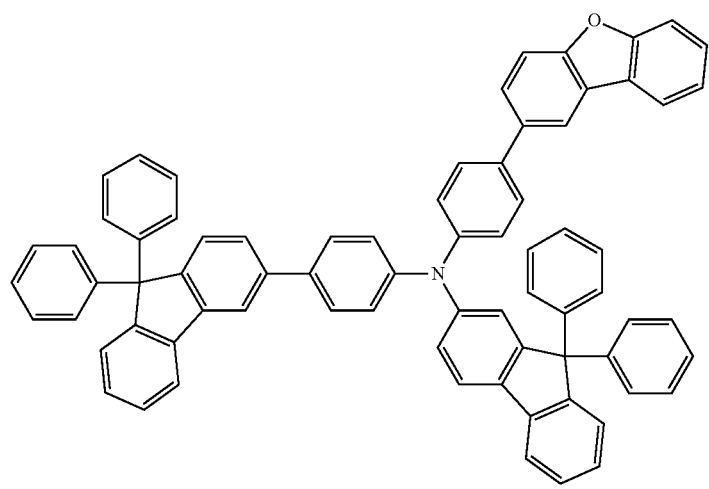

-continued
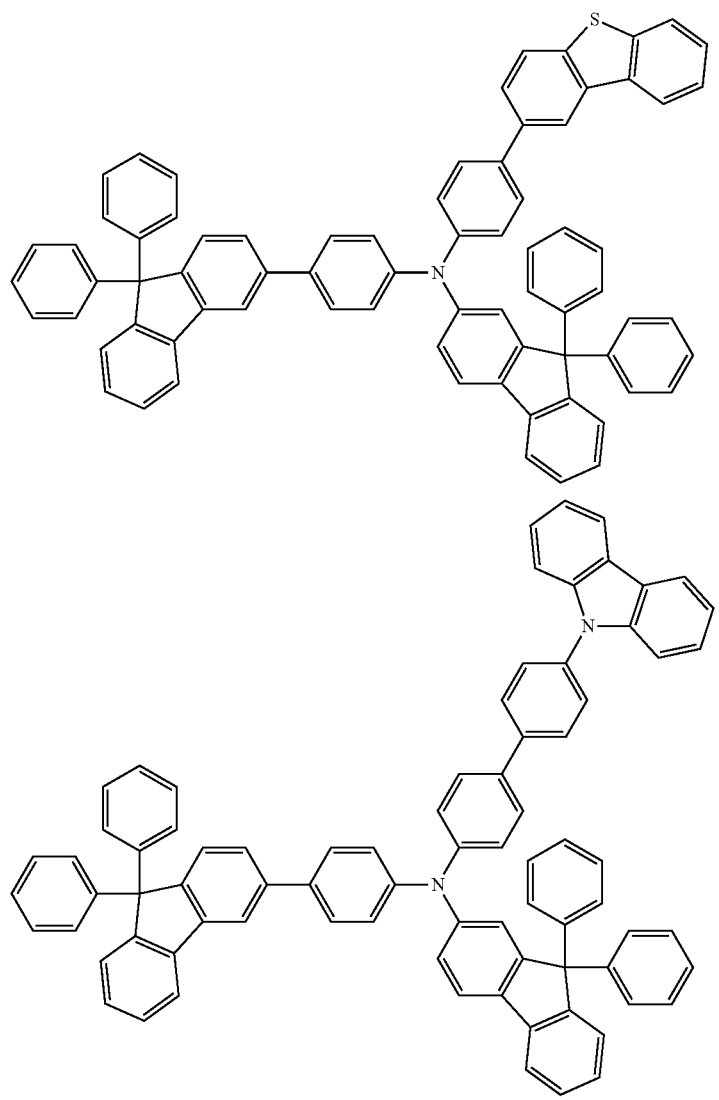
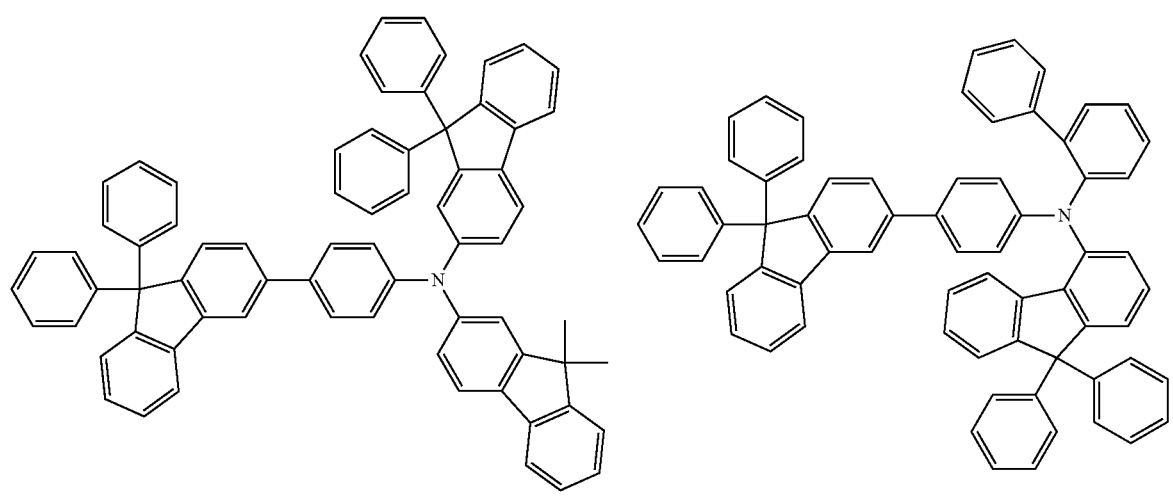

-continued
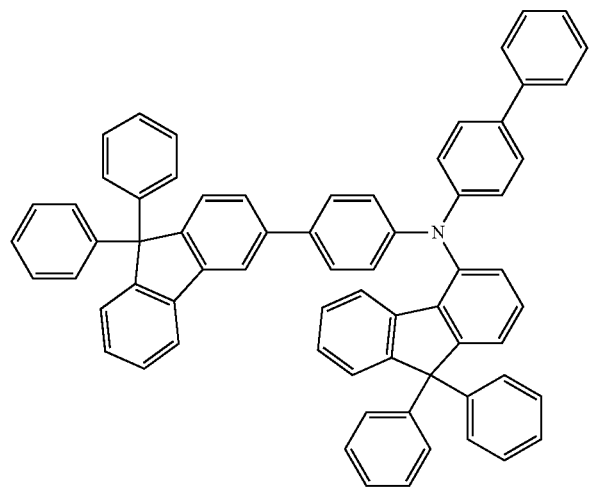
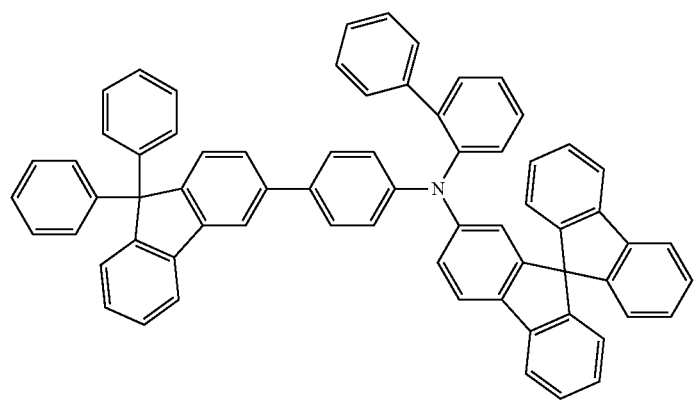
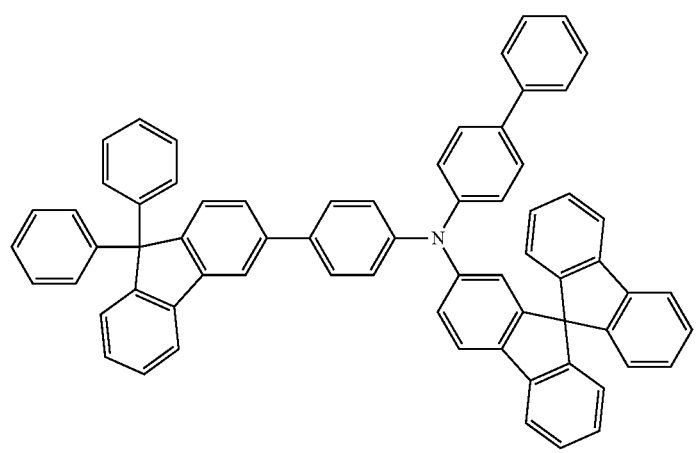

-continued
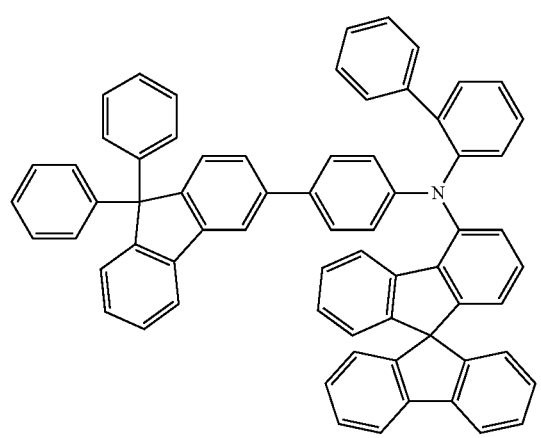
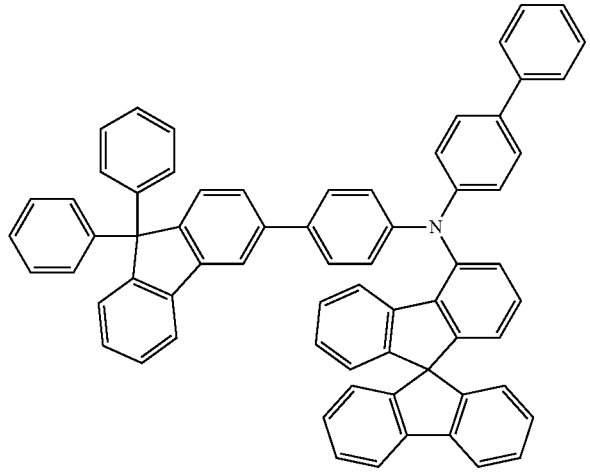
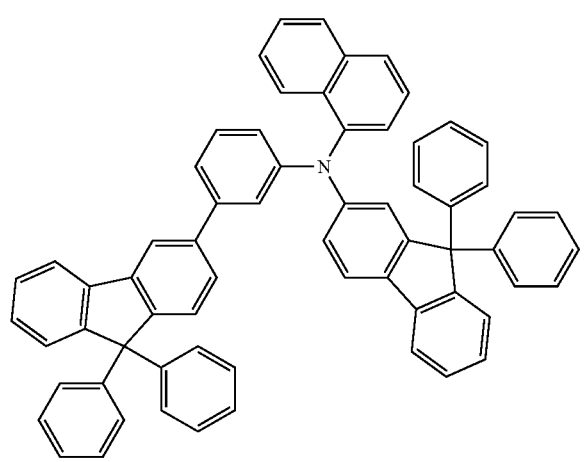
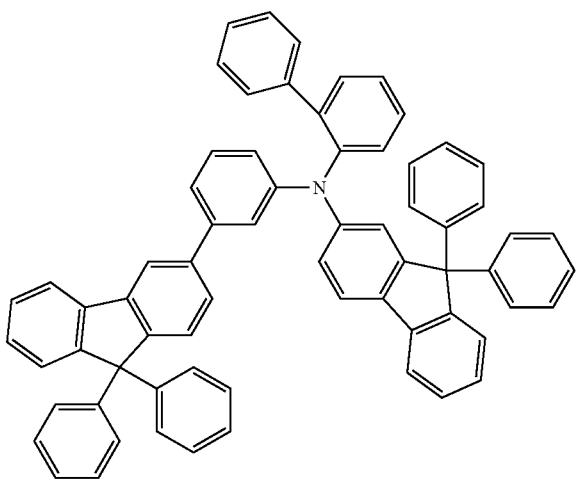
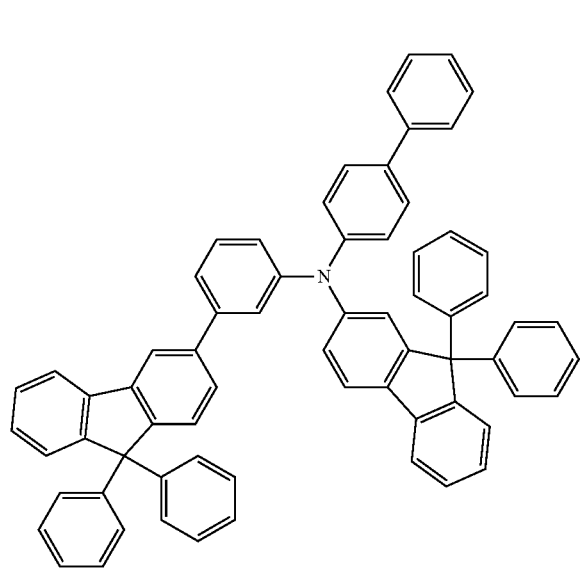
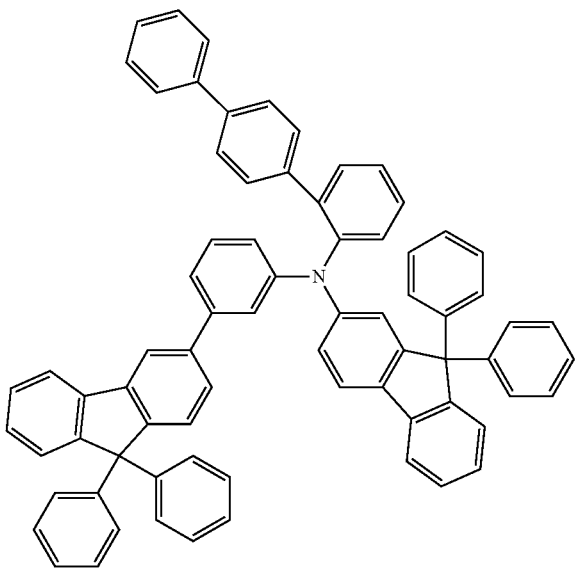

-continued
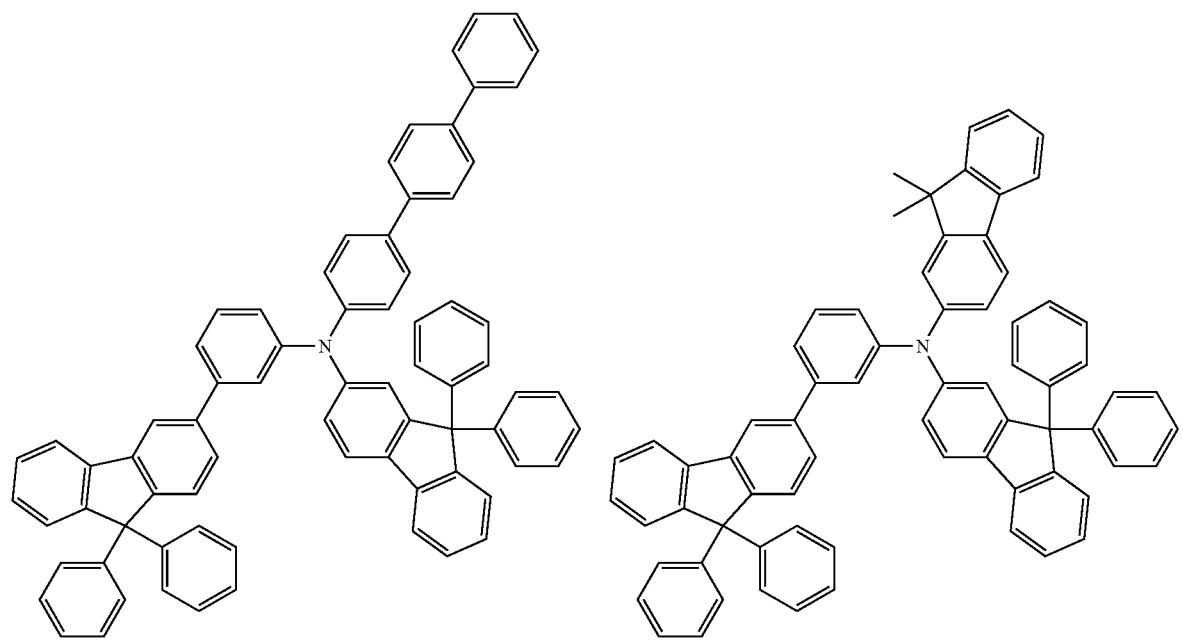
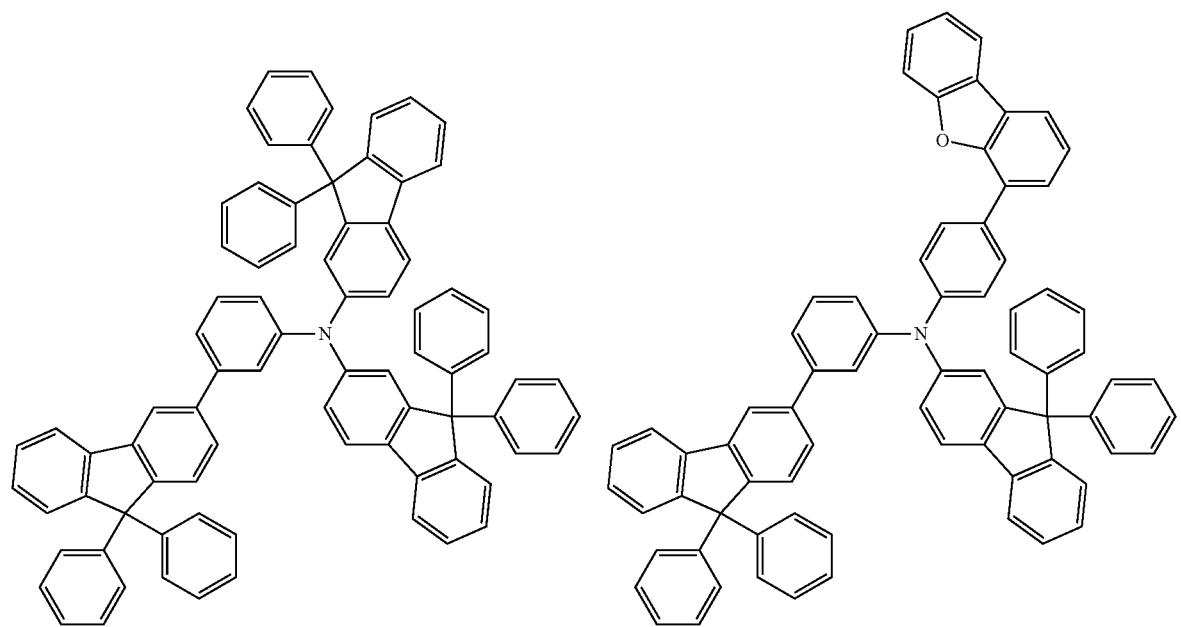

-continued
201
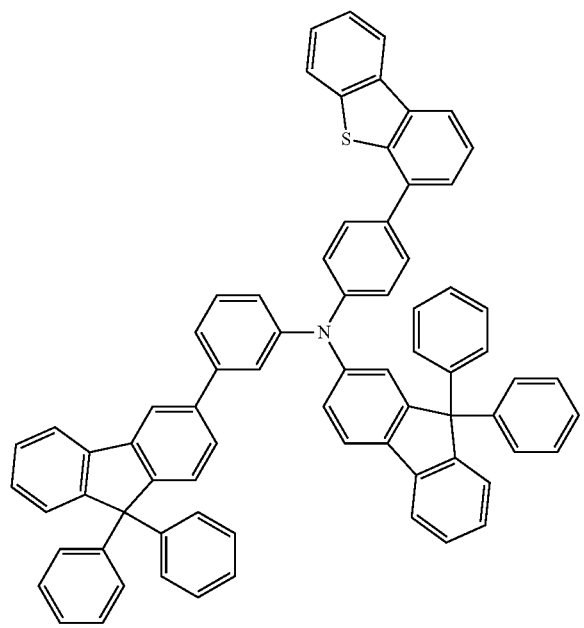
202
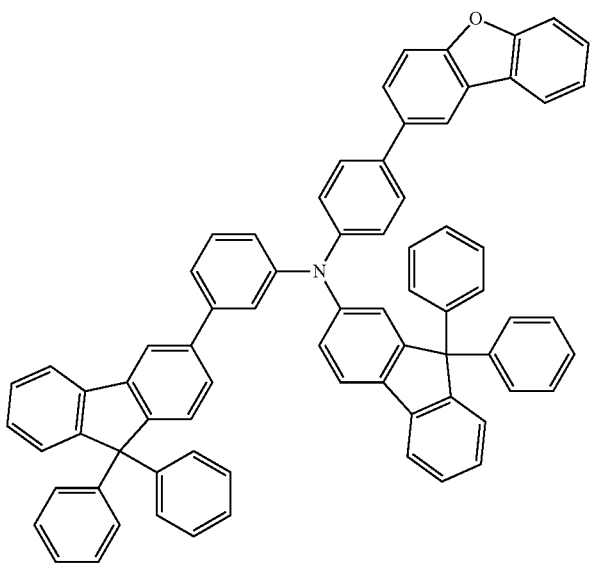
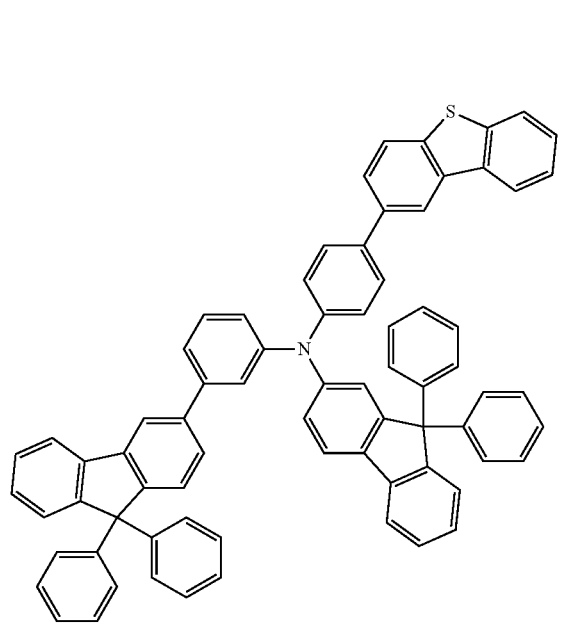
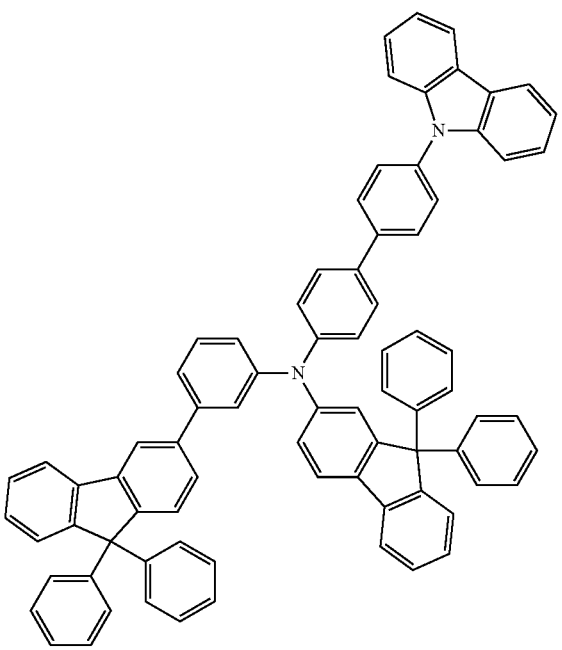

-continued
203
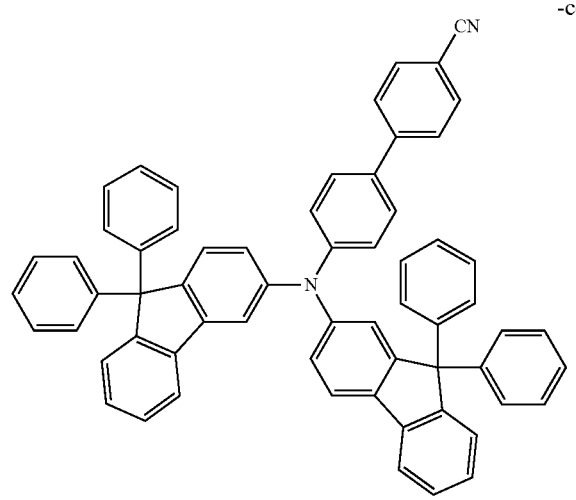
204
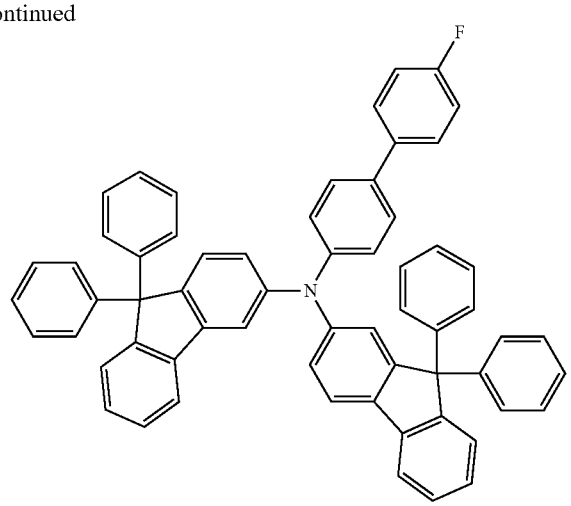
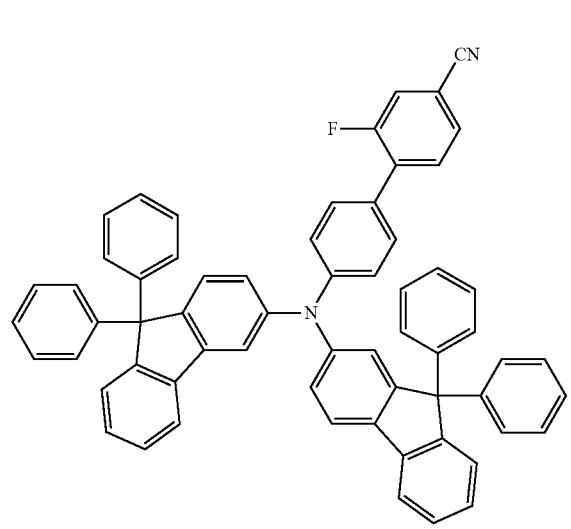
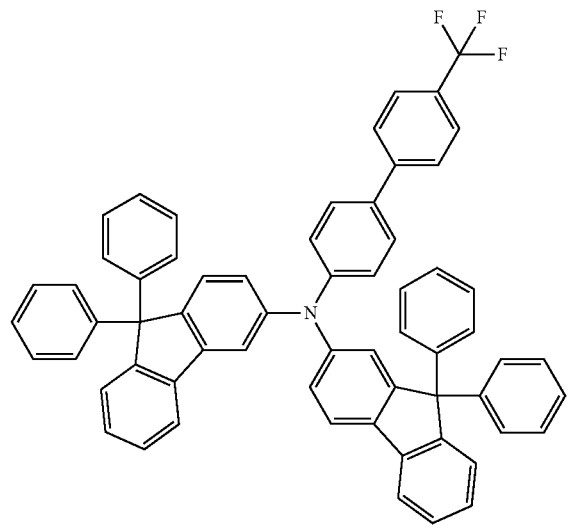
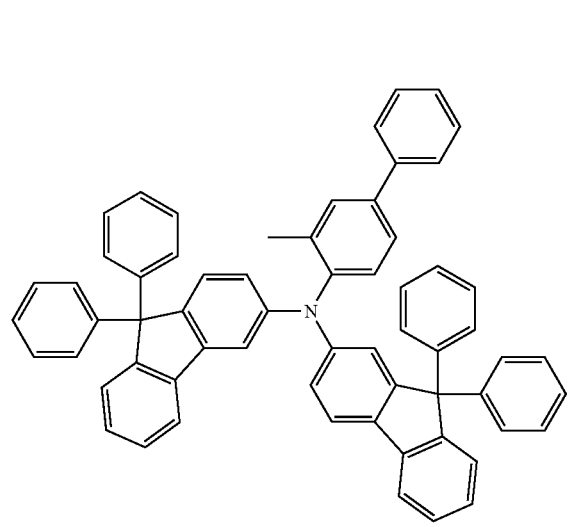
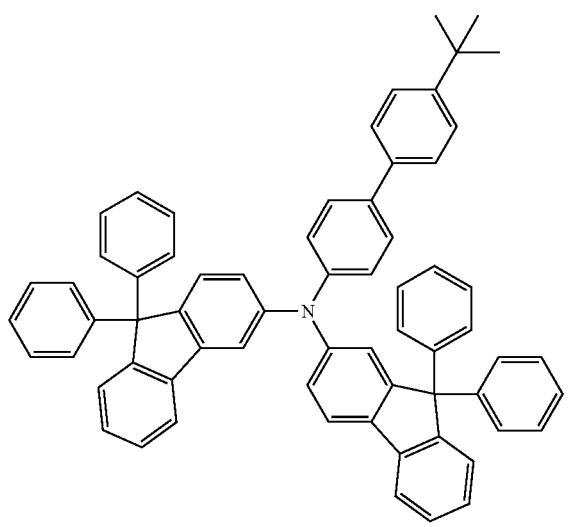

-continued
| 205 | 206 |
|---|---|
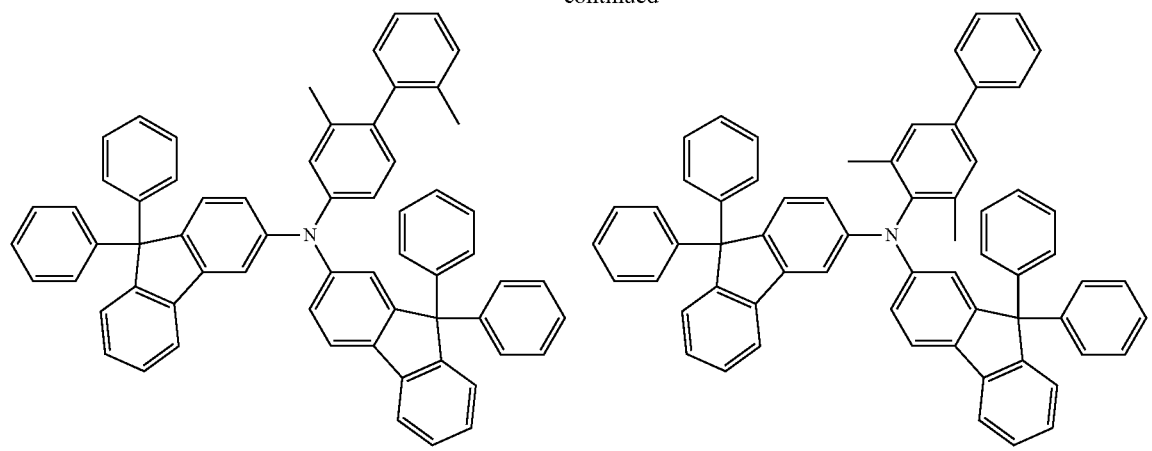
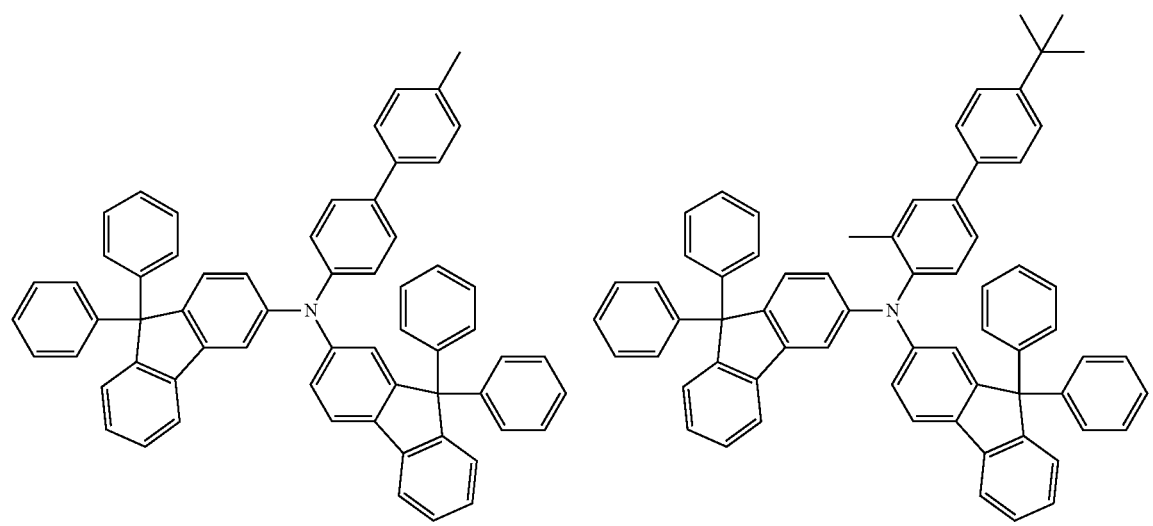
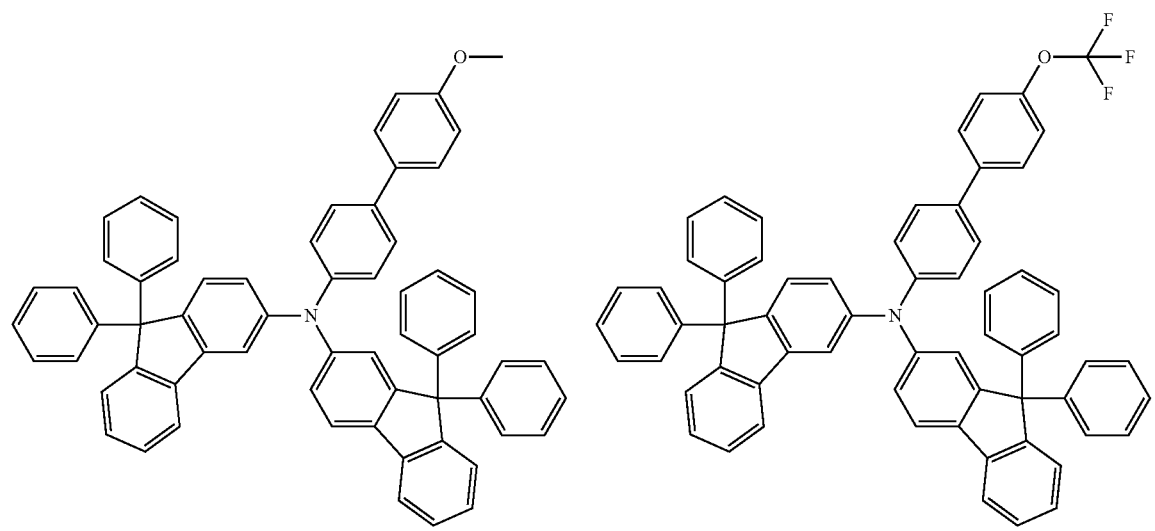

-continued
207
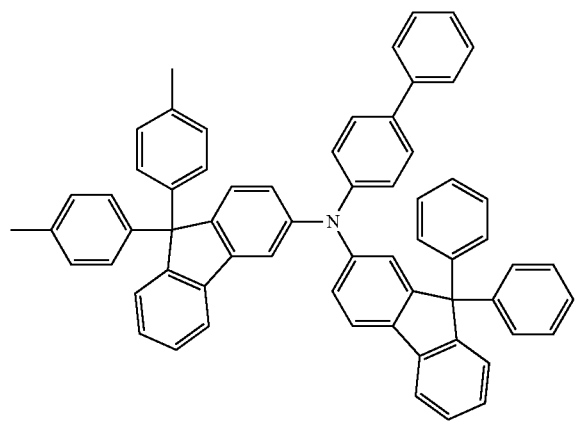
208
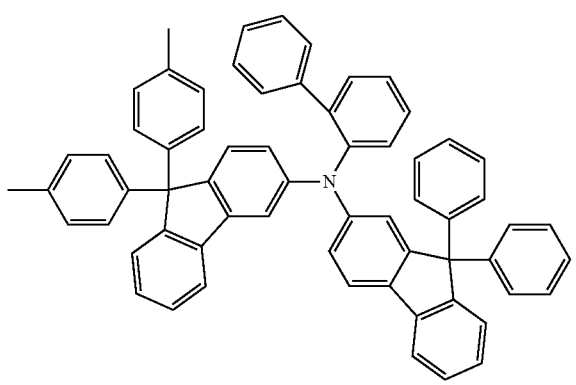
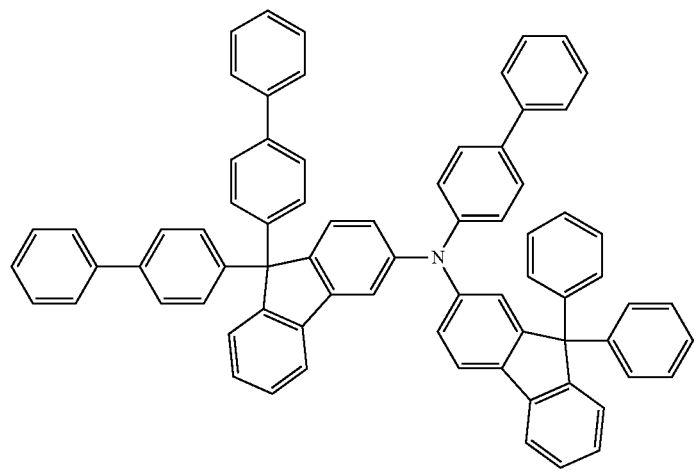
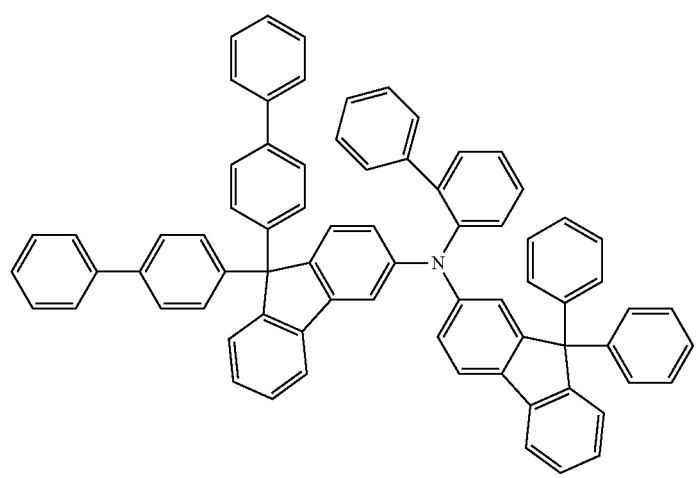

-continued
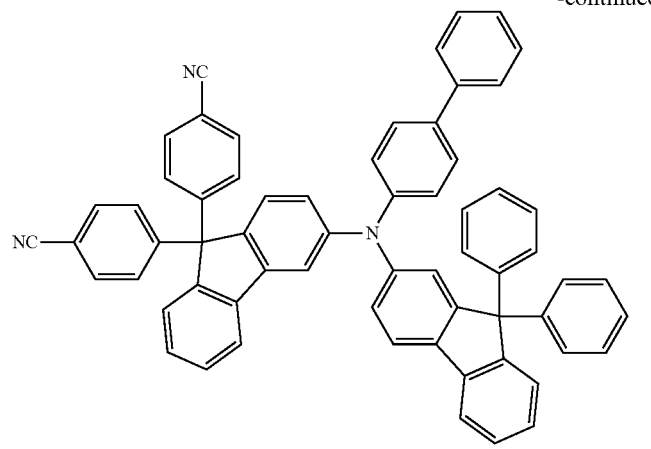
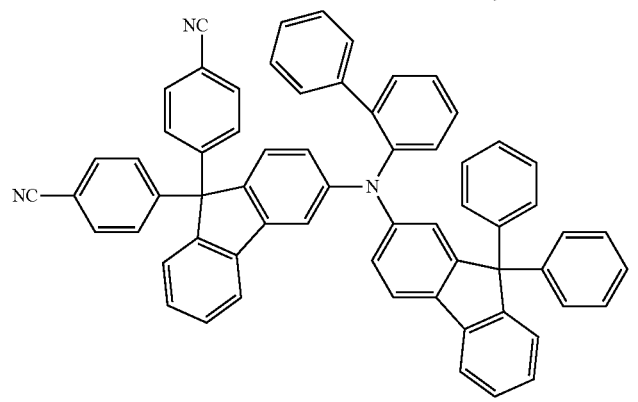
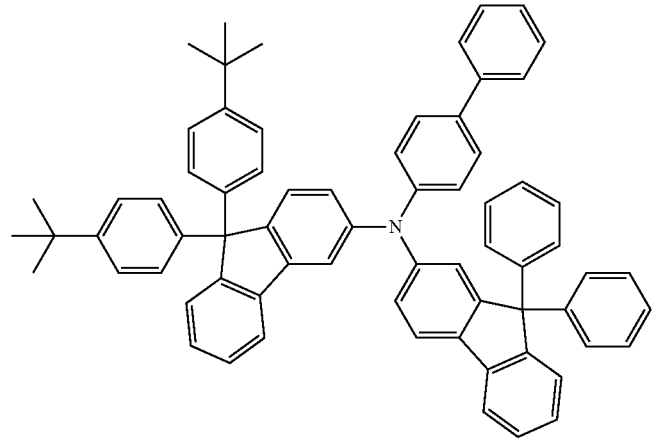
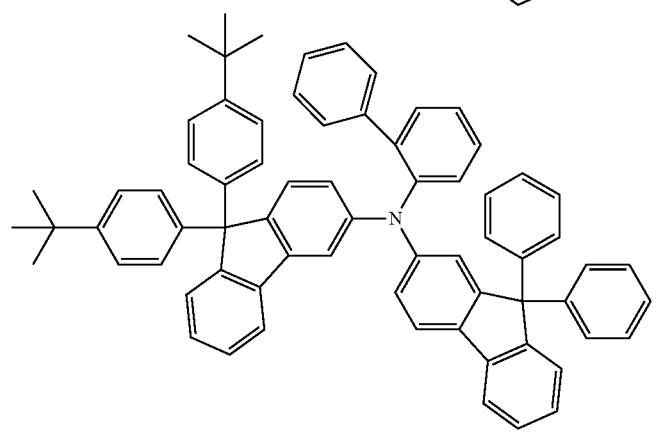

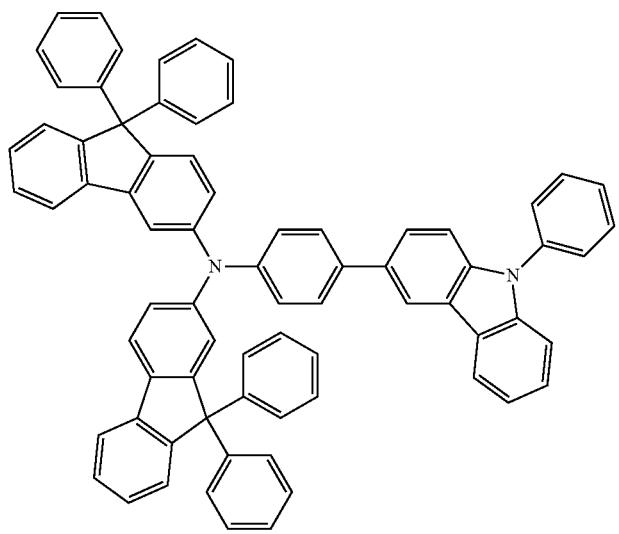
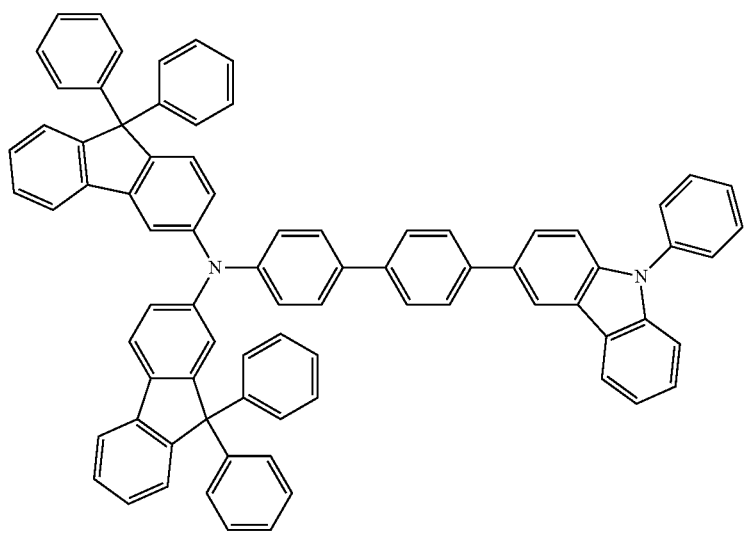
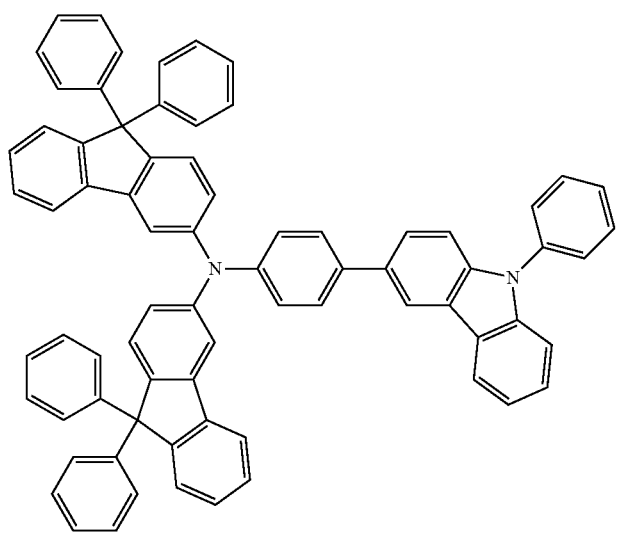

-continued
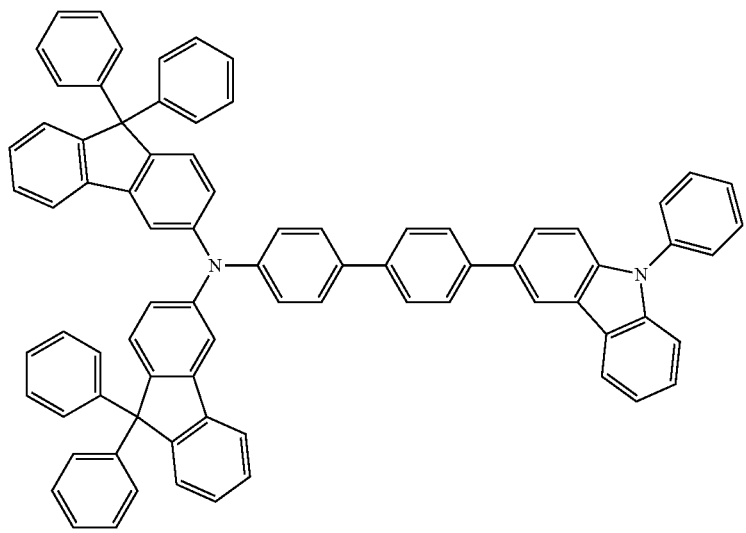
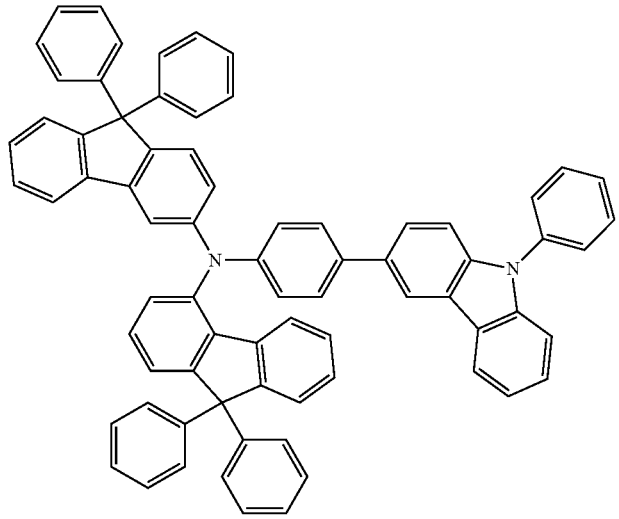
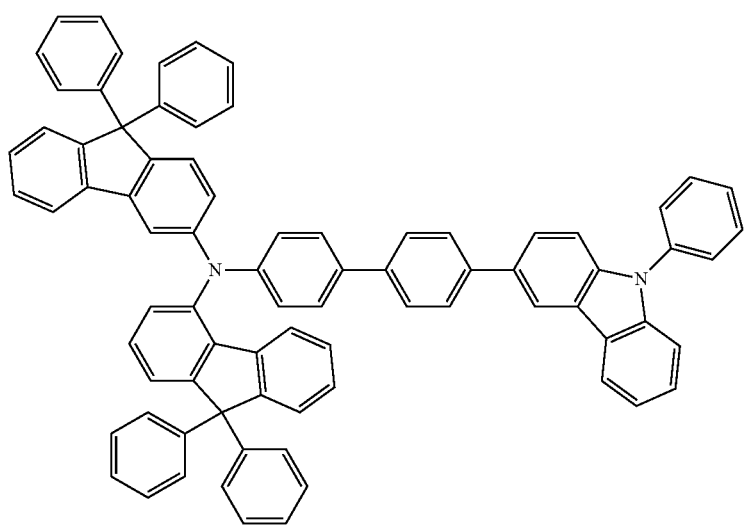

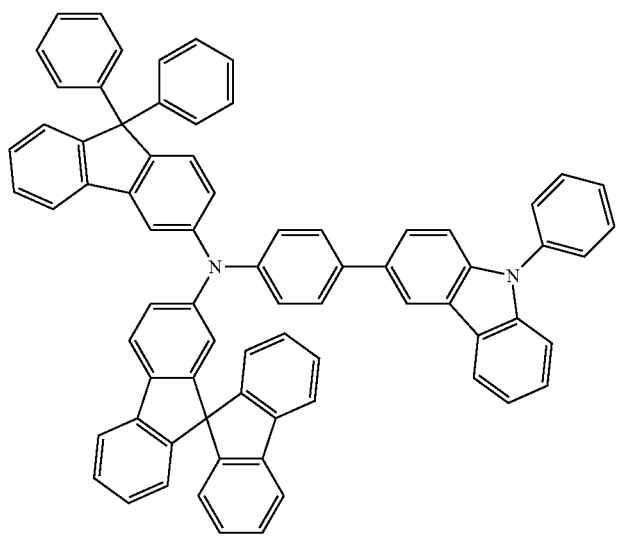
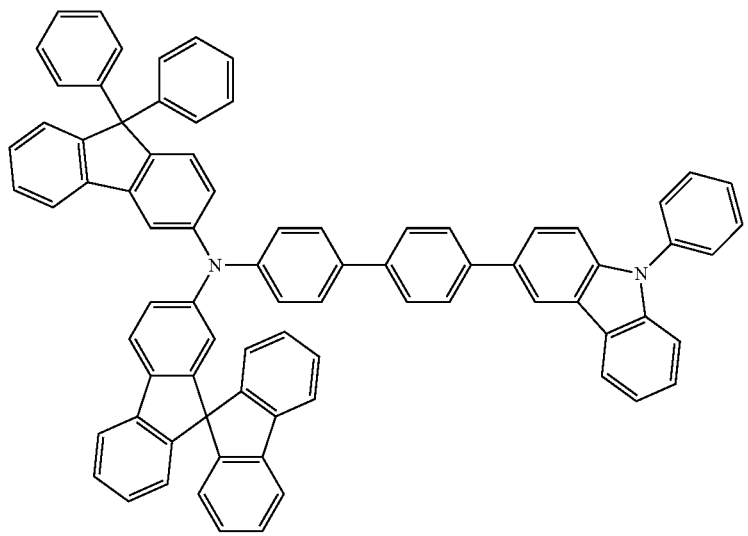
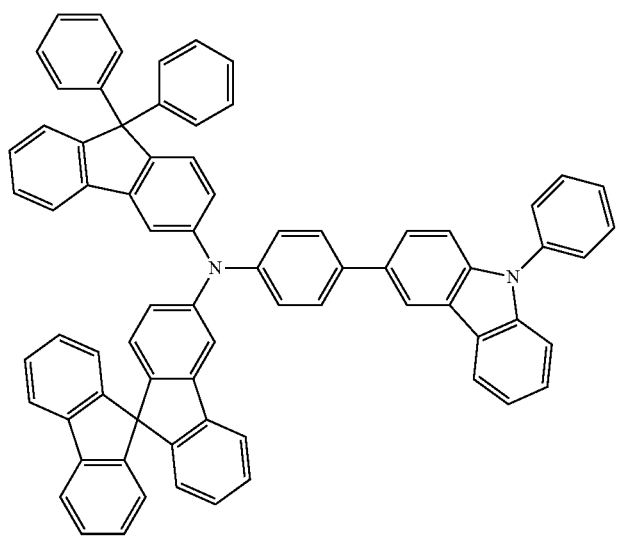

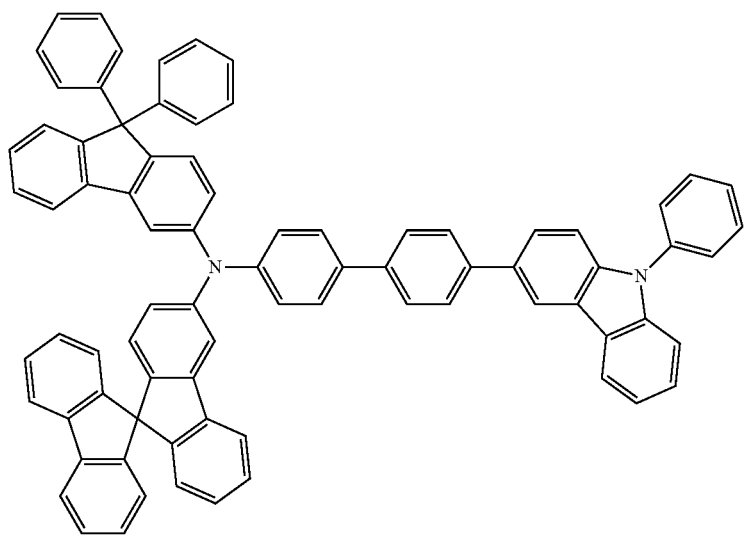
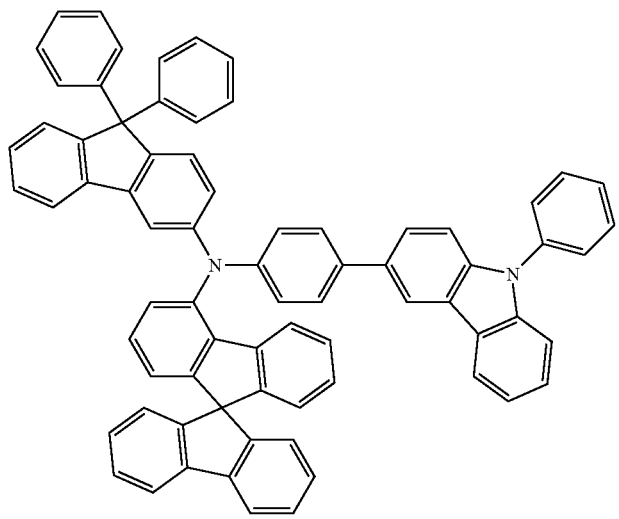
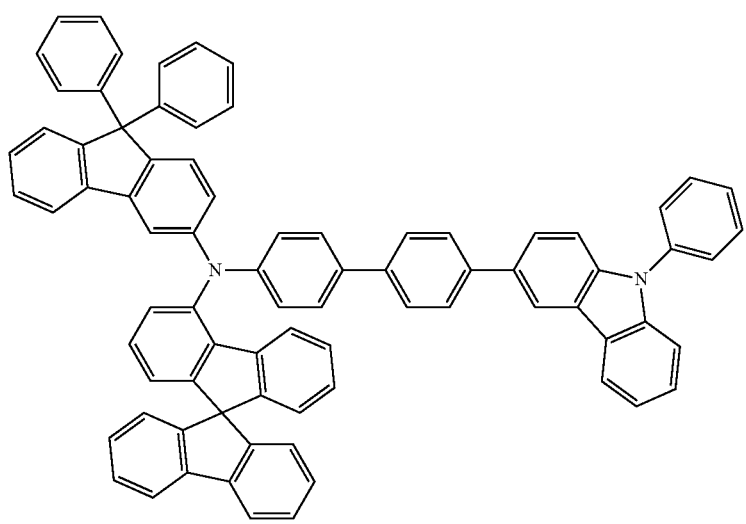

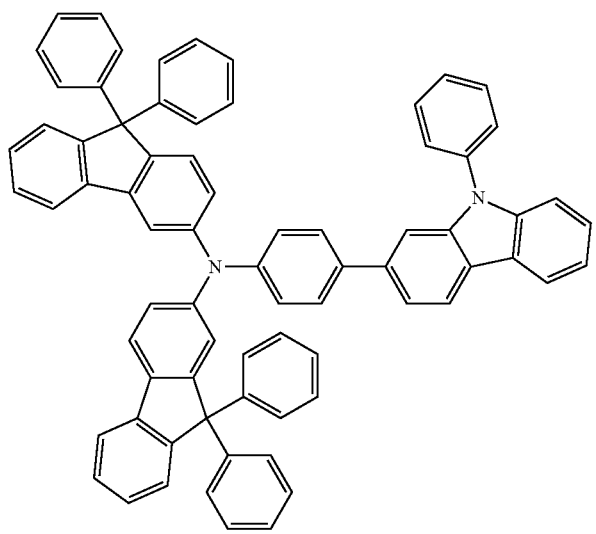
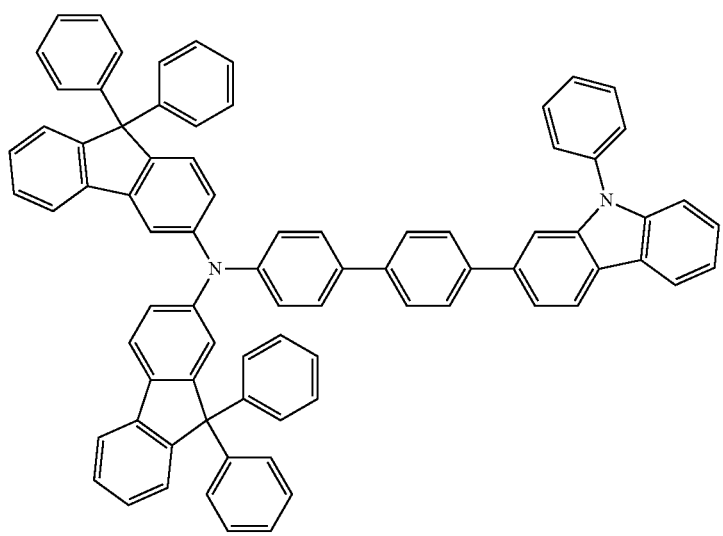
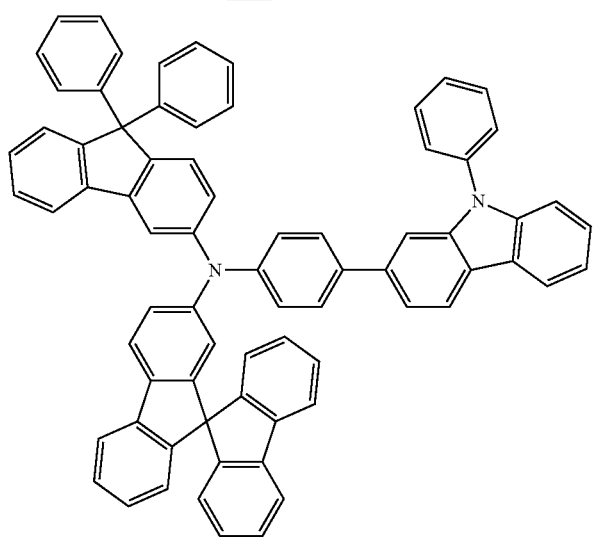

-continued
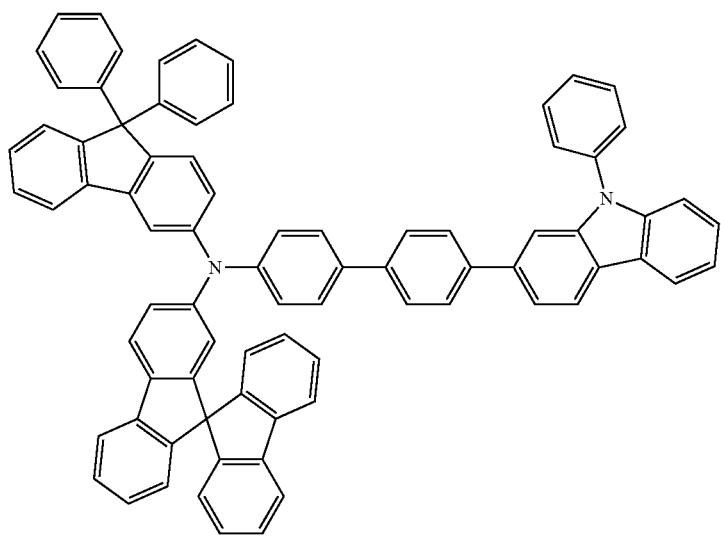
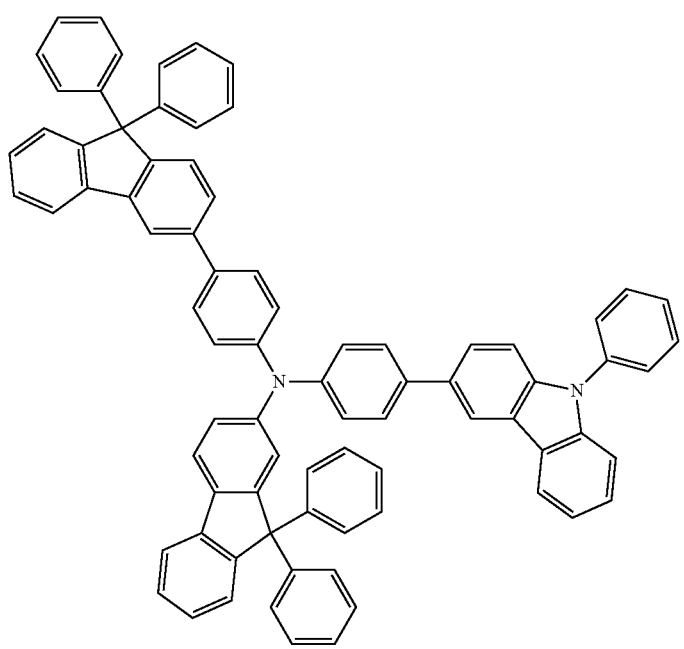

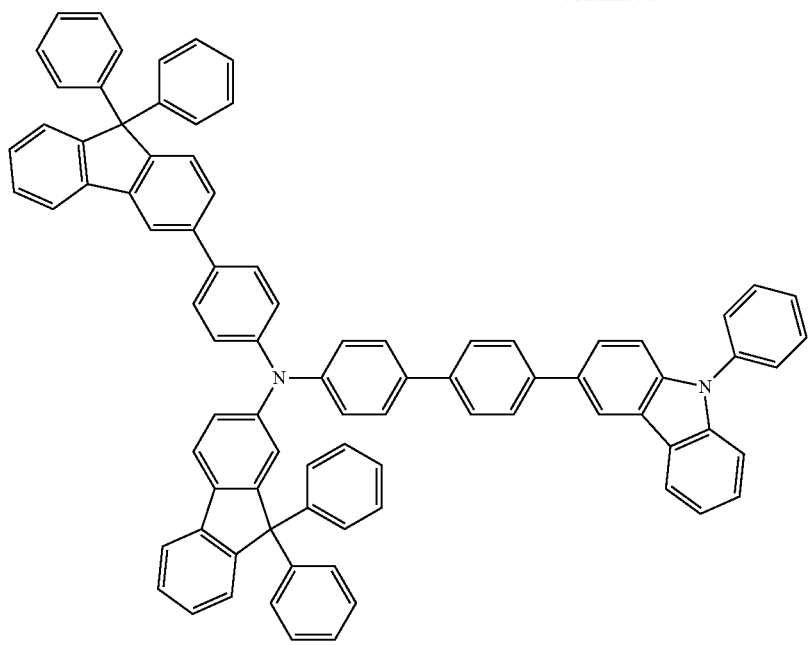
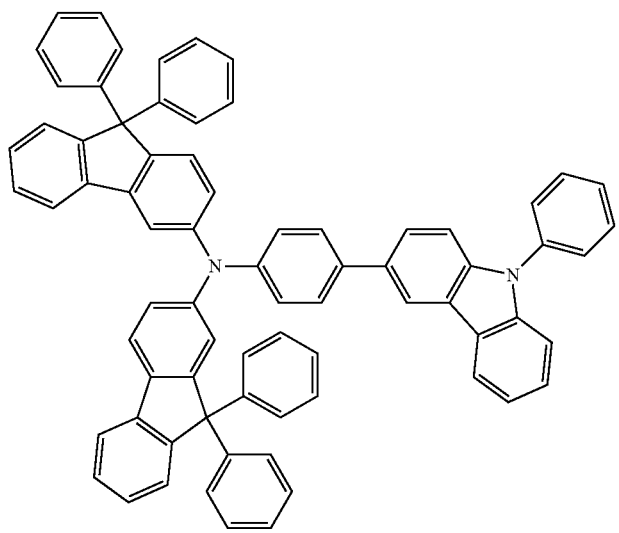
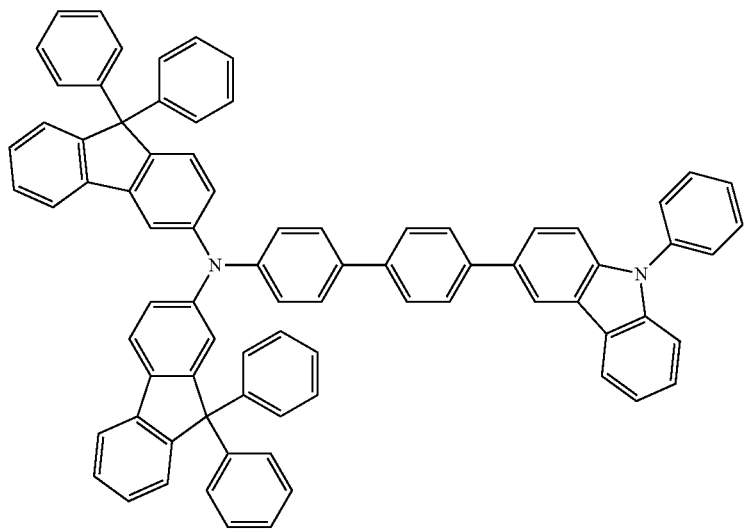

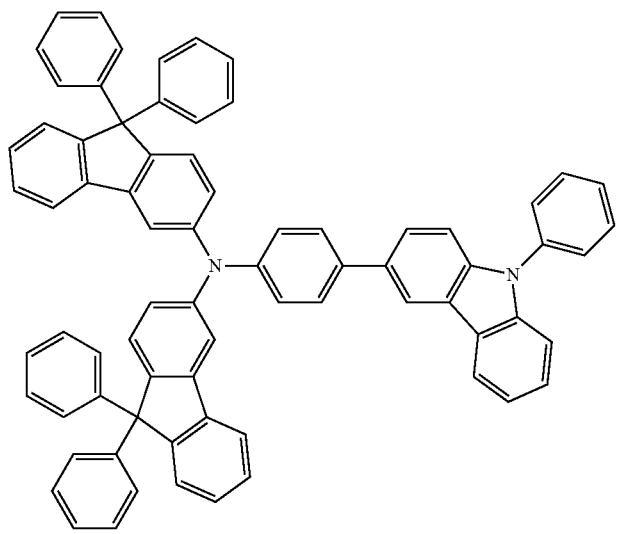
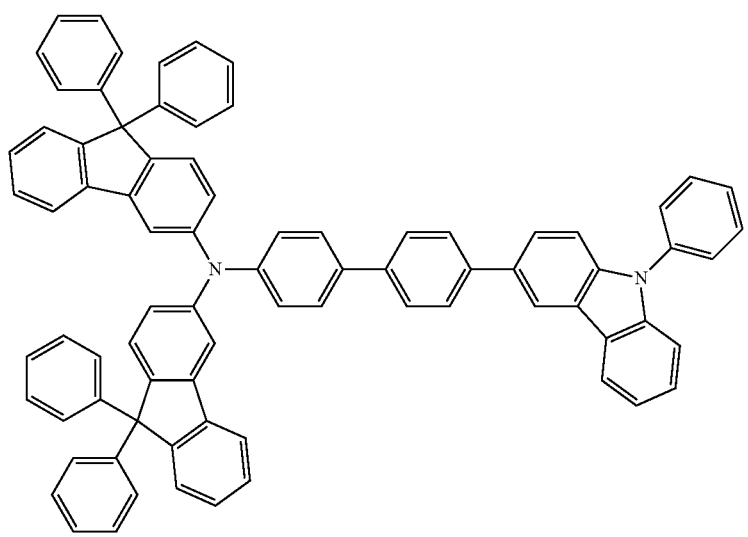
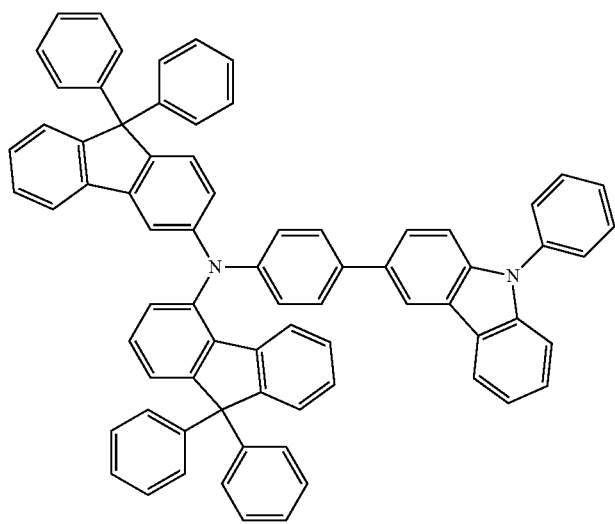

-continued
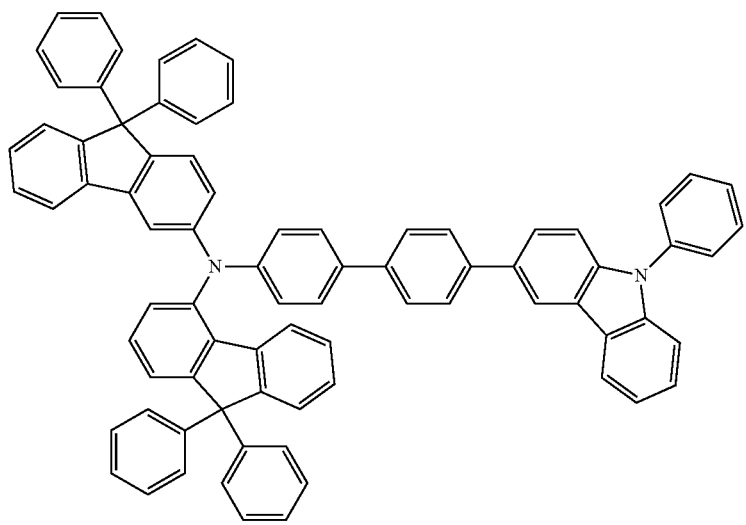
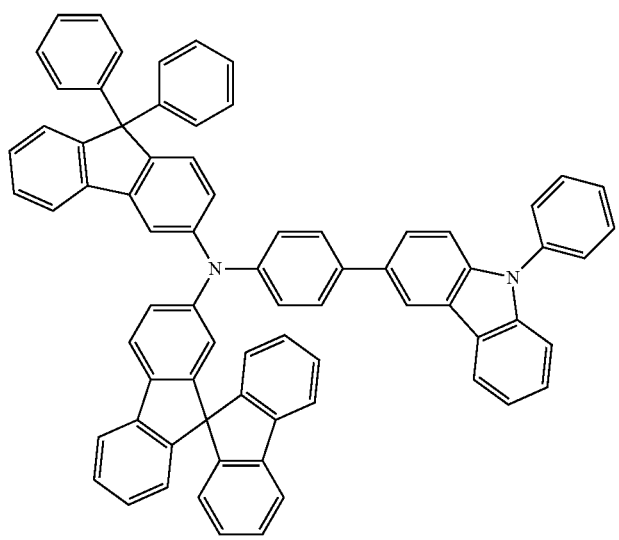
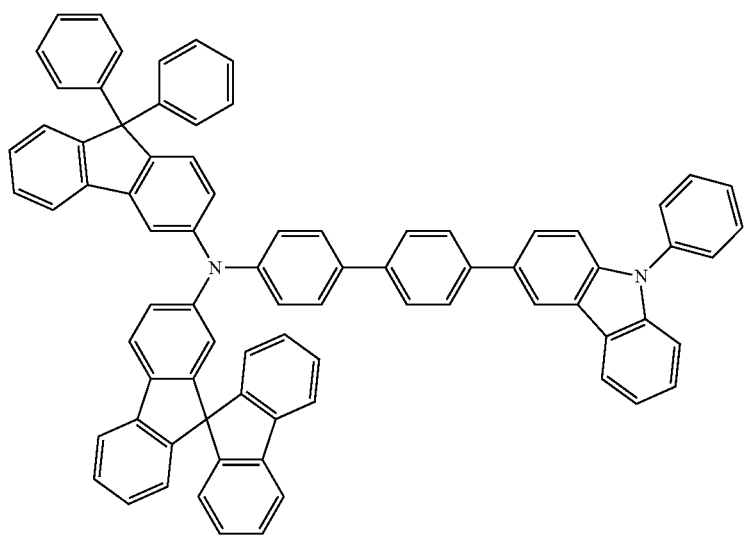

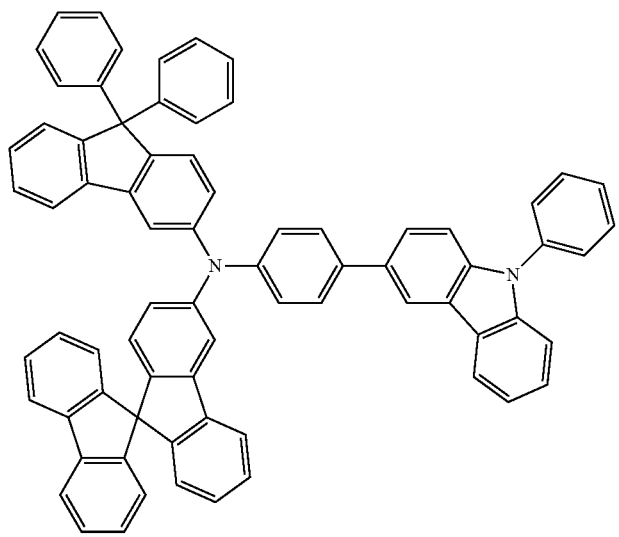
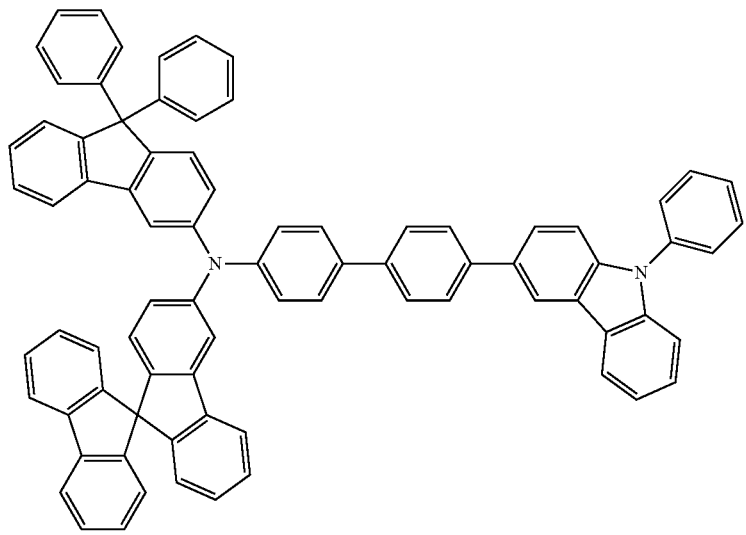
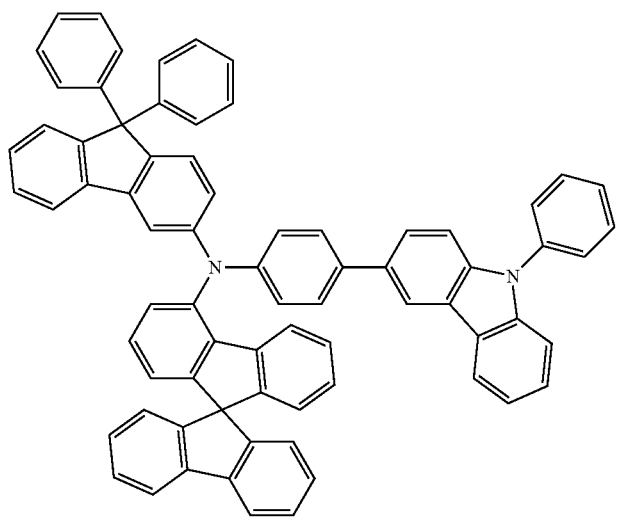

-continued
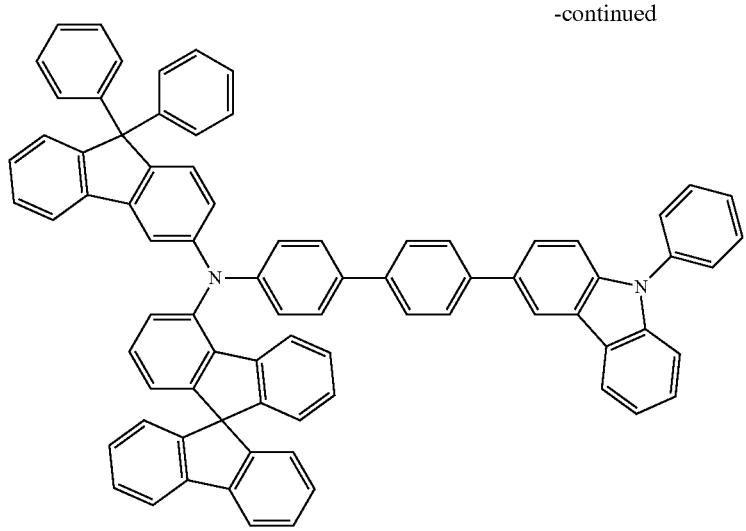
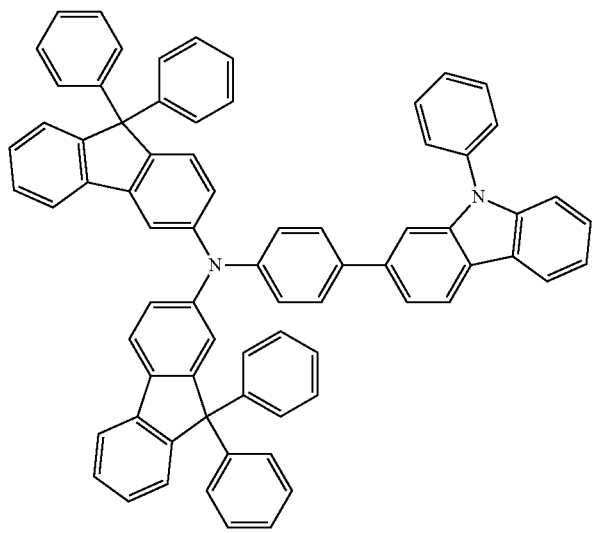
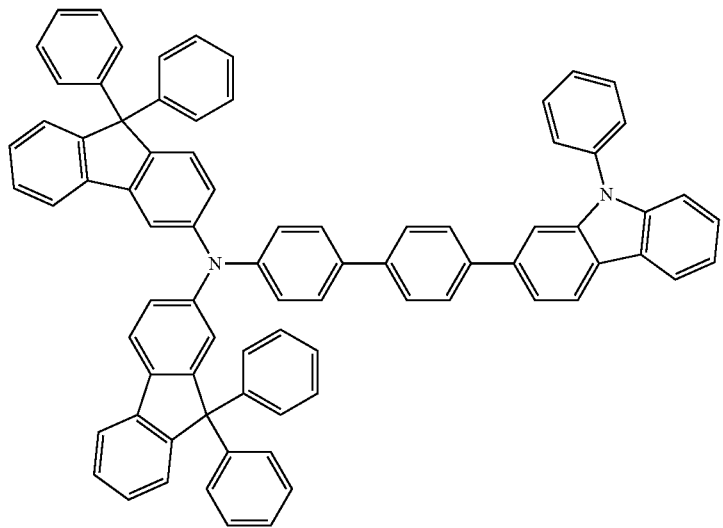

-continued
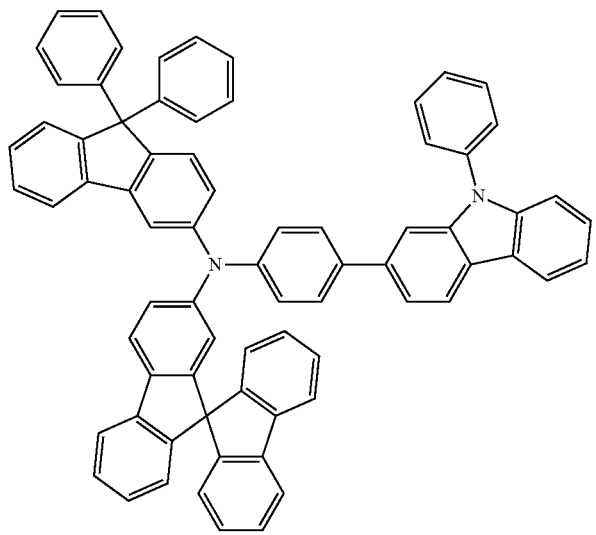
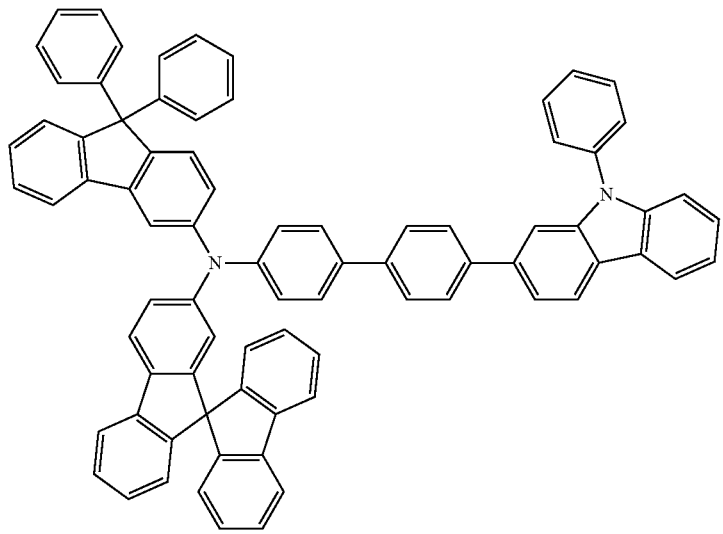
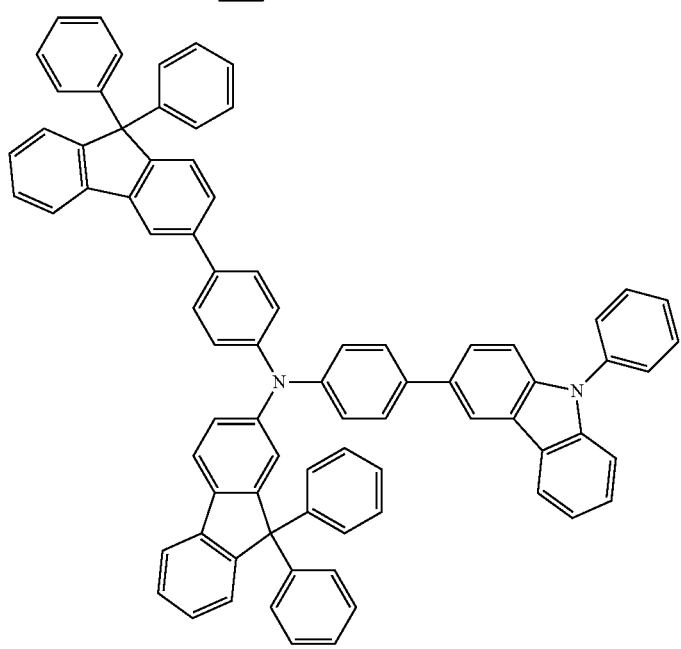

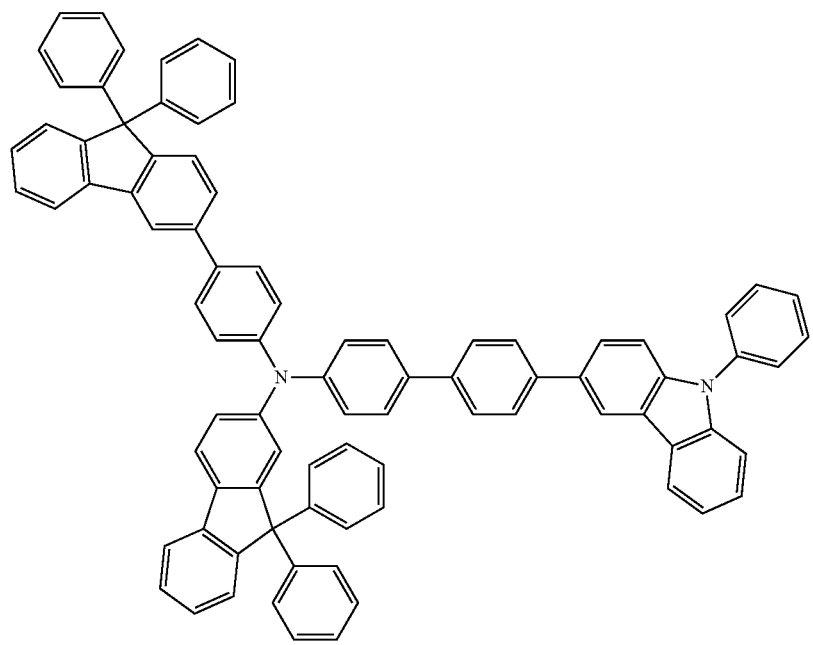
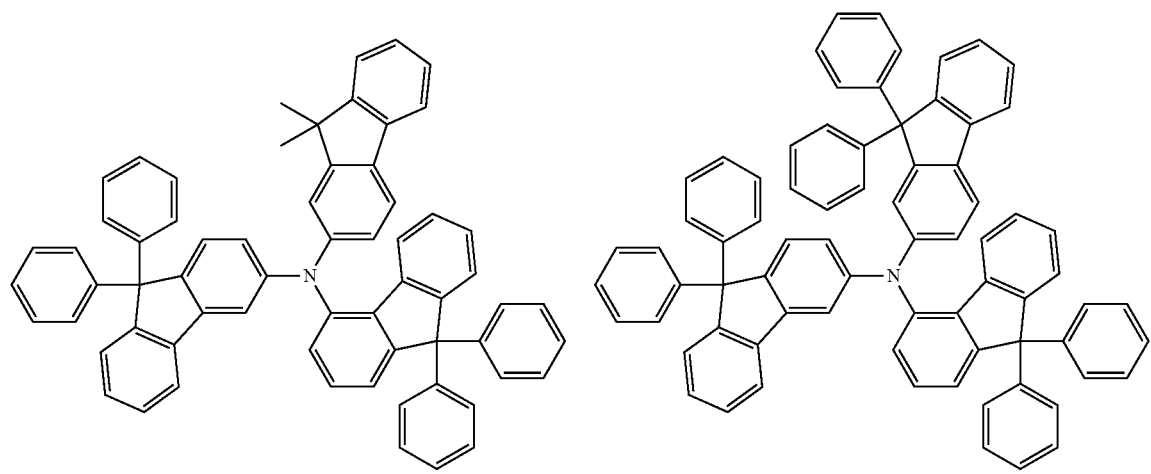
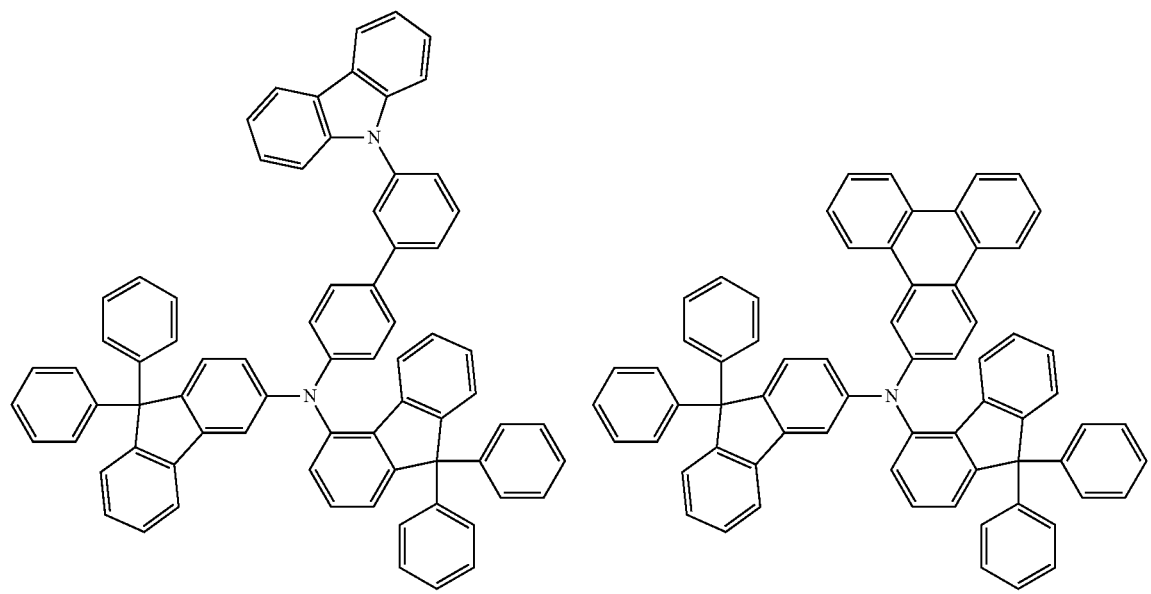

237 238
-continued
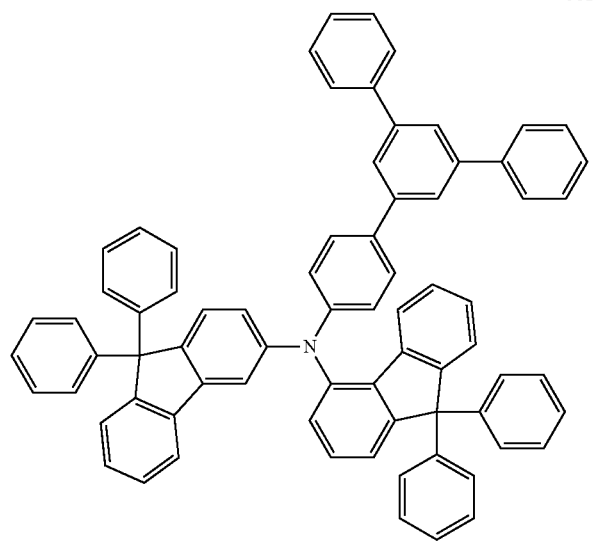 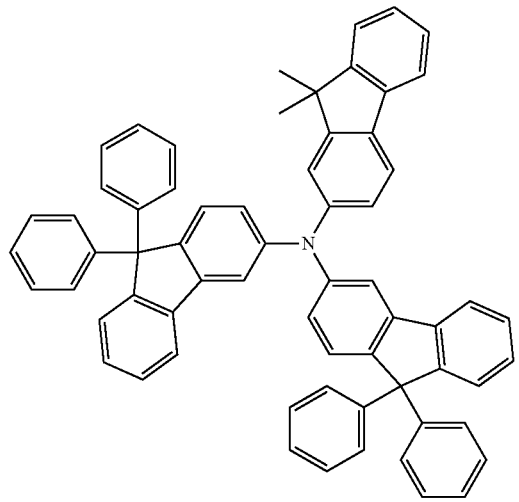
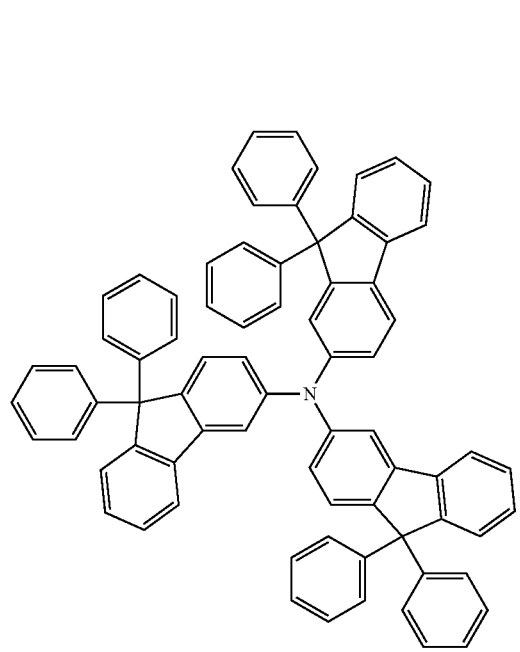 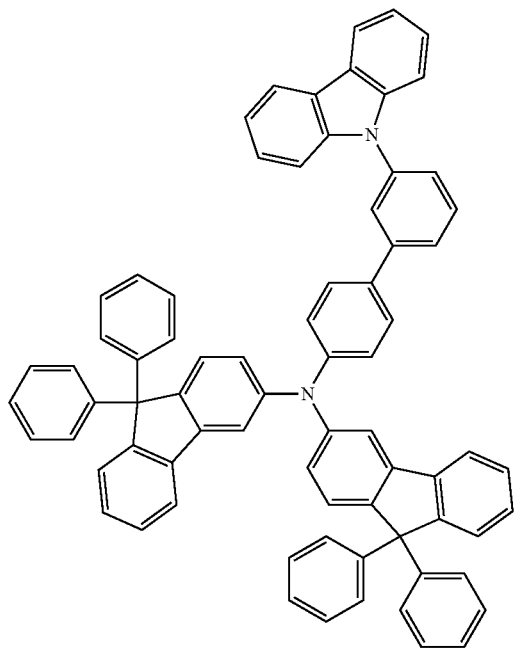

-continued
239
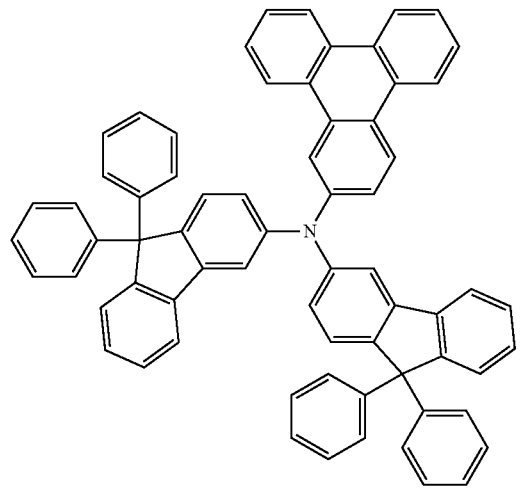
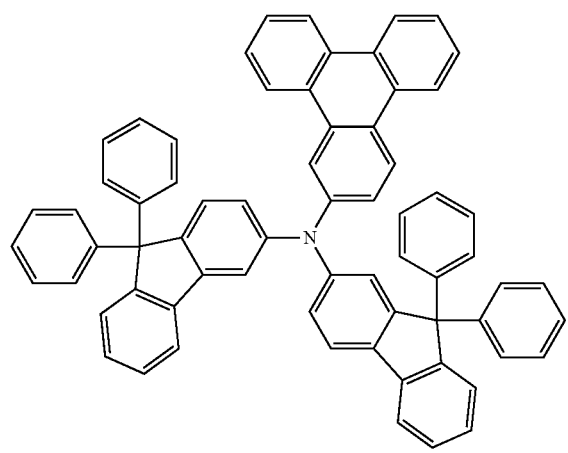
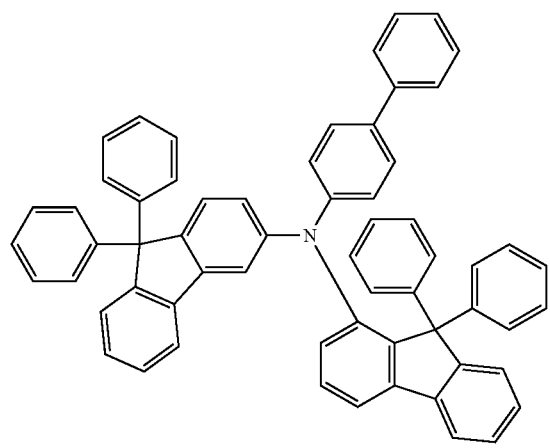
240
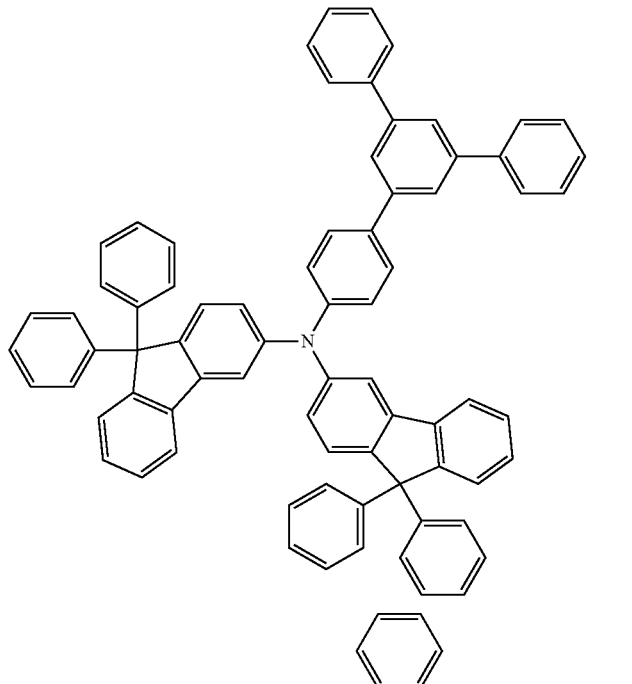
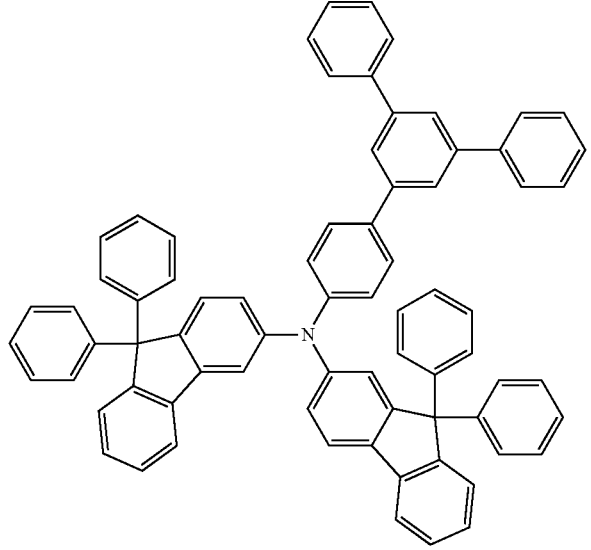
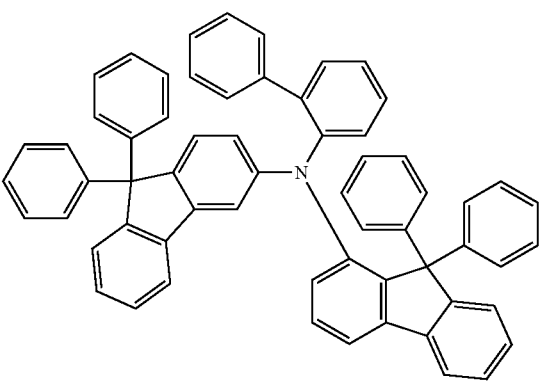

-continued
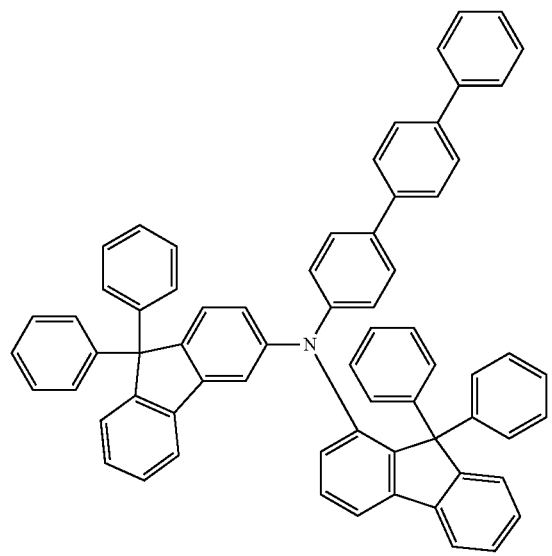
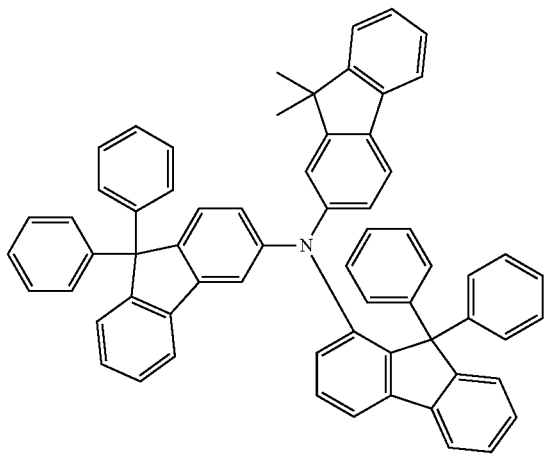
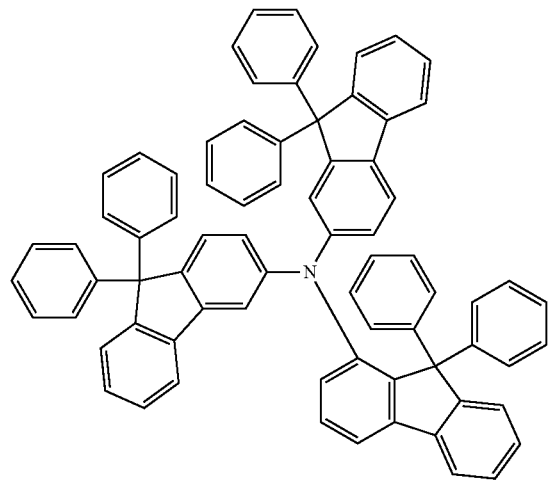
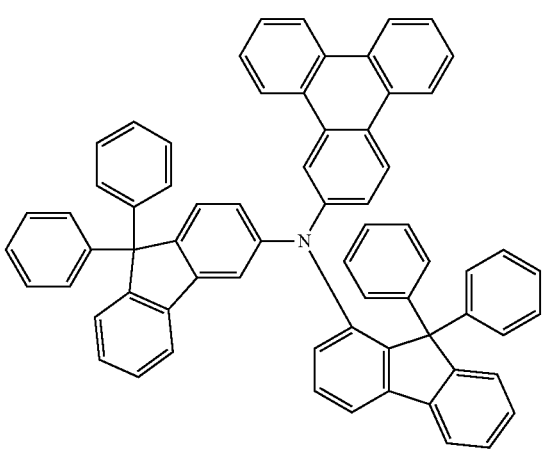
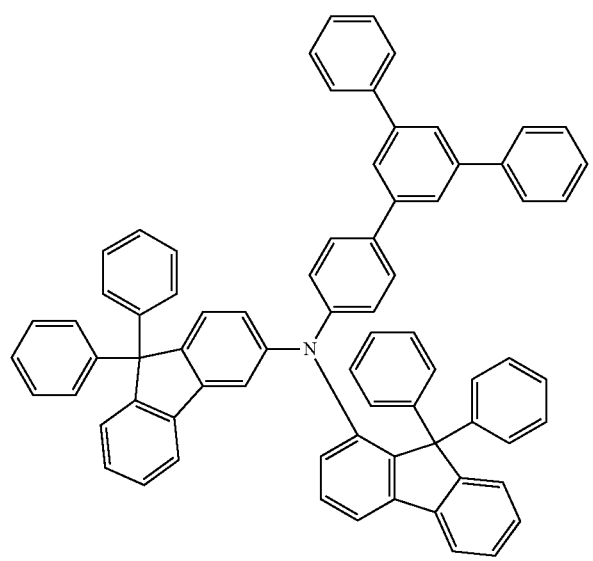
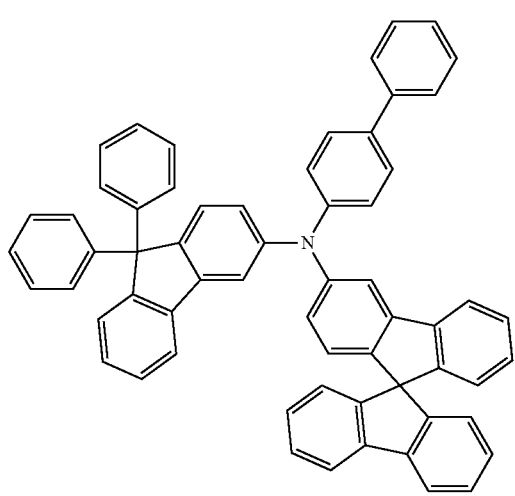

243 244
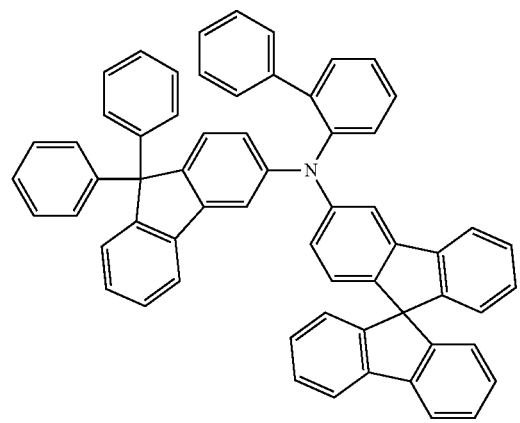 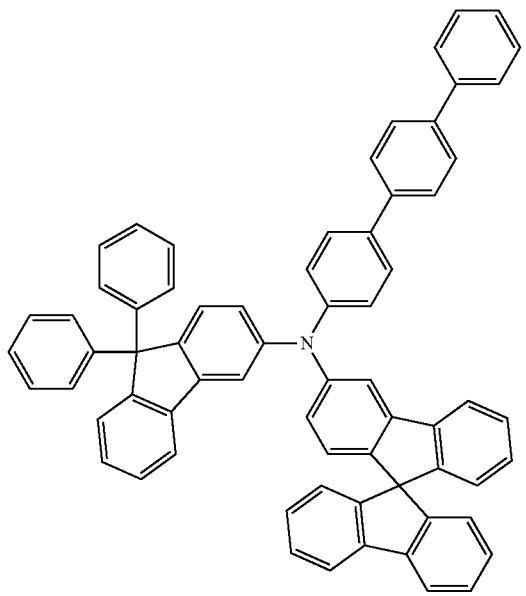
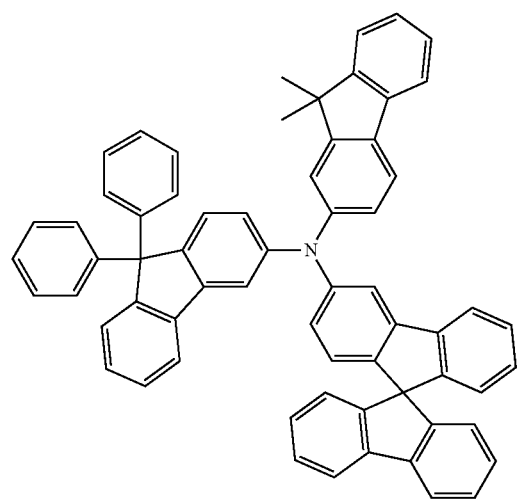 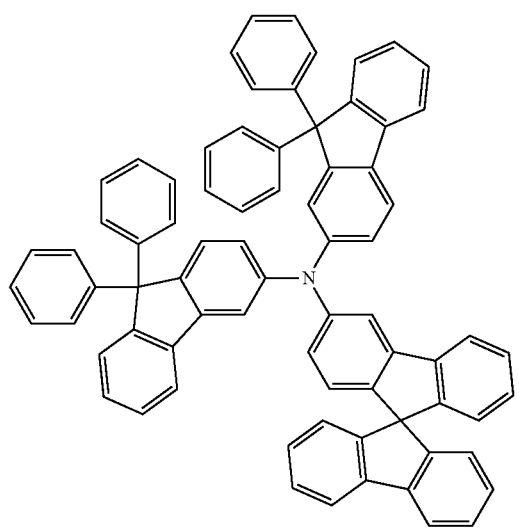
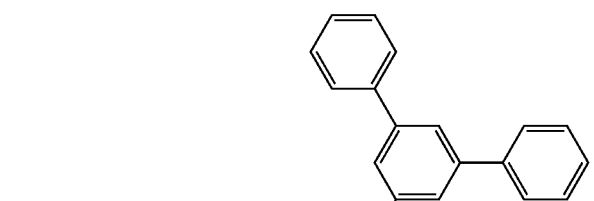
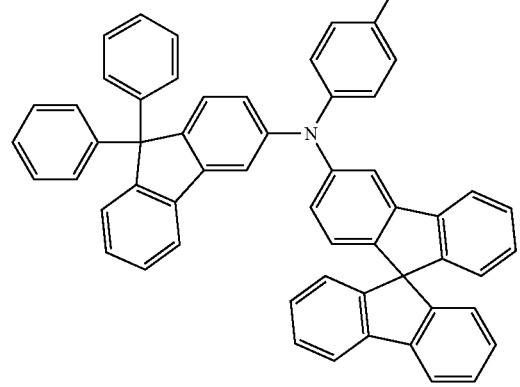 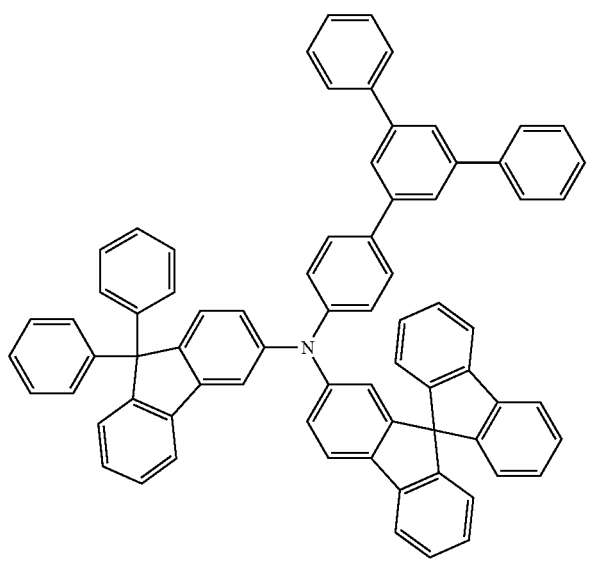

-continued
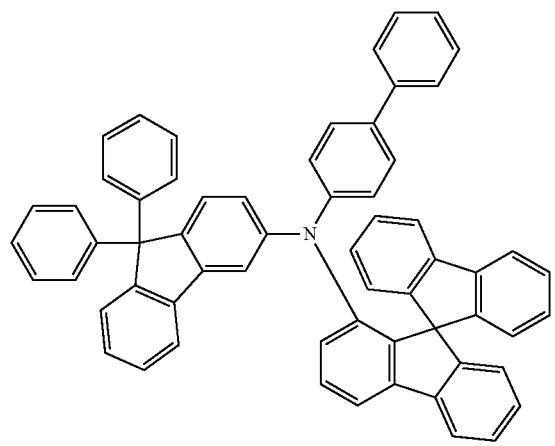
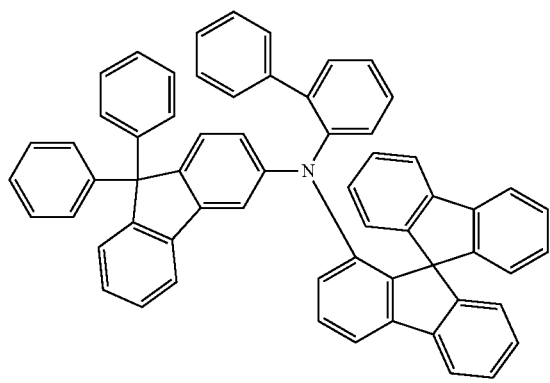
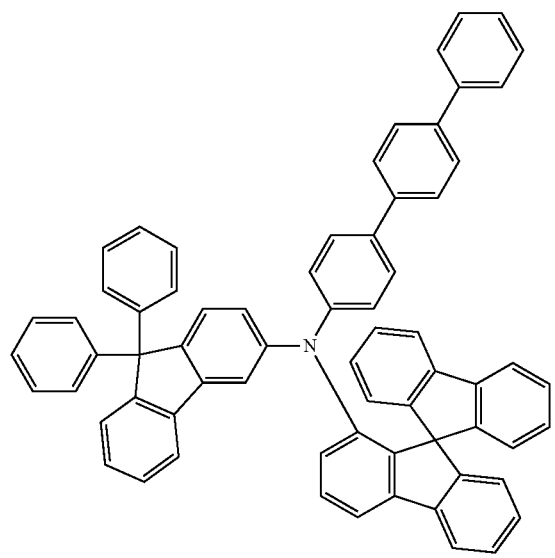
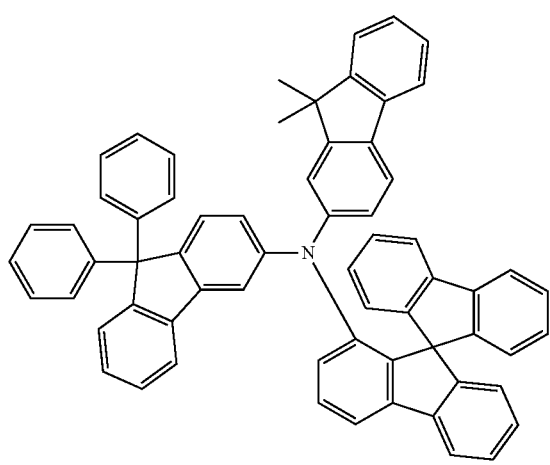
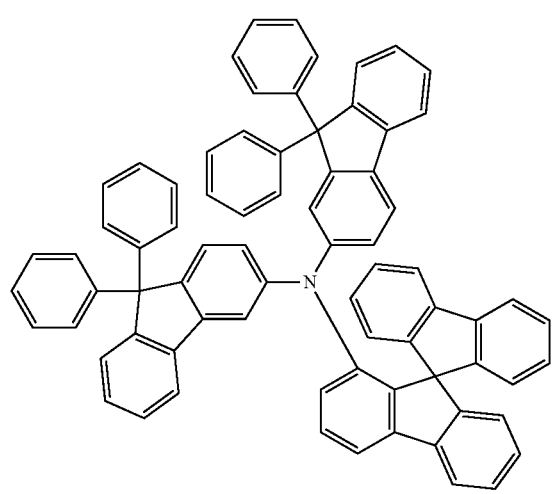
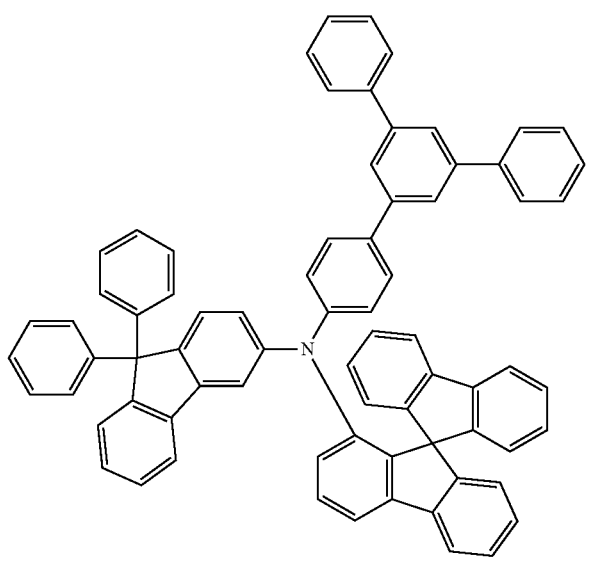

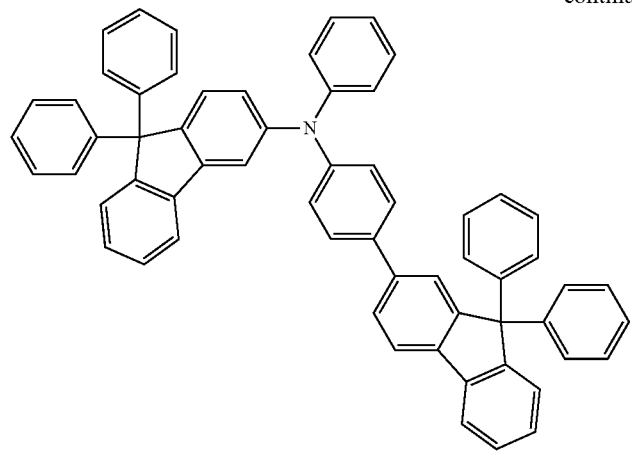
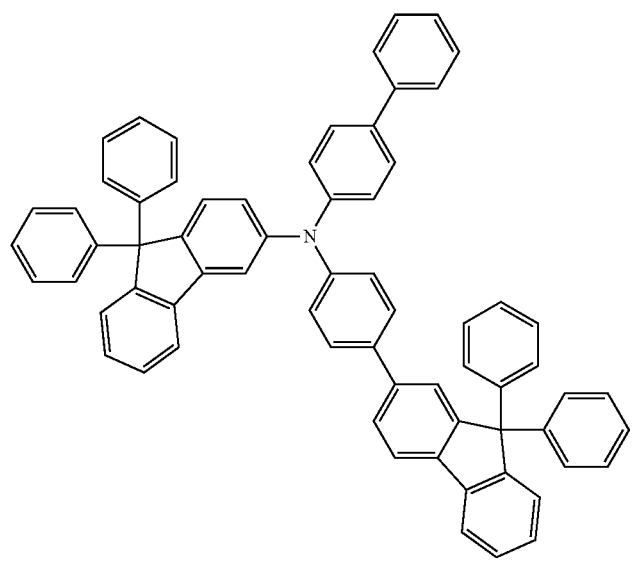
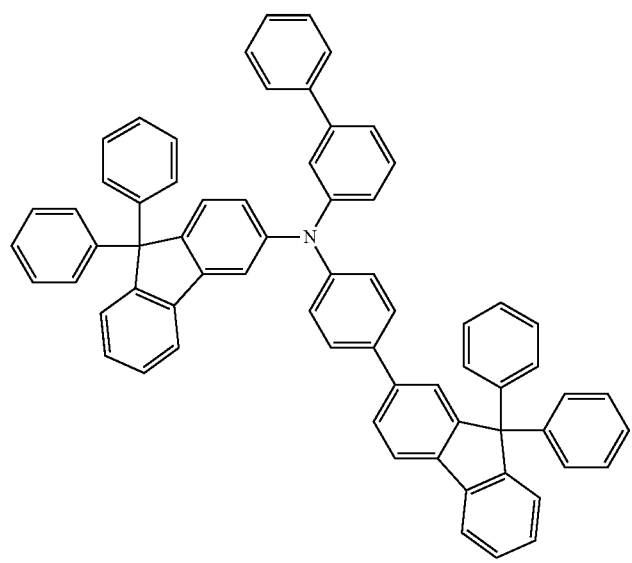

-continued
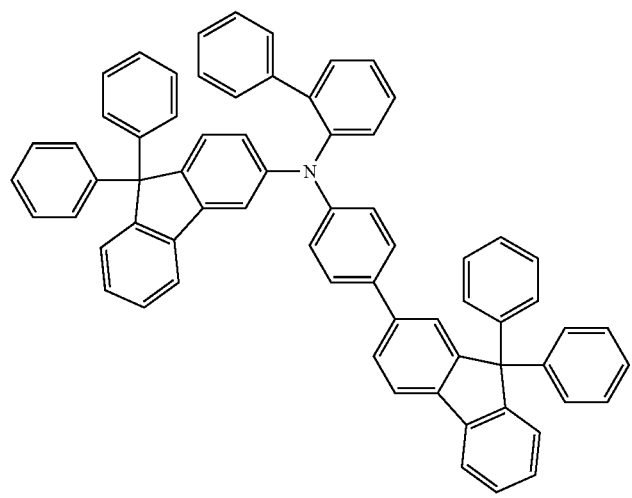
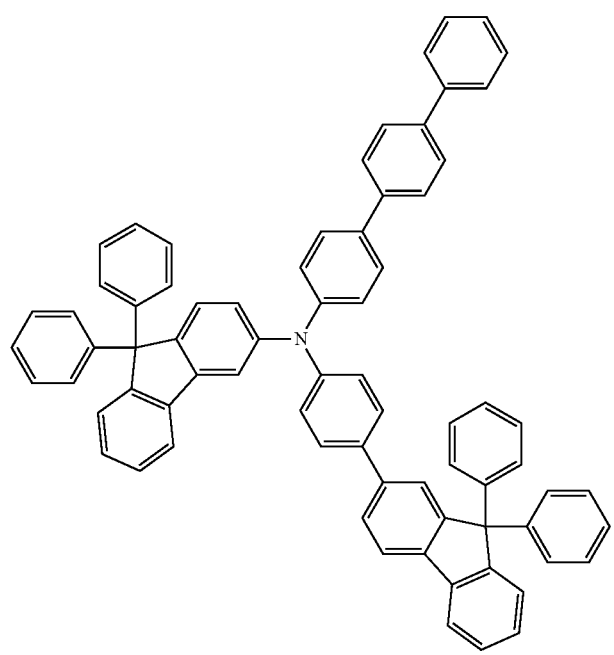

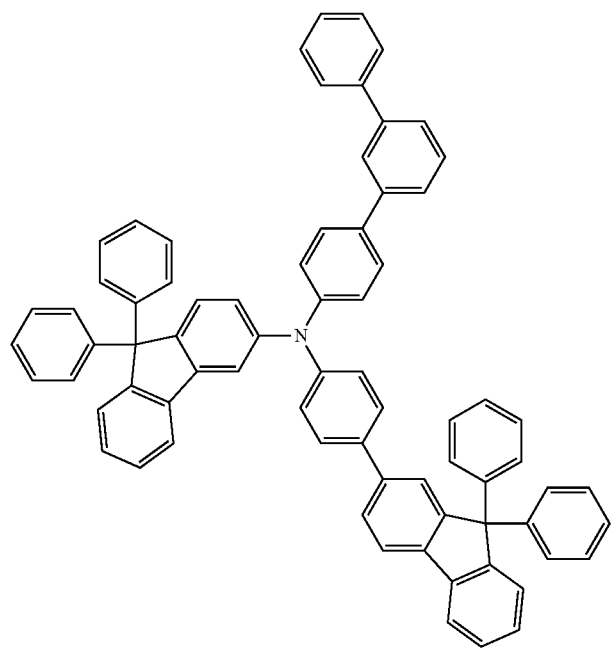
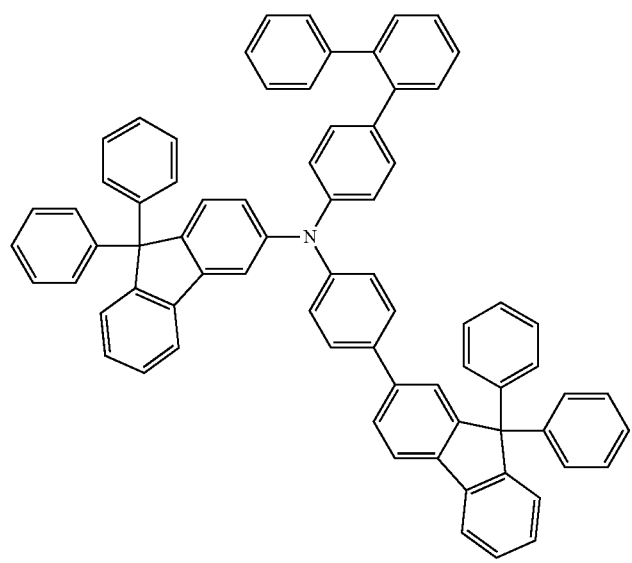

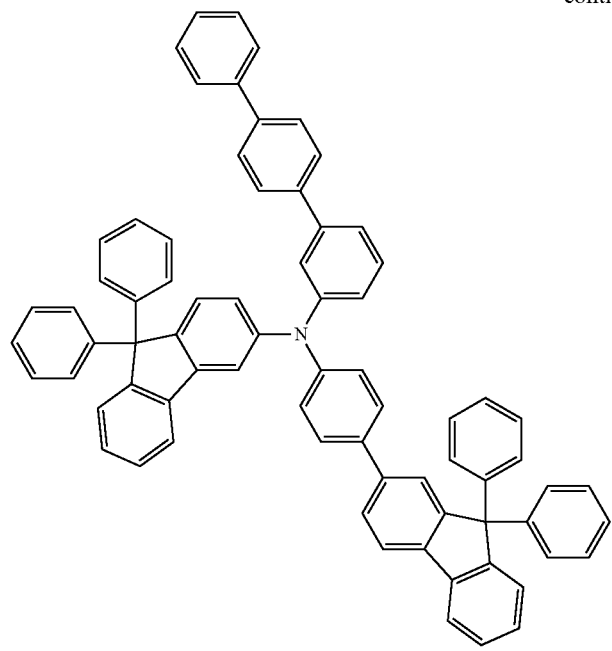
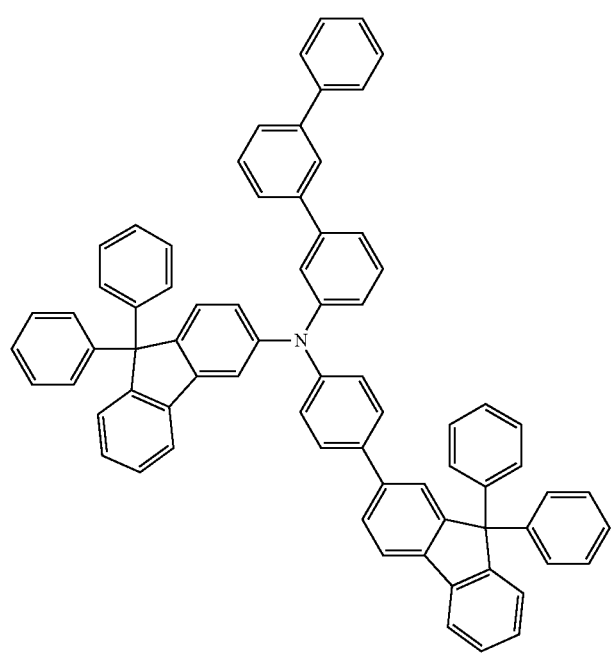

-continued
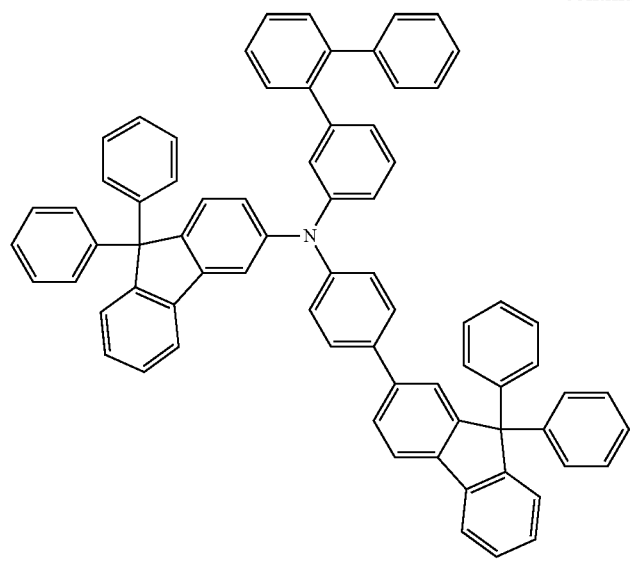
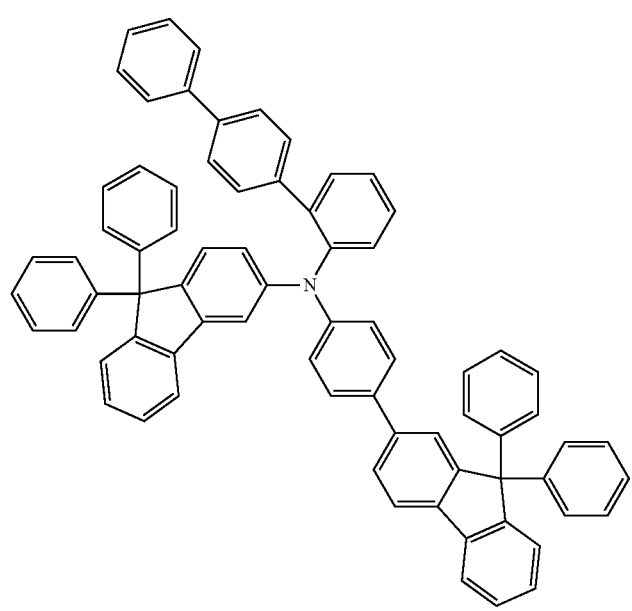

-continued
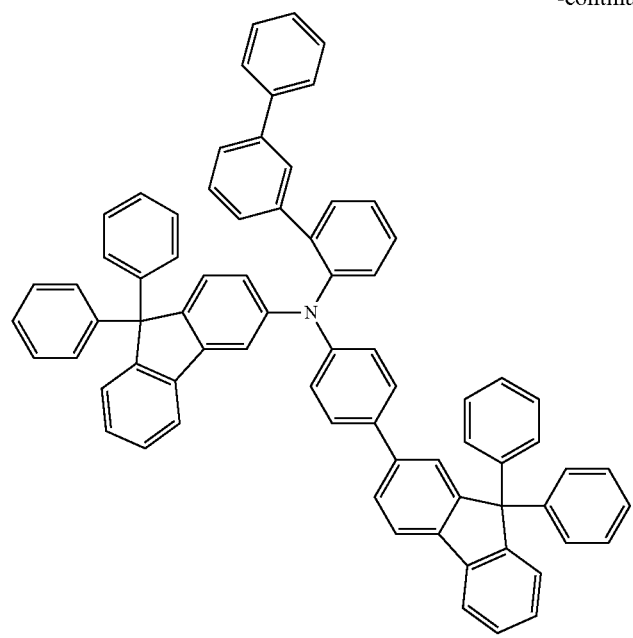
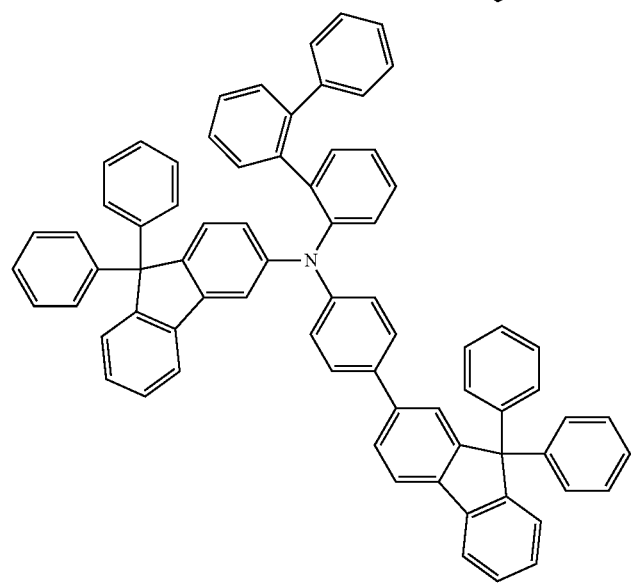
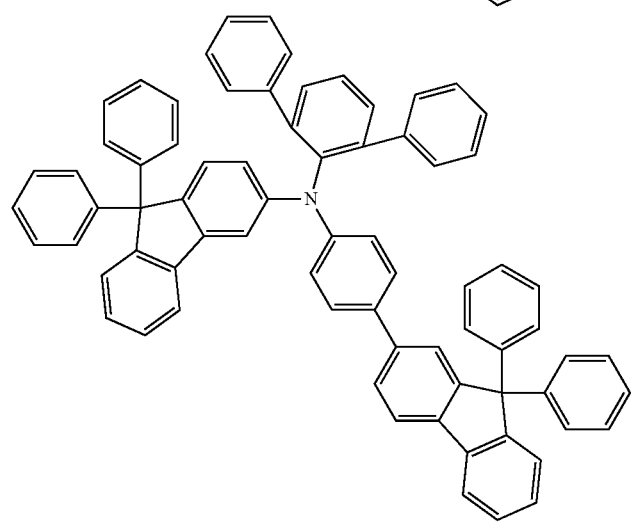

-continued
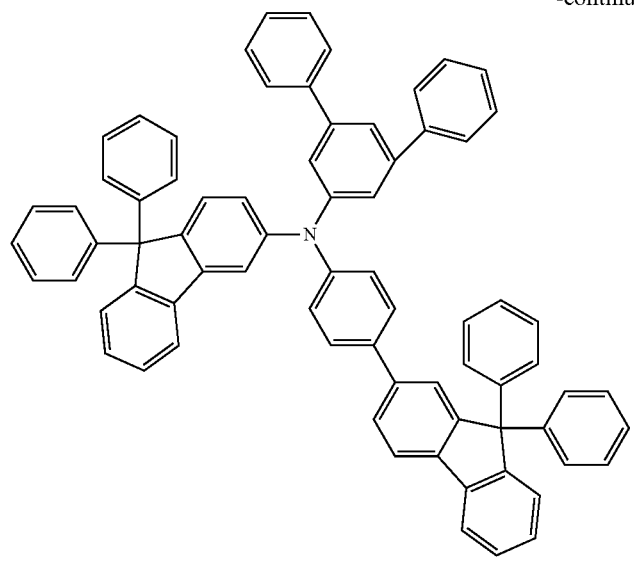
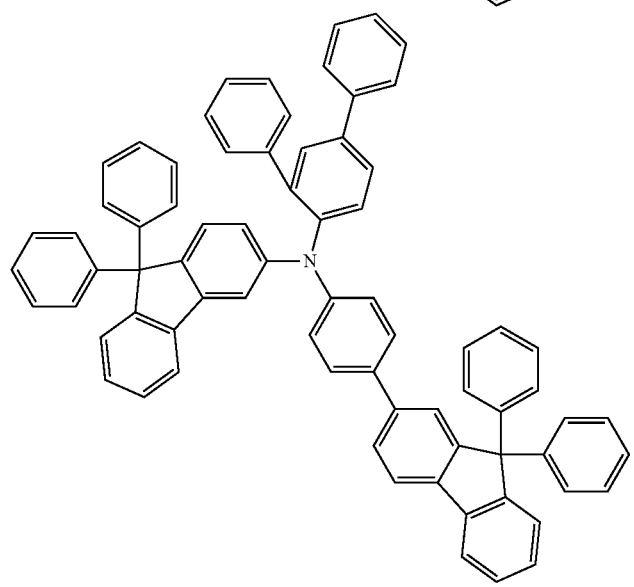
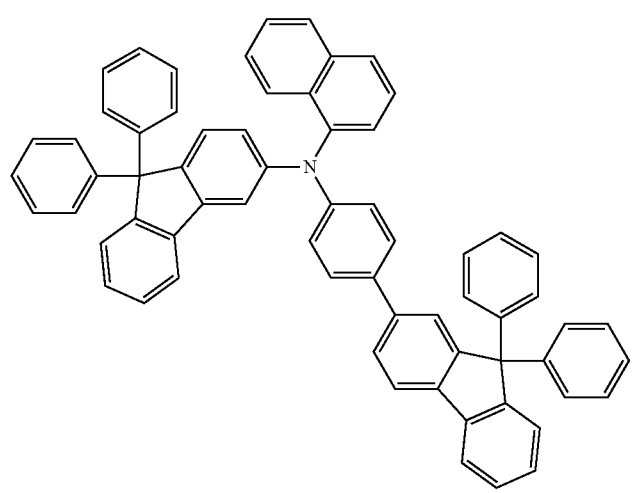

-continued
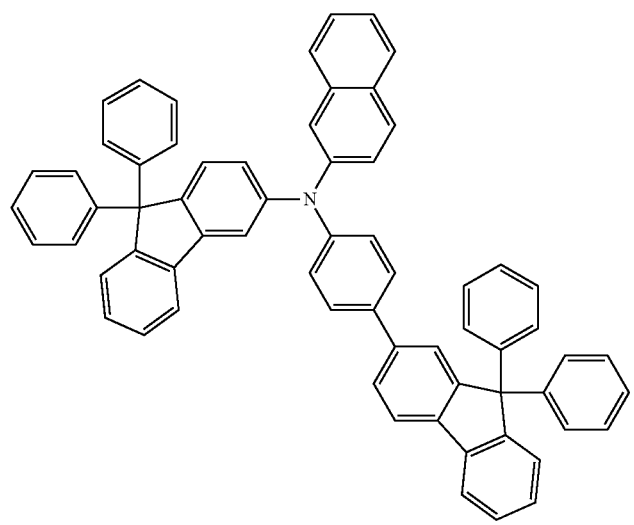
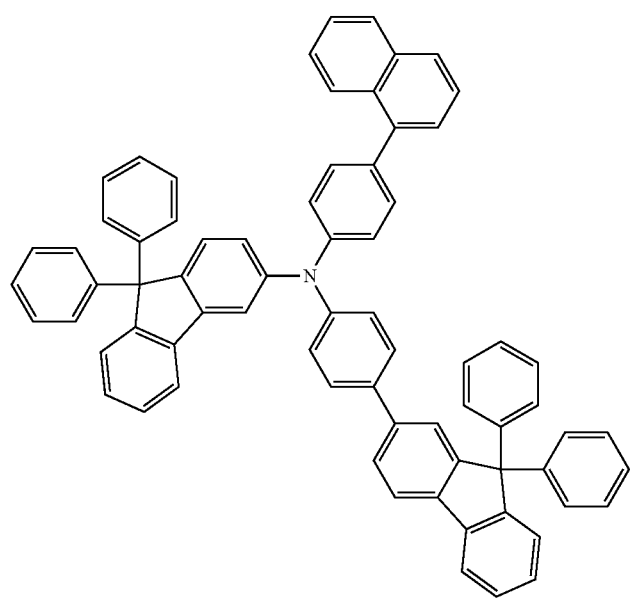

-continued
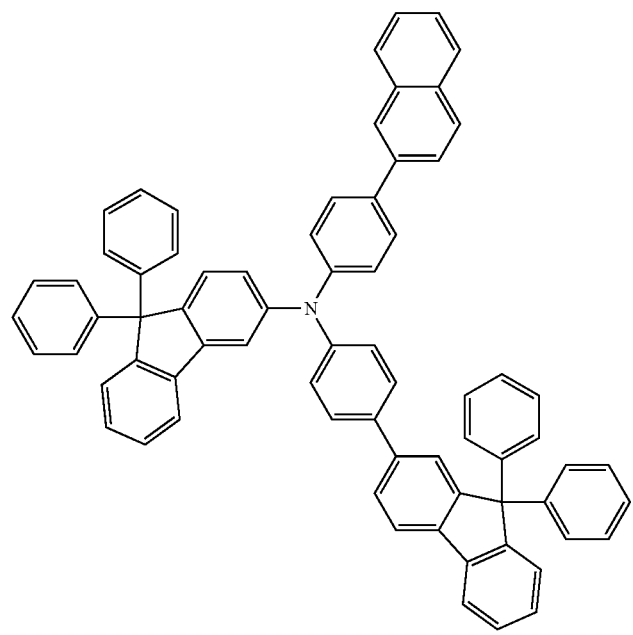
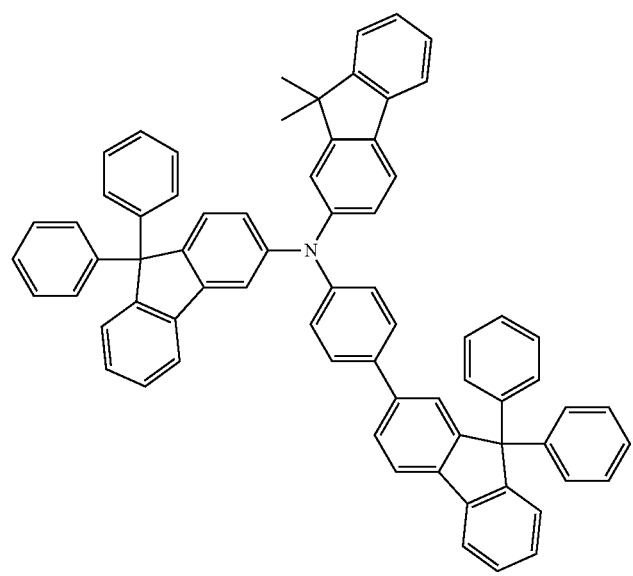

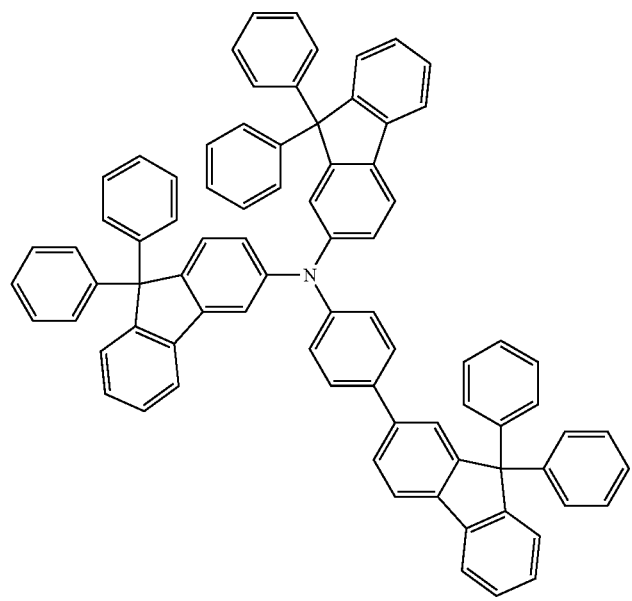
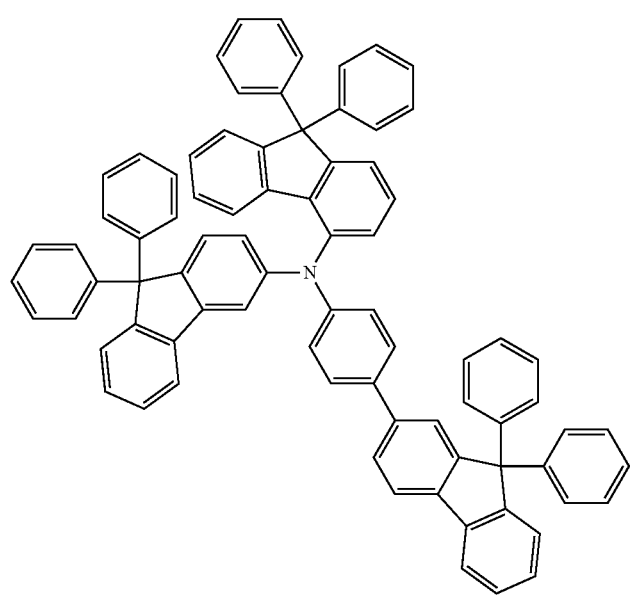

-continued
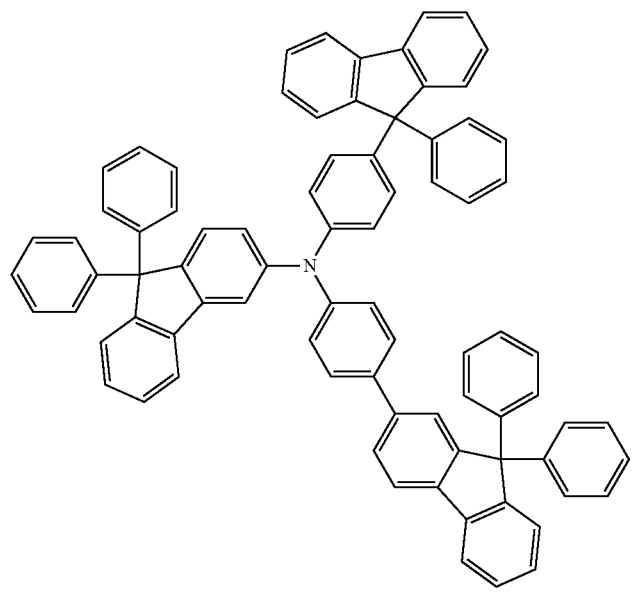
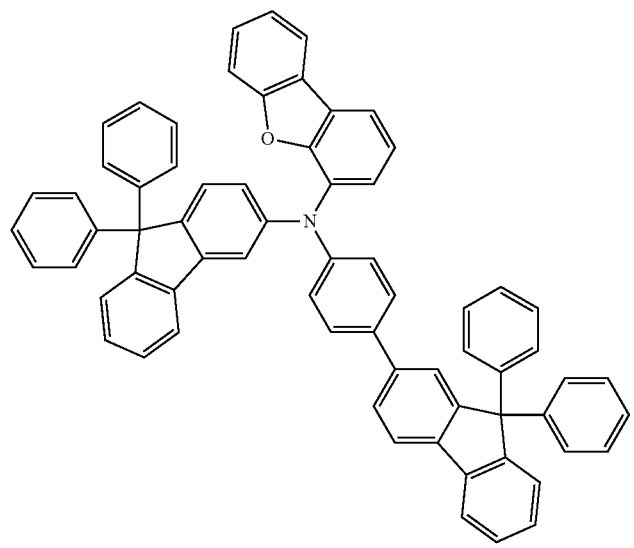
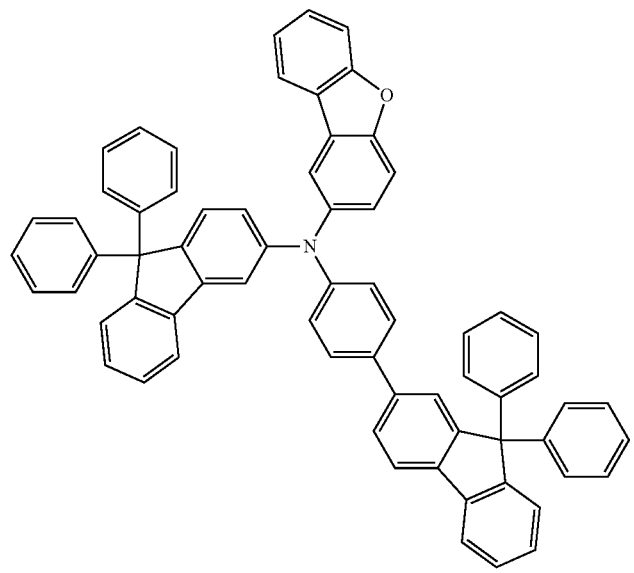

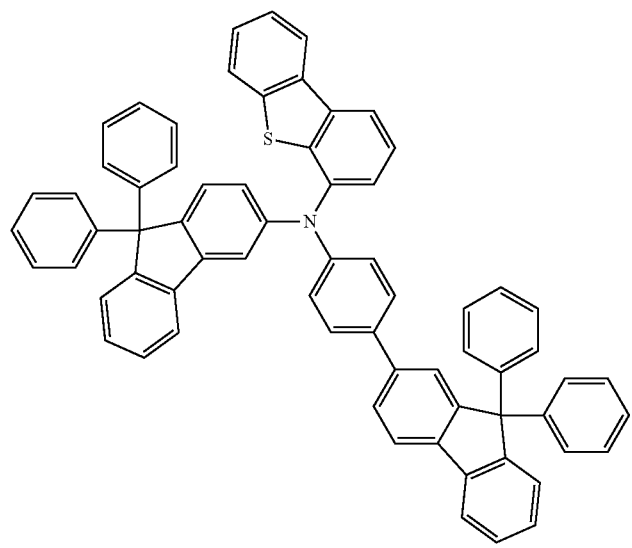
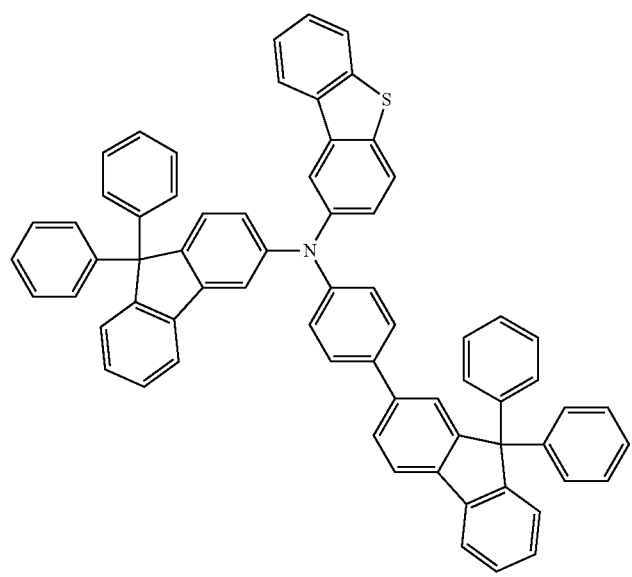
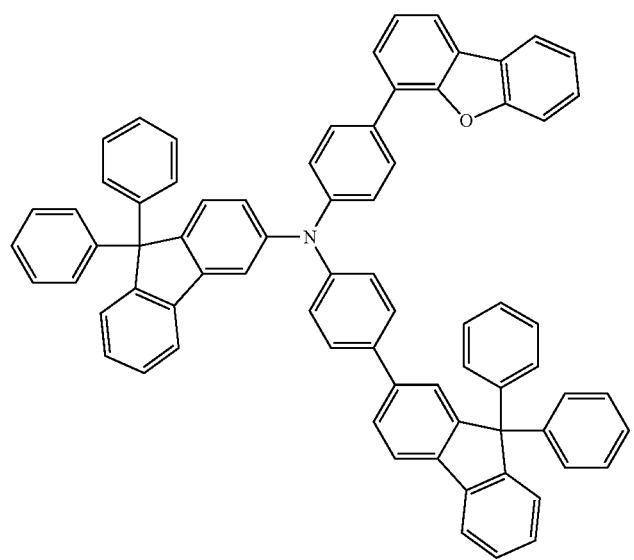

-continued
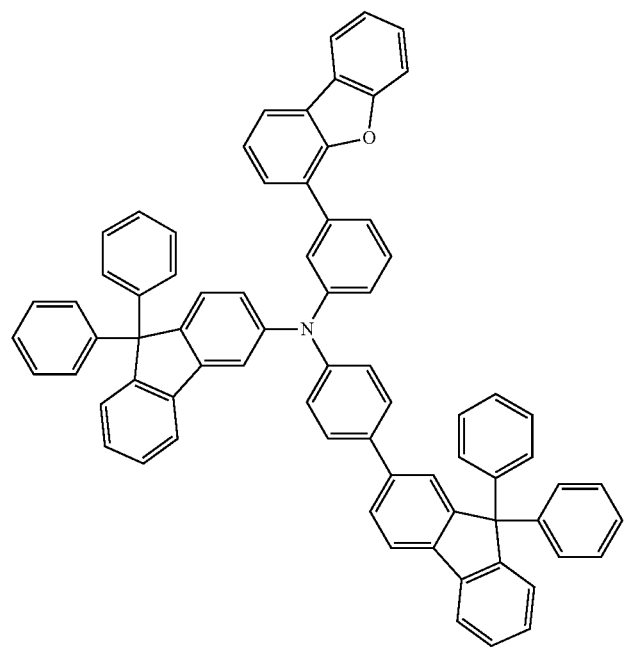
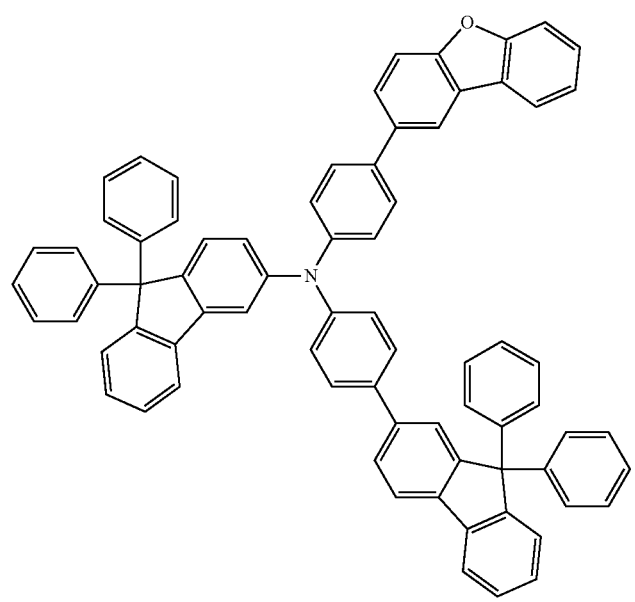

-continued
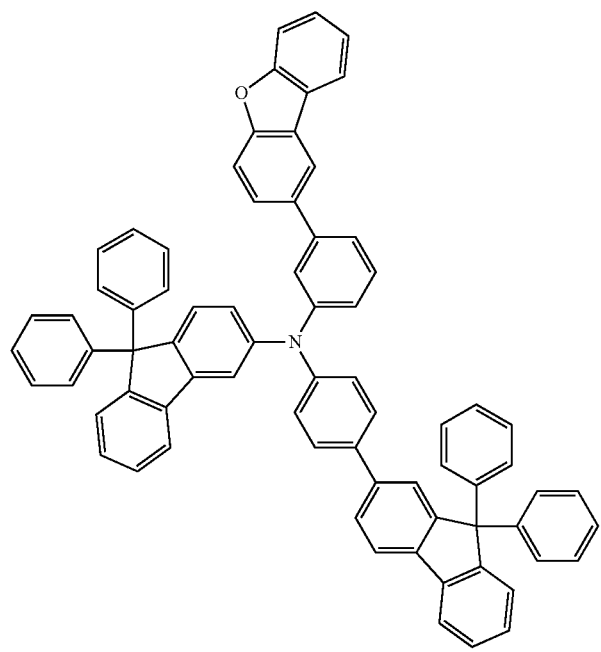
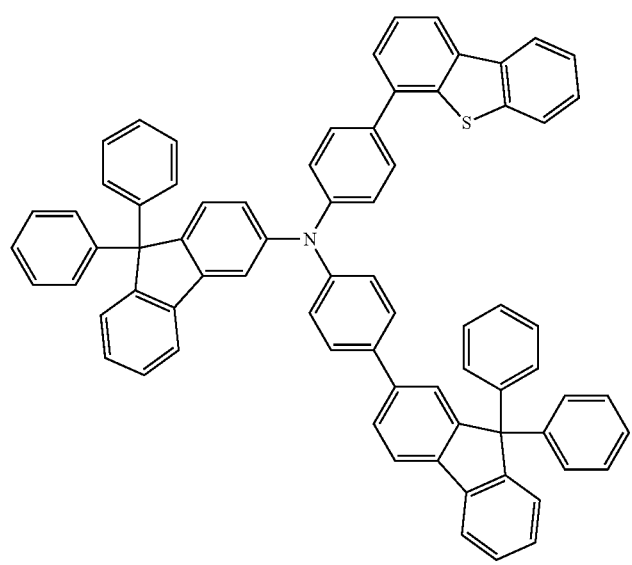

-continued
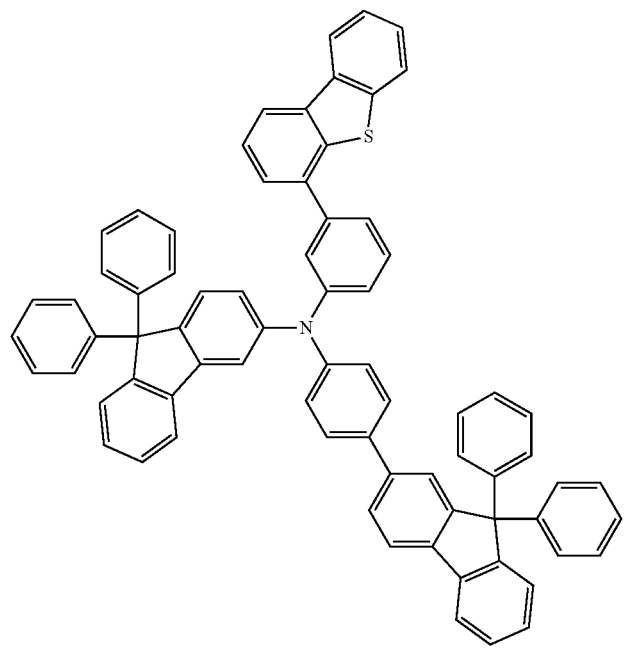
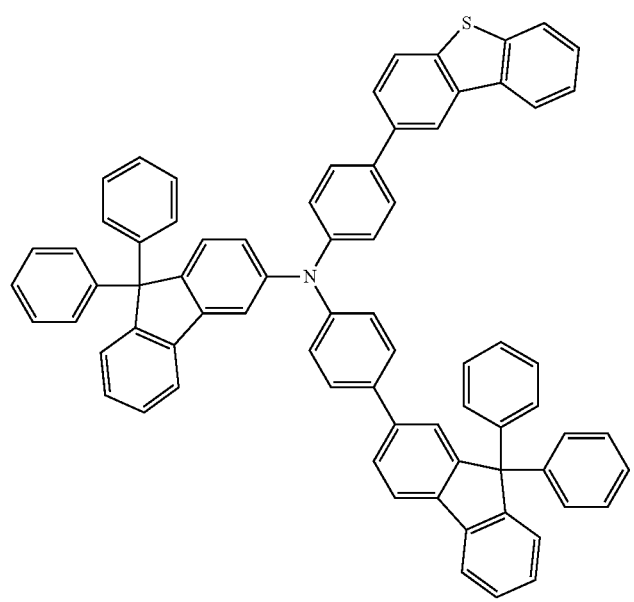

-continued
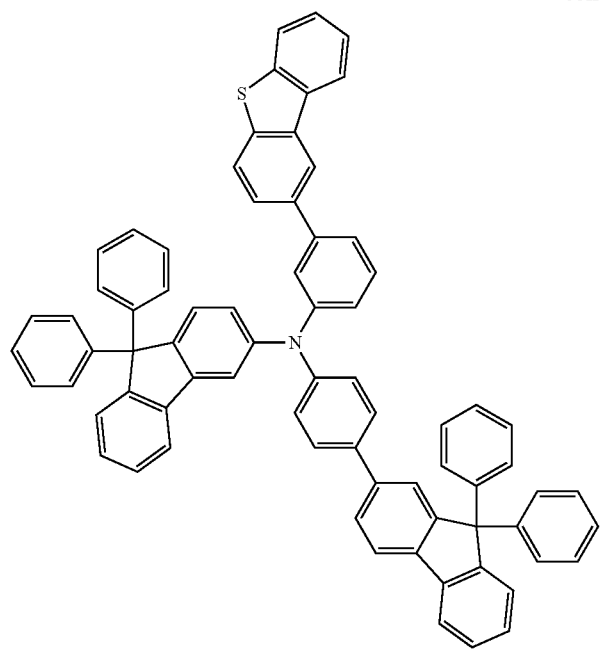
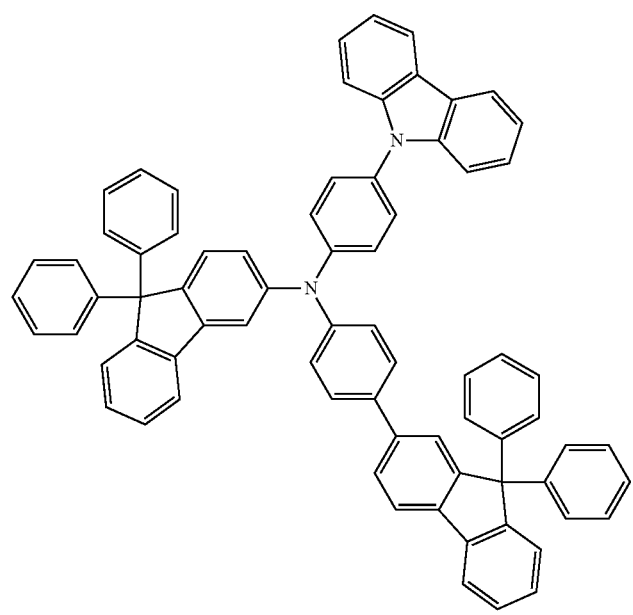

279 280
-continued
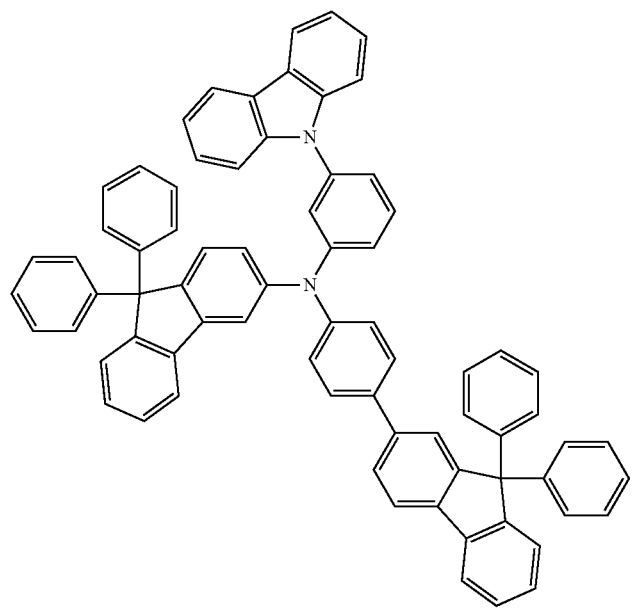
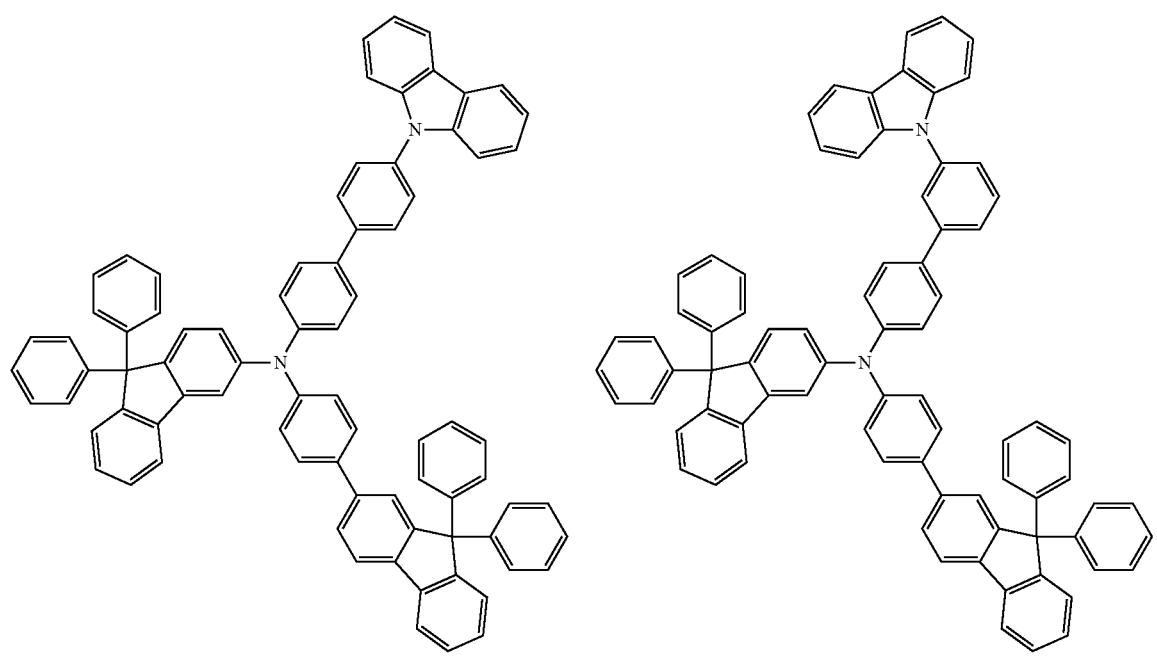

-continued
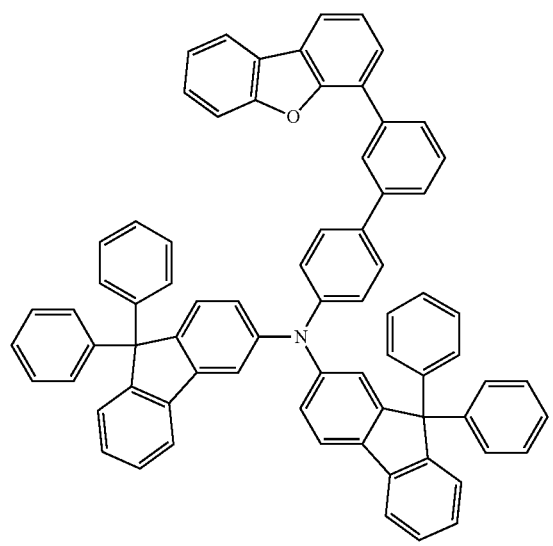
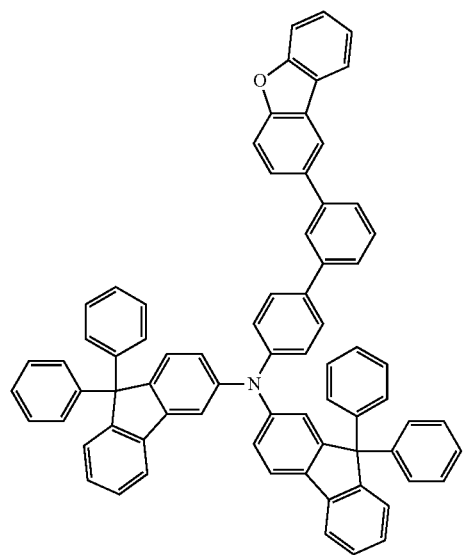
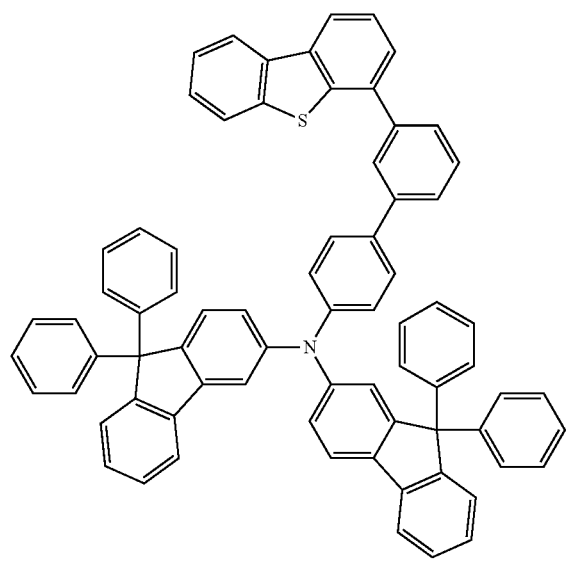

-continued
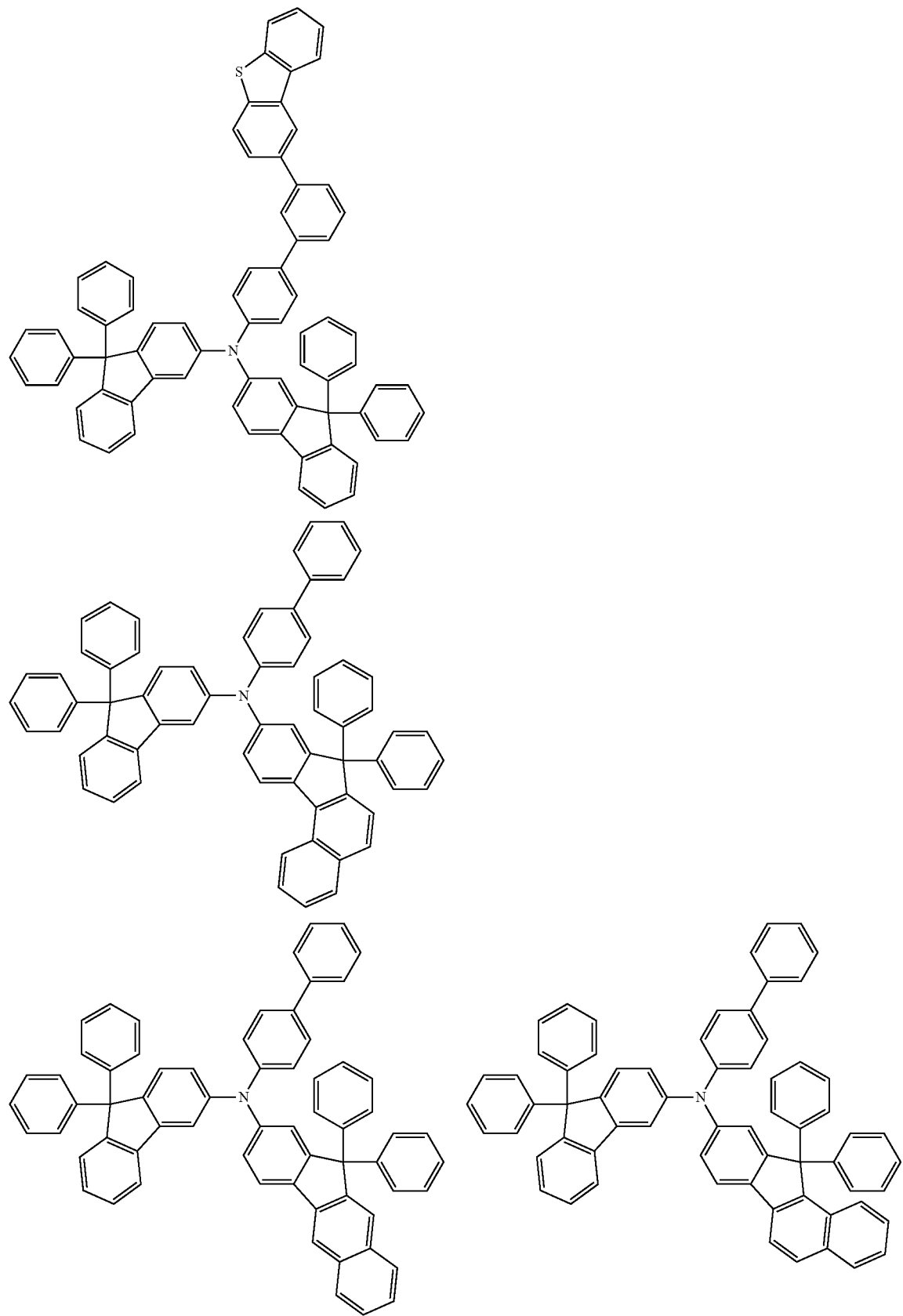

Of the above, the compound (B) is preferably any of the following compounds (H-B1) to (H-B20):
(H-B1)
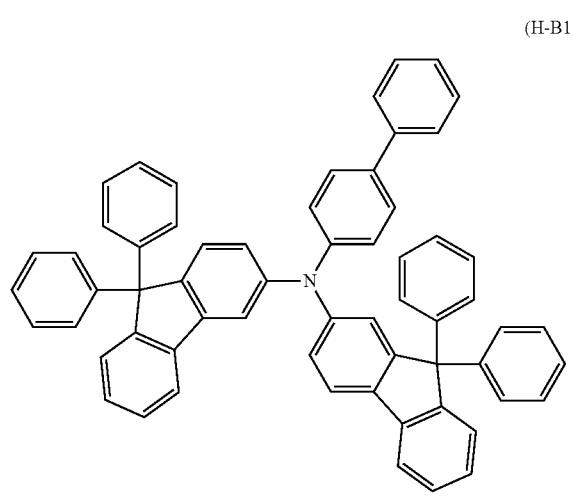
(H-B2)
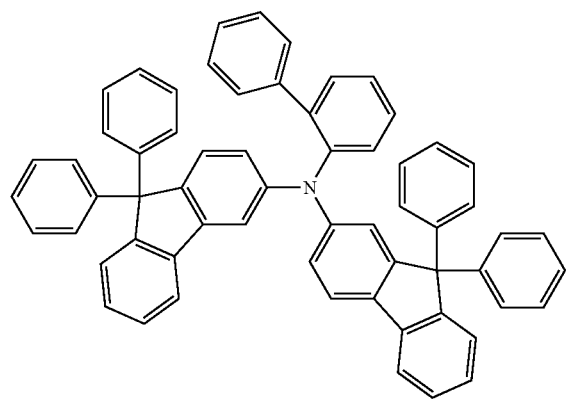
(H-B3)
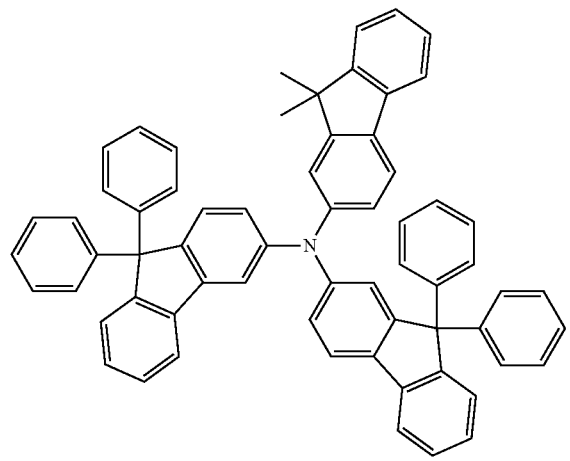
(H-B4)
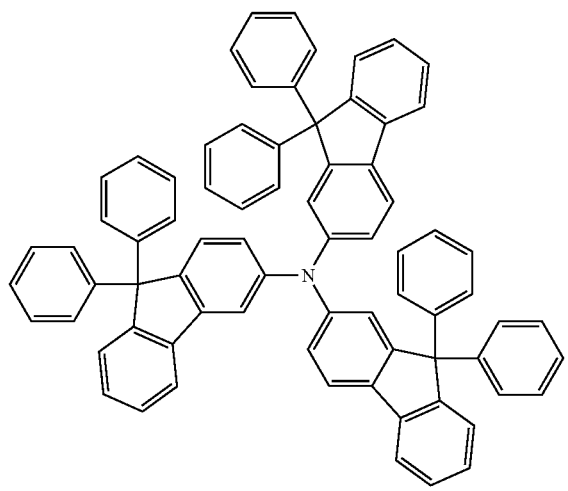
(H-B5)
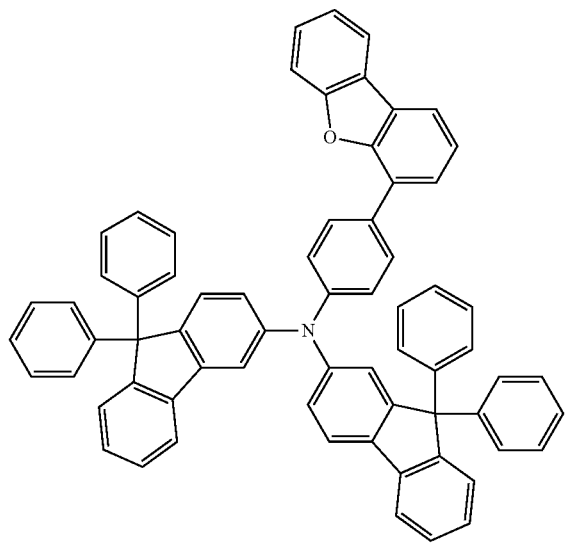
(H-B6)
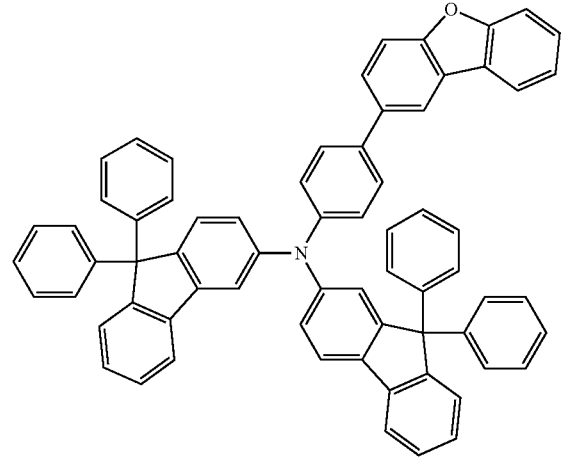

-continued
(H-B7)
(H-B8)
(H-B9)
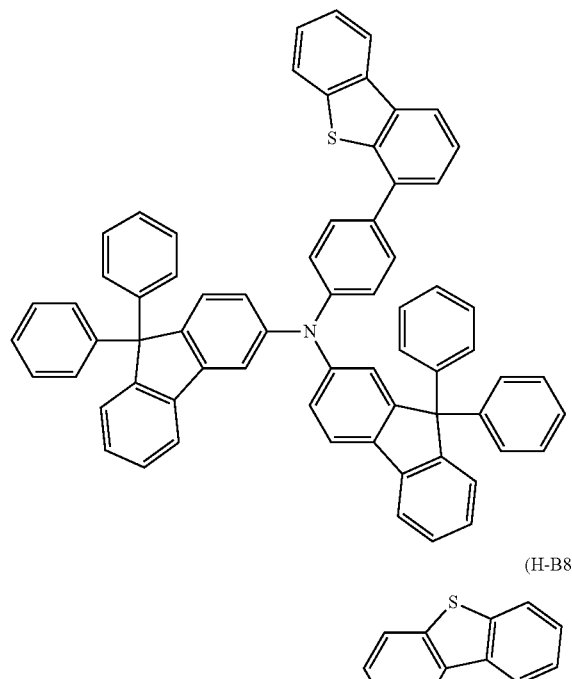
(H-B10)
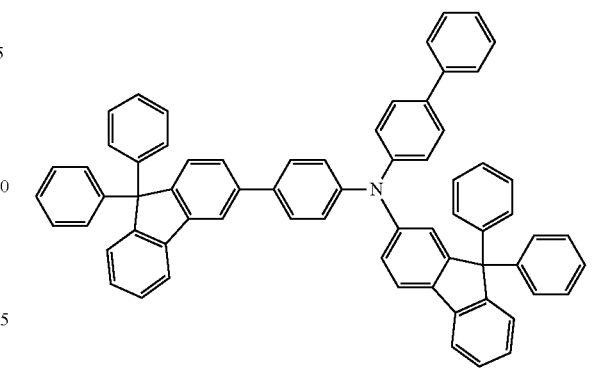
(H-B11)
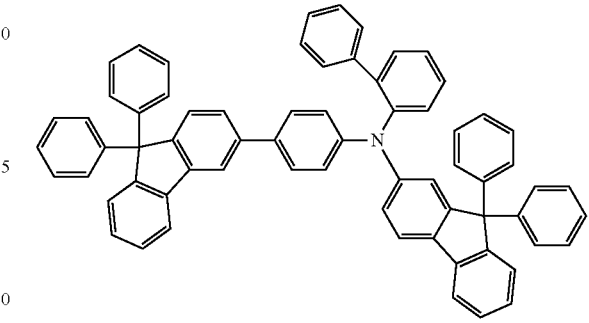
(H-B12)
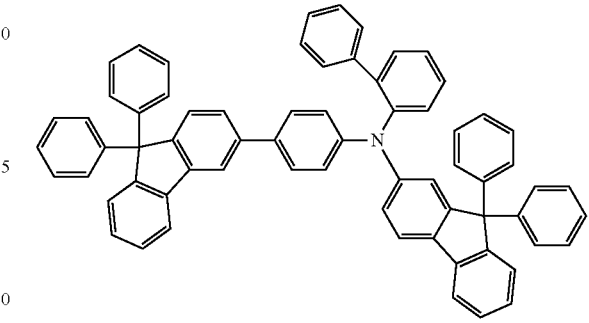
(H-B13)
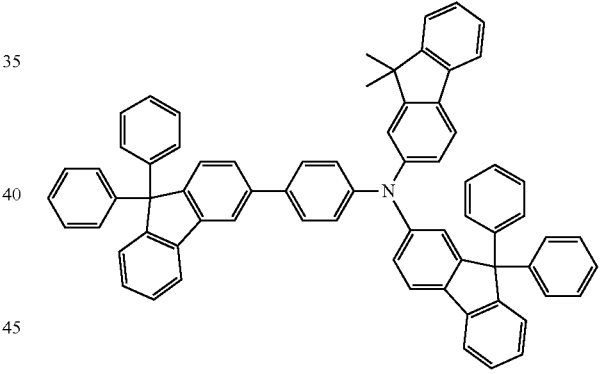

(H-B14)
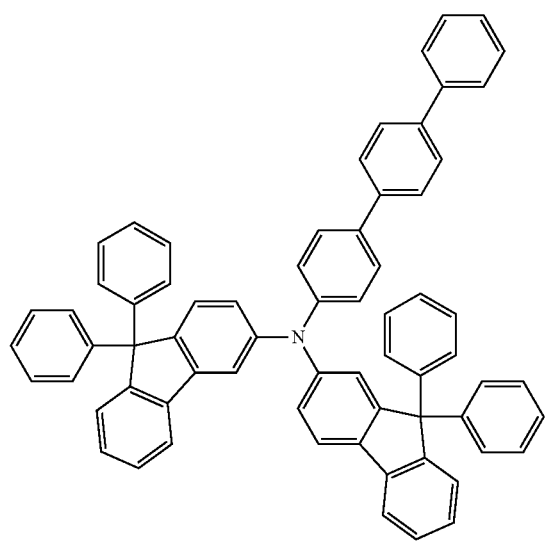
(H-B15)
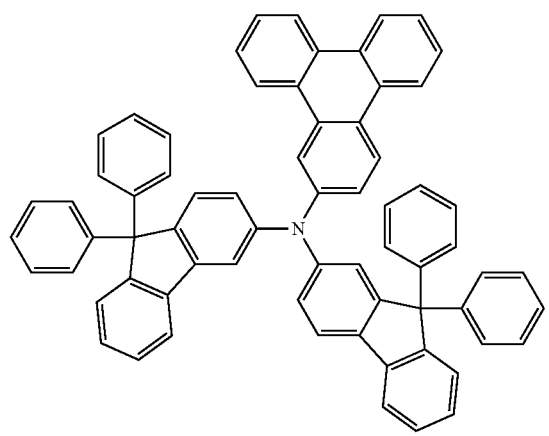
(H-B16)
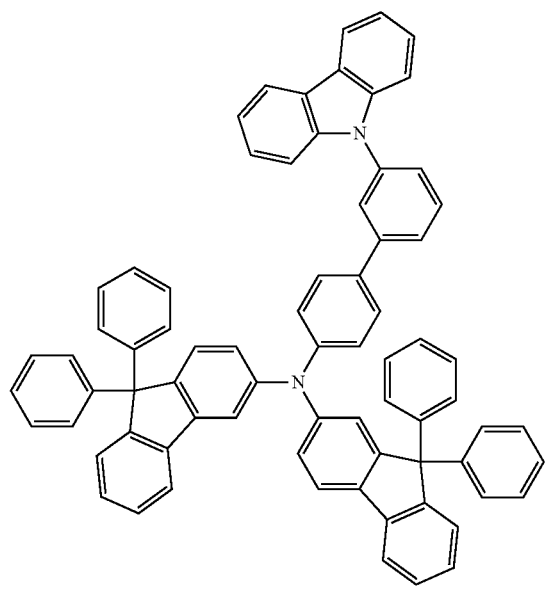
(H-B17)
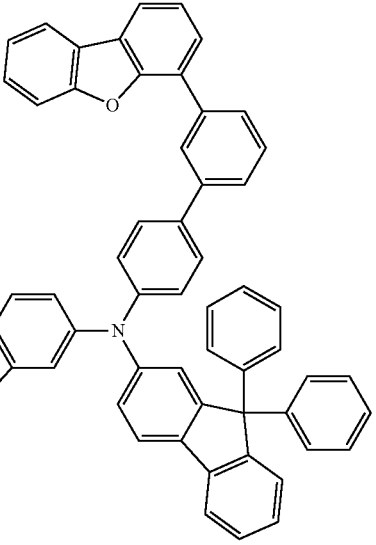
(H-B18)
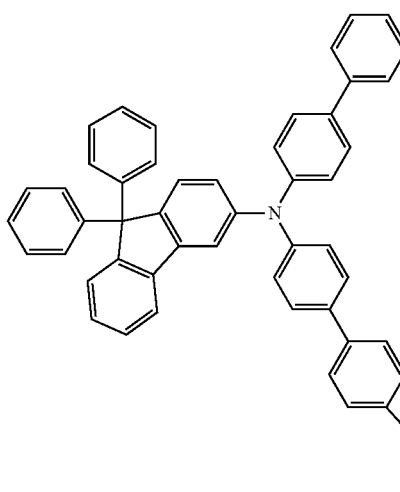
(H-B19)
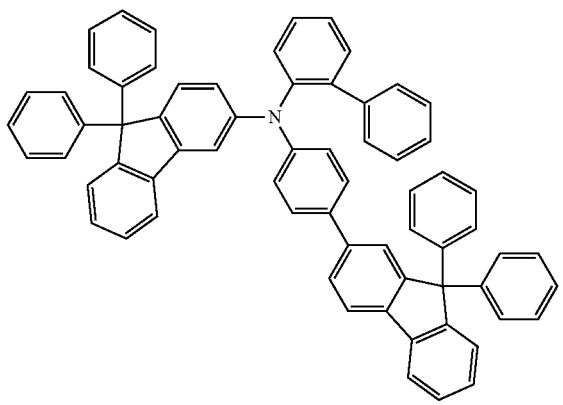

-continued (H-B20)

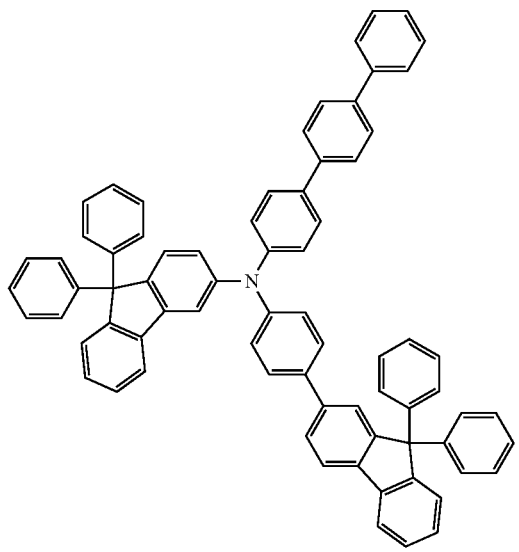

Material for Organic EL Devices

The material for organic EL devices in an aspect of the invention comprises the compound (A), the compound (B), and both the compounds (A) and the compound (B). The material for organic EL devices preferably comprises a compound selected from the compounds (A-1) to (A-4), the compounds (B-0) to (B-4), the compound (A-2-1), and the compound (B-2-1).

The following description with respect to the compound (A) is equally applicable to the compounds (A-1) to (A-4) and (A-2-1), and the following description with respect to the compound (B) is equally applicable to the compounds (B-0) to (B-4) and (B-2-1).

The material for organic EL devices in an aspect of the invention is useful as a material for producing an organic EL device, for example, as a material for at least one organic thin film layer disposed between an anode and a cathode, particularly as a material for a hole transporting layer or a hole injecting layer.

Organic EL Device

The organic EL device in an aspect of the invention will be described below.

Representative device structures (1) to (13) are shown below, although not limited thereto. The device structure (8) is preferably used.

(1) anode/light emitting layer/cathode;
(2) anode/hole injecting layer/light emitting layer/cathode;
(3) anode/light emitting layer/electron injecting layer/cathode;
(4) anode/hole injecting layer/light emitting layer/electron injecting layer/cathode;
(5) anode/organic semiconductor layer/light emitting layer/cathode;
(6) anode/organic semiconductor layer/electron blocking layer/light emitting layer/cathode;
(7) anode/organic semiconductor layer/light emitting layer/adhesion improving layer/cathode;
(8) anode/hole injecting layer/hole transporting layer/light emitting layer/(electron transporting layer/) electron injecting layer/cathode;
(9) anode/insulating layer/light emitting layer/insulating layer/cathode;
(10) anode/inorganic semiconductor layer/insulating layer/light emitting layer/insulating layer/cathode;
(11) anode/organic semiconductor layer/insulating layer/light emitting layer/insulating layer/cathode;
(12) anode/insulating layer/hole injecting layer/hole transporting layer/light emitting layer/insulating layer/cathode; and
(13) anode/insulating layer/hole injecting layer/hole transporting layer/light emitting layer/(electron transporting layer/) electron injecting layer/cathode.

A schematic structure of an example of the organic EL device in an aspect of the invention is shown in FIG. 1, wherein the organic EL device 1 comprises a substrate 2, an anode 3, a cathode 4, and an emission unit 10 disposed between the anode 3 and the cathode 4. The emission unit 10 comprises a light emitting layer 5 which comprises a host material and a dopant (light emitting material). A hole injecting/transporting layer 6, etc. may be disposed between the light emitting layer 5 and the anode 3, and an electron injecting/transporting layer 7, etc. may be disposed between the light emitting layer 5 and the cathode 4. An electron blocking layer may be disposed on the anode 3 side of the light emitting layer 5, and a hole blocking layer may be disposed on the cathode 4 side of the light emitting layer 5. With these blocking layers, electrons and holes are confined in the light emitting layer 5 to increase the exciton generation in the light emitting layer 5.

The organic EL device in an aspect of the invention comprises an anode, a cathode, and at least one organic thin film layer between the cathode and the anode. The at least one organic thin film layer comprises a light emitting layer and at least one layer of the at least one organic thin film layer comprise at least one selected from the compound (A) represented by formula (A-0) and the compound (B) represented by formula (B-0).

Examples of the organic thin film layer comprising the compound (A) and/or the compound (B) include an anode-side organic thin film layer formed between an anode and a light emitting layer (hole transporting layer, hole injecting layer, etc.), a light emitting layer, a cathode-side organic thin film layer formed between a cathode and a light emitting layer (electron transporting layer, electron injecting layer, etc.), a space layer, and a blocking layer, although not limited thereto.

The compound (A) and the compound (B) may be used in any of the organic thin film layers of an organic EL device. In view of driving at a lower voltage, the compound (A) and the compound (B) are preferably used in a hole injecting layer or a hole transporting layer, more preferably used in a hole transporting layer.

Namely, the organic EL device in an aspect of the invention is more preferably an organic EL device wherein the at least one organic thin film layer comprises a hole injecting layer comprising the compound (A) and/or the compound (B), a hole transporting layer comprising the compound (A) and/or the compound (B), or both layers.

The content of the compound (A) in the organic thin film layer, preferably in a hole injecting layer or a hole transporting layer, is preferably 30 to 100 mol %, more preferably 50 to 100 mol %, still more preferably 80 to 100 mol %, and further preferably 95 to 100 mol % each based on the total molar amount (100 mol %) of the components in the organic thin film layer.

Similarly, the content of the compound (B) in the organic thin film layer, preferably in a hole injecting layer or a hole transporting layer, is preferably 30 to 100 mol %, more preferably 50 to 100 mol %, still more preferably 80 to 100 mol %, and further preferably 95 to 100 mol % each based on the total molar amount (100 mol %) of the components in the organic thin film layer.

Substrate

The substrate is a support for the emitting device and made of, for example, glass, quartz, and plastics. The substrate may be a flexible substrate, for example, a plastic substrate made of, for example, polycarbonate, polyarylate, polyether sulfone, polypropylene, polyester, polyvinyl fluoride, and polyvinyl chloride. An inorganic deposition film is also usable.

Anode

The anode is formed on the substrate preferably from a metal, an alloy, an electrically conductive compound, and a mixture thereof, each having a large work function, for example, 4.5 eV or more. Examples of the material for the anode include indium oxide-tin oxide (ITO: indium tin oxide), indium oxide-tin oxide doped with silicon or silicon oxide, indium oxide-zinc oxide, indium oxide doped with tungsten oxide and zinc oxide, and graphene. In addition, gold (Au), platinum (Pt), nickel (Ni), tungsten (W), chromium (Cr), molybdenum (Mo), iron (Fe), cobalt (Co), copper (Cu), palladium (Pd), titanium (Ti), and a metal nitride (for example, titanium nitride) are also usable.

These materials are made into a film generally by a sputtering method. For example, a film of indium oxide-zinc oxide is formed by sputtering an indium oxide target doped with 1 to 10% by mass of zinc oxide, and a film of indium oxide doped with tungsten oxide and zinc oxide is formed by sputtering an indium oxide target doped with 0.5 to 5% by mass of tungsten oxide and 0.1 to 1% by mass of zinc oxide. In addition, a vacuum vapor deposition method, a coating method, an inkjet method, and a spin coating method are usable.

A hole injecting layer to be formed in contact with the anode is formed from a composite material which is capable of easily injecting holes independently of the work function of the anode. Therefore a material, for example, a metal, an alloy, an electroconductive compound, a mixture thereof, and a group 1 element and a group 2 element of the periodic table are usable as the electrode material.

A material having a small work function, for example, the group 1 element and the group 2 element of the periodic table, i.e., an alkali metal, such as lithium (Li) and cesium (Cs), an alkaline earth metal, such as magnesium (Mg), calcium (Ca), and strontium (Sr), and an alloy thereof, such as MgAg and AlLi, are also usable. In addition, a rare earth metal, such as europium (Eu) and ytterbium (Yb), and an alloy thereof are also usable. The alkali metal, the alkaline earth metal, and the alloy thereof can be made into the anode by a vacuum vapor deposition or a sputtering method. When a silver paste, etc. is used, a coating method and an inkjet method are usable.

Hole Injecting Layer

The hole injecting layer comprises a highly hole-transporting material.

The hole injecting layer of the organic EL device in an aspect of the invention preferably comprises at least one selected from the compound (A) and the compound (B) in an aspect of the invention.

Such a hole injecting layer may comprise at least one selected from the compound (A) and the compound (B), or may comprise at least one selected from the compound (A) and the compound (B) in combination with the following compound.

Examples of the highly hole-transporting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

The following low molecular aromatic amine compound is also usable: 4,4',4"-tris(N,N-diphenylamino)triphenylamine (TDATA), 4,4',4"-tris[N-(3-methylphenyl)-N-phenylamino]triphenylamine (MTDATA), 4,4'-bis[N-(4-diphenylaminophenyl)-N-phenylamino]biphenyl (DPAB), 4,4'-bis(N-{4-[N'-(3-methylphenyl)-N'-phenylamino]phenyl}-N-phenylamino)biphenyl (DNTPD), 1,3,5-tris[N-(4-diphenylaminophenyl)-N-phenylamino]benzene (DPA3B), 3-[N-(9-phenylcarbazole-3-yl)-N-phenylamino]-9-phenylcarbazole (PCzPCA1), 3,6-bis[N-(9-phenylcarbazole-3-yl)-N-phenylamino]-9-phenylcarbazole (PCzPCA2), and 3-[N-(1-naphthyl)-N-(9-phenylcarbazole-3-yl)amino]-9-phenylcarbazole (PCzPCN1).

A polymeric compound, such as an oligomer, a dendrimer, a polymer, is also usable. Examples thereof include poly(N-vinylcarbazole) (PVK), poly(4-vinyltriphenylamine) (PVTPA), poly[N-(4-{N'-[4-(4-diphenylamino)phenyl]phenyl-N'-phenylamino}phenyl)methacrylamide](PTPDMA), and poly[N,N'-bis(4-butylphenyl)-N,N'-bis(phenyl)benzidine](Poly-TPD). An acid-added polymeric compound, such as poly(3,4-ethylenedioxythiophene)/poly(styrenesulfonic acid) (PEDOT/PSS) and polyalinine/poly(styrenesulfonic acid) (PAni/PSS), is also usable.

Hole Transporting Layer

The hole transporting layer comprises a highly hole-transporting material.

The hole transporting layer of the organic EL device in an aspect of the invention preferably comprises at least one selected from the compound (A) and the compound (B) in an aspect of the invention.

Such a hole transporting layer may comprise at least one selected from the compound (A) and the compound (B), or may comprise at least one selected from the compound (A) and the compound (B) in combination with the following compound.

The hole transporting layer may comprise an aromatic amine compound, a carbazole derivative, an anthracene derivative, etc., for examples, an aromatic amine compound, such as 4,4'-bis[N-(1-naphthyl)-N-phenylamino]biphenyl (NPB), N,N'-bis(3-methylphenyl)-N,N'-diphenyl-[1,1'-biphenyl]-4,4'-diamine (TPD), 4-phenyl-4'-(9-phenylfluorene-9-yl)triphenylamine (BAFLP), 4,4'-bis[N-(9,9-dimethylfluorene-2-yl)-N-phenylamino]biphenyl (DFLDPBi), 4,4',4"-tris(N,N-diphenylamino)triphenylamine (TDATA), 4,4',4"-tris[N-(3-methylphenyl)-N-phenylamino]triphenylamine (MTDATA), and 4,4'-bis[N-(spiro-9,9'-bifluorene-2-yl)-N-phenylamino]biphenyl (BSPB). The above compounds have a hole mobility of mainly $10^{-6}$ cm$^2$/Vs or more.

In addition, the hole transporting layer may contain a carbazole derivative, such as CBP, CzPA, and PCzPA, an anthracene derivative, such as t-BuDNA, DNA, and DPAnth, and a polymeric compound, such as poly(N-vinylcarbazole) (PVK) and poly(4-vinyltriphenylamine) (PVTPA).

Other materials are also usable if their hole transporting ability is higher than their electron transporting ability. The layer comprising a highly hole-transporting material may be a single layer or a laminate of two or more layers each comprising the material mentioned above. For example, the hole transporting layer may be made into a two-layered structure of a first hole transporting layer (anode side) and a second hole transporting layer (light emitting layer side).

In such a two-layered structure, the compound (A) and/or the compound (B) in an aspect of the invention may be used in either of the first hole transporting layer and the second hole transporting layer.

In the organic EL device in an aspect of the invention, a layer comprising an electron-accepting compound (acceptor material) may be formed on the anode-side of the hole transporting layer or the first hole transporting layer, because it is expected that the driving voltage is lowered and the production cost is reduced.

A compound represented by formula (EA) is preferably used as the acceptor compound:

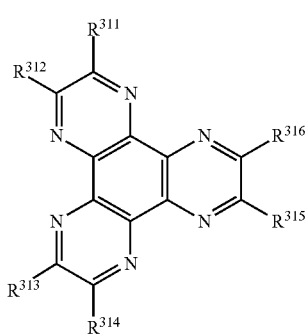

(EA)

wherein $R^{311}$ to $R^{316}$ may be the same or different and each independently represent a cyano group, —$CONH_2$, a carboxyl group, or —$COOR^{317}$ wherein $R^{317}$ represents an alkyl group having 1 to 20 carbon atoms or a cycloalkyl group having 3 to 20 carbon atoms; and $R^{311}$ and $R^{312}$, $R^{313}$ and $R^{314}$, or $R^{315}$ and $R^{316}$ may be bonded to each other to form a group represented by —CO—O—CO—.

Examples of alkyl group for $R^{317}$ include a methyl group, an ethyl group, a n-propyl group, an isopropyl group, a n-butyl group, an isobutyl group, and a t-butyl group. Examples of cycloalkyl group include a cyclopentyl group and a cyclohexyl group.

The thickness of the layer comprising the acceptor compound is preferably 5 to 20 nm, although not particularly limited thereto.

Guest Material of Light Emitting Layer

The light emitting layer comprises a highly light-emitting material and may be formed from a various kind of materials. For example, a fluorescent emitting compound and a phosphorescent emitting compound are usable as the highly light-emitting material. The fluorescent emitting compound is a compound capable of emitting light from a singlet excited state, and the phosphorescent emitting compound is a compound capable of emitting light from a triplet excited state.

Examples of blue fluorescent emitting material for use in the light emitting layer include a pyrene derivative, a styrylamine derivative, a chrysene derivative, a fluoranthene derivative, a fluorene derivative, a diamine derivative, and a triarylamine derivative, such as N,N'-bis[4-(9H-carbazole-9-yl)phenyl]-N,N'-diphenylstilbene-4,4'-diamine (YGA2S), 4-(9H-carbazole-9-yl)-4'-(10-phenyl-9-anthryl)triphenylamine (YGAPA), and 4-(10-phenyl-9-anthryl)-4'-(9-phenyl-9H-carbazole-3-yl)triphenylamine (PCBAPA).

Examples of green fluorescent emitting material for use in the light emitting layer include an aromatic amine derivative, such as N-(9,10-diphenyl-2-anthryl)-N,9-diphenyl-9H-carbazole-3-amine (2PCAPA), N-[9,10-bis(1,1'-biphenyl-2-yl)-2-anthryl]-N,9-diphenyl-9H-carbazole-3-amine (2PCABPhA), N-(9,10-diphenyl-2-anthryl)-N,N',N'-triphenyl-1,4-phenylenediamine (2DPAPA), N-[9,10-bis(1,1'-biphenyl-2-yl)-2-anthryl]-N,N',N'-triphenyl-1,4-phenylenediamine (2DPABPhA), N-[9,10-bis(1,1'-biphenyl-2-yl)]-N-[4-(9H-carbazole-9-yl)phenyl]-N-phenylanthracene-2-amine (2YGABPhA), and N,N,9-triphenylanthracene-9-amine (DPhAPhA).

Examples of red fluorescent emitting material for use in the light emitting layer include a tetracene derivative and a diamine derivative, such as N,N,N',N'-tetrakis(4-methylphenyl)tetracene-5,11-diamine (p-mPhTD) and 7,14-diphenyl-N,N,N',N'-tetrakis(4-methylphenyl)acenaphtho[1,2-a]fluoranthene-3,10-diamine (p-mPhAFD).

Examples of blue phosphorescent emitting material for use in the light emitting layer include a metal complex, such as an iridium complex, an osmium complex, and a platinum complex. Examples thereof include bis[2-(4',6'-difluorophenyl)pyridinato-N,C2']iridium(III) tetrakis(1-pyrazolyl)borato (FIrs), bis[2-(4',6'-difluorophenyl)pyridinato-N,C2']iridium(III) picolinato (FIrpic), bis[2-(3',5'-bistrifluoromethylphenyl)pyridinato-N,C2']iridium(III) picolinato (Ir(CF3ppy)$_2$(pic)), and bis[2-(4',6'-difluorophenyl)pyridinato-N,C2']iridium(III) acetylacetonato (FIracac).

Examples of green phosphorescent emitting material for use in the light emitting layer include an iridium complex, such as tris(2-phenylpyridinato-N,C2')iridium(III) (Ir(ppy)$_3$), bis(2-phenylpyridinato-N,C2')iridium(III) acetylacetonato (Ir(ppy)$_2$(acac)), bis(1,2-diphenyl-1H-benzimidazolato)iridium(III) acetylacetonato (Ir(pbi)$_2$(acac)), and bis(benzo[h]quinolinato)iridium(III) acetylacetonato (Ir(bzq)$_2$(acac)).

Examples of red phosphorescent emitting material for use in the light emitting layer include a metal complex, such as an iridium complex, a platinum complex, a terbium complex, and a europium complex. Examples thereof include an organometallic complex, such as bis[2-(2'-benzo[4,5-a]thienyl)pyridinato-N,C3']iridium(III) acetylacetonato (Ir(btp)$_2$(acac)), bis(1-phenylisoquinolinato-N,C2')iridium(III) acetylacetonato (Ir(piq)$_2$(acac)), (acetylacetonato)bis[2,3-bis(4-fluorophenyl)quinoxalinato]iridium(III) (Ir(Fdpq)$_2$(acac)), and 2,3,7,8,12,13,17,18-octaethyl-21H,23H-porphyrin platinum(II) (PtOEP).

The following rare earth metal complex, such as tris(acetylacetonato) (monophenanthroline) terbium(III) (Tb(acac)$_3$(Phen)), tris(1,3-diphenyl-1,3-propanedionato) (monophenanthroline)europium(III) (Eu(DBM)$_3$(Phen)), and tris[1-(2-thenoyl)-3,3,3-trifluoroacetonato](monophenanthroline)europium(III) (Eu(TTA)$_3$(Phen)), emits light from the rare earth metal ion (electron transition between different multiple states), and therefore, usable as a phosphorescent emitting compound.

Host Material for Light Emitting Layer

The light emitting layer may be formed by dispersing the highly light-emitting material (guest material) mentioned above in another material (host material). The material in which the highly light-emitting material is to be dispersed may be selected from various kinds of materials and is preferably a material having a lowest unoccupied molecular orbital level (LUMO level) higher than that of the highly light-emitting material and a highest occupied molecular orbital level (HOMO level) lower than that of the highly light-emitting material.

The material in which the highly light-emitting material is to be dispersed may include, for example, (1) a metal complex, such as an aluminum complex, a beryllium complex, and a zinc complex;
(2) a heterocyclic compound, such as an oxadiazole derivative, a benzimidazole derivative, and a phenanthroline derivative;
(3) a fused aromatic compound, such as a carbazole derivative, an anthracene derivative, a phenanthrene derivative, a pyrene derivative, and a chrysene derivative; and
(4) an aromatic amine compound, such as a triarylamine derivative and a fused aromatic polycyclic amine derivative.

Examples thereof include:

a metal complex, such as tris(8-quinolinolato)aluminum (III) (Alq), tris(4-methyl-8-quinolinolato)aluminum(III) (Almq$_3$), bis(10-hydroxybenzo[h]quinolinato)beryllium(II) (BeBq$_2$), bis(2-methyl-8-quinolinolato)(4-phenylphenolato)aluminum(III) (BAlq), bis(8-quinolinolato)zinc(II) (Znq), bis[2-(2-benzoxazolyl)phenolato]zinc(II) (ZnPBO), and bis[2-(2-benzothiazolyl)phenolato]zinc(II) (ZnBTZ);

a heterocyclic compound, such as 2-(4-biphenylyl)-5-(4-tert-butylphenyl)-1,3,4-oxadiazole (PBD), 1,3-bis[5-(p-tert-butylphenyl)-1,3,4-oxadiazole-2-yl]benzene (OXD-7), 3-(4-biphenylyl)-4-phenyl-5-(4-tert-butylphenyl)-1,2,4-triazole (TAZ), 2,2',2''-(1,3,5-benzenetriyl)tris(1-phenyl-1H-benzimidazole) (TPBI), bathophenanthroline (BPhen), and bathocuproin (BCP);

a fused aromatic compound, such as 9-[4-(10-phenyl-9-anthryl)phenyl]-9H-carbazole (CzPA), 3,6-diphenyl-9-[4-(10-phenyl-9-anthryl)phenyl]-9H-carbazole (DPCzPA), 9,10-bis(3,5-diphenylphenyl)anthracene (DPPA), 9,10-di(2-naphthyl)anthracene (DNA), 2-tert-butyl-9,10-di(2-naphthyl)anthracene (t-BuDNA), 9,9'-bianthryl (BANT), 9,9'-(stilbene-3,3'-diyl)diphenanthrene (DPNS), 9,9'-(stilbene-4,4'-diyl)diphenanthrene (DPNS2), 3,3',3''-(benzene-1,3,5-triyl)tripyrene (TPB3), 9,10-diphenylanthracene (DPAnth), and 6,12-dimethoxy-5,11-diphenylchrysene; and an aromatic amine compound, such as N,N-diphenyl-9-[4-(10-phenyl-9-anthryl)phenyl]-9H-carbazole-3-amine (CzA1PA), 4-(10-phenyl-9-anthryl)triphenylamine (DPhPA), N,9-diphenyl-N-[4-(10-phenyl-9-anthryl)phenyl]-9H-carbazole-3-amine (PCAPA), N,9-diphenyl-N-{4-[4-(10-phenyl-9-anthryl)phenyl]phenyl}-9H-carbazole-3-amine (PCAPBA), N-(9,10-diphenyl-2-anthryl)-N,9-diphenyl-9H-carbazole-3-amine (2PCAPA), NPB (or α-NPD), TPD, DFLDPBi, and BSPB.

The material (host material) for dispersing the highly light-emitting material (guest material) may be used alone or in combination of two or more.

Electron Transporting Layer

The electron transporting layer comprises a highly electron-transporting material, for example,
(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a polymeric compound.

Examples of the low molecular organic compound include a metal complex, such as Alq, tris(4-methyl-8-quinolinolato)aluminum (Almq$_3$), bis(10-hydroxybenzo[h]quinolinato)beryllium (BeBq$_2$), BAlq, Znq, ZnPBO, and ZnBTZ; and a heteroaromatic compound, such as 2-(4-biphenylyl)-5-(4-tert-butylphenyl)-1,3,4-oxadiazole (PBD), 1,3-bis[5-(ptert-butylphenyl)-1,3,4-oxadiazole-2-yl]benzene (OXD-7), 3-(4-tert-butylphenyl)-4-phenyl-5-(4-biphenylyl)-1,2,4-triazole (TAZ), 3-(4-tert-butylphenyl)-4-(4-ethylphenyl)-5-(4-biphenylyl)-1,2,4-triazole (p-EtTAZ), bathophenanthroline (BPhen), bathocuproine (BCP), and 4,4'-bis(5-methylbenzoxazole-2-yl)stilbene (BzOs).

The above compounds have an electron mobility of mainly $10^{-6}$ cm$^2$Vs or more. Other materials are also usable in the electron transporting layer if their electron transporting ability is higher than their hole transporting ability. The electron transporting layer may be a single layer or a laminate of two or more layers each comprising the material mentioned above.

A polymeric compound is also usable in the electron transporting layer. Examples thereof include poly[(9,9-dihexylfluorene-2,7-diyl)-co-(pyridine-3,5-diyl)](PF-Py), and poly[(9,9-dioctylfluorene-2,7-diyl)-co-(2,2'-bipyridine-6,6'-diyl)](PF-BPy).

Electron Injecting Layer

The electron injecting layer comprises a highly electron-injecting material, for example, an alkali metal, an alkaline earth metal, and a compound of these metals, such as lithium (Li), cesium (Cs), calcium (Ca), lithium fluoride (LiF), cesium fluoride (CsF), calcium fluoride(CaF2), and lithium oxide (LiOx). In addition, an electron transporting material which is incorporated with an alkali metal, an alkaline earth metal or a compound thereof, for example, Alq doped with magnesium (Mg), is also usable. By using such a material, electrons are efficiently injected from the cathode.

A composite material obtained by mixing an organic compound and an electron donor is also usable in the electron injecting layer. Such a composite material is excellent in the electron injecting ability and the electron transporting ability, because the electron donor donates electrons to the organic compound. The organic compound is preferably a material excellent in transporting the received electrons. Examples thereof are the materials for the electron transporting layer mentioned above, such as the metal complex and the aromatic heterocyclic compound. Any material capable of giving its electron to another organic compound is usable as the electron donor. Preferred examples thereof are an alkali metal, an alkaline earth metal, and a rare earth metal, such as lithium, cesium, magnesium, calcium, erbium, and ytterbium; an alkali metal oxide and an alkaline earth metal oxide, such as, lithium oxide, calcium oxide, and barium oxide; a Lewis base, such as magnesium oxide; and an organic compound, such as tetrathiafulvalene (TTF).

Cathode

The cathode is formed preferably from a metal, an alloy, an electrically conductive compound, and a mixture thereof, each having a small work function, for example, a work function of 3.8 eV or less. Examples of the material for the cathode include a metal of the group 1 or 2 of the periodic table, for example, an alkali metal, such as lithium (Li) and cesium (Cs), an alkaline earth metal, such as magnesium (Mg), an alloy containing these metals (for example, MgAg and AlLi), a rare earth metal, such as europium (Eu) and ytterbium (Yb), and an alloy containing a rare earth metal.

The alkali metal, the alkaline earth metal, and the alloy thereof can be made into the cathode by a vacuum vapor deposition or a sputtering method. When a silver paste, etc. is used, a coating method and an inkjet method are usable.

When the electron injecting layer is formed, the material for the cathode can be selected independently from the work function and various electroconductive materials, such as Al, Ag, ITO, graphene, and indium oxide-tin oxide doped with silicon or silicon oxide, are usable. These electroconductive materials are made into films by a sputtering method, an inkjet method, and a spin coating method.

Each layer of the organic EL device is formed by a dry film-forming method, such as vacuum vapor deposition, sputtering, plasma, and ion plating, and a wet film-forming method, such as spin coating, dip coating, and flow coating.

In the wet film-forming method, the material for each layer is dissolved or dispersed in a suitable solvent, such as ethanol, chloroform, tetrahydrofuran, and dioxane, and then the obtained solution or dispersion is made into a film. To improve the film-forming properties and prevent pin holes on the film, the solution and the dispersion may include a resin or an additive. Examples of the resin include an insulating resin and a copolymer thereof, such as polystyrene, polycarbonate, polyarylate, polyester, polyamide, polyurethane, polysulfone, polymethyl methacrylate, polymethyl acrylate, and cellulose; and a photoconductive resin, such as poly-N-vinylcarbazole and polysilane; and an electroconductive resin, such as polythiophene and polypyrrole. Examples of the additive include an antioxidant, an ultraviolet absorber, and a plasticizer.

The thickness of each layer is not particularly limited and selected so as to obtain a good device performance. If extremely thick, a large applied voltage is needed to obtain a desired emission output, thereby reducing the efficiency. If extremely thin, pinholes occur on the film to make it difficult to obtain a sufficient luminance even when applying an electric field. The thickness is generally 5 nm to 10 μm and preferably 10 nm to 0.2 μm.

The thickness of the light emitting layer is, but not particularly limited to, preferably 5 to 100 nm, more preferably 7 to 70 nm, and still more preferably 10 to 50 nm.

The thickness of the hole transporting layer is preferably 10 to 300 nm.

When the hole transporting layer is made into a two-layered structure as described above, the thickness of the first hole transporting layer is preferably 50 to 300 nm, more preferably 50 to 250 nm, still more preferably 50 to 200 nm, and further preferably 50 to 150 nm, and the thickness of the second hole transporting layer is preferably 5 to 100 nm, more preferably 5 to 50 nm, still more preferably 5 to 30 nm, and further preferably 5 to 20 nm, although not limited thereto.

Electronic Equipment

The electronic equipment in an aspect of the invention comprises the organic EL device in an aspect of the invention mentioned above.

Examples of the electronic equipment include display parts, such as organic EL panel module; display devices of television sets, mobile phones, personal computer, etc.; and light emitting sources of lighting equipment and vehicle lighting equipment.

EXAMPLES

The present invention will be described in more detail with reference to the examples and comparative examples. However, it should be noted that the scope of the invention is not limited thereto.

The compounds recited in the claims of this application can be synthesized by referring to the following synthetic reactions while using a known synthetic reaction and a starting material in accordance with the target compound.

Intermediates Commonly Used in Synthesis of Compounds (A) and (B)

Intermediate Synthesis 1-1

Synthesis of Intermediate (1-1)

Under an argon atmosphere, into a mixture of 28.3 g (100.0 mmol) of 4-iodobromobenzene, 22.3 g (105.0 mmol) of dibenzofuran-4-boronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 26.2 g of a white solid (yield: 81%), which was identified by FD-MS analysis (field desorption mass spectrometric analysis) as the intermediate (1-1).

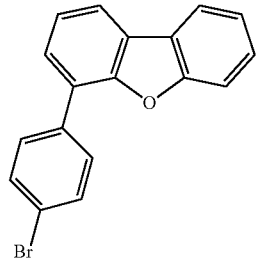

(1-1)

Intermediate Synthesis 1-2

Synthesis of Intermediate (1-2)

In the same manner as in Intermediate Synthesis 1-1 except for using 22.3 g (105.0 mmol) of dibenzofuran-2-boronic acid in place of dibenzofuran-4-boronic acid, 27.4 g of a white solid was obtained (yield: 85%), which was identified by FD-MS analysis as the following intermediate (1-2).

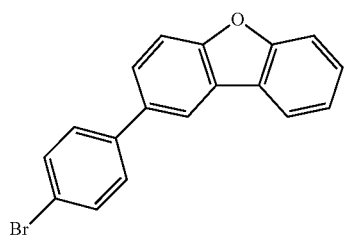

(1-2)

Intermediate Synthesis 1-3

Synthesis of Intermediate (1-3)

Under an argon atmosphere, into a mixture of 28.3 g (100.0 mmol) of 4-iodobromobenzene, 23.9 g (105.0 mmol) of dibenzothophene-4-boronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 27.1 g of a white solid (yield: 80%), which was identified by FD-MS analysis as the following intermediate (1-3).

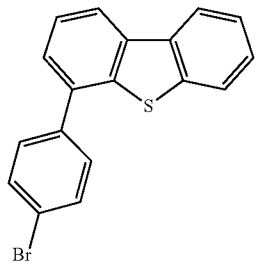

(1-3)

Intermediate Synthesis 1-4

Synthesis of Intermediate (1-4)

In the same manner as in Intermediate Synthesis 1-3 except for using 23.9 g (105.0 mmol) of dibenzothiophene-2-boronic acid in place of dibenzothophene-4-boronic acid, 27.2 g of a white solid was obtained (yield: 80%), which was identified by FD-MS analysis as the following intermediate (1-4).

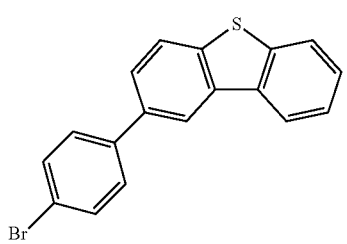

(1-4)

Intermediate Synthesis 1-5

Synthesis of Intermediate (1-5)

Under an argon atmosphere, into a mixture of 28.3 g (100.0 mmol) of 4-iodobromobenzene, 30.1 g (105.0 mmol) of 3-(9H-carbazole-9-yl)phenylboronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 27.2 g of a white solid (yield: 68%), which was identified by FD-MS analysis as the following intermediate (1-5).

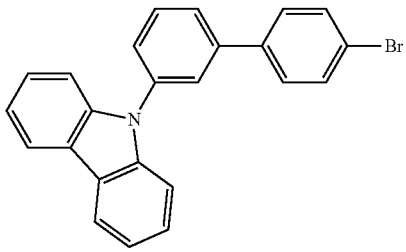

(1-5)

Intermediate Synthesis 1-6

Synthesis of Intermediate (1-6)

In the same manner as in Intermediate Synthesis 1-5 except for using 30.3 g (105.0 mmol) of 3-(dibenzofuran-4-yl)phenylboronic acid in place of 3-(9H-carbazole-9-yl)phenylboronic acid, 24.0 g of a white solid was obtained (yield: 60%), which was identified by FD-MS analysis as the following intermediate (1-6).

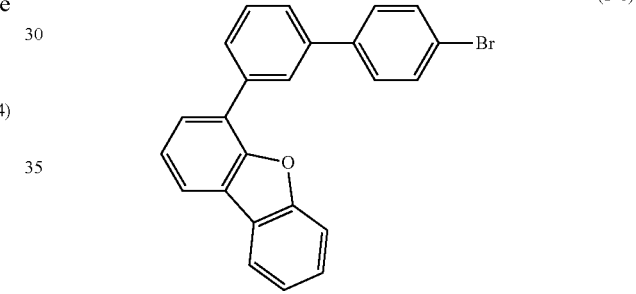

(1-6)

Intermediate Synthesis 1-7

Synthesis of Intermediate (1-7)

Under an argon atmosphere, into a mixture of 17.2 g (100.0 mmol) of 4-bromoaniline, 38.0 g (105.0 mmol) of 9,9'-diphenylfluorene-2-boronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 17.6 g of a white solid (yield: 43%), which was identified by FD-MS analysis as the following intermediate (1-7).

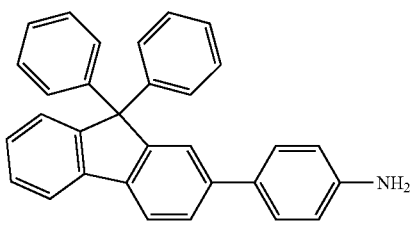

(1-7)

Synthesis of Compound (A)

Intermediate Synthesis A-1-1

Synthesis of Intermediate (A-1-1)

Under an argon atmosphere, into a mixture of 28.3 g (100.0 mmol) of 4-iodobromobenzene, 30.1 g (105.0 mmol) of 4-(9H-carbazole-9-yl)phenylboronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 29.9 g of a white solid (yield: 75%), which was identified by FD-MS analysis as the following intermediate (A-1-1).

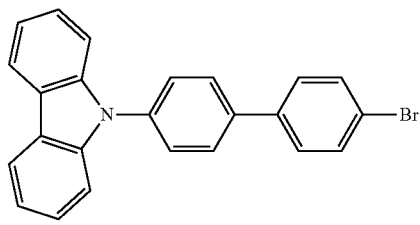

(A-1-1)

Intermediate Synthesis A-1-2

Synthesis of Intermediate (A-1-2)

Under an argon atmosphere, into a mixture of 39.7 g (100.0 mmol) of 4-bromo-9,9'-diphenylfluorene, 16.4 g (105.0 mmol) of 4-chlorophenylboronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 34.3 g of a white solid (yield: 80%), which was identified by FD-MS analysis as the following intermediate (A-1-2).

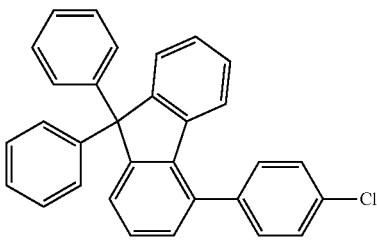

(A-1-2)

Intermediate Synthesis A-2-1

Synthesis of Intermediate (A-2-1)

Under an argon atmosphere, into a mixture of 19.9 g (50.0 mmol) of 4-bromo-9,9'-diphenylfluorene, 16.7 g (50.0 mmol) of 2-amino-9,9'-diphenylfluorene, and 9.6 g (100.0 mmol) of sodium t-butoxide, 250 ml of dehydrated toluene was added, and the resultant mixture was stirred. After further adding 225 mg (1.0 mmol) of palladium acetate and 202 mg (1.0 mmol) of tri-t-butylphosphine, the mixture was allowed to react at 80° C. for 8 h.

After cooling, the reaction mixture was filtered through celite/silica gel, and the filtrate was concentrated under reduced pressure. The obtained residue was recrystallized from toluene, and the precipitated crystal was collected by filtration and dried to obtain 24.4 g of a white crystal (yield: 75%), which was identified by FD-MS analysis as the following intermediate (A-2-1).

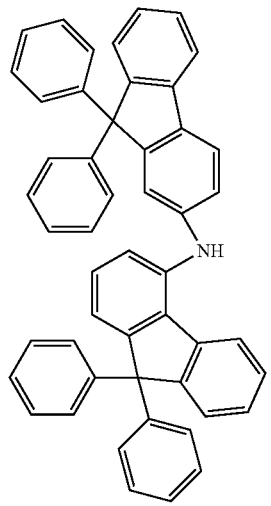

(A-2-1)

Intermediate Synthesis A-2-2

Synthesis of Intermediate (A-2-2)

Under an argon atmosphere, into a mixture of 21.4 g (50.0 mmol) of the intermediate (A-1-2), 16.7 g (50.0 mmol) of 2-amino-9,9'-diphenylfluorene, and 9.6 g (100.0 mmol) of sodium t-butoxide, 250 ml of dehydrated toluene was added, and the resultant mixture was stirred. After further adding 225 mg (1.0 mmol) of palladium acetate and 202 mg (1.0 mmol) of tri-t-butylphosphine, the mixture was allowed to react at 80° C. for 8 h.

After cooling, the reaction mixture was filtered through celite/silica gel, and the filtrate was concentrated under reduced pressure. The obtained residue was recrystallized from toluene, and the precipitated crystal was collected by filtration and dried to obtain 25.4 g of a white crystal (yield: 70%), which was identified by FD-MS analysis as the following intermediate (A-2-2).

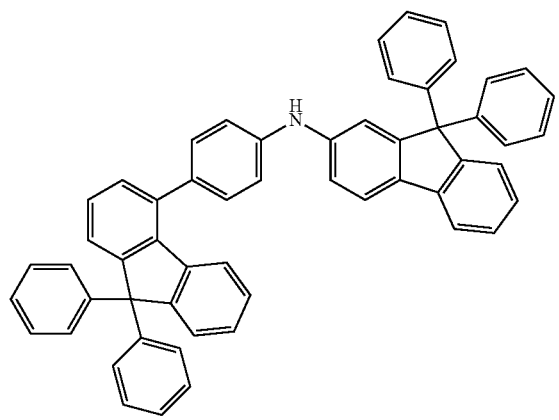

(A-2-2)

Intermediate Synthesis A-2-3

Synthesis of Intermediate (A-2-3)

Under an argon atmosphere, into a mixture of 19.9 g (50.0 mmol) of 4-bromo-9,9'-diphenylfluorene, 20.5 g (50.0 mmol) of the intermediate (1-7), and 9.6 g (100.0 mmol) of sodium t-butoxide, 250 ml of dehydrated toluene was added, and the resultant mixture was stirred. After further adding 225 mg (1.0 mmol) of palladium acetate and 202 mg (1.0 mmol) of tri-t-butylphosphine, the mixture was allowed to react at 80° C. for 8 h.

After cooling, the reaction mixture was filtered through celite/silica gel, and the filtrate was concentrated under reduced pressure. The obtained residue was recrystallized from toluene, and the precipitated crystal was collected by filtration and dried to obtain 24.0 g of a white crystal (yield: 66%), which was identified by FD-MS analysis as the following intermediate (A-2-3).

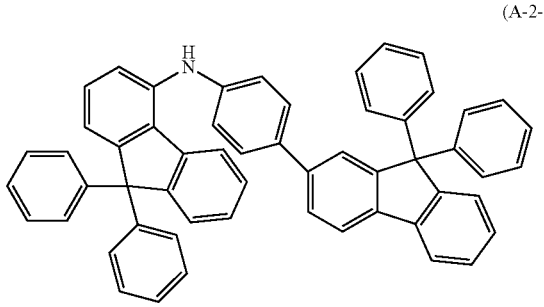

(A-2-3)

Synthesis Example A-1

Synthesis of Compound (H-A1)

Under an argon atmosphere, into a mixture of 2.3 g (10.0 mmol) of 4-bromobiphenyl, 6.5 g (10.0 mmol) of the intermediate (A-2-1), 0.14 g (0.15 mmol) of $Pd_2(dba)_3$, 0.087 g (0.3 mmol) of $P(tBu)_3HBF_4$, and 1.9 g (20.0 mmol) of sodium t-butoxide, 50 ml of dehydrated xylene was added, and the resultant mixture was refluxed for 8 h under heating.

After the reaction, the reaction mixture was cooled to 50° C. and filtered through celite/silica gel. The filtrate was concentrated and the residual concentrate was purified by column chromatography and recrystallized from toluene to obtain 4.0 g of a white crystal (yield: 50%), which was identified by FD-MS analysis as the following compound (H-A1).

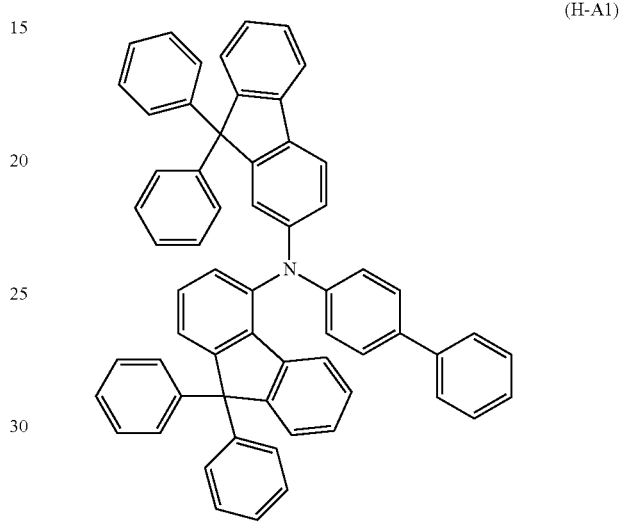

(H-A1)

Synthesis Example A-2

Synthesis of Compound (H-A2)

In the same manner as in Synthesis Example A-1 except for using 2.3 g (10.0 mmol) of 2-bromobiphenyl in place of 4-bromobiphenyl, 3.2 g of a white crystal was obtained (yield: 40%), which was identified by FD-MS analysis as the following compound (H-A2).

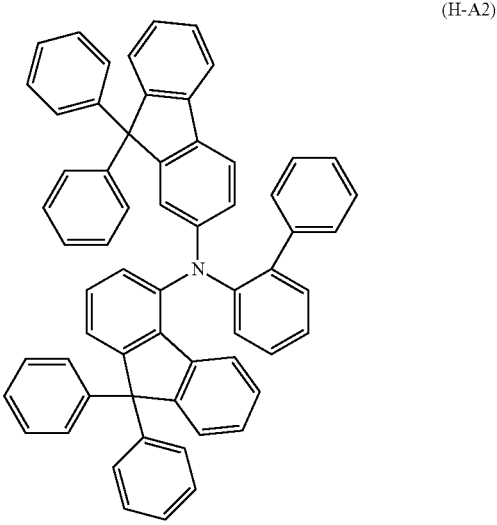 [SMILES: c1ccc(-c2ccccc2N(c2ccc3c(c2)C(c2ccccc2)(c2ccccc2)c2ccccc2-3)c2cccc3c2-c2ccccc2C3(c2ccccc2)c2ccccc2)cc1]

(H-A2)

Synthesis Example A-3

Synthesis of Compound (H-A3)

In the same manner as in Synthesis Example A-1 except for using 4.0 g (10.0 mmol) of 2-bromo-9,9'-diphenylfluorene in place of 4-bromobiphenyl, 2.9 g of a white crystal was obtained (yield: 30%), which was identified by FD-MS analysis as the following compound (H-A3).

(H-A3)

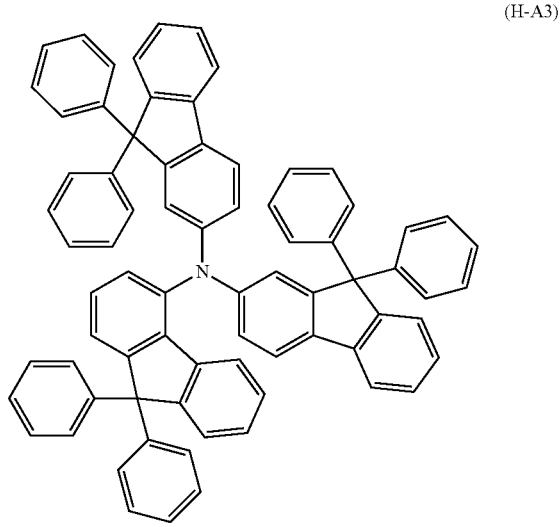 [SMILES: c1ccc(C2(c3ccccc3)c3ccccc3-c3ccc(N(c4ccc5c(c4)C(c4ccccc4)(c4ccccc4)c4ccccc4-5)c4cccc5c4-c4ccccc4C5(c4ccccc4)c4ccccc4)cc32)cc1]

Synthesis Example A-4

Synthesis of Compound (H-A4)

In the same manner as in Synthesis Example A-1 except for using 3.2 g (10.0 mmol) of the intermediate (1-1) in place of 4-bromobiphenyl, 4.0 g of a white crystal was obtained (yield: 45%), which was identified by FD-MS analysis as the following compound (H-A4).

(H-A4)

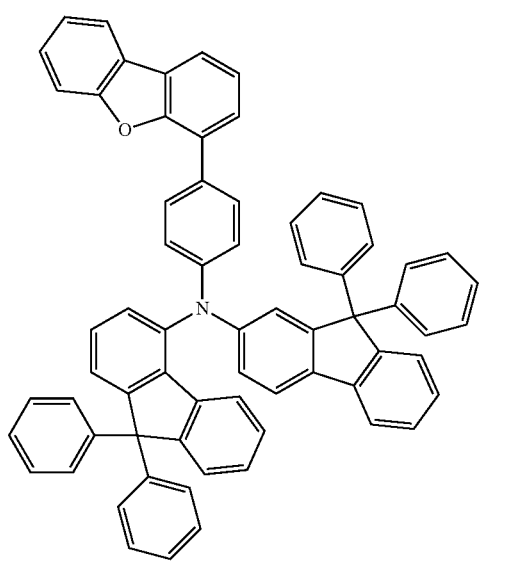

Synthesis Example A-5

Synthesis of Compound (H-A5)

In the same manner as in Synthesis Example A-1 except for using 3.2 g (10.0 mmol) of the intermediate (1-2) in place of 4-bromobiphenyl, 4.6 g of a white crystal was obtained (yield: 52%), which was identified by FD-MS analysis as the following compound (H-A5).

(H-A5)

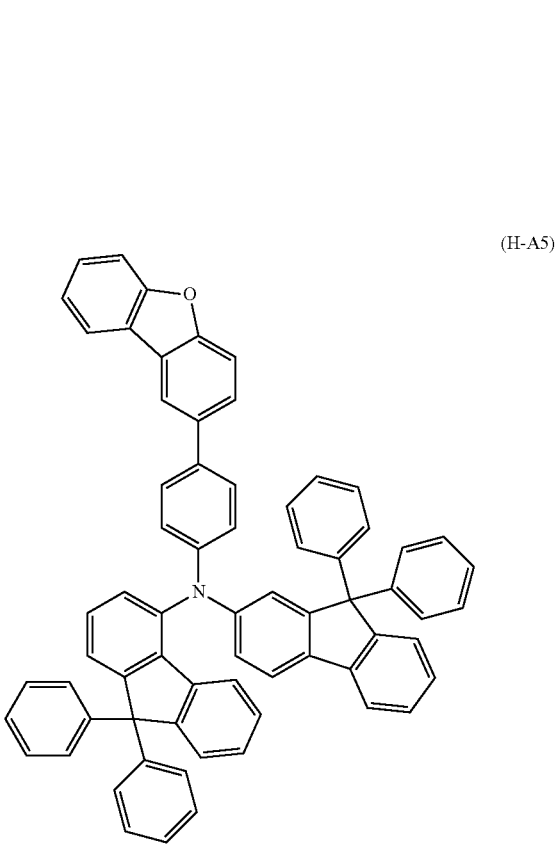 [SMILES: c1ccc(C2(c3ccccc3)c3ccccc3-c3ccc(N(c4ccc(-c5ccc6oc7ccccc7c6c5)cc4)c4cccc5c4-c4ccccc4C5(c4ccccc4)c4ccccc4)cc32)cc1]

Synthesis Example A-6

Synthesis of Compound (H-A6)

In the same manner as in Synthesis Example A-1 except for using 3.4 g (10.0 mmol) of the intermediate (1-3) in place of 4-bromobiphenyl, 4.1 g of a white crystal (yield: 45%), which was identified by FD-MS analysis as the following compound (H-A6).

(H-A6)

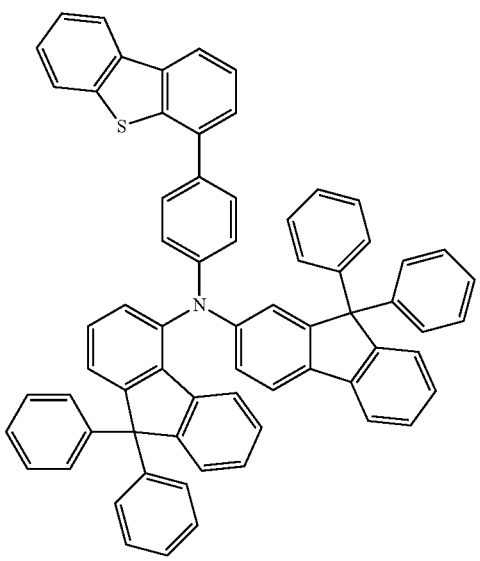

Synthesis Example A-7

Synthesis of Compound (H-A7)

In the same manner as in Synthesis Example A-1 except for using 3.4 g (10.0 mmol) of the intermediate (1-4) in place of 4-bromobiphenyl, 4.4 g of a white crystal was obtained (yield: 48%), which was identified by FD-MS analysis as the following compound (H-A7).

(H-A7)

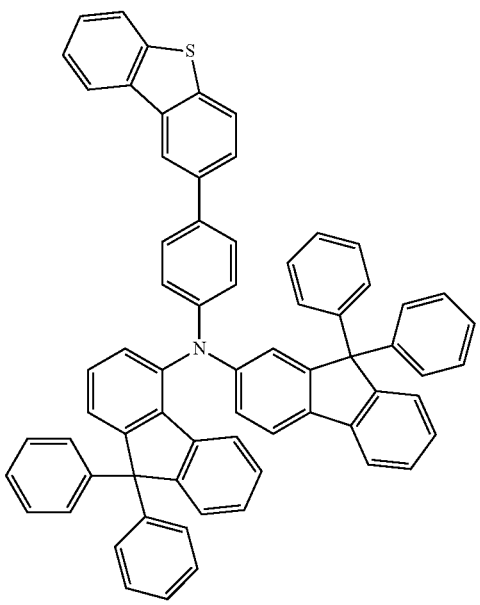

Synthesis Example A-8

Synthesis of Compound (H-A8)

In the same manner as in Synthesis Example A-1 except for using 4.0 g (10.0 mmol) of the intermediate (A-1-1) in place of 4-bromobiphenyl, 4.2 g of a white crystal was obtained (yield: 43%), which was identified by FD-MS analysis as the following compound (H-A8).

(H-A8)

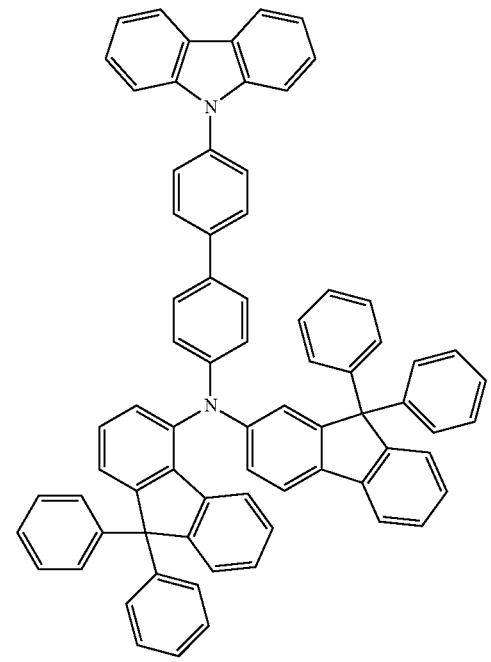

Synthesis Example A-9

Synthesis of Compound (H-A9)

In the same manner as in Synthesis Example A-1 except for using 3.1 g (10.0 mmol) of 4-bromoterphenyl in place of 4-bromobiphenyl, 4.0 g of a white crystal was obtained (yield: 45%), which was identified by FD-MS analysis as the following compound (H-A9).

(H-A9)

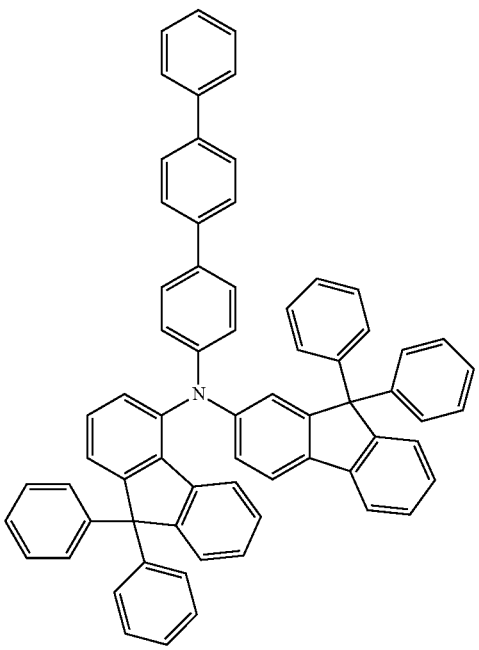

Synthesis Example A-10

Synthesis of Compound (H-A10)

In the same manner as in Synthesis Example A-1 except for using 3.1 g (10.0 mmol) of 2-bromotriphenylene in place of 4-bromobiphenyl, 3.3 g of a white crystal was obtained (yield: 38%), which was identified by FD-MS analysis as the following compound (H-A10).

(H-A10)

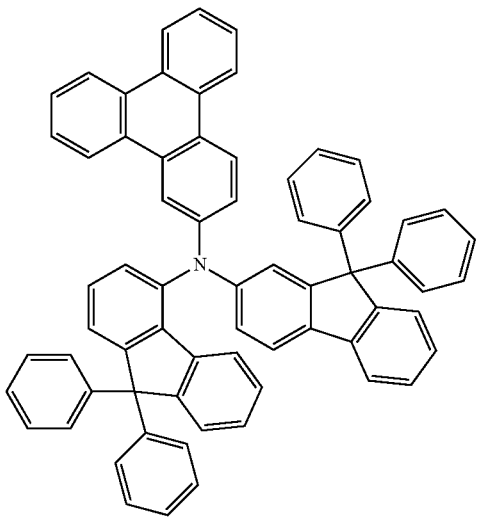

Synthesis Example A-11

Synthesis of Compound (H-A11)

In the same manner as in Synthesis Example A-1 except for using 4.0 g (10.0 mmol) of the intermediate (1-5) in place of 4-bromobiphenyl, 4.0 g of a white crystal was obtained (yield: 41%), which was identified by FD-MS analysis as the following compound (H-A11).

(H-A11)

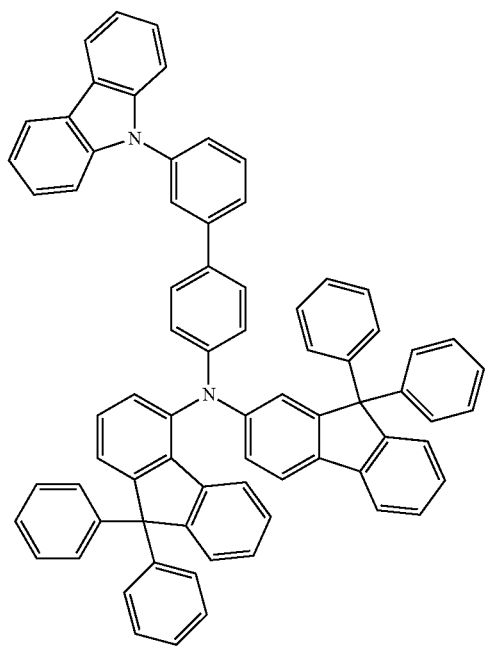

Synthesis Example A-12

Synthesis of Compound (H-A12)

In the same manner as in Synthesis Example A-1 except for using 4.0 g (10.0 mmol) of the intermediate (1-6) in place of 4-bromobiphenyl, 3.6 g of a white crystal was obtained (yield: 37%), which was identified by FD-MS analysis as the following compound (H-A12).

(H-A12)

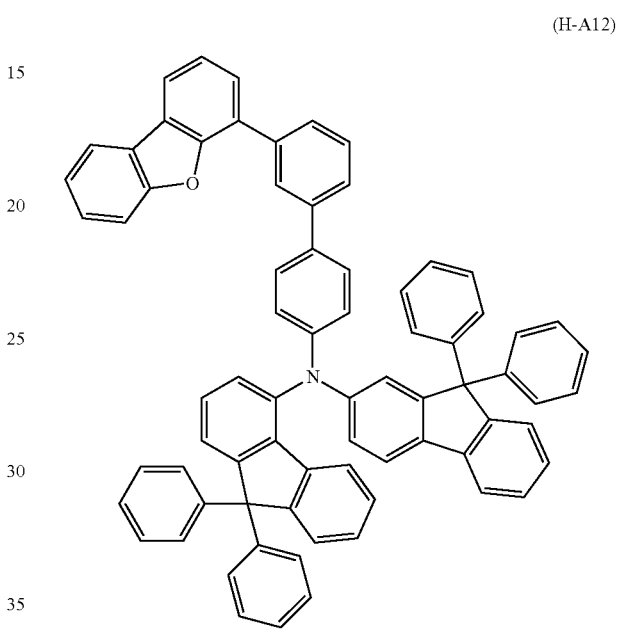

Synthesis Example A-13

Synthesis of Compound (H-A13)

Under an argon atmosphere, into a mixture of 2.3 g (10.0 mmol) of 4-bromobiphenyl, 7.3 g (10.0 mmol) of the intermediate (A-2-2), 0.14 g (0.15 mmol) of $Pd_2(dba)_3$, 0.087 g (0.3 mmol) of $P(tBu)_3HBF_4$, and 1.9 g (20.0 mmol) of sodium t-butoxide, 50 ml of dehydrated xylene was added, and the resultant mixture was refluxed for 8 h under heating.

After the reaction, the reaction mixture was cooled to 50° C. and filtered through celite/silica gel. The filtrate was concentrated and the residual concentrate was purified by column chromatography and recrystallized from toluene to obtain 4.0 g of a white crystal (yield: 45%), which was identified by FD-MS analysis as the following compound (H-A13).

(H-A13)

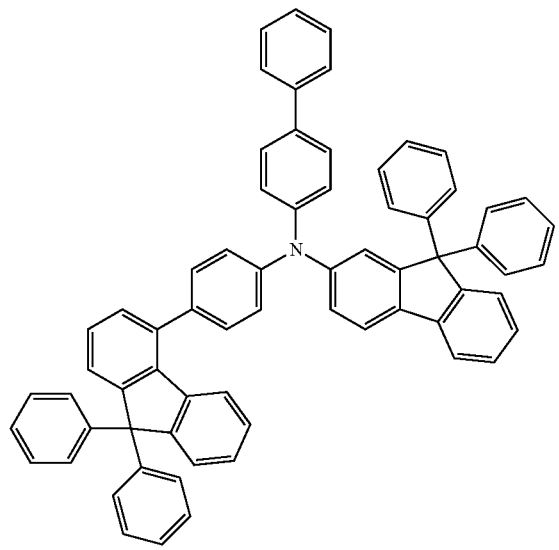

Synthesis Example A-14

Synthesis of Compound (H-A14)

In the same manner as in Synthesis Example A-13 except for using 2.3 g (10.0 mmol) of 2-bromobiphenyl in place of 4-bromobiphenyl, 3.8 g of a white crystal was obtained (yield: 43%), which was identified by FD-MS analysis as the following compound (H-A14).

(H-A14)

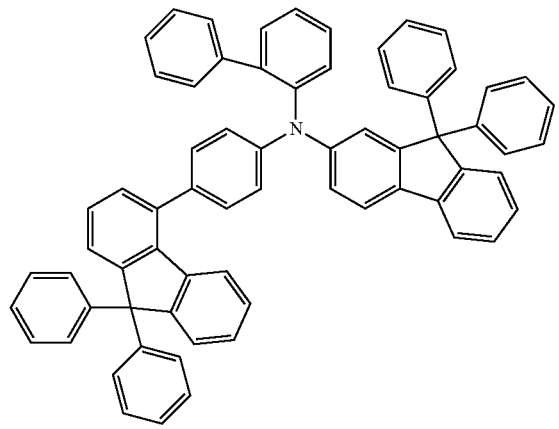

Synthesis Example A-15

Synthesis of Compound (H-A15)

In the same manner as in Synthesis Example A-13 except for using 4.0 g (10.0 mmol) of 2-bromo-9,9'-diphenylfluorene in place of 4-bromobiphenyl, 3.6 g of a white crystal was obtained (yield: 35%), which was identified by FD-MS analysis as the following compound (H-A15).

(H-A15)

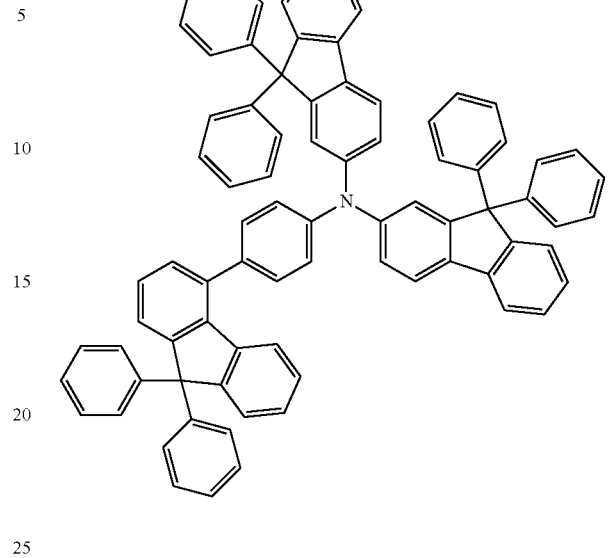

Synthesis Example A-16

Synthesis of Compound (H-A16)

Under an argon atmosphere, into a mixture of 2.3 g (10.0 mmol) of 4-bromobiphenyl, 7.3 g (10.0 mmol) of the intermediate (A-2-3), 0.14 g (0.15 mmol) of $Pd_2(dba)_3$, 0.087 g (0.3 mmol) of $P(tBu)_3HBF_4$, and 1.9 g (20.0 mmol) of sodium t-butoxide, 50 ml of dehydrated xylene was added, and the resultant mixture was refluxed for 8 h under heating.

After the reaction, the reaction mixture was cooled to 50° C. and filtered through celite/silica gel. The filtrate was concentrated and the residual concentrate was purified by column chromatography and recrystallized from toluene to obtain 3.2 g of a white crystal (yield: 37%), which was identified by FD-MS analysis as the following compound (H-A16).

(H-A16)

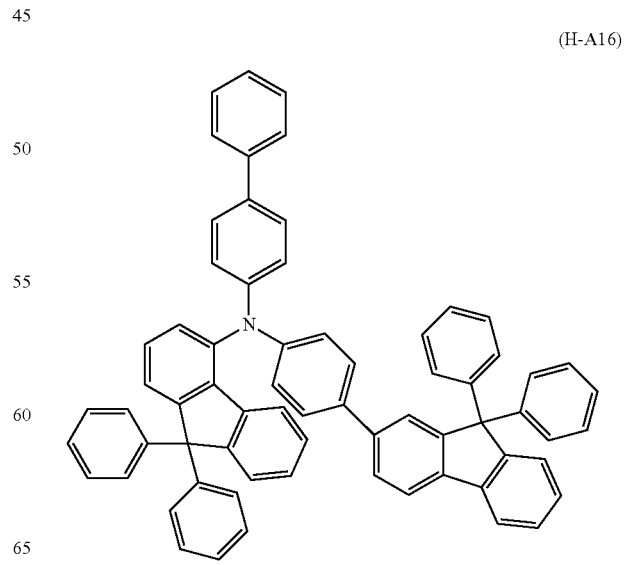

Synthesis Example A-17

Synthesis of Compound (H-A17)

In the same manner as in Synthesis Example A-16 except for using 2.3 g (10.0 mmol) of 2-bromobiphenyl in place of 4-bromobiphenyl, 3.1 g of a white crystal was obtained (yield: 35%), which was identified by FD-MS analysis as the following compound (H-A17).

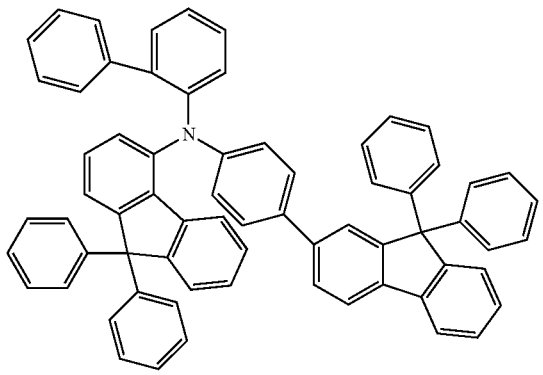
(H-A17)

Synthesis Example A-18

Synthesis of Compound (H-A18)

In the same manner as in Synthesis Example A-16 except for using 3.1 g (10.0 mmol) of 4-bromoterphenyl in place of 4-bromobiphenyl, 3.8 g of a white crystal was obtained (yield: 40%), which was identified by FD-MS analysis as the following compound (H-A18).

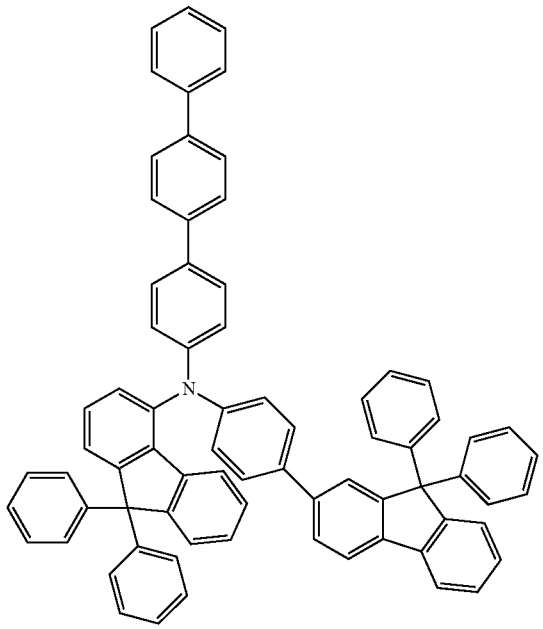
(H-A18)

Synthesis of Compound (B)

Intermediate Synthesis B-1-1

Synthesis of Intermediate (B-1-1)

Under an argon atmosphere, into a mixture of 47.0 g (201.6 mmol) of 4-bromobiphenyl, 23 g (90.6 mmol) of iodine, and 9.4 g (41.2 mmol) of periodic acid dihydrate, 42 ml of water, 360 ml of acetic acid, and 11 ml of sulfuric acid were added, and the resultant mixture was stirred at 65° C. for 30 min and further stirred at 90° C. for 6 h.

After the reaction, the reaction mixture was poured into iced water and filtered. After washing with water and then methanol, 67 g of a white solid was obtained (yield: 93%), which was identified by FD-MS analysis as the following compound (B-1-1).

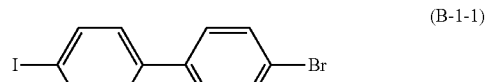
(B-1-1)

Intermediate Synthesis B-1-2

Synthesis of Intermediate (B-1-2)

Under an argon atmosphere, into a mixture of 35.9 g (100.0 mmol) of the intermediate (B-1-1), 16.7 g (100.0 mmol) of carbazole, 0.2 g (1.00 mmol) of copper iodide (CuI), and 42.4 g (210.0 mmol) of tripotassium phosphate, 2 ml of trans-1,2-cyclohexane diamine and 300 ml of 1,4-dioxane were added, and the resultant mixture was stirred at 100° C. for 20 h.

After the reaction, the reaction mixture was liquid-liquid separated after adding 300 ml of water and then the aqueous layer was removed. The organic layer was dried over sodium sulfate and then concentrated. The obtained residue was purified by silica gel column chromatography to obtain 23.1 g of a white solid (yield: 58%), which was identified by FD-MS analysis as the following intermediate (B-1-2).

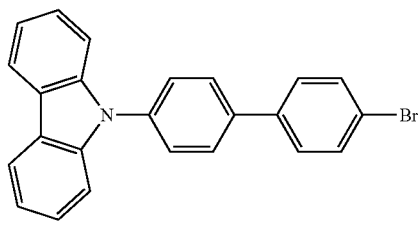
(B-1-2)

Intermediate Synthesis B-1-3

Synthesis of Intermediate (B-1-3)

Under an argon atmosphere, into a mixture of 39.7 g (100.0 mmol) of 3-bromo-9,9'-diphenylfluorene, 16.4 g (105.0 mmol) of 4-chlorophenylboronic acid, and 2.31 g (2.00 mmol) of Pd[PPh$_3$]$_4$, 150 ml of toluene, 150 ml of dimethoxyethane, and 150 ml (300.0 mmol) of a 2 M aqueous solution of Na$_2$CO$_3$ were added, and the resultant mixture was refluxed for 10 h under heating and stirring.

After the reaction, the reaction mixture was cooled to room temperature and extracted with dichloromethane in a separating funnel. The organic layer was dried over MgSO$_4$, filtered, and concentrated. The residual concentrate was purified by column chromatography to obtain 34.3 g of a white solid (yield: 80%), which was identified by FD-MS analysis as the following intermediate (B-1-3).

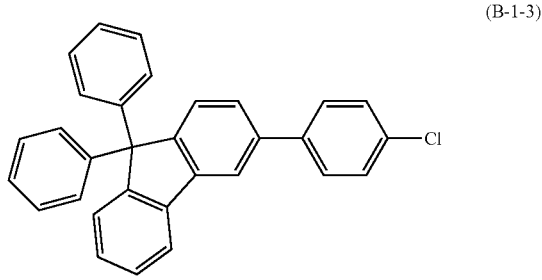 [SMILES: Clc1ccc(-c2ccc3c(c2)-c2ccccc2C3(c2ccccc2)c2ccccc2)cc1]

(B-1-3)

Intermediate Synthesis B-2-1

Synthesis of Intermediate (B-2-1)

Under an argon atmosphere, into a mixture of 19.9 g (50.0 mmol) of 3-bromo-9,9'-diphenylfluorene, 16.7 g (50.0 mmol) of 2-amino-9,9'-diphenylfluorene, and 9.6 g (100.0 mmol) of sodium t-butoxide, 250 ml of dehydrated toluene was added, and the resultant mixture was stirred. After further adding 225 mg (1.0 mmol) of palladium acetate and 202 mg (1.0 mmol) of tri-t-butylphosphine, the mixture was allowed to react at 80° C. for 8 h.

After cooling, the reaction mixture was filtered through celite/silica gel, and the filtrate was concentrated under reduced pressure. The obtained residue was recrystallized from toluene, and the crystal collected by filtration was dried to obtain 22.7 g of a white crystal (yield: 70%), which was identified by FD-MS analysis as the following intermediate (B-2-1).

(B-2-1)

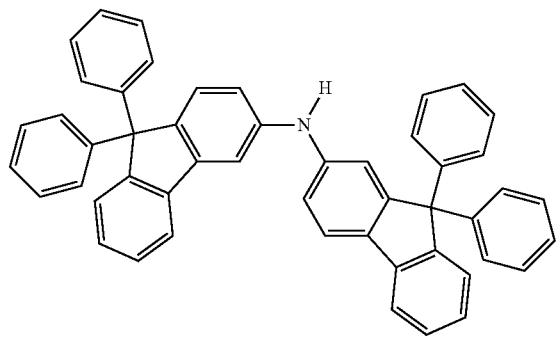

Intermediate Synthesis B-2-2

Synthesis of Intermediate (B-2-2)

Under an argon atmosphere, into a mixture of 19.9 g (50.0 mmol) of 3-bromo-9,9'-diphenylfluorene, 20.5 g (50.0 mmol) of the intermediate (1-7), and 9.6 g (100.0 mmol) of sodium t-butoxide, 250 ml of dehydrated toluene was added, and the resultant mixture was stirred. After further adding 225 mg (1.0 mmol) of palladium acetate and 202 mg (1.0 mmol) of tri-t-butylphosphine, the mixture was allowed to react at 80° C. for 8 h.

After cooling, the reaction mixture was filtered through celite/silica gel, and the filtrate was concentrated under reduced pressure. The obtained residue was recrystallized from toluene, and the precipitated crystal was collected by filtration and dried to obtain 21.8 g of a white crystal (yield: 60%), which was identified by FD-MS analysis as the following intermediate (B-2-2).

(B-2-2)

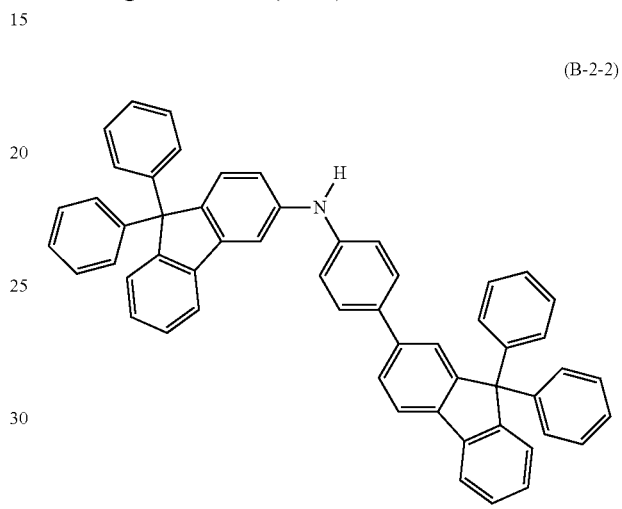

Synthesis Example B-1

Synthesis of Compound (H-B1)

Under an argon atmosphere, into a mixture of 2.3 g (10.0 mmol) of 4-bromobiphenyl, 6.5 g (10.0 mmol) of the intermediate (B-2-1), 0.14 g (0.15 mmol) of Pd$_2$(dba)$_3$, 0.087 g (0.3 mmol) of P(t-Bu)$_3$HBF$_4$, and 1.9 g (20.0 mmol) of sodium t-butoxide, 50 ml of dehydrated xylene was added, and the resultant mixture was refluxed for 8 h under heating.

After the reaction, the reaction mixture was cooled to 50° C. and filtered through celite/silica gel. The filtrate was concentrated and the residual concentrate was purified by column chromatography to obtain a white solid. The crude product was recrystallized from toluene to obtain 2.8 g of a white crystal (yield: 35%), which was identified by FD-MS analysis as the following compound (H-B1).

(H-B1)

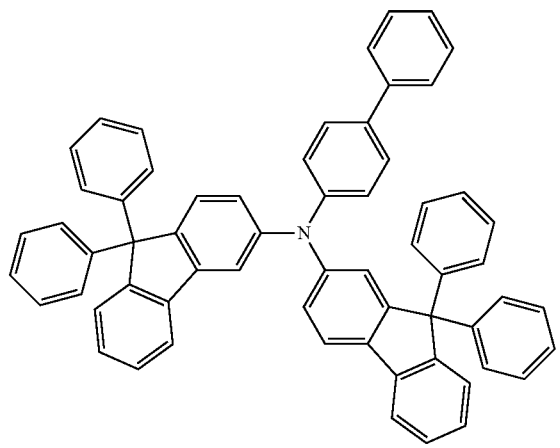

Synthesis Example B-2

Synthesis of Compound (H-B2)

In the same manner as in Synthesis Example B-1 except for using 2.3 g (10.0 mmol) of 2-bromobiphenyl in place of 4-bromobiphenyl, 3.2 g of a white crystal was obtained (yield: 40%), which was identified by FD-MS analysis as the following compound (H-B2).

(H-B2)

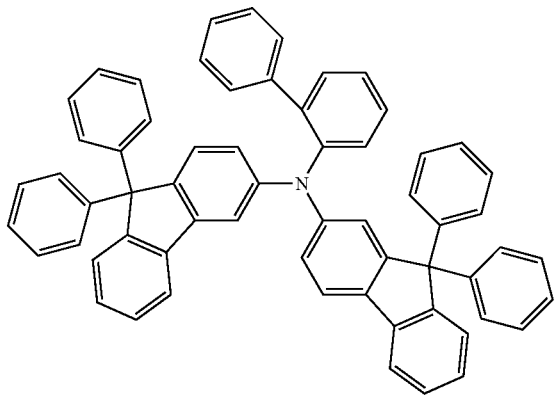

Synthesis Example B-3

Synthesis of Compound (H-B3)

In the same manner as in Synthesis Example B-1 except for using 2.7 g (10.0 mmol) of 2-bromo-9,9'-dimethylfluorene in place of 4-bromobiphenyl, 3.2 g of a white crystal was obtained (yield: 38%), which was identified by FD-MS analysis as the following compound (H-B3).

(H-B3)

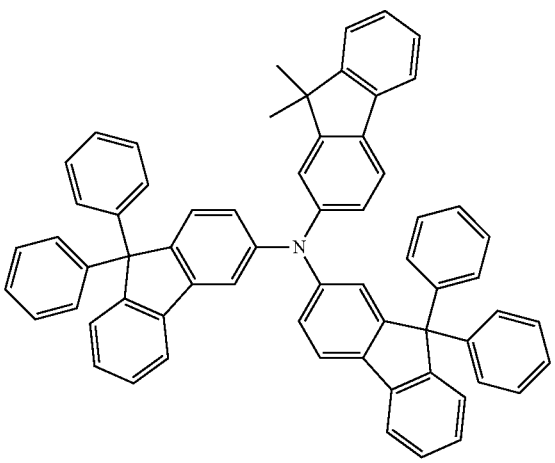

Synthesis Example B-4

Synthesis of Compound (H-B4)

In the same manner as in Synthesis Example B-1 except for using 4.0 g (10.0 mmol) of 2-bromo-9,9'-diphenylfluorene in place of 4-bromobiphenyl, 3.9 g of a white crystal was obtained (yield: 40%), which was identified by FD-MS analysis as the following compound (H-B4).

(H-B4)

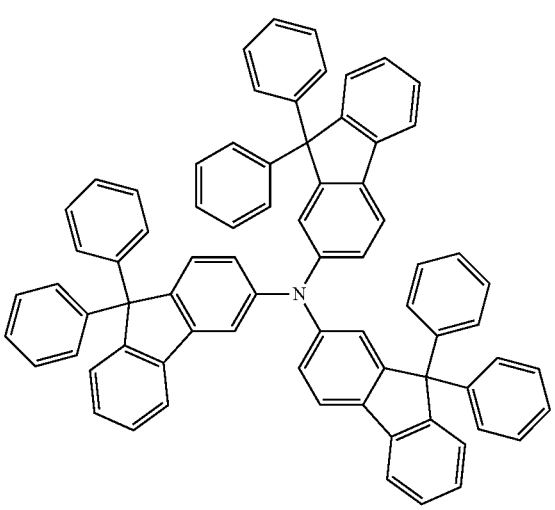

Synthesis Example B-5

Synthesis of Compound (H-B5)

In the same manner as in Synthesis Example B-1 except for using 3.2 g (10.0 mmol) of the intermediate (1-1) in place of 4-bromobiphenyl, 3.1 g of a white crystal was obtained (yield: 35%), which was identified by FD-MS analysis as the following compound (H-B5).

(H-B5)

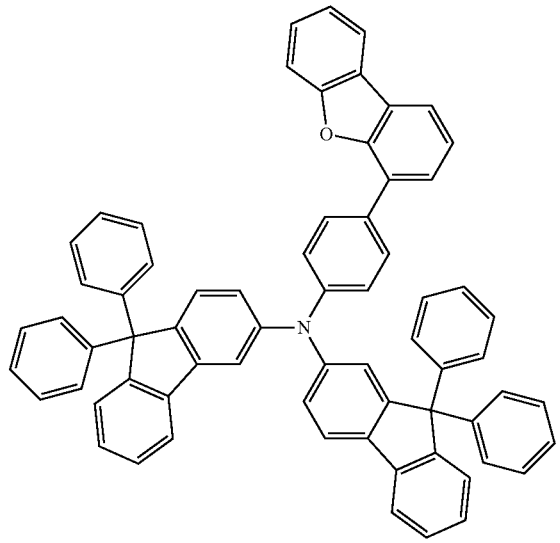

(H-B7)

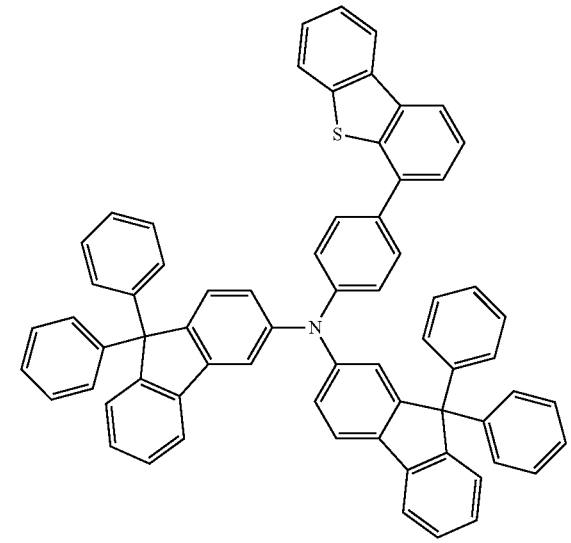

Synthesis Example B-6

Synthesis of Compound (H-B6)

In the same manner as in Synthesis Example B-1 except for using 3.2 g (10.0 mmol) of the intermediate (1-2) in place of 4-bromobiphenyl, 3.3 g of a white crystal was obtained (yield: 37%), which was identified by FD-MS analysis as the following compound (H-B6).

Synthesis Example B-8

Synthesis of Compound (H-B8)

In the same manner as in Synthesis Example B-1 except for using 3.4 g (10.0 mmol) of the intermediate (1-4) in place of 4-bromobiphenyl, 2.9 g of a white crystal was obtained (yield: 32%), which was identified by FD-MS analysis as the following compound (H-B8).

(H-B6)

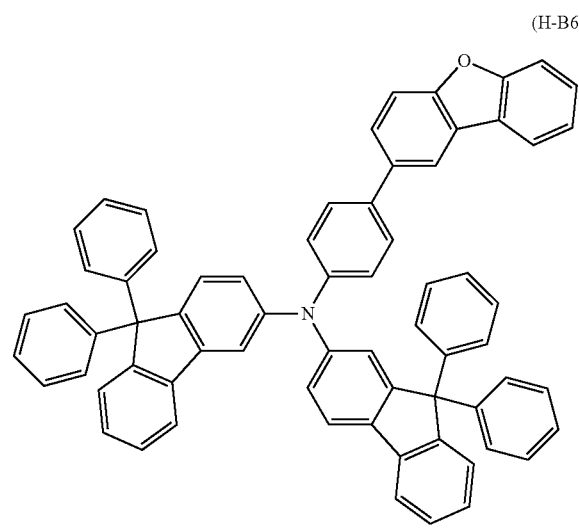

(H-B8)

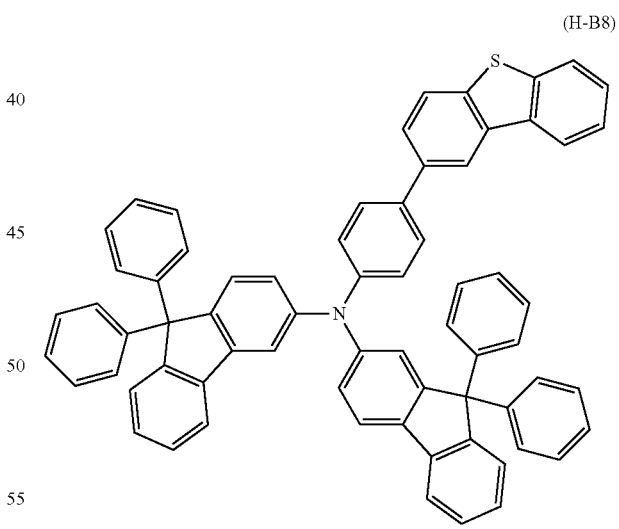

Synthesis Example B-7

Synthesis of Compound (H-B7)

In the same manner as in Synthesis Example B-1 except for using 3.4 g (10.0 mmol) of the intermediate (1-3) in place of 4-bromobiphenyl, 2.7 g or a white crystal was obtained (yield: 30%), which was identified by FD-MS analysis as the following compound (H-B7).

Synthesis Example B-9

Synthesis of Compound (H-B9)

In the same manner as in Synthesis Example B-1 except for using 4.0 g (10.0 mmol) of the intermediate (B-1-2) in place of 4-bromobiphenyl, 2.6 g of a white crystal was obtained (yield: 27%), which was identified by FD-MS analysis as the following compound (H-B9).

(H-B9)

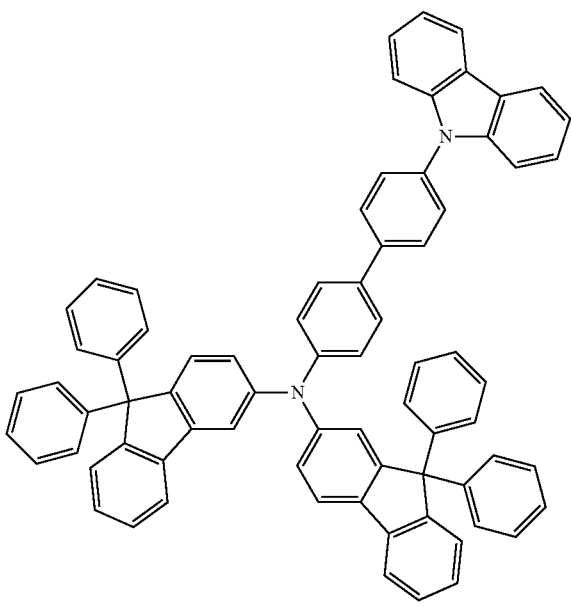

Synthesis Example B-10

Synthesis of Compound (H-B10)

Under an argon atmosphere, into a mixture of 4.3 g (10.0 mmol) of the intermediate (B-1-3), 4.9 g (10.0 mmol) of N-(biphenyl-4-yl)-9,9'-diphenylfluorene-2-amine, 0.14 g (0.15 mmol) of $Pd_2(dba)_3$, 0.087 g (0.3 mmol) of $P(t\text{-Bu})_3HBF_4$, and 1.9 g (20.0 mmol) of sodium t-butoxide, 50 ml of dehydrated xylene was added, and the resultant mixture was refluxed for 8 h under heating.

After the reaction, the reaction mixture was cooled to 50° C. and filtered through celite/silica gel. The filtrate was concentrated and the residual concentrate was purified by column chromatography to obtain a white solid. The crude product was recrystallized from toluene to obtain 2.8 g of a white crystal (yield: 32%), which was identified by FD-MS analysis as the following compound (H-B10).

(H-B10)

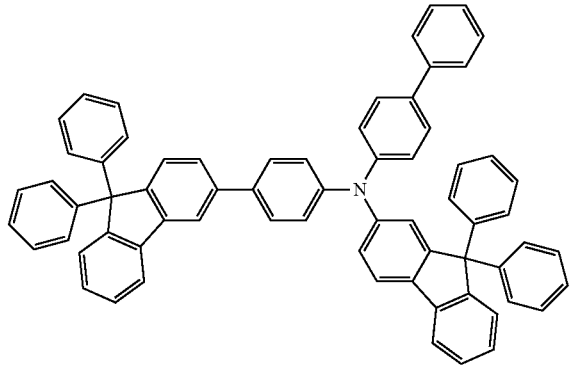

Synthesis Example B-11

Synthesis of Compound (H-B11)

In the same manner as in Synthesis Example B-10 except for using 4.9 g (10.0 mmol) of N-(biphenyl-2-yl)-9,9'-diphenylfluorene-2-amine in place of N-(biphenyl-4-yl)-9,9'-diphenylfluorene-2-amine, 3.1 g of a white crystal was obtained (yield: 35%), which was identified by FD-MS analysis as the following compound (H-B11).

(H-B11)

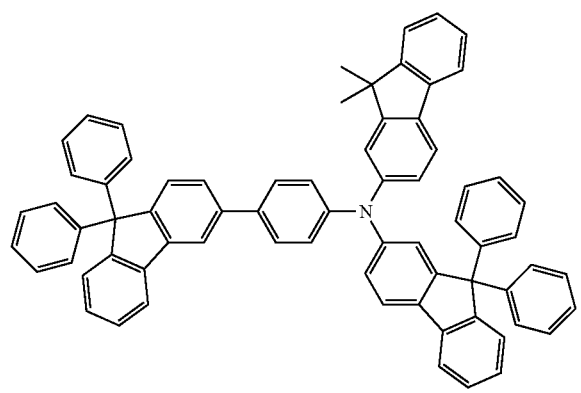

Synthesis Example B-12

Synthesis of Compound (H-B12)

In the same manner as in Synthesis Example B-10 except for using 5.3 g (10.0 mmol) of N-(9,9'-dimethylfluorene-2-yl)-9,9'-diphenylfluorene-2-amine in place of N-(biphenyl-4-yl)-9,9'-diphenylfluorene-2-amine, 2.9 g of a white crystal was obtained (yield: 32%), which was identified by FD-MS analysis as the following compound (H-B12).

(H-B12)

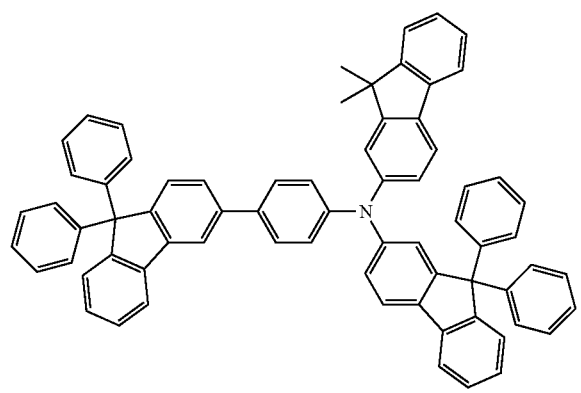

Synthesis Example B-13

Synthesis of Compound (H-B13)

In the same manner as in Synthesis Example B-10 except for using 6.5 g (10.0 mmol) of N,N-bis(9,9'-diphenylfluorene-2-yl) amine in place of N-(biphenyl-4-yl)-9,9'-diphenylfluorene-2-amine, 3.9 g of a white crystal was obtained (yield: 37%), which was identified by FD-MS analysis as the following compound (H-B13).

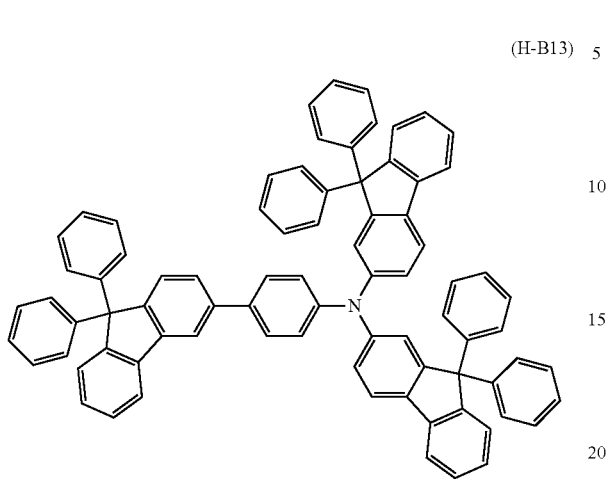

(H-B13)

Synthesis Example B-14

Synthesis of Compound (H-B14)

In the same manner as in Synthesis Example B-1 except for using 3.1 g (10.0 mmol) of 4-bromoterphenyl in place of 4-bromobiphenyl, 3.3 g of a white crystal was obtained (yield: 38%), which was identified by FD-MS analysis as the following compound (H-B14).

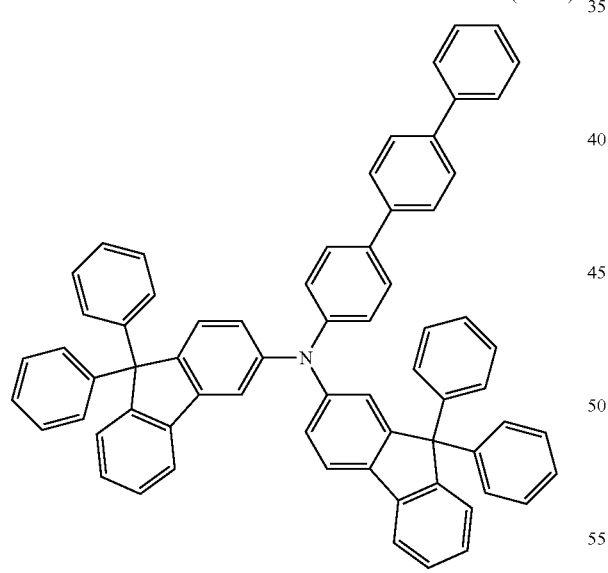

(H-B14)

Synthesis Example B-15

Synthesis of Compound (H-B15)

In the same manner as in Synthesis Example B-1 except for using 3.1 g (10.0 mmol) of 2-bromophenanthrene in place of 4-bromobiphenyl, 3.5 g of a white crystal was obtained (yield: 40%), which was identified by FD-MS analysis as the following compound (H-B15).

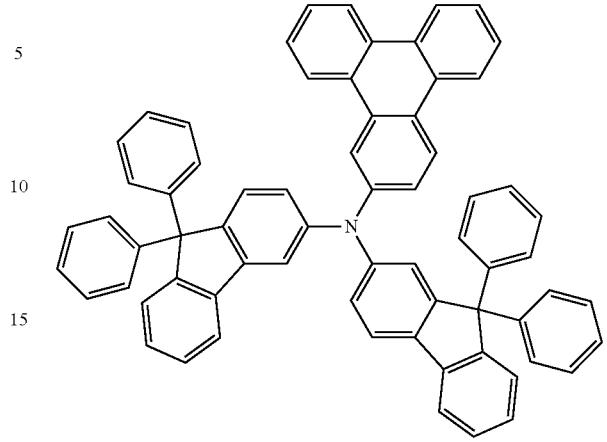

(H-B15)

Synthesis Example B-16

Synthesis of Compound (H-B16)

In the same manner as in Synthesis Example B-1 except for using 4.0 g (10.0 mmol) of the intermediate (1-5) in place of 4-bromobiphenyl, 3.9 g of a white crystal was obtained (yield: 40%), which was identified by FD-MS analysis as the following compound (H-B16).

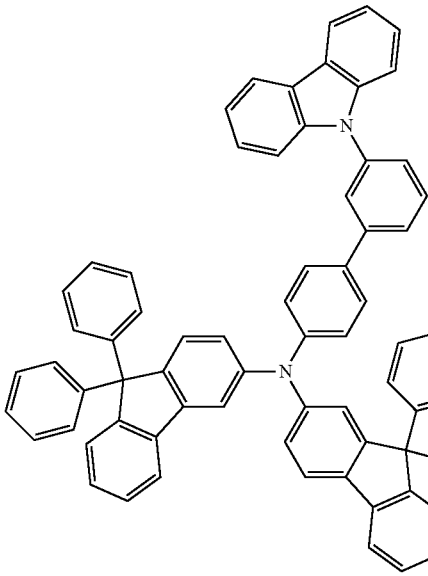

(H-B16)

Synthesis Example B-17

Synthesis of Compound (H-B17)

In the same manner as in Synthesis Example B-1 except for using 4.0 g (10.0 mmol) of the intermediate (1-6) in place of 4-bromobiphenyl, 3.4 g of a white crystal was obtained (yield: 35%), which was identified by FD-MS analysis as the following compound (H-B17).

(H-B17)

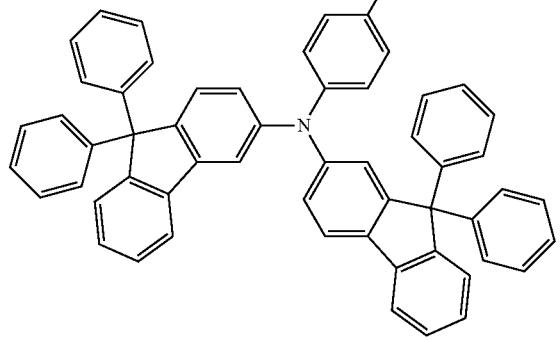

Synthesis Example B-18

Synthesis of Compound (H-B18)

Under an argon atmosphere, into a mixture of 2.3 g (10.0 mmol) of 4-bromobiphenyl, 7.3 g (10.0 mmol) of the intermediate (B-2-2), 0.14 g (0.15 mmol) of Pd$_2$(dba)$_3$, 0.087 g (0.3 mmol) of P(tBu)$_3$HBF$_4$, and 1.9 g (20.0 mmol) of sodium t-butoxide, 50 ml of dehydrated xylene was added, and the resultant mixture was refluxed for 8 h under heating.

After the reaction, the reaction mixture was cooled to 50° C. and filtered through celite/silica gel. The filtrate was concentrated and the residual concentrate was purified by column chromatography and recrystallized from toluene to obtain 3.1 g of a white crystal (yield: 35%), which was identified by FD-MS analysis as the following compound (H-B18).

(H-B18)

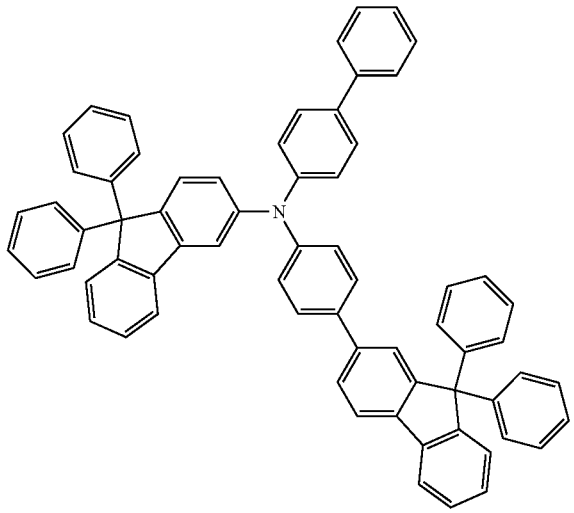

Synthesis Example B-19

Synthesis of Compound (H-B19)

In the same manner as in Synthesis Example B-18 except for using 2.3 g (10.0 mmol) of 2-bromobiphenyl in place of 4-bromobiphenyl, 2.6 g of a white crystal was obtained (yield: 30%), which was identified by FD-MS analysis as the following compound (H-B19).

(H-B19)

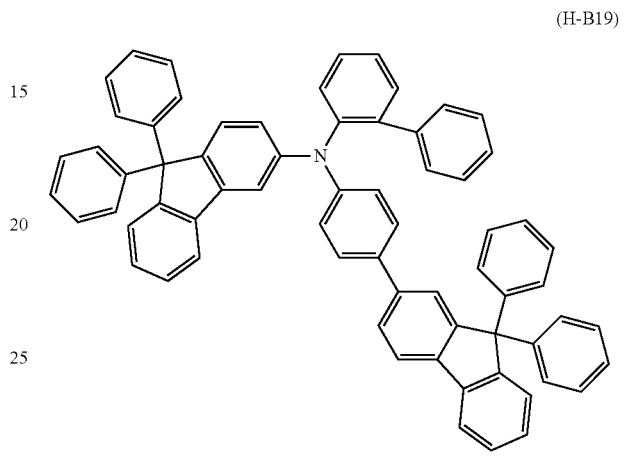

Synthesis Example B-20

Synthesis of Compound (H-B20)

In the same manner as in Synthesis Example B-18 except for using 3.1 g (10.0 mmol) of 4-bromoterphenyl in place of 4-bromobiphenyl, 3.7 g of a white crystal was obtained (yield: 39%), which was identified by FD-MS analysis as the following compound (H-B20).

(H-B20)

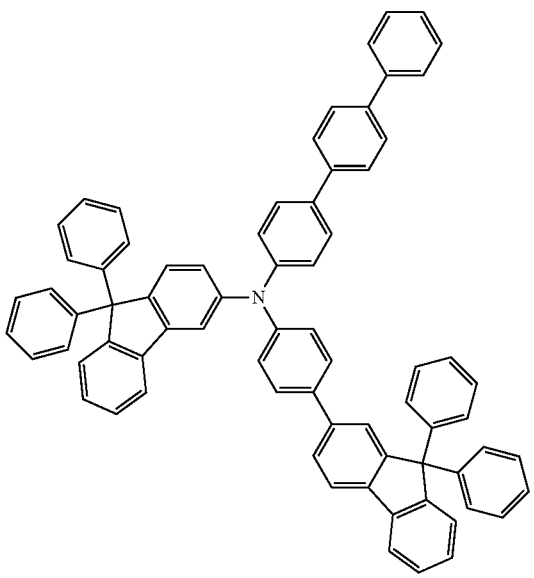

Production of Organic EL Device Using Compound (A)

Examples A1-1 to A1-18

Production of Organic EL Device

A glass substrate of 25 mm×75 mm×1.1 mm having an ITO transparent electrode (product of Geomatec Company) was cleaned by ultrasonic cleaning in isopropyl alcohol for 5 min and then UV (ultraviolet) ozone cleaning for 30 min.

The cleaned glass substrate having a transparent electrode line was mounted to a substrate holder of a vacuum vapor deposition apparatus. First, the following electron-accepting compound (EA1) was vapor-deposited so as to cover the transparent electrode to form a film (EA1) with a thickness of 10 nm.

On the film (EA1), the following aromatic amine derivative (X1) as a first hole transporting material was vapor-deposited to form a first hole transporting layer with a thickness of 80 nm. Successively after forming the first hole transporting layer, each of the compounds (H-A1) to (H-A18) obtained in Synthesis Examples A-1 to A-18 as a second hole transporting material was vapor-deposited to form a second hole transporting layer with a thickness of 10 nm.

On the second hole transporting layer, the following host compound (BH) and dopant compound (BD) as fluorescent emitting materials were vapor co-deposited to form a light emitting layer with a thickness of 25 nm. The concentration of the dopant compound (BD) in the light emitting layer was 4% by mass.

Thereafter, on the light emitting layer, the following compound (ET1), compound (ET2), and LiF were vapor co-deposited into a thickness of 25 nm, 10 nm, and 1 nm, respectively to form an electron transporting/injecting layer.

Further, metallic Al was deposited into a thickness of 80 nm, thereby producing each organic EL device of Examples A1-1 to A1-18.

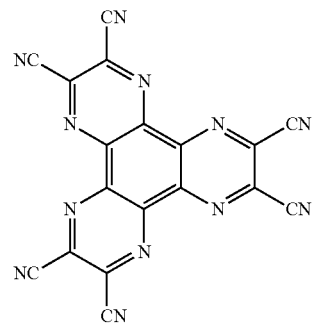
(EA1)

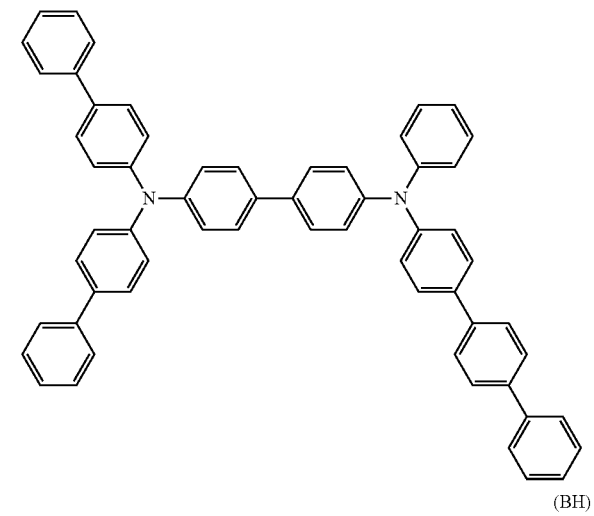
(X1)

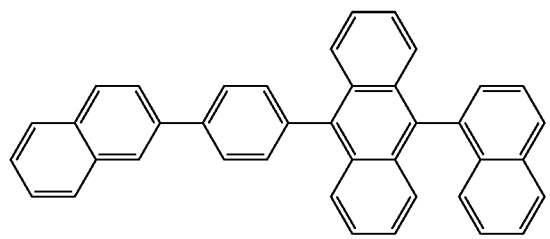
(BH)

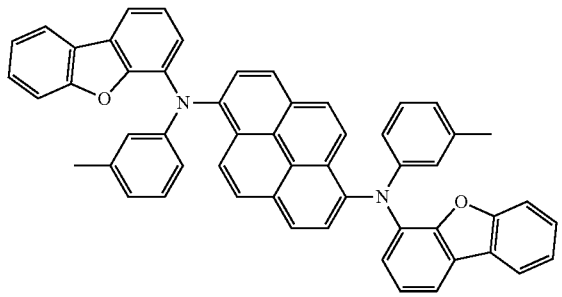
(BD)

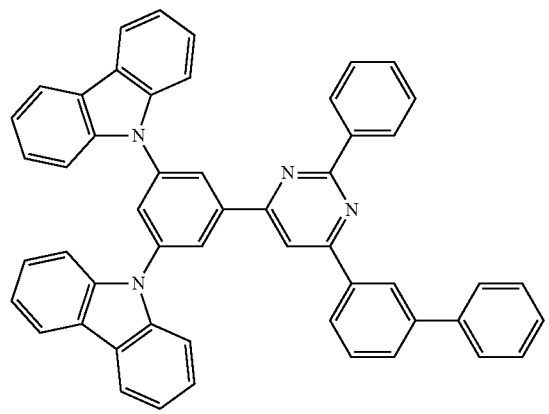
(ET1)

(ET2)
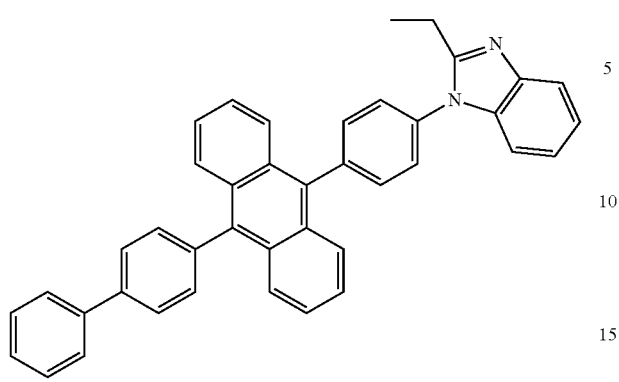
The compounds (H-A1) to (H-A18) obtained Synthesis Examples A-1 to A-18 are shown below.
(H-A1)
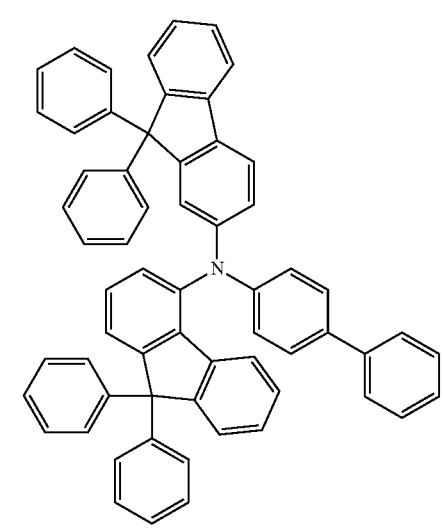
(H-A2)
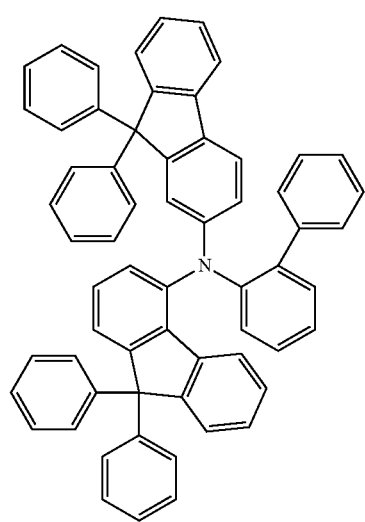
(H-A3)
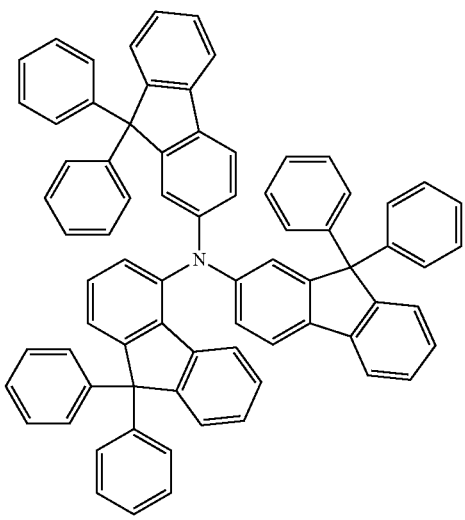
(H-A4)
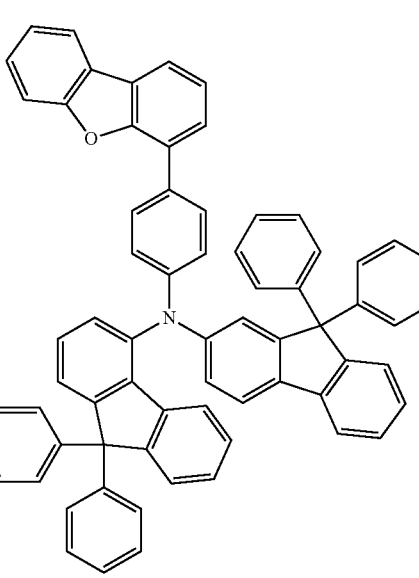

333
-continued
(H-A5)
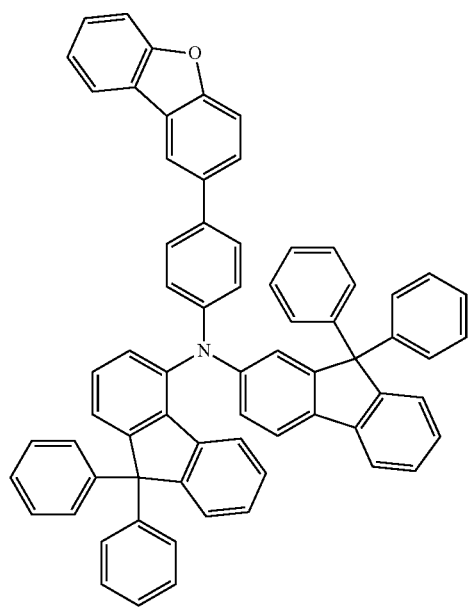
334
-continued
(H-A7)
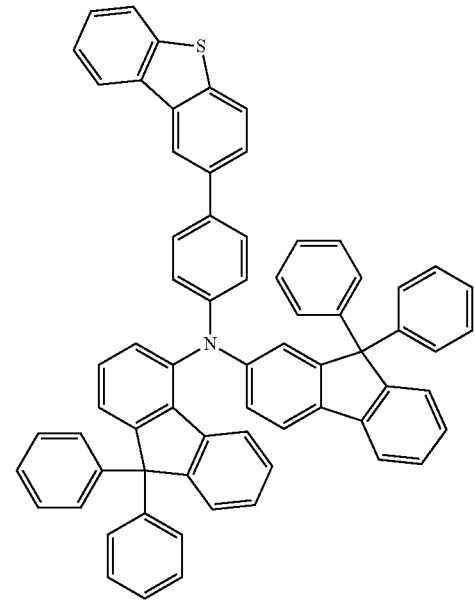
(H-A6)
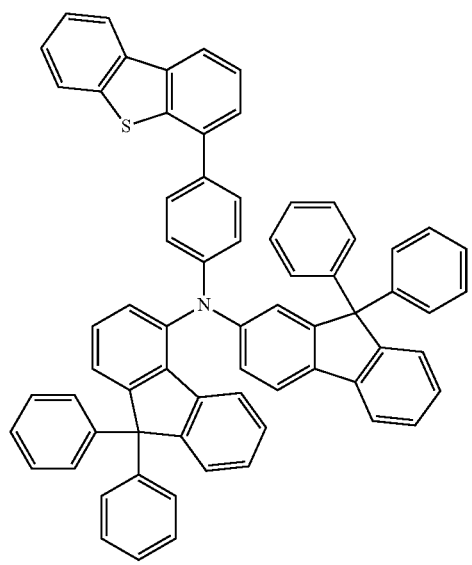
(H-A8)
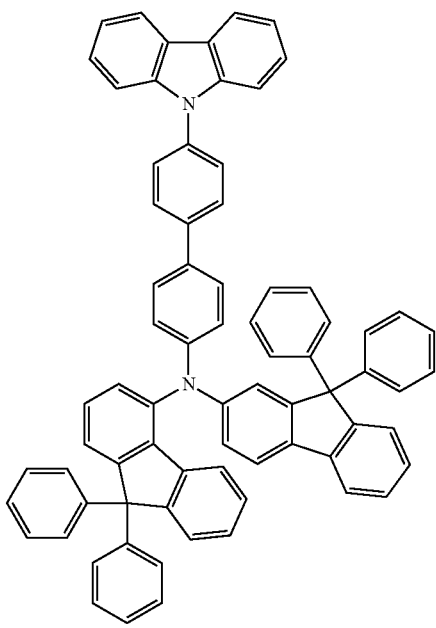

(H-A9)
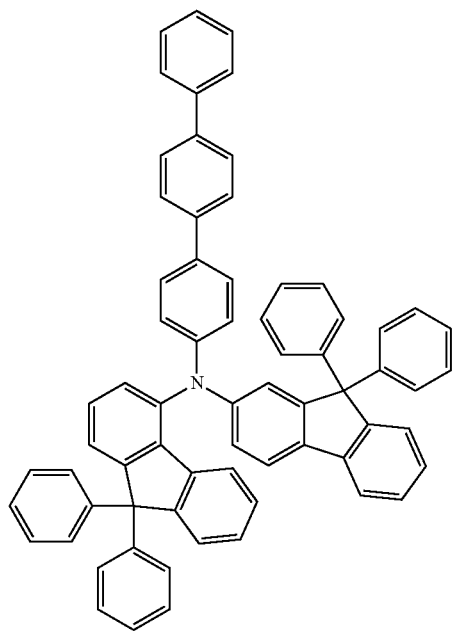
(H-A11)
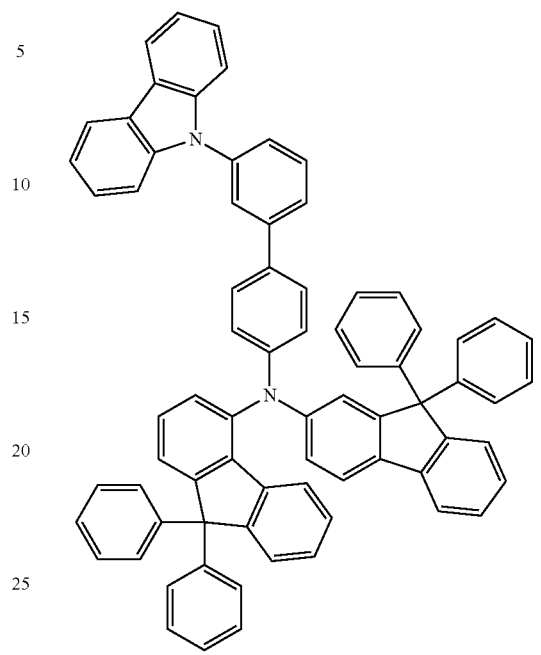
(H-A10)
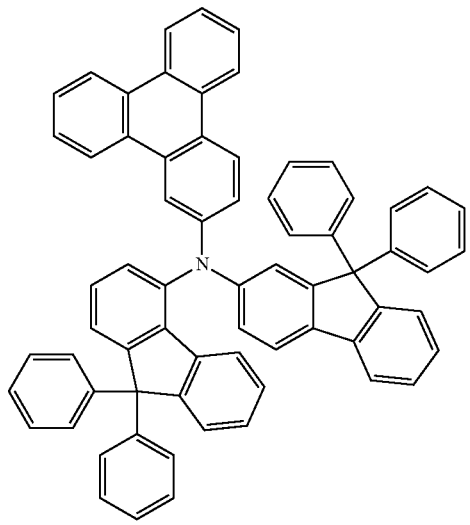
(H-A12)
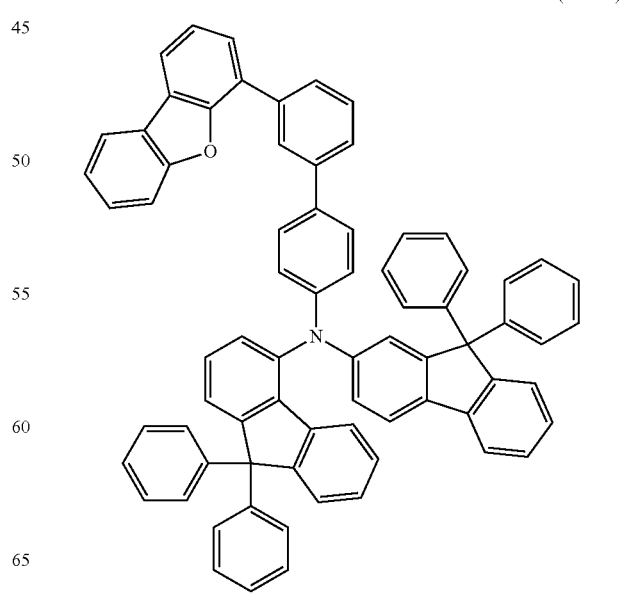

(H-A13)
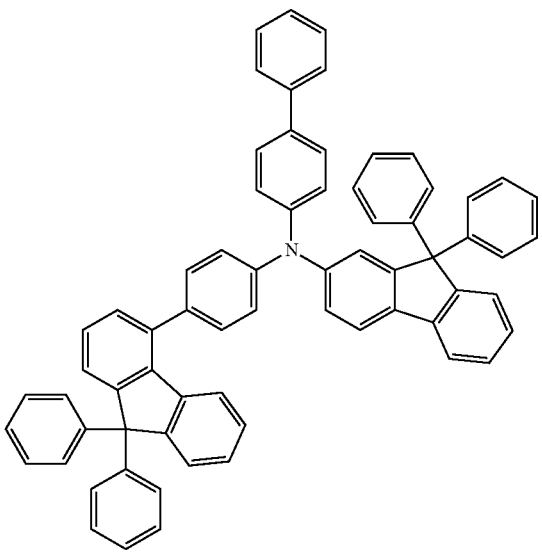
(H-A14)
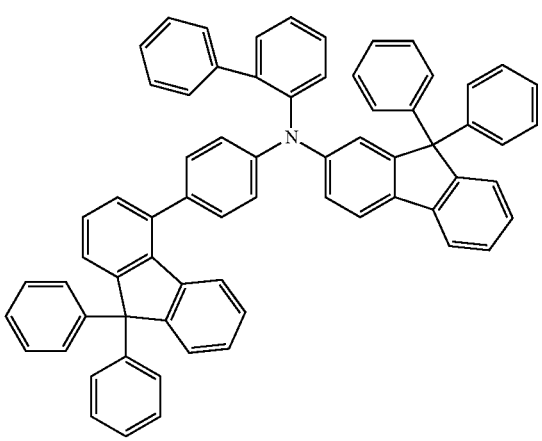
(H-A15)
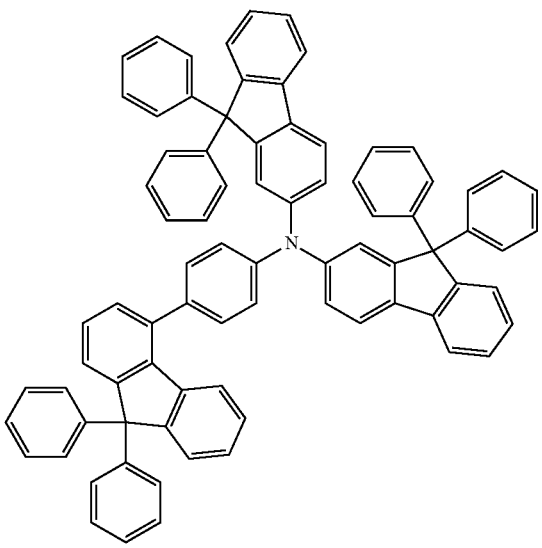
(H-A16)
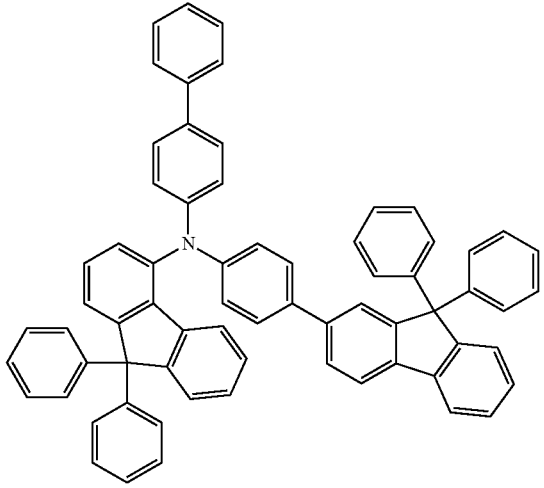
(H-A17)
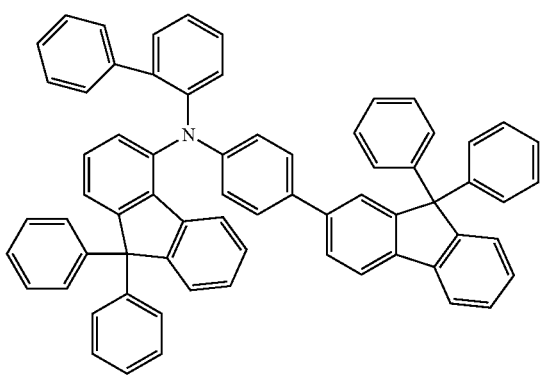
(H-A18)
Comparative Example a1-1 to a1-4
Each organic EL device of Comparative Example a1-1 to a1-4 was produced in the same manner as in Example A1-1 except for forming the second hole transporting layer by using each of the following compounds (a1) to (a4) as the second hole transporting material.

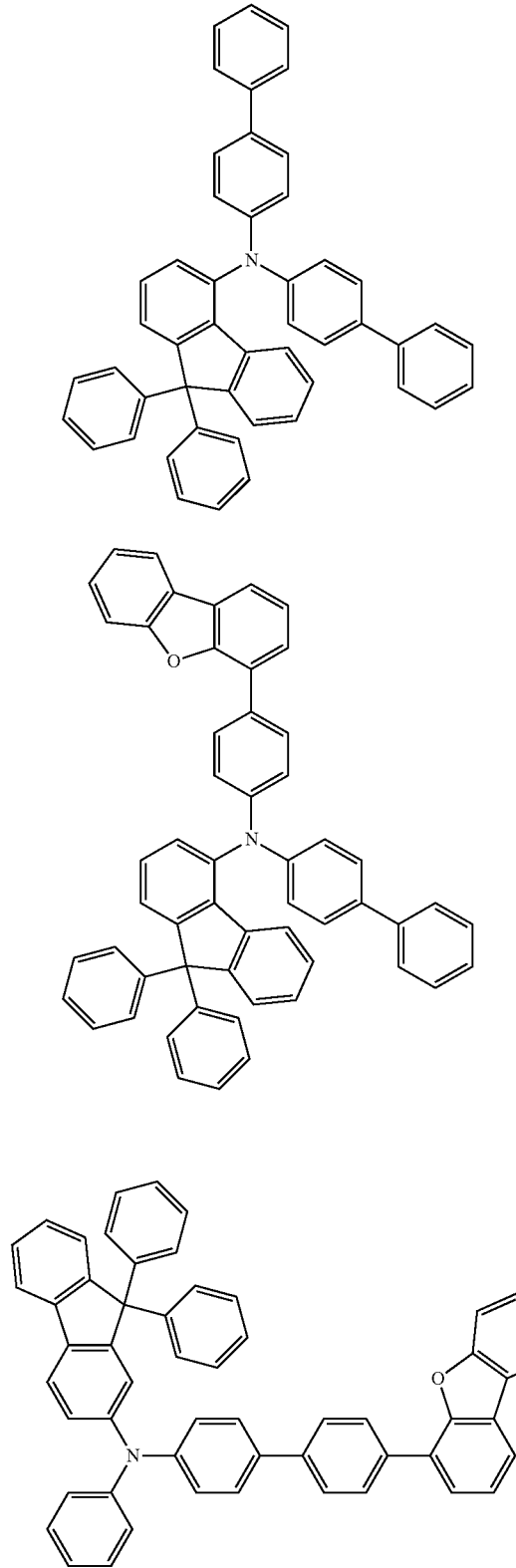

(a1)

(a2)

(a3)

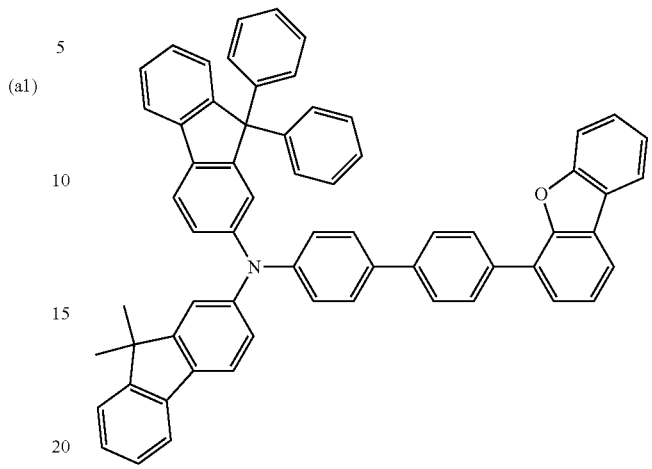

(a4)

Evaluation of Emission Efficiency of Organic EL Device

Each organic EL device thus produced was allowed to emit light by driving at a constant current to measure the luminance (L) and the current density. From the measured results, the emission efficiency (cd/A) and the driving voltage (V) at a current density of 10 mA/cm² were determined. In addition, the 80% lifetime at a current density of 50 mA/cm² was determined. The 80% lifetime is the time taken until the luminance is reduced to 80% of the initial luminance when driving at a constant current. The results are shown in Table A-1.

TABLE A-1

|  | First hole transporting material | Second hole transporting material | Emission efficiency (cd/A) @10 mA/cm² | Driving voltage (V) @10 mA/cm² | 80% lifetime (h) @50 mA/cm² |
|---|---|---|---|---|---|
| Examples |
| A1-1 | X1 | H-A1 | 9.5 | 4.5 | 280 |
| A1-2 | X1 | H-A2 | 9.6 | 4.5 | 280 |
| A1-3 | X1 | H-A3 | 9.5 | 4.4 | 290 |
| A1-4 | X1 | H-A4 | 9.6 | 4.5 | 300 |
| A1-5 | X1 | H-A5 | 9.7 | 4.4 | 290 |
| A1-6 | X1 | H-A6 | 9.6 | 4.5 | 300 |
| A1-7 | X1 | H-A7 | 9.7 | 4.4 | 290 |
| A1-8 | X1 | H-A8 | 9.7 | 4.6 | 320 |
| A1-9 | X1 | H-A9 | 9.5 | 4.3 | 320 |
| A1-10 | X1 | H-A10 | 9.5 | 4.3 | 290 |
| A1-11 | X1 | H-A11 | 9.7 | 4.8 | 300 |
| A1-12 | X1 | H-A12 | 9.7 | 4.8 | 300 |
| A1-13 | X1 | H-A13 | 9.4 | 4.4 | 280 |
| A1-14 | X1 | H-A14 | 9.5 | 4.4 | 290 |
| A1-15 | X1 | H-A15 | 9.4 | 4.3 | 290 |
| A1-16 | X1 | H-A16 | 9.8 | 4.5 | 300 |
| A1-17 | X1 | H-A17 | 9.8 | 4.6 | 290 |
| A1-18 | X1 | H-A18 | 9.7 | 4.4 | 320 |
| Comparative Examples |
| a1-1 | X1 | a1 | 9.8 | 4.8 | 200 |
| a1-2 | X1 | a2 | 9.8 | 4.9 | 220 |
| a1-3 | X1 | a3 | 8.2 | 4.5 | 220 |
| a1-4 | X1 | a4 | 7.8 | 4.3 | 250 |

Examples A2-1 to A2-18

Production of Organic EL Device

Each organic EL device of Examples A2-1 to A2-18 was produced in the same manner as in Example A1-1 except for forming the film (EA2) with a thickness of 10 nm by vapor-depositing the following compound (EA2) as the electron-accepting compound; forming the first hole transporting layer with a thickness of 80 nm by using each of the compounds (H-A1) to (H-A18) obtained in Synthesis Examples A-1 to A-18; and forming the second hole transporting layer with a thickness of 10 nm on the first hole transporting layer by using the following aromatic amine derivative (Y1) as the second hole transporting material.

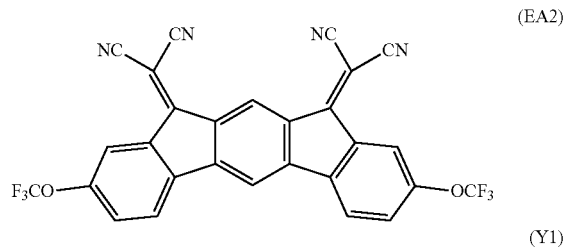
(EA2)

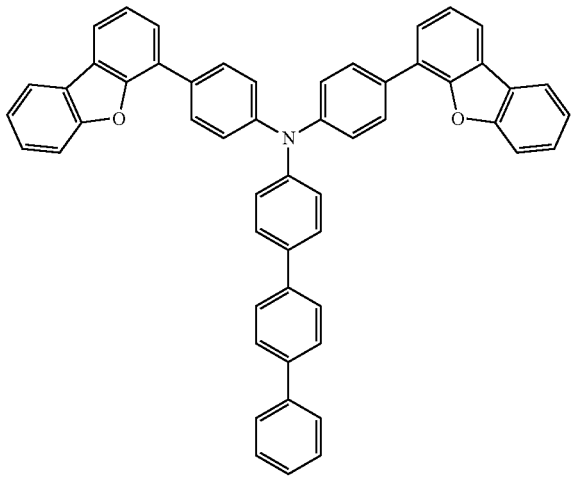
(Y1)

Comparative Examples a2-1 and a2-2

Production Organic EL Device

Each organic EL device of Comparative Examples a2-1 and a2-2 was produced in the same manner as in Example A2-1 except for forming the first hole transporting layer by using the above comparative compound (a1) or (a2) as the first hole transporting material.

Evaluation of Emission Efficiency of Organic EL Device

Each organic EL device thus produced was allowed to emit light by driving at a constant current to measure the luminance (L) and the current density. From the measured results, the current efficiency (L/J) and the driving voltage (V) at a current density of 10 mA/cm$^2$ were determined. In addition, the 80% lifetime at a current density of 50 mA/cm$^2$ was determined. The 80% lifetime is the time taken until the luminance is reduced to 80% of the initial luminance when driving at a constant current. The results are shown in Table A-2.

TABLE A-2

| First hole transporting material | Second hole transporting material | Emission efficiency (cd/A) @10 mA/cm$^2$ | Driving voltage (V) @10 mA/cm$^2$ | 80% lifetime (h) @50 mA/cm$^2$ |
|---|---|---|---|---|
| Examples | | | | |
| A2-1  H-A1  | Y1 | 9.5  | 4.4 | 300 |
| A2-2  H-A2  | Y1 | 9.5  | 4.3 | 300 |
| A2-3  H-A3  | Y1 | 9.3  | 4.3 | 310 |
| A2-4  H-A4  | Y1 | 9.3  | 4.4 | 300 |
| A2-5  H-A5  | Y1 | 9.7  | 4.4 | 300 |
| A2-6  H-A6  | Y1 | 9.3  | 4.4 | 290 |
| A2-7  H-A7  | Y1 | 9.6  | 4.4 | 290 |
| A2-8  H-A8  | Y1 | 9.5  | 4.4 | 300 |
| A2-9  H-A9  | Y1 | 9.5  | 4.2 | 350 |
| A2-10 H-A10 | Y1 | 9.4  | 4.2 | 300 |
| A2-11 H-A11 | Y1 | 10.1 | 4.7 | 310 |
| A2-12 H-A12 | Y1 | 10.1 | 4.6 | 300 |
| A2-13 H-A13 | Y1 | 9.5  | 4.3 | 310 |
| A2-14 H-A14 | Y1 | 9.5  | 4.2 | 320 |
| A2-15 H-A15 | Y1 | 9.5  | 4.2 | 310 |
| A2-16 H-A16 | Y1 | 9.5  | 4.4 | 320 |
| A2-17 H-A17 | Y1 | 9.8  | 4.3 | 320 |
| A2-18 H-A18 | Y1 | 9.4  | 4.4 | 350 |
| Comparative Examples | | | | |
| a2-1  a1    | Y1 | 9.5  | 4.8 | 250 |
| a2-2  a2    | Y1 | 9.5  | 5.4 | 220 |

As seen from Tables A-1 and A-2, it can be found that an organic EL device having high emission efficiency even when driving at a low voltage and long lifetime is obtained by using each of the compounds (H-A1) to (H-A18) within the compound (A) in an aspect of the invention.

The compound (A), such as the compounds (H-A1) to (H-A18), comprises more than one diphenylfluorene skeleton and at least one diphenylfluorene skeleton is boned at its 4-position. With such a structure, the electron blocking ability and the hole injecting ability are high to provide an organic EL device capable of driving at a low voltage and having long lifetime while maintaining the emission efficiency high.

Production of Organic EL Device Using Compound (B)

Examples B1-1 to B1-20

Production of Organic EL Device

Each organic EL device of Examples B1-1 to B1-20 was produced in the same manner as in Example A1-1 except for forming the second hole transporting layer by using each of the compounds (H-B1) to (H-B20) obtained in Synthesis Examples B-1 to B-20 as the second hole transporting material.

The compounds (H-B1) to (H-B20) obtained in Synthesis Examples B-1 to B-20 which were used in these examples are shown below.

(H-B1)
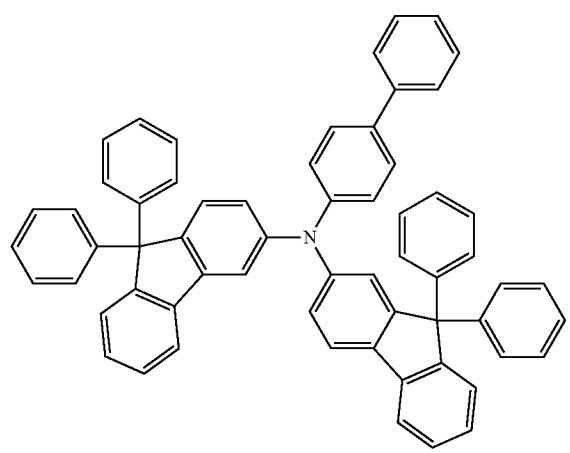
(H-B2)
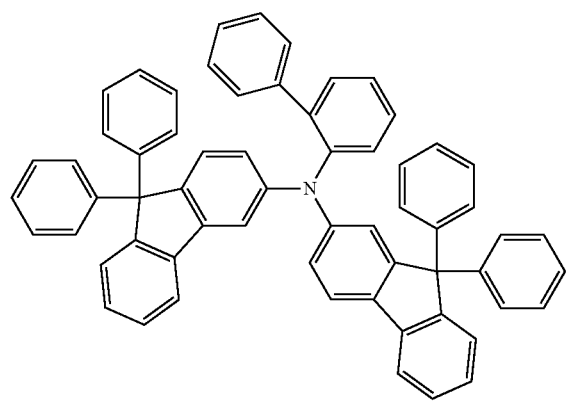
(H-B3)
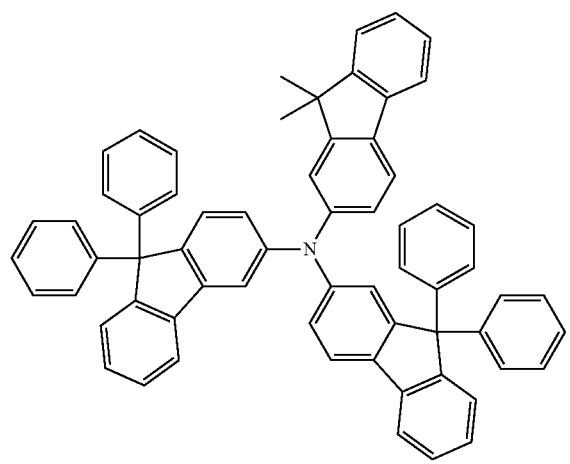
-continued
(H-B4)
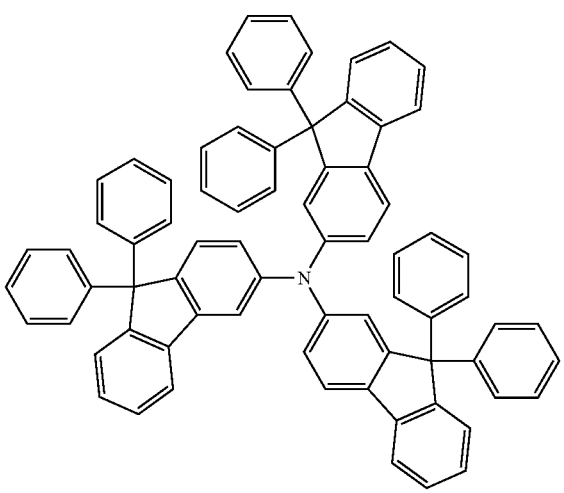
(H-B5)
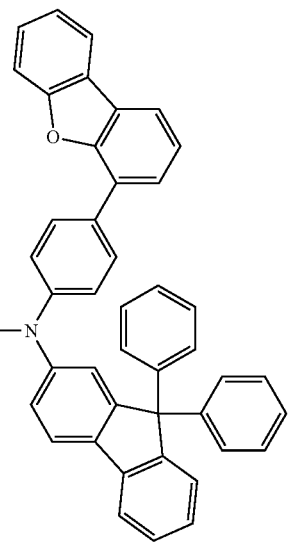
(H-B6)
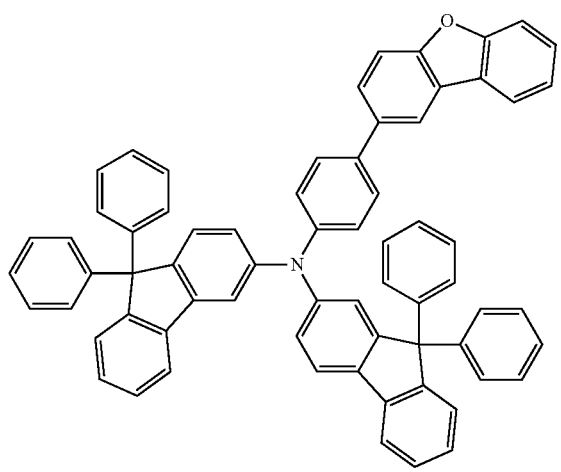

(H-B7)
(H-B8)
(H-B9)
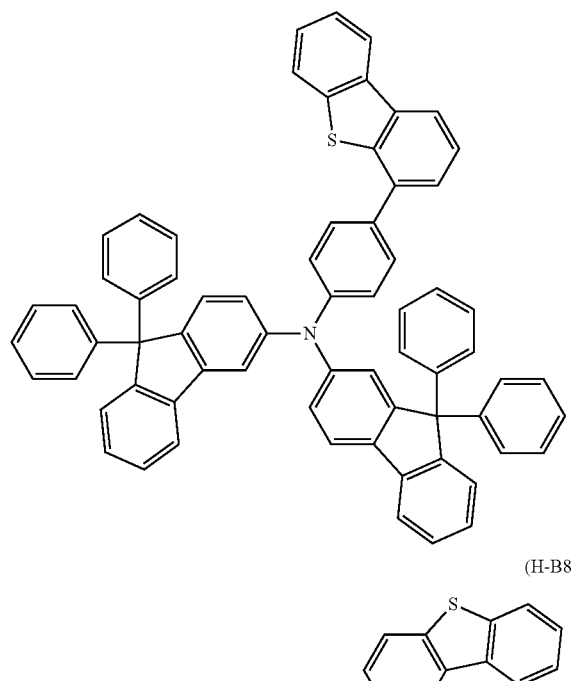
(H-B10)
(H-B11)
(H-B12)
(H-B13)
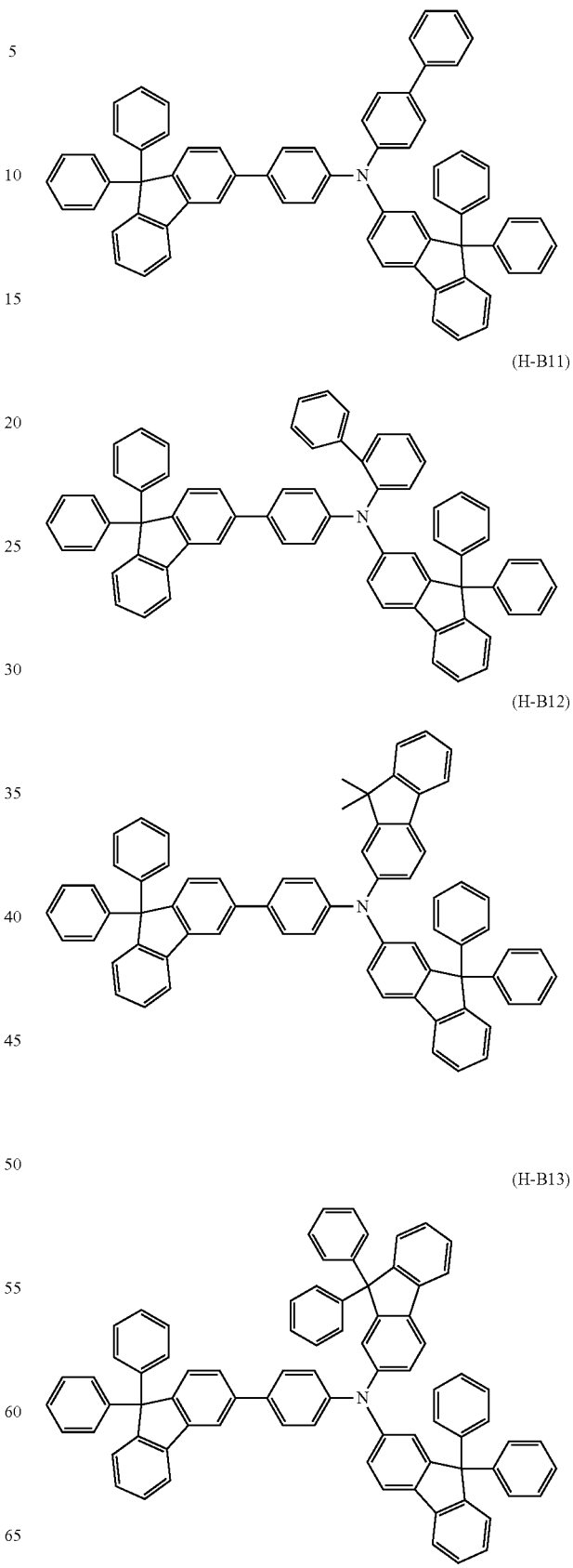

(H-B14)
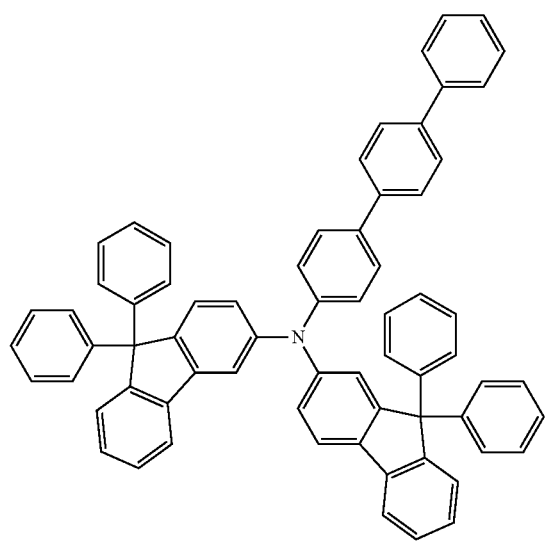
(H-B15)
(H-B16)
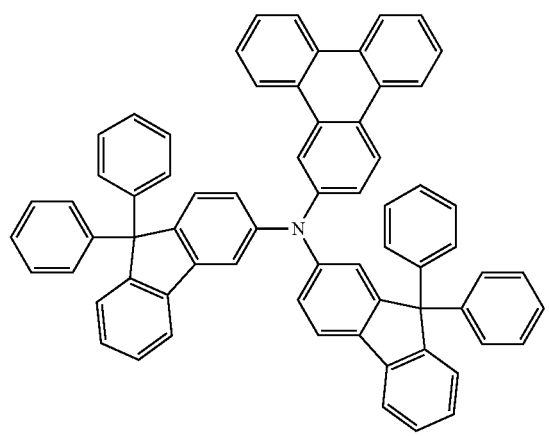
(H-B17)
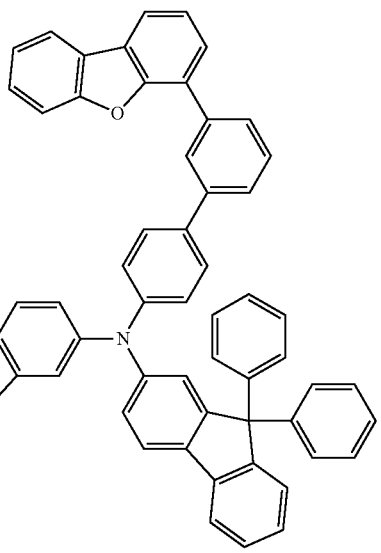
(H-B18)
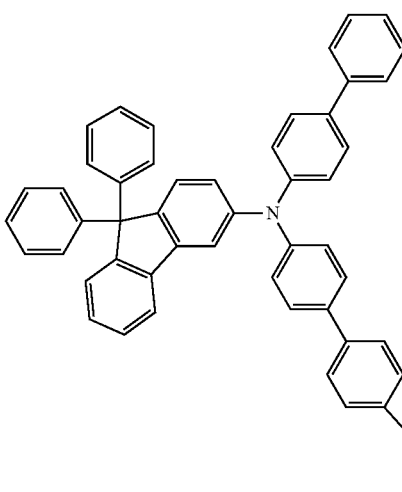
(H-B19)
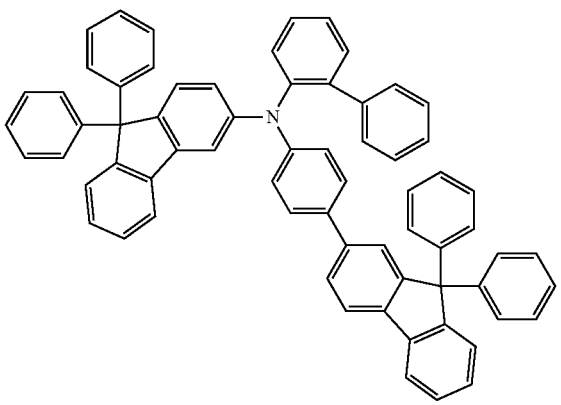

-continued (H-B20)

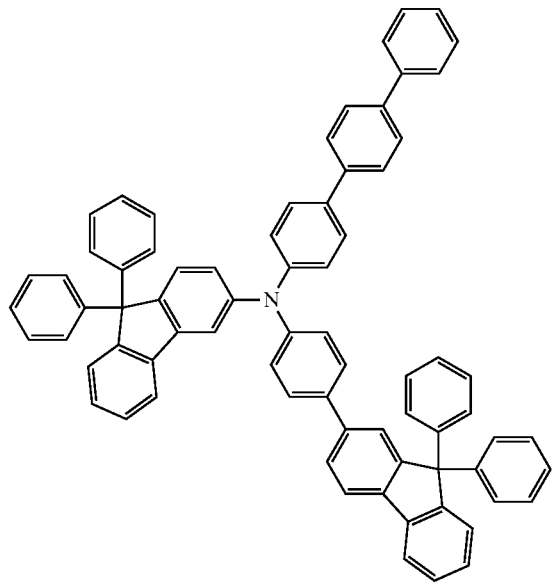

Comparative Examples b1-1 and b1-2

Production of Organic EL Device

Each organic EL device of Comparative Examples b1-1 and b1-2 was produced in the same manner as in Example B1-1 except for forming the second hole transporting layer by using the following comparative compound (b1) or (b2) as the second hole transporting material.

(b1)

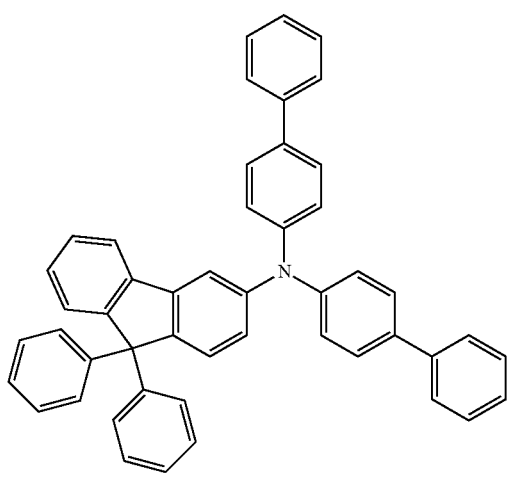

-continued (b2)

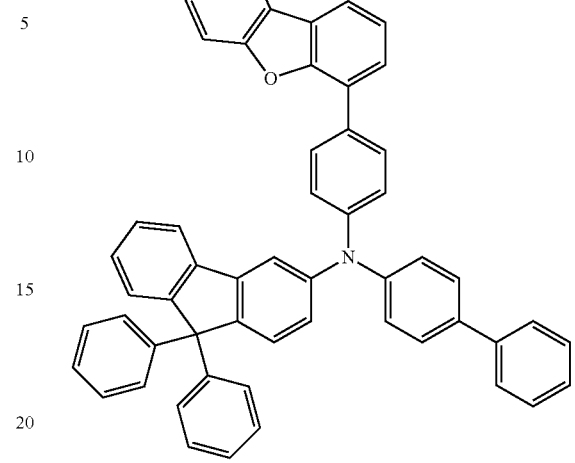

Evaluation of Emission Efficiency of Organic EL Device

Each organic EL device thus produced was allowed to emit light by driving at a constant current to measure the luminance (L) and the current density. From the measured results, the current efficiency (L/J) and the driving voltage (V) at a current density of 10 mA/cm$^2$ were determined. In addition, the 80% lifetime at a current density of 50 mA/cm$^2$ was determined. The 80% lifetime is the time taken until the luminance is reduced to 80% of the initial luminance when driving at a constant current. The results are shown in Table B-1.

TABLE B-1

| | | | Measured results | | |
|---|---|---|---|---|---|
| | First hole transporting material | Second hole transporting material | Emission efficiency (cd/A) @10 mA/cm$^2$ | Driving voltage (V) @10 mA/cm$^2$ | 80% lifetime (h) @50 mA/cm$^2$ |
| Examples | | | | | |
| B1-1 | X1 | H-B1 | 9.4 | 4.0 | 290 |
| B1-2 | X1 | H-B2 | 9.5 | 4.0 | 290 |
| B1-3 | X1 | H-B3 | 9.3 | 3.9 | 300 |
| B1-4 | X1 | H-B4 | 9.3 | 3.9 | 300 |
| B1-5 | X1 | H-B5 | 9.6 | 4.2 | 300 |
| B1-6 | X1 | H-B6 | 9.8 | 4.2 | 290 |
| B1-7 | X1 | H-B7 | 9.6 | 4.2 | 280 |
| B1-8 | X1 | H-B8 | 9.8 | 4.2 | 260 |
| B1-9 | X1 | H-B9 | 9.8 | 4.1 | 300 |
| B1-10 | X1 | H-B10 | 9.3 | 3.9 | 300 |
| B1-11 | X1 | H-B11 | 9.3 | 3.9 | 300 |
| B1-12 | X1 | H-B12 | 9.3 | 3.7 | 280 |
| B1-13 | X1 | H-B13 | 9.3 | 3.8 | 290 |
| B1-14 | X1 | H-B14 | 9.4 | 3.9 | 330 |
| B1-15 | X1 | H-B15 | 9.3 | 3.7 | 300 |
| B1-16 | X1 | H-B16 | 10.0 | 4.3 | 300 |
| B1-17 | X1 | H-B17 | 10.0 | 4.2 | 300 |
| B1-18 | X1 | H-B18 | 9.4 | 3.9 | 310 |
| B1-19 | X1 | H-B19 | 9.6 | 3.9 | 310 |
| B1-20 | X1 | H-B20 | 9.3 | 3.8 | 330 |
| Comparative Examples | | | | | |
| b1-1 | X1 | b1 | 9.5 | 3.8 | 200 |
| b1-2 | X1 | b2 | 9.8 | 3.9 | 220 |

Examples B2-1 to B2-20

Production Organic EL Device

Each organic EL device of Examples B2-1 to B2-20 was produced in the same manner as in Example A1-1 except for forming first hole transporting layer with a thickness of 80 nm by using each of the compounds (H-B1) to (H-B20) obtained in Synthesis Examples B-1 to B-20 as the first hole transporting material, and forming the second hole transporting layer with a thickness of 10 nm on the first hole transporting layer by using the following aromatic amine derivative (Y1) as the second hole transporting material.

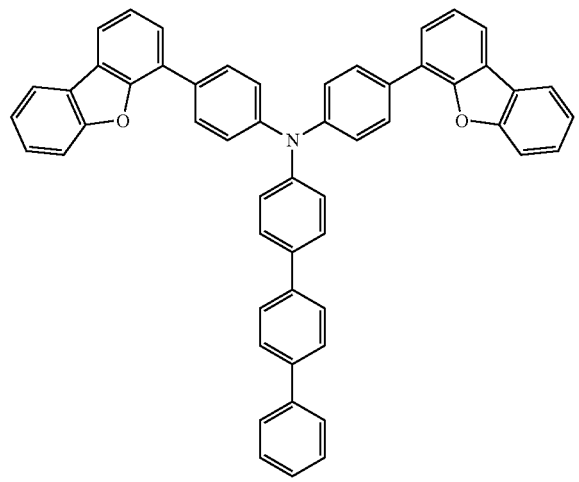

(Y1)

Comparative Examples b2-1 and b2-2

Production of Organic EL Device

Each organic EL device of Comparative Examples b2-1 and b2-2 was produced in the same manner as in Example B2-1 except for forming the first hole transporting layer by using the above comparative compound (b1) or (b2) as the first hole transporting material.

Examples B2-21 to B2-24

Production of Organic EL Device

Each organic EL device of Examples B2-21 to B2-24 was produced in the same manner as in Example A1-1 except for forming the film (EA2) with a thickness of 10 nm by vapor-depositing the following compound (EA2) as the electron-accepting compound; forming the first hole transporting layer with a thickness of 80 nm by using each of the compounds (H-B1) to (H-B4) obtained in Synthesis Examples B-1 to B-4 as the first hole transporting material; and forming the second hole transporting layer with a thickness of 10 nm on the first hole transporting layer by using the following aromatic amine derivative (Y1) as the second hole transporting material.

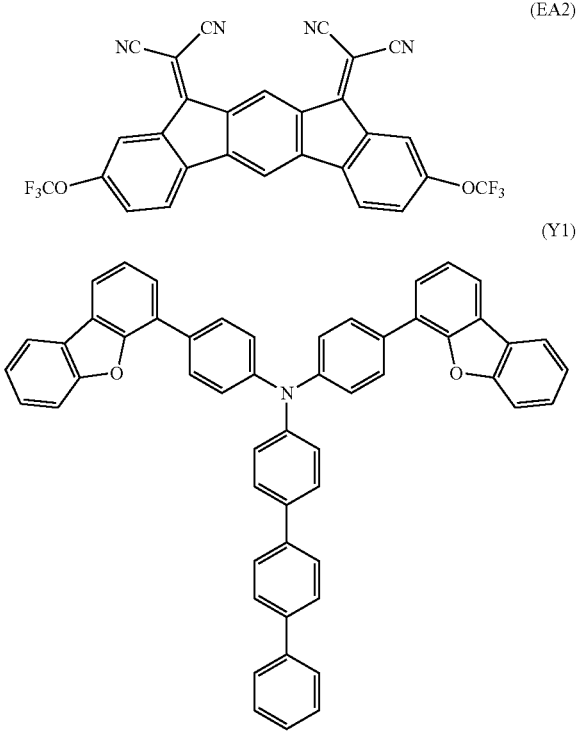

Comparative Examples b2-3 and b2-4

Production of Organic EL Device

Each organic EL device of Comparative Examples b2-3 and b2-4 was produced in the same manner as in Examples B2-21 to B2-24 except for forming the first hole transporting layer by using the above comparative compound (b1) or (b2) as the first hole transporting material.

Evaluation of Emission Efficiency of Organic EL Device

Each organic EL device thus produced was allowed to emit light by driving at a constant current to measure the luminance (L) and the current density. From the measured results, the current efficiency (L/J) and the driving voltage (V) at a current density of 10 mA/cm$^2$ were determined. In addition, the 80% lifetime at a current density of 50 mA/cm$^2$ was determined. The 80% lifetime is the time taken until the luminance is reduced to 80% of the initial luminance when driving at a constant current. The results are shown in Table B-2.

TABLE B-2

| | | | Measured results | | |
|---|---|---|---|---|---|
| | First hole transporting material | Second hole transporting material | Emission efficiency (cd/A) @10 mA/cm$^2$ | Driving voltage (V) @10 mA/cm$^2$ | 80% lifetime (h) @50 mA/cm$^2$ |
| Examples | | | | | |
| B2-1 | H-B1 | Y1 | 9.7 | 3.8 | 320 |
| B2-2 | H-B2 | Y1 | 9.7 | 3.8 | 320 |
| B2-3 | H-B3 | Y1 | 9.5 | 3.6 | 330 |
| B2-4 | H-B4 | Y1 | 9.5 | 3.7 | 330 |
| B2-5 | H-B5 | Y1 | 9.6 | 3.9 | 330 |

TABLE B-2-continued

| | First hole transporting material | Second hole transporting material | Emission efficiency (cd/A) @10 mA/cm² | Driving voltage (V) @10 mA/cm² | 80% lifetime (h) @50 mA/cm² |
|---|---|---|---|---|---|
| B2-6 | H-B6 | Y1 | 10.0 | 3.9 | 330 |
| B2-7 | H-B7 | Y1 | 9.5 | 3.9 | 320 |
| B2-8 | H-B8 | Y1 | 9.9 | 3.9 | 320 |
| B2-9 | H-B9 | Y1 | 9.9 | 3.8 | 300 |
| B2-10 | H-B10 | Y1 | 9.7 | 3.8 | 340 |
| B2-11 | H-B11 | Y1 | 9.7 | 3.8 | 330 |
| B2-12 | H-B12 | Y1 | 9.6 | 3.6 | 340 |
| B2-13 | H-B13 | Y1 | 9.6 | 3.7 | 340 |
| B2-14 | H-B14 | Y1 | 9.7 | 3.7 | 350 |
| B2-15 | H-B15 | Y1 | 9.9 | 3.6 | 300 |
| B2-16 | H-B16 | Y1 | 10.2 | 4.0 | 300 |
| B2-17 | H-B17 | Y1 | 10.2 | 4.0 | 300 |
| B2-18 | H-B18 | Y1 | 9.7 | 3.6 | 330 |
| B2-19 | H-B19 | Y1 | 9.8 | 3.5 | 320 |
| B2-20 | H-B20 | Y1 | 9.7 | 3.6 | 350 |
| B2-21 | H-B1 | Y1 | 9.7 | 3.5 | 330 |
| B2-22 | H-B2 | Y1 | 9.8 | 3.5 | 330 |
| B2-23 | H-B3 | Y1 | 9.6 | 3.4 | 340 |
| B2-24 | H-B4 | Y1 | 9.6 | 3.5 | 330 |
| Comparative Examples | | | | | |
| b2-1 | b1 | Y1 | 9.5 | 3.9 | 250 |
| b2-2 | b2 | Y1 | 9.5 | 4.0 | 220 |
| b2-3 | b1 | Y1 | 9.5 | 3.7 | 260 |
| b2-4 | b2 | Y1 | 9.5 | 3.8 | 220 |

As seen from Tables B-1 and B-2, it can be found that an organic EL device having high emission efficiency even when driving at a low voltage and long lifetime is obtained by using each of the compounds (H-B1) to (H-B20) within the compound (B) in an aspect of the invention.

The compound (B), such as the compounds (H-B1) to (H-B20), comprises more than one diphenylfluorene skeleton and at least one diphenylfluorene skeleton is boned at its 3-position. With such a structure, the electron blocking ability and the hole injecting ability are high to provide an organic EL device capable of driving at a low voltage and having long lifetime while maintaining the emission efficiency high.

Example B3-1

Production of Organic EL Device

A glass substrate of 25 mm×75 mm×1.1 mm thickness having an ITO transparent electrode (product of Geomatec Company) was cleaned by ultrasonic cleaning in isopropyl alcohol for 5 min and then UV ozone cleaning for 30 min. The thickness of the ITO transparent electrode was 130 nm.

The cleaned glass substrate having a transparent electrode line was mounted to a substrate holder of a vacuum vapor deposition apparatus. First, the following electron-accepting compound (EA2) was vapor-deposited so as to cover the transparent electrode to form a film (EA2) with a thickness of 5 nm.

On the film (EA2), the compound (H-B1) obtained in Synthesis Example B-1 as a hole transporting material was vapor-deposited to form a hole transporting layer with a thickness of 210 nm.

On the hole transporting layer, the following host compound (RH-1) and the following dopant compound (RD-1) were vapor co-deposited to form a light emitting layer with a thickness of 40 nm. The concentration of the dopant compound (RD-1) in the light emitting layer was 2.0% by mass.

On the light emitting layer, the following compound (ET) (50% by mass) and an electron-donating dopant Liq (8-hydroxyquinolinolatolithium) (50% by mass) were vapor binary-deposited to form an electron transporting layer with a thickness of 30 nm.

Next, on the electron transporting layer, Liq was vapor-deposited into a Liq film with a thickness of 1 nm at a film-forming speed of 0.1 Å/min to form an electron injecting layer.

Further, on the Liq film, metallic Al was vapor-deposited into a metallic Al film with a thickness of 80 nm to form a cathode, thereby producing an organic EL device of Example B3-1.

Example B3-2

Production of Organic EL Device

An organic EL device of Example B3-2 was produced in the same manner as in Example B3-1 except for using the following host compound (RH-2) as the host material.

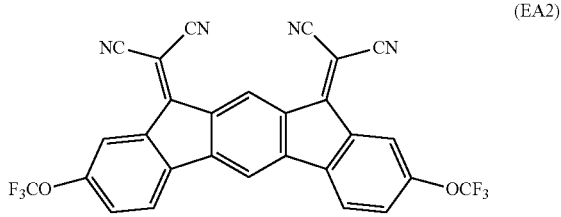

(EA2)

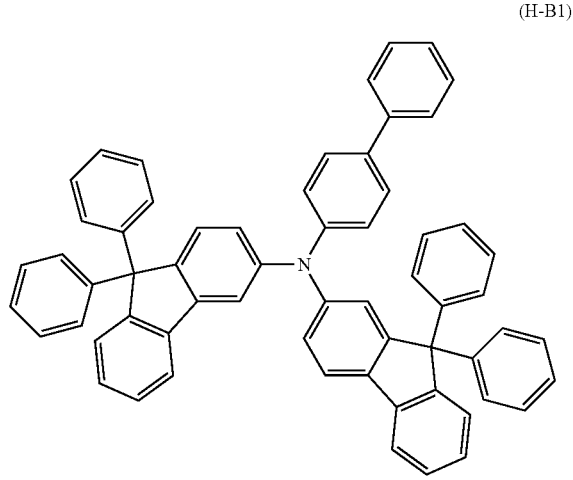 [SMILES: c1ccc(-c2ccc(N(c3ccc4c(c3)-c3ccccc3C4(c3ccccc3)c3ccccc3)c3ccc4c(c3)C(c3ccccc3)(c3ccccc3)c3ccccc3-4)cc2)cc1]

(H-B1)

-continued (RH-1)

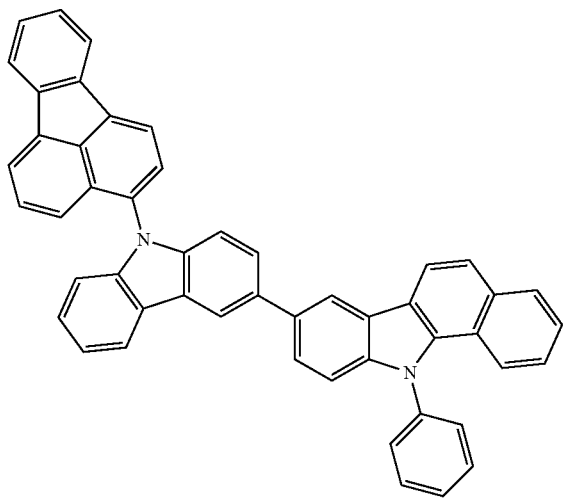

(RH-2)

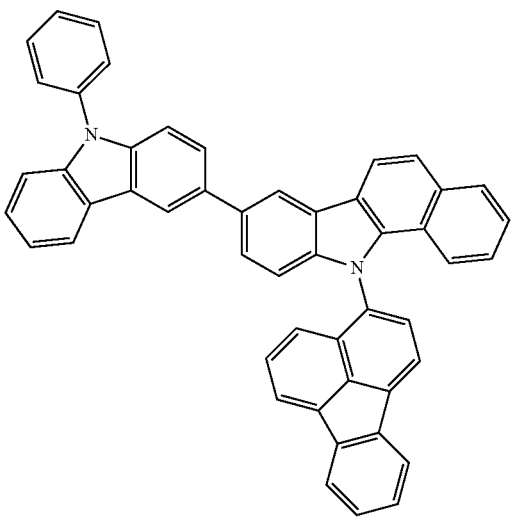

(RD-1)

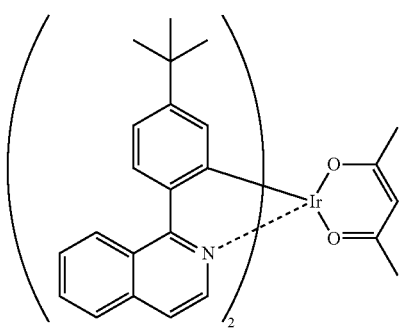

-continued (ET)

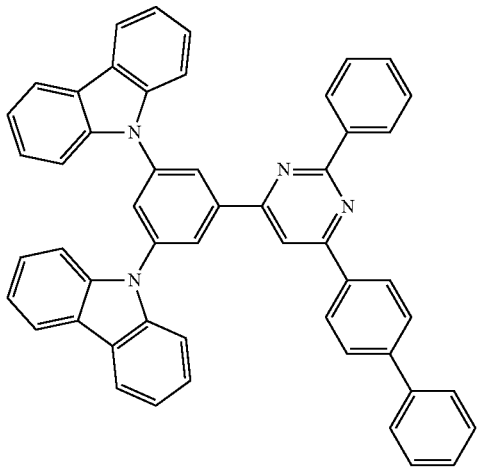

Comparative Example b3-1

Production of Organic EL Device

An organic EL device of Comparative Example b3-1 was produced in the same manner as in Example B3-1 except for forming the hole transporting layer by using the above comparative compound (b1) as the hole transporting material.

Comparative Example b3-2

Production of Organic EL Device

An organic EL device was produced in the same manner as in Example B3-1 except for forming the hole transporting layer by using the above comparative compound (b1) and using the above host compound (RH-2) as the host material.
Evaluation of Emission Efficiency of Organic EL Device Each organic EL device thus produced was allowed to emit light by driving at a constant current to measure the luminance (L) and the current density. From the measured results, the external quantum efficiency (L/JEQE) and the driving voltage (V) at a current density of 10 mA/cm² were determined. In addition, the 80% lifetime at a current density of 50 mA/cm² was determined. The 80% lifetime is the time taken until the luminance is reduced to 80% of the initial luminance when driving at a constant current. The results are shown in Table B-3.

TABLE B-3

| | | | Measured results | | |
|---|---|---|---|---|---|
| | First hole transporting material | Second hole transporting material | External quantum efficiency (EQE) @10 mA/cm² | Driving voltage (V) @10 mA/cm² | 80% lifetime (h) @50 mA/cm² |
| Examples | | | | | |
| B3-1 | H-B1 | RH-1 | 17.0 | 4.2 | 530 |
| B3-2 | H-B1 | RH-2 | 18.0 | 4.4 | 300 |

TABLE B-3-continued

|  |  | Measured results | | |
|---|---|---|---|---|
| First hole transporting material | Second hole transporting material | External quantum efficiency (EQE) @10 mA/cm² | Driving voltage (V) @10 mA/cm² | 80% lifetime (h) @50 mA/cm² |
| Comparative Examples | | | | |
| b3-1 | b1 | RH-1 | 7.5 | 5.2 | 110 |
| b3-2 | b1 | RH-2 | 7.2 | 5.5 | 60 |

As seen from Table B-3, the compound (H-B1) in an aspect of the invention has a high hole mobility and a high ability of injecting holes into the light emitting layer. Therefore, even when used as a material for a hole transporting layer with a larger thickness, an organic EL device capable of driving at a low voltage and having high emission efficiency and long lifetime is obtained.

REFERENCE SIGNS LIST

1: Organic EL device
2: Substrate
3: Anode
4: Cathode
5: Light emitting layer
6: Anode-side organic thin film layer
7: Cathode-side organic thin film layer
10: Emission unit

What is claimed is:

1. A compound represented by formula (A-2) or (B-2):

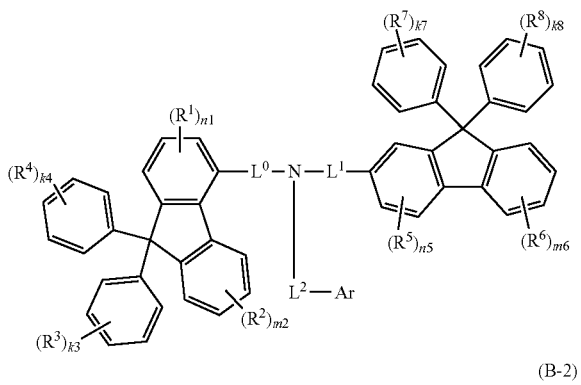

(A-2)

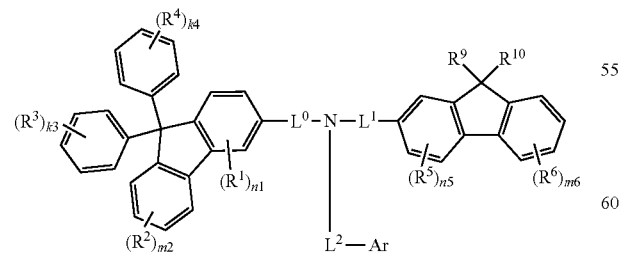

(B-2)

wherein $R^1$ to $R^8$ each independently represent a substituted or unsubstituted alkyl group having 1 to 20 carbon atoms, a substituted or unsubstituted aryl group having 6 to 50 ring carbon atoms, a substituted or unsubstituted heteroaryl group having 5 to 50 ring atoms, a halogen atom, a substituted or unsubstituted fluoroalkyl group having 1 to 20 carbon atoms, a substituted or unsubstituted alkoxy group having 1 to 20 carbon atoms, a substituted or unsubstituted fluoroalkoxy group having 1 to 20 carbon atoms, a substituted or unsubstituted aryloxy group having 6 to 50 ring carbon atoms, or a cyano group;

when $R^1$ to $R^8$ are each plural in number, groups $R^1$ to groups $R^8$ may be the same or different, two selected from $R^5$ to $R^8$ in formula (A-2) may be bonded to each other to form a ring structure, and two selected from $R^5$ and $R^6$ in formula (B-2) may be bonded to each other to form a ring structure;

$R^9$ and $R^{10}$ are each an unsubstituted phenyl group;

k3, k4, k7, and k8 each independently represent an integer of 0 to 5, m2 and m6 each independently represent an integer of 0 to 4, and n1 and n5 each independently represent an integer of 0 to 3;

$L^1$ is a single bond;

in (A-2) $L^0$ and $L^2$ each independently represent a single bond, or a group represented by any of formulae (i) and (ii):

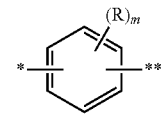

(i)

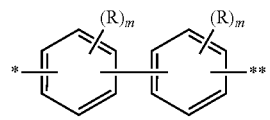

(ii)

wherein each R is independently the same as defined with respect to $R^1$, when more than one R occurs, groups R may be the same or different, two selected from groups R may be bonded to each other to form a ring structure, each m independently represents an integer of 0 to 4, and * and ** each represent a bonding site;

in (B-2) $L^0$ and $L^2$ each independently represent a single bond, a substituted or unsubstituted arylene group having 6 to 50 ring carbon atoms, or a substituted or unsubstituted heteroarylene group having 5 to 50 ring atoms; and in (A-2) Ar is a group selected from the group consisting of formulae (c), (g) to (j) and a triphenylene group, in (B-2) Ar is a group selected from the group consisting of (c), (d), (f) to (j) and a triphenylene group:

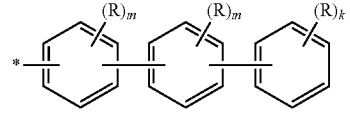

(c)

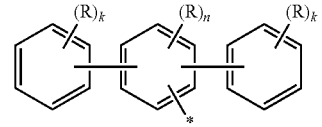

(d)

(f)

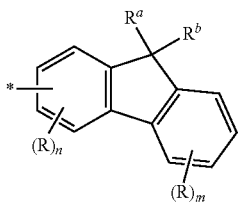

(g)

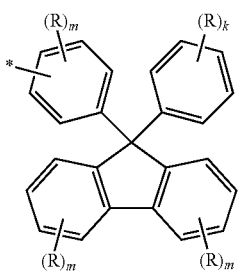

(h)

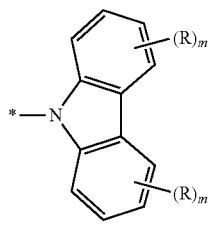

(i)

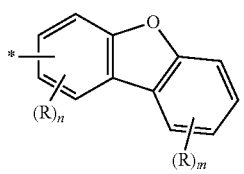

(j)

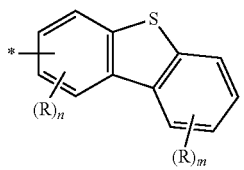

wherein $R^a$ and $R^b$ are each —$CH_3$,
R is $R^1$ as defined above,
and
k, m and n are each 0.

2. The compound according to claim 1, wherein the compound is represented by formula (A-2-1):

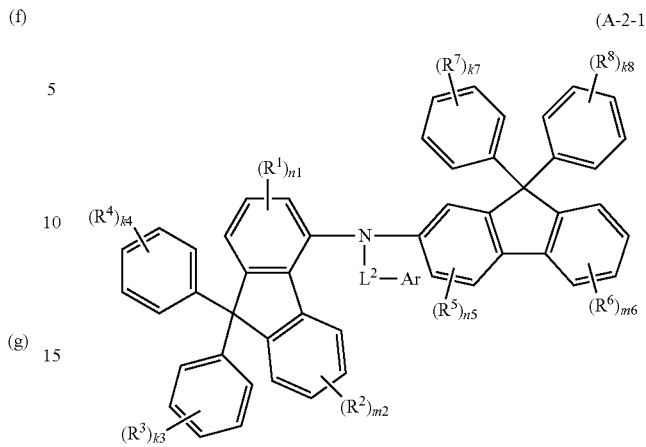

(A-2-1)

wherein $R^1$ to $R^8$, n1, m2, k3, k4, n5, m6, k7, k8, $L^2$, and Ar are as defined in claim 1.

3. The compound according to claim 1, wherein the compound is represented by the formula (A-2) and wherein k3, k4, k7, and k8 are each 0.

4. The compound according to claim 1, wherein the compound is represented by the formula (A-2) and wherein k3, k4, k7, and k8 are each 0, m2 and m6 are each 0, and n1 and n5 are each 0.

5. The compound according to claim 1, represented by the formula (A-2), wherein $L^0$ represents a single bond.

6. The compound according to claim 1, wherein the compound is represented by the formula (B-2):

wherein $L^0$ is a single bond.

7. The compound according to claim 1, wherein the compound is represented by the formula (B-2) wherein k3 and k4 are each 0.

8. The compound according to claim 1, wherein the compound is represented by the formula (B-2) wherein K3, k4, m2, m6, n1 and n5 are each 0.

9. The compound according to claim 1, wherein in (A-2) Ar represents a group represented by any of formulae (c-1), and (c-2), and in (B-2) (c-1), (c-2) and (d-1):

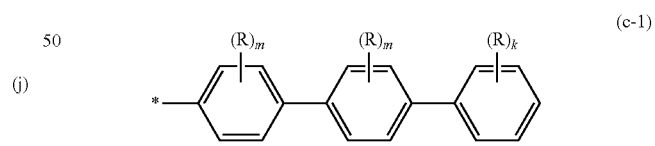

(c-1)

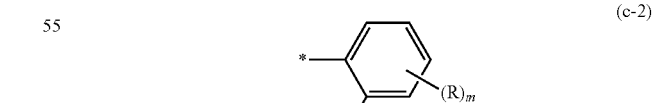

(c-2)

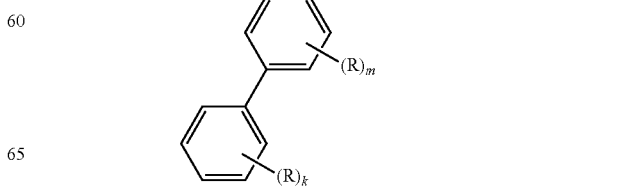

-continued

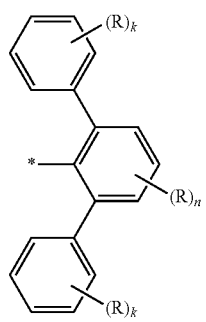

(d-1)

wherein R, k, m, n, and * are as defined in claim 1.

10. The compound according to claim 1, wherein the compound is represented by the formula (B-2), and wherein $L^0$ and $L^2$ each independently represent a single bond or a group represented by any of formulae (i) and (ii):

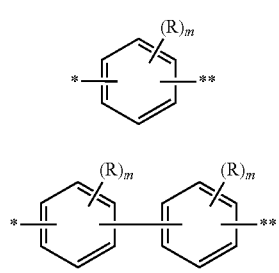

(ii)

(ii)

wherein each R is independently the same as defined with respect to $R^1$ in claim 1, when more than one R occurs, groups R may be the same or different, two selected from groups R may be bonded to each other to form a ring structure, each m independently represents an integer of 0 to 4, and * and ** each represent a bonding site.

11. The compound according to claim 1, wherein $-L^2$-Ar represents any of the following groups:

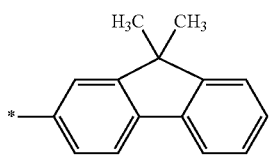

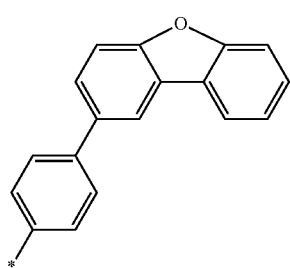

-continued

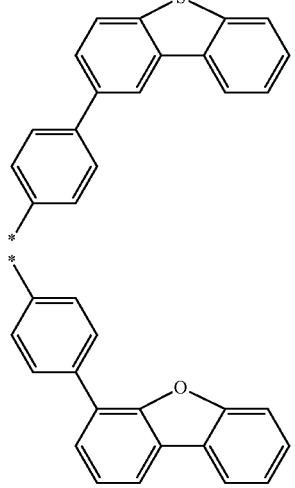

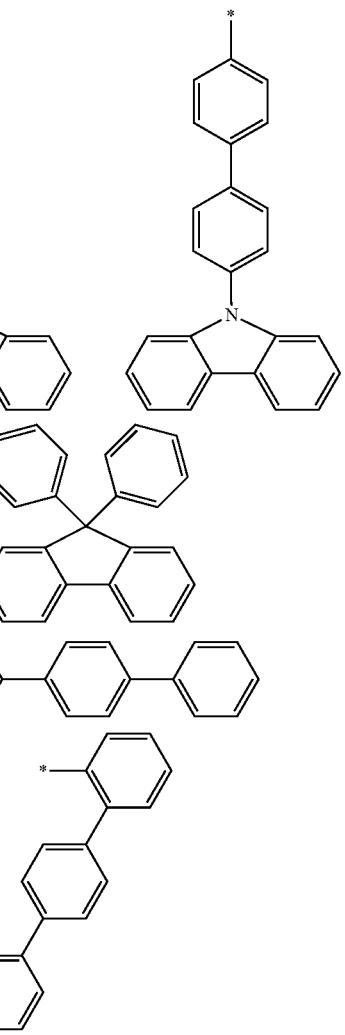

wherein * represents a bonding site to a nitrogen atom and $R^c$ represents a hydrogen atom, a substituted or unsubstituted alkyl group having 1 to 20 carbon atoms, a substituted or unsubstituted aryl group having 6 to 50 ring carbon atoms, or a substituted or unsubstituted heteroaryl group having 5 to 50 ring atoms.

12. The compound according to claim 1, wherein the compound is any of the following compounds (H-A3) to (HA-12) and (HA-15):
(H-A3)
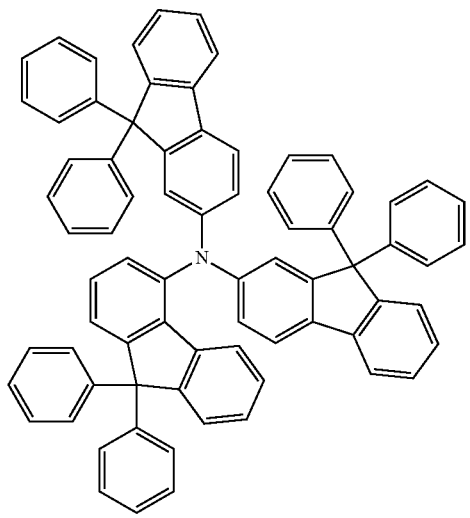
(H-A4)
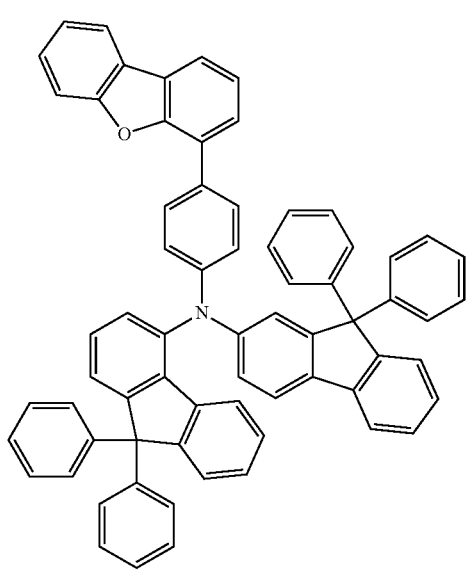
(H-A5)
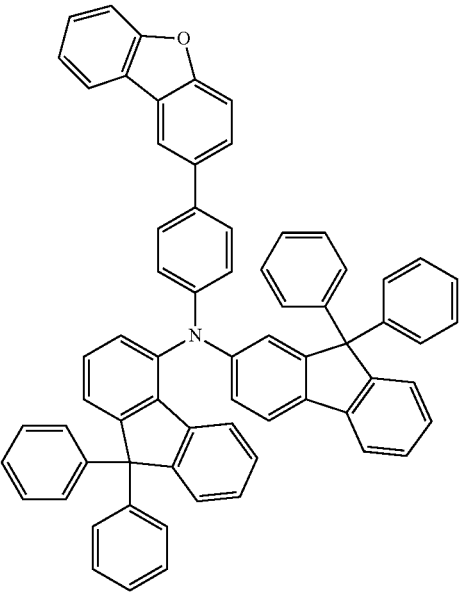
(H-A6)
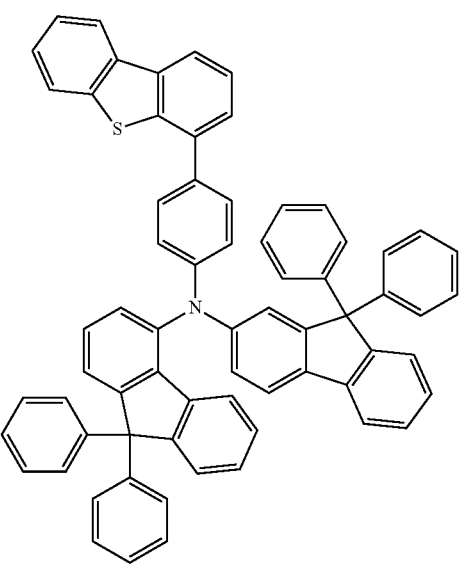

365
-continued
(H-A7)
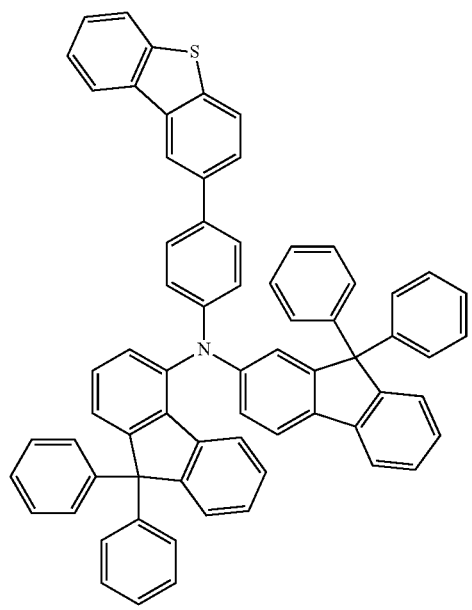
(H-A8)
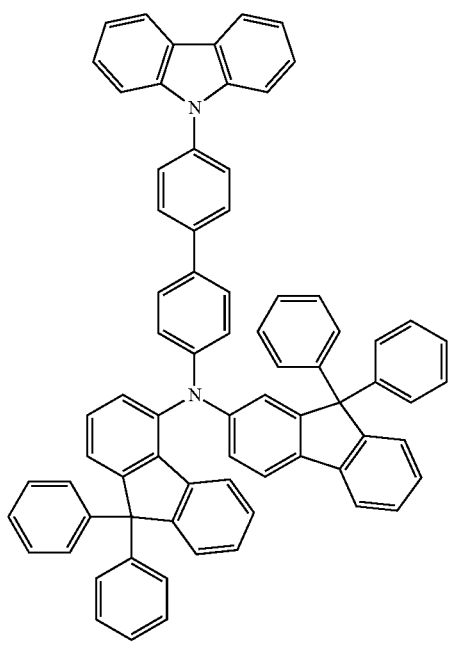
366
-continued
(H-A9)
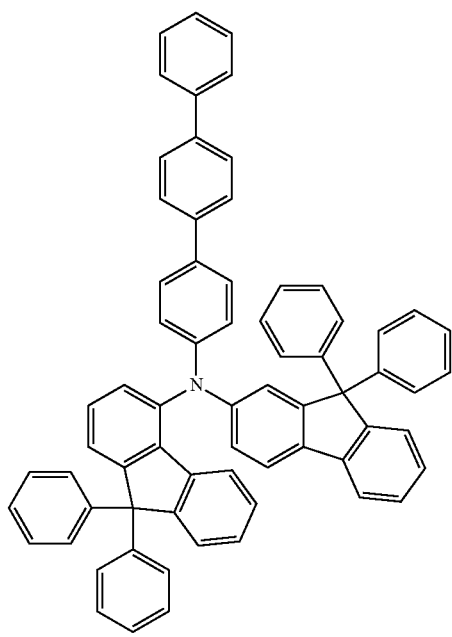
(H-A10)
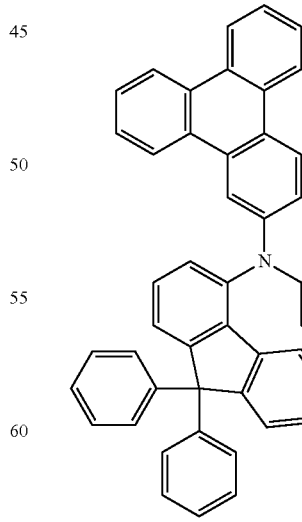

(H-A11)
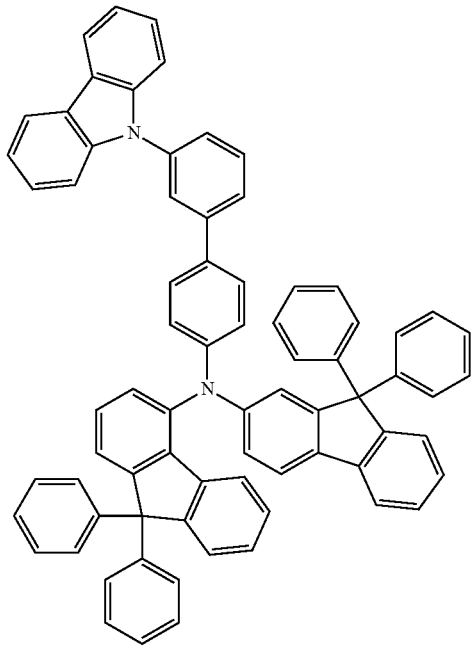
(H-A15)
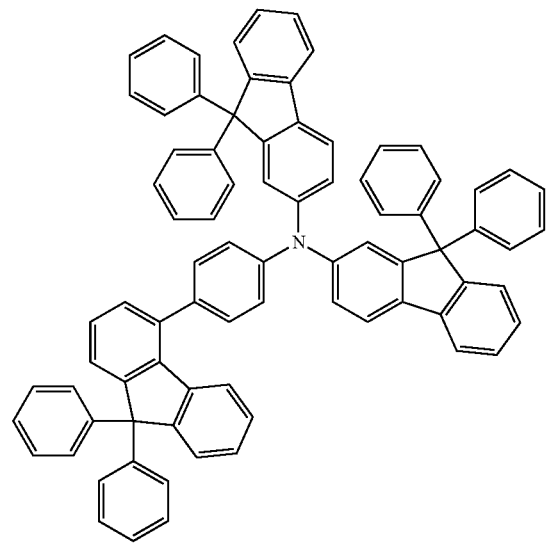
(H-A12)
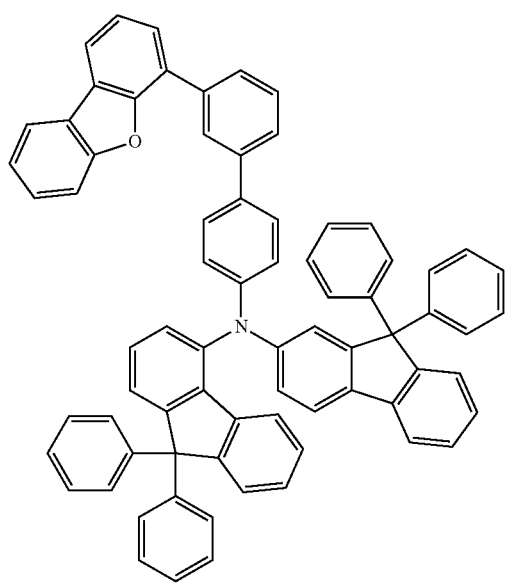
13. The compound according to claim 1, wherein the compound is any of the following compounds (HB-3) to (HB-9) and (HB-12) to (HB-17):
(H-B3)
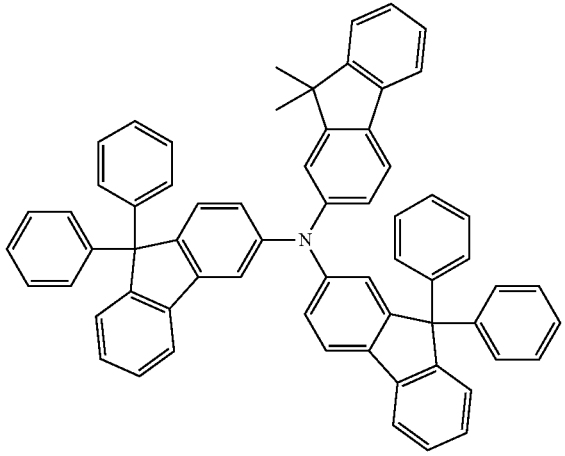

(H-B4)
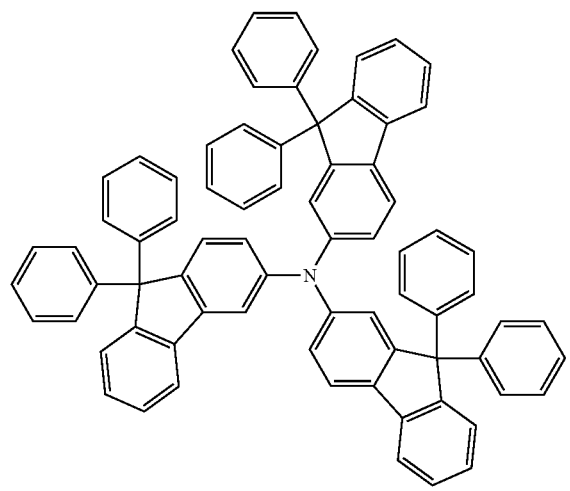
(H-B5)
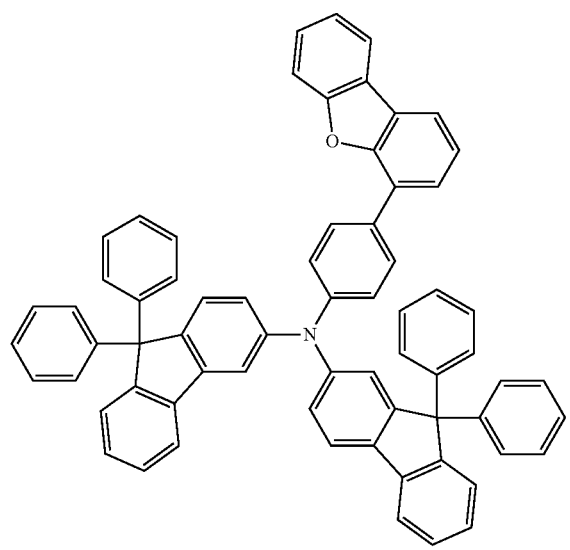
(H-B6)
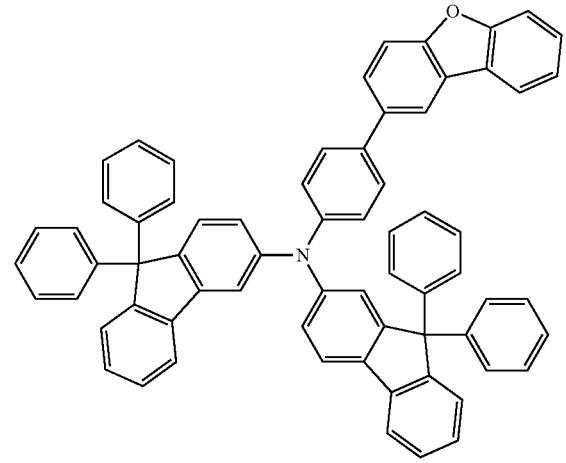
(H-B7)
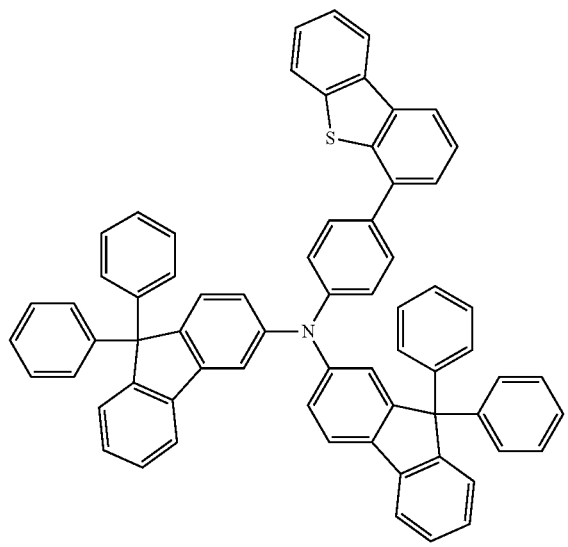
(H-B8)
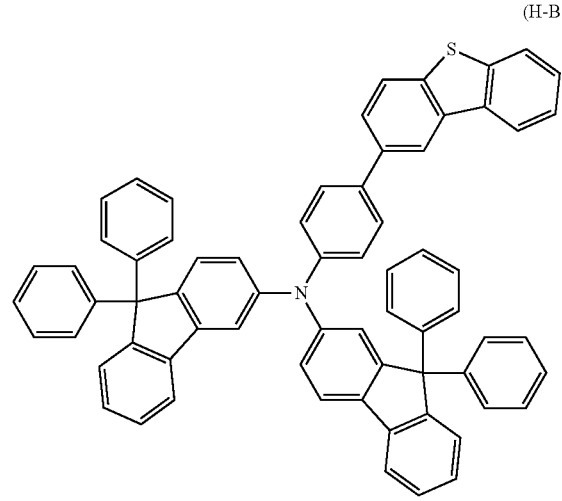
(H-B9)
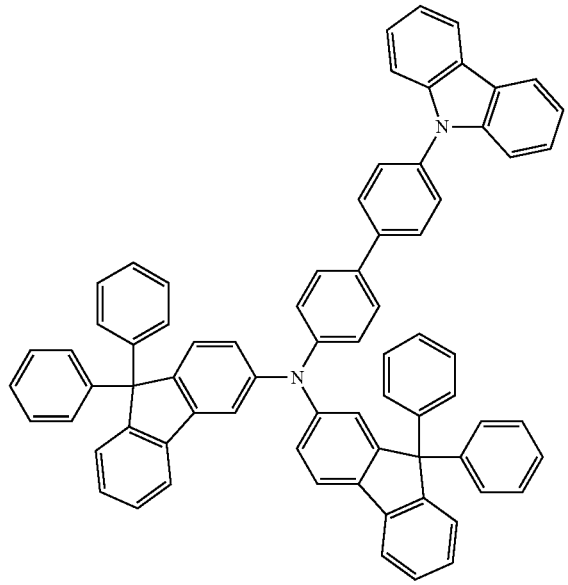

(H-B12)
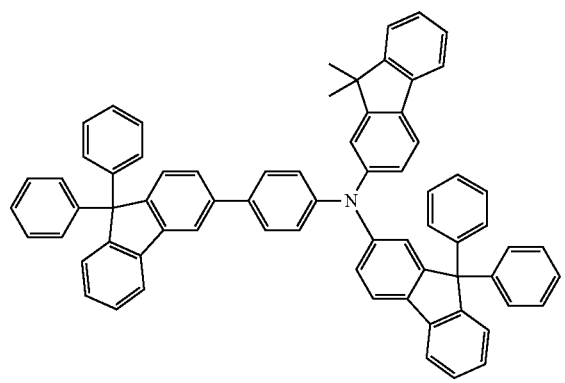
(H-B13)
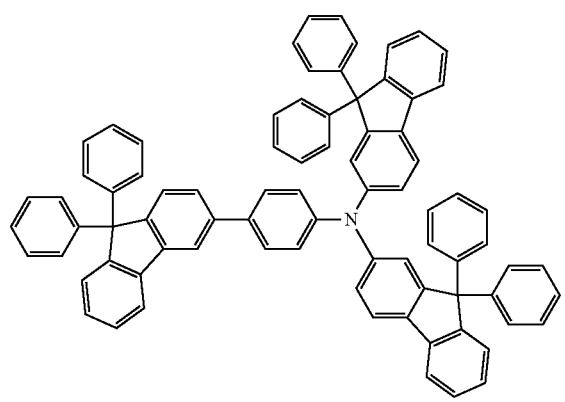
(H-B14)
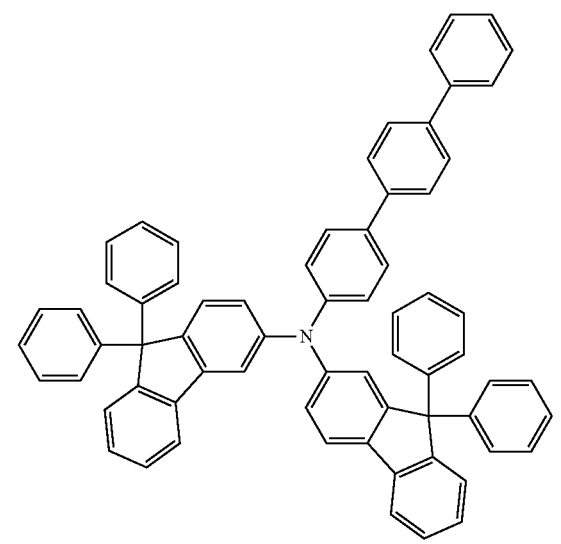
(H-B15)
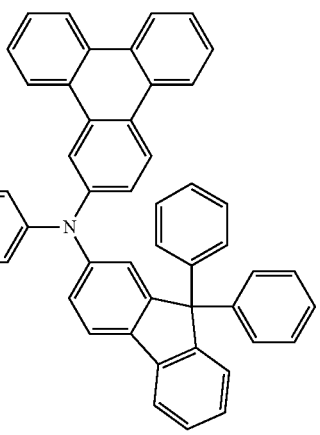
(H-B16)
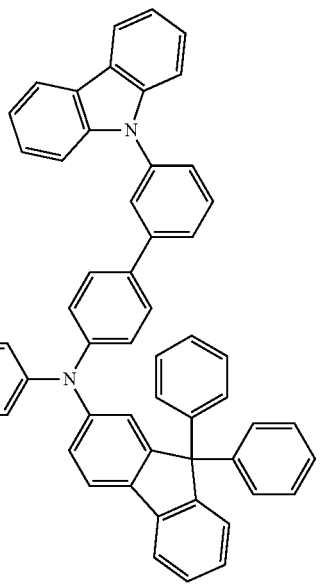
(H-B17)
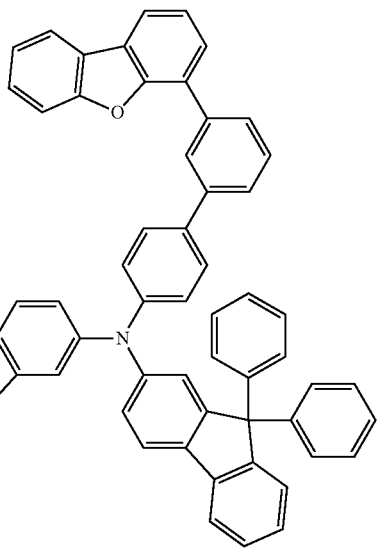

14. A material comprising the compound according to claim 1.

15. An organic electroluminescence device comprising a cathode, an anode, and an organic thin film layer disposed between the cathode and the anode, wherein the organic thin film layer comprises a light emitting layer and at least one layer of the organic thin film layer comprises the compound according to claim 1.

16. The organic electroluminescence device according to claim 15, wherein the organic thin film layer comprises at least one selected from the group consisting of (i) a hole injecting layer comprising the compound and (ii) a hole transporting layer comprising the compound.

17. An electronic equipment comprising the organic electroluminescence device according to claim 15.

* * * * *